United States Patent
Blatter et al.

(10) Patent No.: US 11,059,829 B2
(45) Date of Patent: Jul. 13, 2021

(54) CRYSTAL FORMS OF (S)-4-(8-AMINO-3-(1-(BUT-2-YNOYL) PYRROLIDIN-2-YL)IMIDAZO[1,5-A] PYRAZIN-1-YL)-N-(PYRIDIN-2-YL) BENZAMIDE MALEATE

(71) Applicant: Acerta Pharma B.V., Oss (NL)

(72) Inventors: Fritz Blatter, Reinach (CH); Tim Ingallinera, San Francisco, CA (US); Tjeerd Barf, Ravenstein (NL); Edwin Aret, Almere (NL); Cecile Krejsa, Seattle, WA (US); Jerry Evarts, Bellevue, WA (US)

(73) Assignee: Acerta Pharma B.V., Oss (NL)

( * ) Notice: Subject to any disclaimer, the term of this patent is extended or adjusted under 35 U.S.C. 154(b) by 0 days.

(21) Appl. No.: 16/863,033

(22) Filed: Apr. 30, 2020

(65) Prior Publication Data
US 2020/0255437 A1    Aug. 13, 2020

Related U.S. Application Data

(63) Continuation of application No. 16/177,927, filed on Nov. 1, 2018, now Pat. No. 10,640,509, which is a continuation of application No. 15/707,508, filed on Sep. 18, 2017, now Pat. No. 10,167,291, which is a continuation of application No. 15/200,875, filed on Jul. 1, 2016, now Pat. No. 9,796,721.

(60) Provisional application No. 62/188,468, filed on Jul. 2, 2015, provisional application No. 62/271,708, filed on Dec. 28, 2015.

(51) Int. Cl.
| A61K 31/4985 | (2006.01) |
| C07D 487/04 | (2006.01) |
| A61K 45/06 | (2006.01) |
| A61K 47/36 | (2006.01) |

(52) U.S. Cl.
CPC ........ *C07D 487/04* (2013.01); *A61K 31/4985* (2013.01); *A61K 45/06* (2013.01); *A61K 47/36* (2013.01); *C07B 2200/13* (2013.01)

(58) Field of Classification Search
CPC .......................... A61K 31/4985; C07D 487/04
USPC .......................................... 514/249; 544/350
See application file for complete search history.

(56) References Cited

U.S. PATENT DOCUMENTS

| 7,459,554 B2 | 12/2008 | Dong et al. |
| 7,825,118 B2 | 11/2010 | Honigberg et al. |
| 7,960,396 B2 | 6/2011 | Honigberg et al. |
| 8,377,946 B1 | 2/2013 | Chen et al. |
| 8,658,794 B2 | 2/2014 | deMan et al. |
| 9,290,504 B2 | 3/2016 | Barf et al. |
| 2006/0084654 A1 | 4/2006 | Beck et al. |
| 2008/0076921 A1 | 3/2008 | Honigberg et al. |
| 2011/0257203 A1 | 10/2011 | Honigberg et al. |
| 2012/0053189 A1 | 3/2012 | Loury |
| 2012/0095026 A1 | 4/2012 | Honigberg et al. |
| 2012/0129821 A1 | 5/2012 | Honigberg et al. |
| 2012/0135944 A1 | 5/2012 | Honigberg et al. |
| 2012/0165328 A1 | 6/2012 | Honigberg et al. |
| 2013/0018032 A1 | 1/2013 | Chen et al. |
| 2013/0079327 A1 | 3/2013 | Yamamoto et al. |
| 2014/0073593 A1 | 3/2014 | Conklin et al. |
| 2014/0206681 A1 | 7/2014 | Kim et al. |
| 2014/0212425 A1 | 7/2014 | Chang et al. |

FOREIGN PATENT DOCUMENTS

| CN | 103889987 A | 6/2014 |
| EA | 014739 B1 | 2/2011 |
| EP | 2548877 | 1/2013 |
| EP | 2734522 B1 | 10/2018 |
| JP | 2012-188438 A | 10/2012 |
| JP | 2013-522241 A | 6/2013 |
| JP | 2014-520866 | 8/2014 |
| JP | 2014-520870 | 8/2014 |
| RU | 2012138456 A | 3/2014 |
| WO | 2001/016106 A1 | 3/2001 |
| WO | 2001019828 | 3/2001 |
| WO | 2007064993 | 6/2001 |
| WO | 2002080926 | 10/2002 |
| WO | 2003065995 | 8/2003 |
| WO | 2005037836 | 4/2005 |
| WO | 2005097800 | 10/2005 |
| WO | 2007061737 | 5/2007 |
| WO | 2007064883 | 6/2007 |
| WO | 2007106503 | 9/2007 |
| WO | 2008121742 | 10/2008 |
| WO | 2009076170 | 6/2009 |

(Continued)

OTHER PUBLICATIONS

Office Action dated Sep. 18, 2020 for Japanese Patent Application No. 2017-568182, 3 pages.

(Continued)

*Primary Examiner* — Douglas M Willis
(74) *Attorney, Agent, or Firm* — Morgan, Lewis & Bockius LLP

(57) ABSTRACT

In some embodiments, the invention relates to crystalline solid forms, including hydrates, polymorphs, and salt forms, of (S)-4-(8-amino-3-(1-(but-2-ynoyl)pyrrolidin-2-yl)imidazo[1,5-a]pyrazin-1-yl)-N-(pyridin-2-yl)benzamide. In some embodiments, the invention relates to amorphous solid forms of (S)-4-(8-amino-3-(1-(but-2-ynoyl)pyrrolidin-2-yl) imidazo[1,5-a]pyrazin-1-yl)-N-(pyridin-2-yl)benzamide. In some embodiments, the invention also relates to pharmaceutical compositions containing the solid forms, and methods for treating conditions or disorders by administering to a subject a pharmaceutical composition that includes the forms, including pharmaceutical compositions and methods for overcoming the effects of acid reducing agents.

42 Claims, 73 Drawing Sheets

(56) References Cited

FOREIGN PATENT DOCUMENTS

| WO | 2010126960 | 11/2010 |
|---|---|---|
| WO | 2011095556 | 8/2011 |
| WO | 2011119663 | 9/2011 |
| WO | 2011152351 | 12/2011 |
| WO | 2011153514 | 12/2011 |
| WO | 2012158843 | 11/2012 |
| WO | 2013003629 | 1/2013 |
| WO | 2013010380 | 1/2013 |
| WO | 2013010868 | 1/2013 |
| WO | 2013010869 | 1/2013 |
| WO | 2013059738 | 4/2013 |
| WO | 2014143807 | 9/2014 |
| WO | 2014/166820 A1 | 10/2014 |
| WO | 2014159745 | 10/2014 |
| WO | 2014168975 | 10/2014 |
| WO | 2015018522 | 2/2015 |
| WO | 2015057992 | 4/2015 |

OTHER PUBLICATIONS

Examination Report No. 2 dated Sep. 10, 2020 for Australian Patent Application No. 2016286548, 4 pages.
Brittain, H.G. ed., 2016. Polymorphism in pharmaceutical solids. CRC Press.
United States Pharmacopeia contains a general chapter on XRPD, [retrieved from internet on Sep. 10, 2020] (https://www.usp.org/sites/default/files/usp/document/harmonization/gen-chapter/g14_pf_35_3_2009.pdf).
Berge et al., Pharmaceutical salts, 66(1) J. Pharm. Sci. 1-19 (1977).
Bingham et al., Over one hundred solvates of sulfathlazole, Chem. Commun. (7) 603-04 (2001).
Caira et al., \Preparation and Crystal Characterization of a Polymorph, a Monohydrate, and an Ethyl Acetate Solvate of the Antifungal Fluconazole, 93(3) J. Pharma. Sci. 601-11 (2004).
Davis et al., Chronic active B-cell-receptor signaling in diffuse large B-cell lymphoma, 463 Nature 88-92 (2010).
Dhar et al., Synthesis and SAR of p38a MAP kinase inhibitors based on heterobicyclic scaffolds, 17 Bioorg. Med. Chem. Lett. 5019-24 (2007).
Gaudet et al., A Homogeneous Fluorescence Polarization Assay Adaptable for a Range of Protein Serine/Threonine and TyrosIne Kinases, 8(2) J. Biomol. Screening 164-75 (2003).
Gilfillan et al., The tyrosine kinase network regulating mast cell activation, 288 Immun. Rev. 149-69 (2009).
Gould, Salt selection for basic drugs, 33 Int'l J. Pharmaceutics 201-217 (1986).
Harder et al., Gain- and Loss-of-Function Lyn Mutant Mice Define a Critical Inhibitory Role for Lyn in the Myeloid Lineage, 15 Immunity 603-15 (2001).
Hartz et al., Synthesis and Evaluation of imidazo[1,5-a]pyrazines as Corticotrophin Releasing Hormone Receptor Ligands, 12 Bioorg. Med. Chem. Lett. 291-94 (2002).
Ji et al., A novel, potent, and selective insulin-like growth factor-I receptor kinase inhibitor blocks insulin-like growth factor-I receptor signaling in vitro and inhibits insulin-like growth factor-Ireceptor-dependent tumor growth in vivo, 6(8) Mol. Cancer Ther. 2158-67 (2007).
King et al., Nucleofugallty effects in the pyridine promoted formation of esters from 2-substituted ethanesulfonyl chlorides, 66 Can. J. Chem. 1109-16 (1988).
Klinghoffer et al., Src family kinases are required for integrin but not PDGFR signal transduction, 18(9) EMBO J. 2459-71 (1999).
Lim et al., Anti-CD20 monoclonal antibodies: historical and future perspectives, 95(1) Hematological 135-43 (2010).
Lowell et al., Deficiency of the Hck and Src Tyrosine Kinases Results in Extreme Levels of Extramedullary Hematopoiesis, 87(5) Blood 1780-92 (1996).
Mitchell et al., Synthesis of C-nucleoside isosteres of 9-(2-hydroxyethoxymethyl)guanine (acyclovir), 21(3) J. Heterocyclic Chem. 697-99 (1984).
Mukalyama et al., Synthesis and c-Src inhibitory activity of imidazo[1,5-a]pyrazine derivatives as an agent for treatment of acute ischemic stroke, 15 Bioog. Med. Chem. 868-85 (2007).
Mulvihill et al., 1,3-Disubstituted-imidazo[1,5-a]pyrazines as insulin-like growth-factor-I receptor (IGF-IR) inhibitors, 17 Bioorg. Med. Chem. Lett. 1091-97 (2007).
Mulvihill et al., Novel 2-phenylquinolin-7-yl-derived imidazo[1,5-a]pyrazines as potent insulin-growth factor-I receptor (IGF-IR) inhibitors, 16 Bioorg. Med. Chem. 1359-75 (2008).
Odom et al., Negative Regulation of immunoglobulin E-dependent Allergic Responses by Lyn Kinase, 199(11) J. Exp. Med. 1491-1502 (2004).
Pan et al., Discovery of Selective Irreversible Inhibitors for Bruton's Tyrosine Kinase, 2 ChemMedChem 58-61 (2007).
Roby et al., Alterations in Reproductive Function in Src Tyrosine Kinase Knockout Mice, 26 Endocrine 169-76 (2005).
Shinohara et al., Tyrosine Kinases Btk and Tec Regulate Osteoclast Differentiation by Linking RANK and ITAM Signals 132 Cell 794-806 (2008).
Van Tonder et al., Preparation and Physicochemical Characterization of 5 Niclosamide Solvates and 1 Hemisolvate, 5(1) AAPS PharmSclTech Article 12 (2004).
Written Opinion dated Aug. 10, 2016 relating to PCT/IB2016/053988.
International Search Report dated Aug. 10, 2016 relating to PCT/IB2016/053988.
Office Action for Israel Patent Application No. 256633 dated Jun. 6, 2018 with English Translations, 4 pages.
Gennaro (ed.), Remington: The Science and Practice of Pharmacy 20th edition (2000).
Greene & Wuts, Protective Groups in Organic Synthesis, 2d Edition (1991).
Higuchi et al. (eds.), Pro-drugs as Novel Delivery Systems. 14 A.C.S Symposium Series (1975).
Roche (ed.), Bioreversible Carriers in Drug Design, Pergamon Press (1987).
Communication Pursuant to Rules 161(1) and 162 from the European Patent Office dated Feb. 14, 2018.
Examination Report dated Nov. 25, 2019 for Australian Patent Application No. 2016286548, 4 pages.
Guidance for Industry, ANDAs: Pharmaceutical Solid Polymorphism, Chemistry, Manufacturing, and Controls Information; U.S. Department of Health and Human Services, Food and Drug Administration, Center for Drug Evaluation and Research (CDER); Jul. 2007, 13 pages.
Examination Report dated Oct. 30, 2019 for Singapore Patent Application No. 11201710679U, 4 pages.
Translation of Office Action dated Jun. 2, 2020 for Japanese Patent Application No. 2017-568182, 5 pages.
Translation of Office Action dated May 29, 2020 for Russian Patent Application No. 2018103913, 6 pages.
J. Bernstein, "Polymorphism in Molecular Crystals", Moscow, Nauka, 2007, Chapter Bioavailability, pp. 324-330.
Sherry L. Morissette et al.: "High-throughput crystallization: polymorphs, salts, co-crystals and solvates of pharmaceutical solids", Advanced Drug Delivery Reviews, 2004, v.56, pp. 275-300.
Richard J.Bastin et al.: "Salt Selection and Optimization Procedures for Pharmaceutical New Chemical Entities", Organic Process Research and Develop, 2000, vol. 4, No. 5, pp. 427-435.
T.G. Khoruzhaya, V.S. Chuchalin Bioformatsiya—nauchnoe napravlenie v razrabotke i sovershenstvovanii lekarstvennyh preparatov [Biopharmaceutics—scientific direction in the development and improvement of medicaments] Textbook for students of the Faculty of Pharmacy, Tomsk, 2006, pp. 6-7.
Translation of Office Action dated Mar. 20, 2020 for Chinese Patent Application No. 201680050713.6, 8 pages.
Translation of Search Report dated Dec. 31, 2019 for Russian Patent Application No. 2018103913, 2 pages.
Office Action dated Nov. 27, 2019 for Chilean Patent Application No. 201703445, 6 pages.

(56) References Cited

OTHER PUBLICATIONS

Communication dated Apr. 29, 2019 for European Patent Application 16735945, 5 pages.
S. Byrn et al., "Pharmaceutical Solids: A Strategic Approach to Regulatory Considerations", Pharmaceutical Research, 1995, 12 (7): 945-954.
J. K. Guillory, Polymorphism in Pharmaceutical Solids, Marcel Dekker, Inc, 1999, Chapter 5, "Generation of Polymorphs, Hydrates, Solvates, and Amorphous Solids", 183-226.
P. H.-L Tran et al., "Dissolution-modulating mechanism of pH modifiers in solid dispersion containing weakly acidic or basic drugs with poor water solubility", Expert Opin. Drug Deliv. 2010, 7(5): 647-661.
D. Chen, "Hygroscopicity of Pharmaceutical Crystals", Dissertation submitted to the Faculty of Graduate School of the University of Minnesota, 2009, Chapters 1 and 2, pp. 1-103.
Official Action dated Feb. 26, 2021 for Russian Patent Application No. 2018103913, 7 pages.
Notice of Opposition dated Jan. 27, 2021 for European Patent Application No. 16735945.4, 23 pages.
Office Action dated Dec. 3, 2020 for Japanese Patent Application No. 2017-568182, 2 pages.
Second Office Action dated Oct. 30, 2020 for Chinese Patent Application No. 201680050713.6, 3 pages.
Standard Patent for Australian Patent Application No. AU 2016286548 B2, Accepted Journal Date of Dec. 10, 2020; 137 pages.
Caira, M. R. 'Crystalline Polymorphism of Organic Compounds', In Topics in Current Chemistry, Edited by E. Weber. Berlin: Springer, 1998, vol. 198, pp. 163-208.
Office Action dated Nov. 12, 2020 for Israel Patent Application No. 274066, 3 pages.

CRYSTAL FORMS OF (S)-4-(8-AMINO-3-(1-(BUT-2-YNOYL) PYRROLIDIN-2-YL)IMIDAZO[1,5-A] PYRAZIN-1-YL)-N-(PYRIDIN-2-YL) BENZAMIDE MALEATE

CROSS-REFERENCE TO RELATED APPLICATIONS

This application claims priority to, and the benefit of, U.S. Provisional Application No. 62/188,468, filed on Jul. 2, 2015, and U.S. Provisional Application No. 62/271,708, filed on Dec. 28, 2015, the entirety of each of which is incorporated herein by reference.

FIELD OF THE INVENTION

In some embodiments, the invention relates to crystalline Form I of (S)-4-(8-amino-3-(1-(but-2-ynoyl)pyrrolidin-2-yl) imidazo[1,5-a]pyrazin-1-yl)-N-(pyridin-2-yl)benzamide. In other embodiments, the invention relates to pharmaceutical compositions including Form I, including pharmaceutical compositions that overcome the effects of acid reducing agents, and methods for treating cancers or other disorders by administering the pharmaceutical compositions to a subject. In some embodiments, the invention relates to crystalline salts of (5)-4-(8-amino-3-(1-(but-2-ynoyl)pyrrolidin-2-yl)imidazo[1,5-a]pyrazin-1-yl)-N-(pyridin-2-yl)benzamide. In other embodiments, the invention relates to pharmaceutical compositions including crystalline salts of (S)-4-(8-amino-3-(1-(but-2-ynoyl)pyrrolidin-2-yl)imidazo[1,5-a] pyrazin-1-yl)-N-(pyridin-2-yl)benzamide, including pharmaceutical compositions that overcome the effects of acid reducing agents, and methods for treating cancers or other disorders by administering the pharmaceutical compositions to a subject.

BACKGROUND OF THE INVENTION

Bruton's Tyrosine Kinase (BTK) is a Tec family non-receptor protein kinase expressed in B cells and myeloid cells. BTK is composed of the pleckstrin homology (PH), Tec homology (TH), Src homology 3 (SH3), Src homology 2 (SH2), and tyrosine kinase or Src homology 1 (TK or SH1) domains. The function of BTK in signaling pathways activated by the engagement of the B cell receptor (BCR) in mature B cells and FCER1 on mast cells is well established. Functional mutations in BTK in humans result in a primary immunodeficiency disease (X-linked agammaglobuinaemia) characterized by a defect in B cell development with a block between pro- and pre-B cell stages. The result is an almost complete absence of B lymphocytes, causing a pronounced reduction of serum immunoglobulin of all classes. These findings support a key role for BTK in the regulation of the production of auto-antibodies in autoimmune diseases.

BTK is expressed in numerous B cell lymphomas and leukemias. Other diseases with an important role for dysfunctional B cells are B cell malignancies, as described in Hendriks, et al., *Nat. Rev. Cancer,* 2014, 14, 219-231. The reported role for BTK in the regulation of proliferation and apoptosis of B cells indicates the potential for BTK inhibitors in the treatment of B cell lymphomas. BTK inhibitors have thus been developed as potential therapies for many of these malignancies, as described in D'Cruz, et al., *Onco-Targets and Therapy* 2013, 6, 161-176; and International Patent Application Publication No. WO 2013/010868 discloses BTK inhibitors including (S)-4-(8-amino-3-(1-(but-2-ynoyl)pyrrolidin-2-yl)imidazo[1,5-a]pyrazin-1-yl)-N-(pyridin-2-yl)benzamide for use in therapy.

The present invention includes the unexpected discovery of novel solid forms of (S)-4-(8-amino-3-(1-(but-2-ynoyl) pyrrolidin-2-yl)imidazo[1,5-a]pyrazin-1-yl)-N-(pyridin-2-yl)benzamide, referred to herein as Formula (1). Formula (1) is a BTK inhibitor that is useful, inter alia, in pharmaceutical compositions and methods for treatment of cancers, inflammation, immune, and autoimmune diseases. The novel solid forms of Formula (1) disclosed herein have surprising and useful properties.

SUMMARY OF THE INVENTION

In an embodiment, the invention provides a composition comprising crystalline (S)-4-(8-amino-3-(1-(but-2-ynoyl) pyrrolidin-2-yl)imidazo[1,5-a]pyrazin-1-yl)-N-(pyridin-2-yl)benzamide free base.

In an embodiment, the invention provides a composition comprising crystalline (S)-4-(8-amino-3-(1-(but-2-ynoyl) pyrrolidin-2-yl)imidazo[1,5-a]pyrazin-1-yl)-N-(pyridin-2-yl)benzamide free base is characterized by an X-ray powder diffraction pattern comprising peaks at 6.4, 8.6, 10.5, 11.6, and 15.7° 2θ±0.2° 2θ.

In an embodiment, the invention provides a composition comprising crystalline (S)-4-(8-amino-3-(1-(but-2-ynoyl) pyrrolidin-2-yl)imidazo[1,5-a]pyrazin-1-yl)-N-(pyridin-2-yl)benzamide free base is characterized by an X-ray powder diffraction pattern comprising peaks at 6.4, 8.6, 10.5, 11.6, and 15.7° 2θ±0.2° 2θ and further comprising peaks at 10.9, 12.7, 13.4, 14.3, 14.9, and 18.2° 2θ±0.2° 2θ.

In an embodiment, the invention provides a composition comprising crystalline (S)-4-(8-amino-3-(1-(but-2-ynoyl) pyrrolidin-2-yl)imidazo[1,5-a]pyrazin-1-yl)-N-(pyridin-2-yl)benzamide free base is characterized by an X-ray powder diffraction pattern comprising peaks at 6.4, 8.6, 10.5, 11.6, and 15.7° 2θ±0.2° 2θ, further comprising peaks at 10.9, 12.7, 13.4, 14.3, 14.9, and 18.2° 2θ±0.2° 2θ and further comprising peaks selected from the group consisting of 11.3, 15.1, 15.7, 16.1, 17.3, 19.2, 19.4, 19.8, 20.7, 21.1, 21.4, 21.6, 21.9, 22.6, 23.3, 23.6, 24.9, 25.2, 25.4, 25.7, 26.1, 26.4, 26.8, 26.9, 27.7, 28.6, 29.1, 29.4, 30.1, 30.5, 31.7, 31.9, 32.2, 32.6, 33.1, 33.4, 34.5, 35.9, 36.1, 36.8, 37.4, 38.1, 38.9, and 39.5° 2θ±0.2° 2θ, and any combination of one or more peaks thereof.

In an embodiment, the invention provides a composition comprising crystalline (5)-4-(8-amino-3-(1-(but-2-ynoyl) pyrrolidin-2-yl)imidazo[1,5-a]pyrazin-1-yl)-N-(pyridin-2-yl)benzamide free base, wherein the crystalline (S)-4-(8-amino-3-(1-(but-2-ynoyl)pyrrolidin-2-yl)imidazo[1,5-a] pyrazin-1-yl)-N-(pyridin-2-yl)benzamide free base is characterized by a transmission X-ray powder diffraction pattern substantially the same as the representative X-ray powder diffraction pattern shown in FIG. 2.

In an embodiment, the invention provides a composition comprising crystalline (S)-4-(8-amino-3-(1-(but-2-ynoyl) pyrrolidin-2-yl)imidazo[1,5-a]pyrazin-1-yl)-N-(pyridin-2-yl)benzamide free base is further characterized by a Raman spectrum comprising peaks at 1620, 1609, 1547, 1514 and 1495 cm$^{-1}$±4 cm$^{-1}$.

In an embodiment, the invention provides a composition comprising crystalline (S)-4-(8-amino-3-(1-(but-2-ynoyl) pyrrolidin-2-yl)imidazo[1,5-a]pyrazin-1-yl)-N-(pyridin-2-yl)benzamide free base is characterized by a Raman spectrum comprising peaks at 1620, 1609, 1547, 1514 and 1495 cm$^{-1}$±4 cm$^{-1}$ and further comprising one or more peaks selected from the group consisting of 1680, 1620, 1609, 1574, 1547, 1514, 1495, 1454, 1433, 1351, 1312, 1255, 1232, 1187, 1046, 995, 706, 406, 280, and any combination of one or more peaks thereof, with peak positions measured in cm$^{-1}$±4 cm$^{-1}$.

In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base is further characterized by an infrared (IR) spectrum comprising peaks at 1621, 1608, 1403, 1303, and 764 cm$^{-1}$±4 cm$^{-1}$.

In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base is characterized by an IR spectrum comprising 1621, 1608, 1403, 1303, and 764 cm$^{-1}$±4 cm$^{-1}$ and comprising one or more peaks selected from the group consisting of 3367, 3089, 2246, 1682, 1621, 1608, 1574, 1514, 1504, 1454, 1428, 1403, 1345, 1303, 1248, 1194, 1177, 1149, 1109, 1049, 1023, 1003, 947, 900, 858, 842, 816, 764, 734, 729, 701, 689, 665, 623, 612, and any combination of one or more peaks thereof, with peak positions measured in cm$^{-1}$±4 cm$^{-1}$.

In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base is further characterized by the absence of water in the crystal structure.

In an embodiment, the invention provides a composition comprising an extragranular acidulant.

In an embodiment, the invention provides a composition wherein extragranular acidulant is selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, Protacid F 120 NM, Protacid AR 1112 (also known as Kelacid NF), and Carbopol 971P (carboxypolymethylene), and combinations thereof.

In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base and an extragranular acidulant, wherein the extragranular acidulant is alginic acid, or a sodium or potassium salt thereof, at a concentration of between about 5% to about 33% by weight.

In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base and an extragranular acidulant, wherein the extragranular acidulant is alginic acid, or a sodium or potassium salt thereof, at a concentration of between about 5% to about 33% by weight, and wherein the composition further comprises at least one pharmaceutically-acceptable excipient.

In an embodiment, the invention provides a method of treating a hyperproliferative disease comprising the step of administering a therapeutically effective amount of a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base Form I to a mammal, wherein the hyperproliferative disease is selected from the group consisting of chronic lymphocytic leukemia, non-Hodgkin's lymphoma, diffuse large B-cell lymphoma, mantle cell lymphoma, follicular lymphoma, B-cell lymphoproliferative disease, B cell acute lymphoblastic leukemia, Waldenström's macroglobulinemia, Burkitt's leukemia, Hodgkin's disease, multiple myeloma, acute myeloid leukemia, juvenile myelomonocytic leukemia, hairy cell leukemia, mast cell leukemia, mastocytosis, myeloproliferative disorders (MPDs), myeloproliferative neoplasms, polycythemia vera (PV), essential thrombocythemia (ET), primary myelofibrosis (PMF), myelodysplastic syndrome, chronic myelogenous leukemia (BCR-ABL1-positive), chronic neutrophilic leukemia, chronic eosinophilic leukemia, primary central nervous system (CNS) lymphoma, primary multifocal lymphoma of peripheral nervous system (PNS), thymus cancer, brain cancer, glioblastoma, lung cancer, squamous cell cancer, skin cancer (e.g., melanoma), eye cancer, retinoblastoma, intraocular melanoma, oral cavity and oropharyngeal cancers, bladder cancer, gastric cancer, stomach cancer, pancreatic cancer, breast cancer, cervical cancer, head and neck cancer, renal cancer, kidney cancer, liver cancer, ovarian cancer, prostate cancer, colorectal cancer, bone cancer (e.g., metastatic bone cancer), esophageal cancer, testicular cancer, gynecological cancer, thyroid cancer, epidermoid cancer, AIDS-related cancer (e.g., lymphoma), viral-induced cervical carcinoma (human papillomavirus), nasopharyngeal carcinoma (Epstein-Barr virus), Kaposi's sarcoma, primary effusion lymphoma (Kaposi's sarcoma herpesvirus), hepatocellular carcinoma (hepatitis B and hepatitis C viruses), T-cell leukemias (Human T-cell leukemia virus-1), benign hyperplasia of the skin, restenosis, benign prostatic hypertrophy, tumor angiogenesis, chronic inflammatory disease, rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, ulcerative colitis, atopic dermatitis, pouchitis, spondylarthritis, uveitis, Behcet's disease, polymyalgia rheumatica, giant-cell arteritis, sarcoidosis, Kawasaki disease, juvenile idiopathic arthritis, hidratenitis suppurativa, Sjögren's syndrome, psoriatic arthritis, juvenile rheumatoid arthritis, ankylosing spondylitis, Crohn's disease, lupus, and lupus nephritis.

In an embodiment, the invention provides a method of treating a hyperproliferative disease comprising the step of administering a therapeutically effective amount of a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base Form I to a mammal, wherein the hyperproliferative disease is selected from the group consisting of chronic lymphocytic leukemia, non-Hodgkin's lymphoma, diffuse large B-cell lymphoma, mantle cell lymphoma, follicular lymphoma, and Waldenström's macroglobulinemia.

In an embodiment, the invention provides a method of treating a hyperproliferative disease comprising the step of administering a therapeutically effective amount of a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base Form I and an extragranular acidulant to a mammal, wherein the hyperproliferative disease is selected from the group consisting of chronic lymphocytic leukemia, non-Hodgkin's lymphoma, diffuse large B-cell lymphoma, mantle cell lymphoma, follicular lymphoma, and Waldenström's macroglobulinemia.

In an embodiment, the invention provides a method of treating a hyperproliferative disease comprising the step of administering a therapeutically effective amount of a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base Form I and an extragranular acidulant to a mammal, further comprising the step of administering a therapeutically effective amount of an acid-reducing agent to the mammal.

In an embodiment, the invention provides a method of treating a hyperproliferative disease comprising the step of administering a therapeutically effective amount of a composition comprising a crystalline fumarate, maleate, phosphate, L-tartrate, citrate, gentisate, oxalate, or sulfate salt of (S)-4-(8-amino-3-(1-(but-2-ynoyl)pyrrolidin-2-yl)imidazo[1,5-a]pyrazin-1-yl)-N-(pyridin-2-yl)benzamide free base Form I to a mammal, further comprising the step of administering a therapeutically effective amount of an acid-reducing agent to the mammal.

BRIEF DESCRIPTION OF THE DRAWINGS

The foregoing summary, as well as the following detailed description of the invention, will be better understood when read in conjunction with the appended drawings.

DETAILED DESCRIPTION OF THE INVENTION

Figure 1:
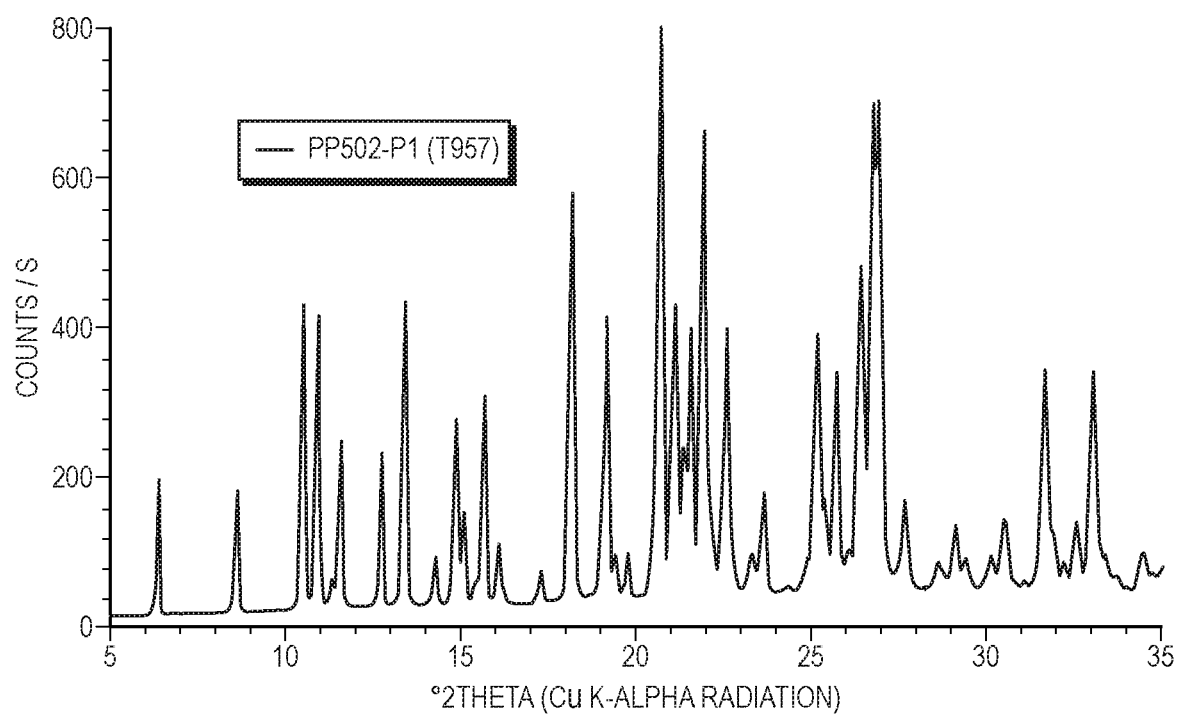
FIG. 1 illustrates a powder X-ray diffraction (PXRD) pattern of Form I (sample PP502-P1) of the free base of Formula (1) measured in reflection mode.

While preferred embodiments of the invention are shown and described herein, such embodiments are provided by way of example only and are not intended to otherwise limit the scope of the invention. Various alternatives to the described embodiments of the invention may be employed in practicing the invention.

Definitions

Unless defined otherwise, all technical and scientific terms used herein have the same meaning as is commonly understood by one of skill in the art to which this invention belongs. All patents and publications referred to herein are incorporated by reference in their entireties.

The term "solid form" may refer to a crystalline solid form or phase, including crystalline free base, crystalline salt, or a cocrystal, as well as an amorphous phase, including an amorphous dispersion.

The terms "co-administration," "co-administering," "administered in combination with," and "administering in combination with" as used herein, encompass administration of two or more agents to a subject so that both agents and/or their metabolites are present in the subject at the same time. Co-administration includes simultaneous administration in separate compositions, administration at different times in separate compositions, or administration in a composition in which two or more agents are present.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

A "therapeutic effect" as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions including fumarate, maleate, phosphate, L-tartrate, citrate, gentisate, oxalate, and sulfate counter ions. Pharmaceutically acceptable acid addition salts can be formed with inorganic acids and organic acids. "Pharmaceutically acceptable carrier" or "pharmaceutically acceptable excipient" is intended to include any and all solvents, dispersion media, coatings, antibacterial and antifungal agents, isotonic and absorption delaying agents. Except insofar as any conventional media or agent is incompatible with the active ingredient, its use in the therapeutic compositions of the invention is contemplated. Supplementary active ingredients can also be incorporated into the described compositions.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "extragranular" refers to substances that are outside of a granule, e.g., a substance added to granules (multiparticle compacts formed by a granulation process) and physically mixed with granules, but not contained within the granules.

The term "intragranular" refers to substances that are within a granule (a multiparticle compact formed by a granulation process). Granules may be formed by processes such as wet granulation (i.e., prepared using moisture or steam, thermal, melt, freeze, foam, and other processes) or dry granulation.

The term "acidulant" refers to a substance that increases acidity.

The terms "transmission" or "transmission mode," when used in conjunction with powder X-ray diffraction, refers to the transmission (also known as Debye-Scherrer) sampling mode. The terms "reflection" or "reflection mode," when used in conjunction with powder X-ray diffraction, refers to the reflection (also known as Bragg-Brentano) sampling mode.

The term "amorphous solid molecular dispersion" refers to dispersions of compounds such as Formula (1) in, e.g., a polymeric excipient, wherein the polymer and compound are mixed intimately, e.g., at a molecular level or at a nanoscale level.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}C$- or $^{14}C$-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" or "approximately" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (9-isomer. If that compound has one isomeric form predominant over the other, for example, 80% (9-isomer and 20% (R)-isomer, the enantiomeric purity of the compound with respect to the (S)-isomeric form is 80%. The enantiomeric purity of a compound can be determined in a number of ways, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions*, Wiley Interscience, New York, 1981; Eliel, *Stereochemistry of Carbon Compounds*, McGraw-Hill, N Y, 1962; and Eliel and Wilen, *Stereochemistry of Organic Compounds*, Wiley-Interscience, New York, 1994.

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. The formation of solid forms in different tautomerization states is known as "desmotropy" and such forms are known as "desmotropes."

Compositions of the invention also include crystalline forms of those compounds, including, for example, polymorphs, pseudopolymorphs, solvates, hydrates, unsolvated polymorphs (including anhydrates), and conformational polymorphs, as well as mixtures thereof "Crystalline form", "form" and "polymorph" are intended to include all crystalline forms of the compound, including, for example, polymorphs, pseudopolymorphs, solvates, hydrates, unsolvated polymorphs (including anhydrates), and conformational polymorphs, as well as mixtures thereof, unless a particular crystalline form is referred to.

"Solvate" refers to a crystalline phase of a compound in physical association with one or more molecules of a solvent. The crystalline phase of a compound in physical association with one or more molecules of water is referred to as a "hydrate."

"Amorphous form" refers to a form of a compound, or a salt or molecular complex of a compound, that lacks long range crystalline order where the x-ray diffraction pattern lacks Bragg reflections.

Crystalline Forms

In an embodiment, the invention provides a crystalline solid form of (S)-4-(8-amino-3-(1-(but-2-ynoyl)pyrrolidin-2-yl)imidazo[1,5-a]pyrazin-1-yl)-N-(pyridin-2-yl)benzamide (Formula (1)). Formula (1) has the following chemical structure:

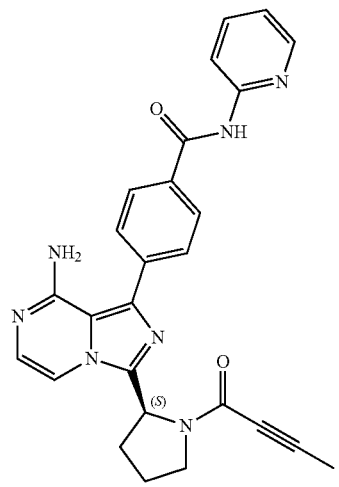

In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide free base is characterized by an X-ray powder diffraction pattern comprising peaks at 6.4, 8.6, 10.5, 11.6, and 15.7° 2θ±0.2° 2θ. In an embodiment, the composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base is characterized by an X-ray powder diffraction pattern comprising peaks at 6.4, 8.6, 10.5, 11.6, and 15.7° 2θ±0.2° 2θ and further comprising peaks at 10.9, 12.7, 13.4, 14.3, 14.9, and 18.2° 2θ±0.2° 2θ. In another embodiment, the composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base is characterized by an X-ray powder diffraction pattern comprising peaks selected from the group consisting of 6.4, 8.6, 10.5, 10.9, 11.3, 11.6, 12.7, 13.4, 14.3, 14.9, 15.1, 15.7, 16.1, 17.3, 18.2, 19.2, 19.39, 19.8, 20.7, 21.1, 21.4, 21.6, 21.9, 22.6, 23.3, 23.6, 24.9, 25.2, 25.4, 25.7, 26.1, 26.4, 26.8, 26.9, 27.7, 28.6, 29.1, 29.4, 30.1, 30.5, 31.7, 31.9, 32.2, 32.6, 33.1, 33.4, 34.5, 35.9, 36.1, 36.8, 37.4, 38.1, 38.9, 39.5, and any combination thereof, with peak positions measured in ° 2θ 0.2° 2θ. In yet another embodiment, the composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base is characterized by a transmission X-ray powder diffraction pattern substantially the same as the representative X-ray powder diffraction pattern shown in FIG. 2. In an embodiment, the X-ray powder diffraction pattern of any of the foregoing embodiments is measured in transmission mode. In an embodiment, the X-ray powder diffraction pattern of any of the foregoing embodiments is measured in reflection mode.

It is known in the art that an X-ray powder diffraction pattern may be obtained which has one or more measurement errors depending on measurement conditions (such as equipment, sample preparation or instrument used). In particular, it is generally known that intensities in an X-ray powder diffraction pattern may vary depending on measurement conditions and sample preparation. For example, persons skilled in the art of X-ray powder diffraction will realise that the relative intensities of peaks may vary according to the orientation of the sample under test and based on the type and settings of the instrument used. The skilled person will also realise that the position of reflections can be affected by the precise height at which the sample sits in the diffractometer, the sample's surface planarity, and the zero calibration of the diffractometer. Hence a person skilled in the art will appreciate that the diffraction pattern data presented herein is not to be construed as absolute and any crystalline form that provides a power diffraction pattern substantially the same as those disclosed herein fall within the scope of the present disclosure. For further information, see Jenkins and Snyder, *Introduction to X-Ray Powder Diffractometry*, John Wiley & Sons, 1996.

In each of the foregoing embodiments, composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide free base is further characterized by at least one of: (1) a Raman spectrum with at least five peaks selected from the group consisting of 1680, 1620, 1609, 1574, 1547, 1514, 1495, 1454, 1433, 1351, 1312, 1255, 1232, 1187, 1046, 995, 706, 406, 280, and any combination thereof, with peak positions measured in $cm^{-1} \pm 4\ cm^{-1}$; (2) an IR spectrum with at least five peaks selected from the group consisting of 3367, 3089, 2246, 1682, 1621, 1608, 1574, 1514, 1504, 1454, 1428, 1403, 1345, 1303, 1248, 1194, 1177, 1149, 1109, 1049, 1023, 1003, 947, 900, 858, 842, 816, 764, 734, 729, 701, 689, 665, 623, 612, and any combination thereof, with peak positions measured in $cm^{-1} \pm 4\ cm^{-1}$; and (3) the absence of water in the crystal structure.

It is also known in the art that IR and Raman spectra may be obtained which may vary depending on measurement conditions. The instrument, sampling mode (e.g., attenuated total reflectance IR sampling versus transmission IR sampling), and the calibration of the instrument may affect the peak positions and intensities. A person skilled in the art will appreciate that the spectra presented herein is not to be construed as absolute and any crystalline form that provides a spectrum substantially the same as those disclosed herein fall within the scope of the present disclosure. For further information, see Colthup, et al., *Introduction to Infrared and Raman Spectroscopy*, 3rd Ed., Academic Press, 1990.

In an embodiment, the invention provides a composition comprising crystalline (S)-4-(8-amino-3-(1-(but-2-ynoyl) pyrrolidin-2-yl)imidazo[1,5-a]pyrazin-1-yl)-N-(pyridin-2-yl)benzamide free base, wherein the crystalline (S)-4-(8-amino-3-(1-(but-2-ynoyl)pyrrolidin-2-yl)imidazo[1,5-a] pyrazin-1-yl)-N-(pyridin-2-yl)benzamide free base is characterized by at least one of: (1) an X-ray powder diffraction pattern with at least five peaks selected from the group consisting of 6.6, 9.9, 11.0, 13.6, 14.0, 14.3, 18.1, 18.4, 18.9, 19.3, 20.2, 21.1, 22.0, 22.2, 22.5, 22.7, 22.9, 23.4, 23.5, 23.9, 24.2, 24.6, 25.0, 26.1, 26.6, 26.9, 27.5, 28.2, 31.0, 32.1, 32.4, 32.7, 33.4, 33.9, 34.4, and any combination thereof, with peak positions measured in ° 2θ±0.2° 2θ; (2) a Raman spectrum with at least five peaks selected from the group consisting of 1668, 1611, 1580, 1564, 1537, 1506, 1493, 1454, 1436, 1416, 1401, 1349, 1321, 1287, 1272, 1252, 1244, 1183, 1165, 1097, 1039, 1025, 996, 950, 871, 853, 776, 730, 645, 633, 375, 352, 279, and 247 and any combination thereof, with peak positions measured in $cm^{-1} \pm 4\ cm^{-1}$; (3) an IR spectrum with at least five peaks selected from the group consisting of 3212, 2206, 1665, 1618, 1577, 1548, 1535, 1504, 1465, 1452, 1432, 1416, 1397, 1348, 1316, 1243, 1208, 1181, 1164, 1149, 1095, 1038, 1004, 948, 891, 869, 821, 776, 736, 716, 643, 617, and any combination thereof, with peak positions measured in $cm^{-1} \pm 4\ cm^{-1}$; and (4) the presence of water in the crystal structure with a stoichiometry relative to Formula (1) that is approximately equivalent to a trihydrate.

In an embodiment, the invention provides a composition comprising crystalline (S)-4-(8-amino-3-(1-(but-2-ynoyl) pyrrolidin-2-yl)imidazo[1,5-a]pyrazin-1-yl)-N-(pyridin-2-yl)benzamide free base, wherein the crystalline (S)-4-(8-amino-3-(1-(but-2-ynoyl)pyrrolidin-2-yl)imidazo[1,5-a] pyrazin-1-yl)-N-(pyridin-2-yl)benzamide free base is characterized by at least one of: (1) an X-ray powder diffraction pattern with at least five peaks selected from the group consisting of 10.4, 12.6, 12.8, 17.9, 21.3, 21.7, 23.1, 24.2, 25.2, 27.0, and any combination thereof, with at least five peak positions measured in ° 2θ±0.2° 2θ; (2) an IR spectrum with at least five peaks selected from the group consisting of 3446, 2248, 1667, 1592, 1531, 1504, 1428, 1349, 1305, 1243, 1189, 1158, 1089, 1001, 896, 862, 829, 780, 759, 736, 699, and any combination thereof, with peak positions measured in $cm^{-1} \pm 4\ cm^{-1}$; and (3) the presence of water in the crystal structure with a stoichiometry relative to Formula (1) that is approximately equivalent to a dihydrate.

In an embodiment, the invention provides a composition comprising crystalline (S)-4-(8-amino-3-(1-(but-2-ynoyl) pyrrolidin-2-yl)imidazo[1,5-a]pyrazin-1-yl)-N-(pyridin-2-yl)benzamide fumarate. In an embodiment, the invention provides a composition comprising crystalline (S)-4-(8-amino-3-(1-(but-2-ynoyl)pyrrolidin-2-yl)imidazo[1,5-a] pyrazin-1-yl)-N-(pyridin-2-yl)benzamide fumarate, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide fumarate is characterized by at least one of: (1) an X-ray powder diffraction pattern with at least five peaks selected from the group consisting of 4.9, 5.4, 7.0, 9.8, 10.8, 11.5, 12.1, 14.1, 16.1, 16.6, 17.8, 18.5, 19.4, 20.3, 20.5, 21.9, 22.1, 22.5, 23.1, 24.0, 24.8, 26.6, 26.8, 27.3, 28.2, and any combination thereof, with peak positions measured in ° 2θ±0.2° 2θ; and (2) the presence of water in the crystal structure with a stoichiometry relative to Formula (1) that is approximately equivalent to a sesquihydrate. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide fumarate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide fumarate Form A is characterized by an X-ray powder diffraction pattern peaks at 4.9, 5.4, 7.0, 10.8, and 11.5° 2θ±0.2° 2θ. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide fumarate Form A, wherein the crystalline (S)-4-(8-amino-3-(1-(but-2-ynoyl)pyrrolidin-2-yl)imidazo[1,5-a] pyrazin-1-yl)-N-(pyridin-2-yl)benzamide fumarate Form A is characterized by an X-ray powder diffraction pattern substantially in agreement with an X-ray powder diffraction pattern of FIG. 41.

In an embodiment, the invention provides a composition comprising crystalline (S)-4-(8-amino-3-(1-(but-2-ynoyl) pyrrolidin-2-yl)imidazo[1,5-a]pyrazin-1-yl)-N-(pyridin-2-yl)benzamide maleate. In an embodiment, the invention provides a composition comprising crystalline (S)-4-(8-amino-3-(1-(but-2-ynoyl)pyrrolidin-2-yl)imidazo[1,5-a] pyrazin-1-yl)-N-(pyridin-2-yl)benzamide maleate, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide maleate is characterized by at least one of: (1) an X-ray powder diffraction pattern with at least five peaks selected from the group consisting of 5.3, 9.8, 10.6, 11.6, 13.5, 13.8, 13.9, 14.3, 15.3, 15.6, 15.8, 15.9, 16.6, 17.4, 17.5, 18.7, 19.3, 19.6, 19.8, 20.0, 20.9, 21.3, 22.1, 22.3, 22.7, 23.2, 23.4, 23.7, 23.9, 24.5, 24.8, 25.2, 25.6, 26.1, 26.4, 26.7, 26.9, 27.1, 27.6, 28.9, 29.5, 30.0, 30.3, 30.9, 31.5, 31.9, 32.5, 33.9, 35.1, and any combination thereof, with peak positions measured in ° 2θ±0.2° 2θ; and (2) the presence of water in the crystal structure with a stoichiometry relative to Formula (1) that is approximately equivalent to a monohydrate. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide maleate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide maleate Form A is characterized by an X-ray powder diffraction pattern comprising peaks at 5.3, 9.8, 10.6, 11.6, and 19.3° 2θ±0.2° 2θ. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide maleate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide maleate Form A is characterized by an X-ray powder diffraction pattern substantially in agreement with the X-ray powder diffraction pattern of FIG. 42. In an embodiment, the X-ray powder diffraction pattern of any of the foregoing embodiments is measured in transmission mode. In an embodiment, the X-ray powder diffraction pattern of any of the foregoing embodiments is measured in reflection mode.

In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide phosphate. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide phosphate, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide phosphate is characterized by at least one of: (1) an X-ray powder diffraction pattern with at least five peaks selected from the group consisting of 4.5, 6.0, 7.2, 10.4, 12.0, 12.5, 13.1, 14.3, 15.5, 17.4, 18.0, 18.3, 18.9, 19.3, 20.2, 20.56, 20.9, 21.4, 21.9, 22.0, 22.6, 22.9, 23.1, 23.3, 24.2, 24.6, 25.0, 25.7, 26.2, 26.4, 26.9, 27.3, 27.5, 29.3, 30.0, 30.3, 30.5, 30.9, 31.2, 31.9, 35.7, and any combination thereof, with peak positions measured in ° 2θ±0.2° 2θ; and (2) the presence of water in the crystal structure with a stoichiometry relative to Formula (1) that is approximately equivalent to a dihydrate. In an embodiment, the X-ray powder diffraction pattern of any of the foregoing embodiments is measured in transmission mode. In an embodiment, the X-ray powder diffraction pattern of any of the foregoing embodiments is measured in reflection mode. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide phosphate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide phosphate Form A is characterized by an X-ray powder diffraction pattern comprising peaks at 4.5, 6.0, 10.4, 12.0, and 14.3° 2θ±0.2° 2θ. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide phosphate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide phosphate Form A is characterized by an X-ray powder diffraction pattern substantially in agreement with the X-ray powder diffraction pattern of FIG. 43. In an embodiment, the X-ray powder diffraction pattern of any of the foregoing embodiments is measured in transmission mode. In an embodiment, the X-ray powder diffraction pattern of any of the foregoing embodiments is measured in reflection mode.

Figure 44:
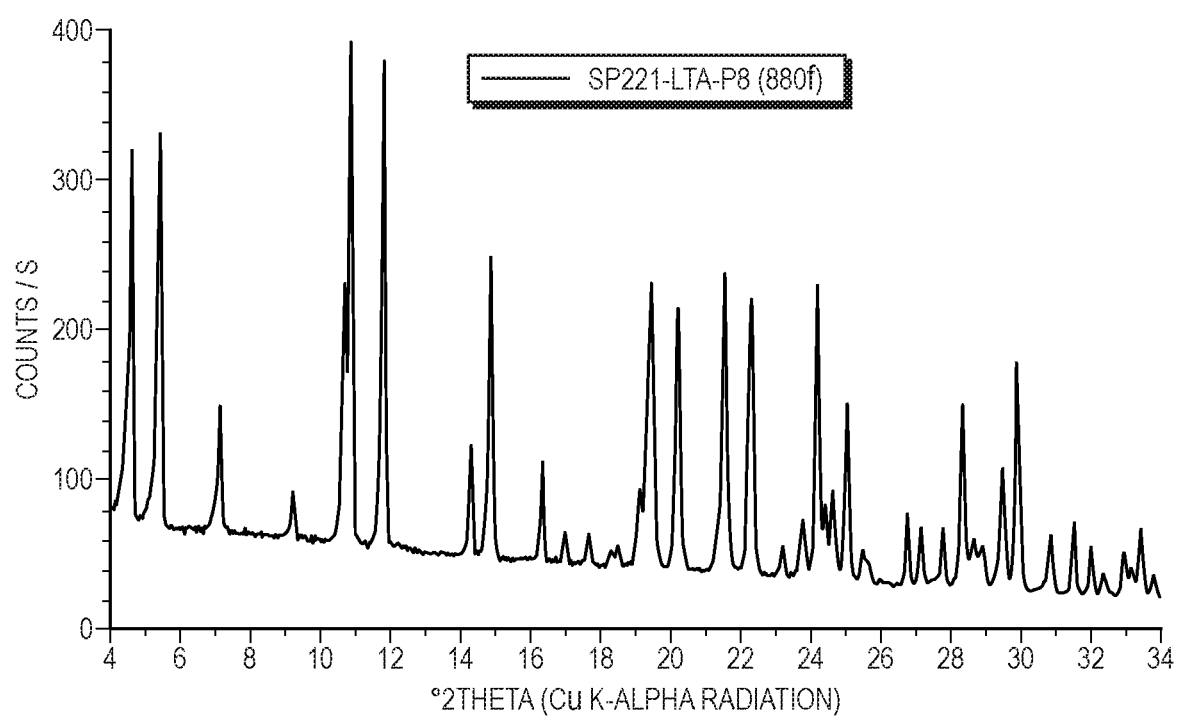
FIG. 44 illustrates a PXRD pattern of the L-tartrate salt of Formula (1).

In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide L-tartrate. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide L-tartrate, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide L-tartrate is characterized by at least one of: (1) an X-ray powder diffraction pattern with at least five peaks selected from the group consisting of 4.6, 5.5, 7.2, 9.3, 10.7, 10.9, 11.8, 14.3, 14.9, 16.4, 17.0, 17.7, 19.2, 19.4, 19.5, 20.3, 21.6, 22.4, 23.3, 23.8, 24.3, 24.5, 24.7, 25.1, 25.6, 26.8, 27.2, 27.8, 28.4, 28.7, 29.0, 29.5, 30.0, 30.9, 31.6, 32.1, 32.4, 33.0, 33.5, 33.9, and any combination thereof, with peak positions measured in ° 2θ±0.2° 2θ; and (2) the presence of water in the crystal structure with a stoichiometry relative to Formula (1) that is approximately equivalent to a sesquihydrate. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide L-tartrate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide L-tartrate Form A is characterized by an X-ray powder diffraction pattern comprising peaks at 4.6, 5.5, 10.9, 11.8, and 14.9° 2θ±0.2° 2θ. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide L-tartrate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide L-tartrate Form A is characterized by an X-ray powder diffraction pattern substantially in agreement with the X-ray powder diffraction pattern of FIG. 44. In an embodiment, the X-ray powder diffraction pattern of any of the foregoing embodiments is measured in transmission mode. In an embodiment, the X-ray powder diffraction pattern of any of the foregoing embodiments is measured in reflection mode.

In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide citrate. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide citrate, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide citrate is characterized by at least one of: (a) an X-ray powder diffraction pattern with at least five peaks selected from the group consisting of 6.1, 6.6, 7.2, 7.9, 8.3, 9.7, 10.8, 11.1, 12.2, 13.5, 14.1, 14.9, 15.9, 16.6, 17.5, 17.9, 18.3, 18.9, 19.5, 20.3, 21.5, 21.9, 22.7, 23.8, 24.3, 24.8, 26.1, 26.3, 27.2, 27.4, 27.9, 29.3, and any combination thereof, with peak positions measured in ° 2θ±0.2° 2θ; (b) a Raman spectrum with at least five peaks selected from the group consisting of 3068, 2921, 2237, 1682, 1612, 1551, 1505, 1436, 1332, 1313, 1241, 1188, 993, 712, and any combination thereof, with peak positions measured in $cm^{-1} \pm 4\ cm^{-1}$; (c) an IR spectrum with at least five peaks selected from the group consisting 3396, 2234, 1673, 1606, 1537, 1428, 1304, 1264, 1200, 1092, 1008, 893, 866, 773, 735, and 693, and any combination thereof, with peak positions measured in $cm^{-1} \pm 4\ cm^{-1}$; and (d) the presence of water in the crystal structure at a concentration between about 0% to 8% by weight. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide citrate, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide citrate is characterized by at least one of: (a) an X-ray powder diffraction pattern with at least five peaks selected from the group consisting of 6.1, 6.4, 7.2, 7.9, 8.2, 9.6, 10.9, 12.0, 13.4, 13.8, 14.0, 14.9, 15.5, 15.9, 16.4, 17.3, 17.5, 18.2, 18.6, 19.3, 20.1, 20.4, 21.4, 21.6, 22.6, 23.2, 23.7, 24.3, 26.0, 27.0, 27.3, 27.8, 29.2, and any combination thereof, with peak positions measured in ° 2θ±0.2° 2θ; (b) a Raman spectrum with at least five peaks selected from the group consisting of 3055, 2920, 2237, 1685, 1612, 1549, 1504, 1436, 1333, 1313, 1286, 1240, 1187, 993, 712, and any combination thereof, with peak positions measured in $cm^{-1} \pm 4\ cm^{-1}$; (c) an IR spectrum with at least five peaks selected from the group consisting 3403, 2960, 2872, 2233, 1678, 1608, 1582, 1538, 1434, 1403, 1352, 1302, 1253, 1201, 1094, 1055, 1010, 967, 895, 813, 772, 750, 735, 693, 612, and any combination thereof, with peak positions measured in $cm^{-1} \pm 4\ cm^{-1}$; and (d) the presence of water in the crystal structure at a concentration between about 0% to about 8% by weight. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide citrate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide citrate Form A is characterized by an X-ray powder diffraction pattern comprising peaks at 6.1, 7.2, 9.7, 11.1, and 12.2° 2θ±0.2° 2θ. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide citrate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide citrate Form A is characterized by an X-ray powder diffraction pattern substantially in agreement with the X-ray powder diffraction pattern of FIG. 58. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide citrate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide citrate Form A is characterized by an X-ray powder diffraction pattern comprising peaks at 6.1, 7.2, 9.6, 10.9, and 12.0° 2θ±0.2° 2θ. In an embodiment, the X-ray powder diffraction pattern of any of the foregoing embodiments is measured in transmission mode. In an embodiment, the X-ray powder diffraction pattern of any of the foregoing embodiments is measured in reflection mode.

In an embodiment, the invention provides a composition comprising crystalline (5)-4-(8-amino-3-(1-(but-2-ynoyl)pyrrolidin-2-yl)imidazo[1,5-a]pyrazin-1-yl)-N-(pyridin-2-yl)benzamide gentisate. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide gentisate, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide gentisate is characterized by at least one of: (a) an X-ray powder diffraction pattern with at least five peaks selected from the group consisting of 4.6, 8.2, 9.0, 9.7, 11.8, 12.9, 13.8, 14.5, 15.5, 16.6, 16.8, 18.4, 19.6, 20.5, 21.1, 24.1, 24.5, 25.5, 25.8, 26.0, 26.6, 26.9, 27.4, 29.8, and any combination thereof, with peak positions measured in ° 2θ±0.2° 2θ; (b) a Raman spectrum with at least five peaks selected from the group consisting of 3057, 2919, 2223, 1681, 1613, 1576, 1552, 1518, 1437, 1333, 1312, 1228, 1192, 1156, 990, 716, 485, 257, and any combination thereof, with peak positions measured in $cm^{-1} \pm 4\ cm^{-1}$; (c) an IR spectrum with at least five peaks selected from the group consisting 2957, 1682, 1668, 1602, 1574, 1523, 1504, 1481, 1429, 1377, 1346, 1302, 1274, 1228, 1157, 1092, 1010, 939, 896, 865, 826, 810, 778, 748, 734, 686, 660, 617, and any combination thereof, with peak positions measured in $cm^{-1} \pm 4\ cm^{-1}$; and (d) the presence of water in the crystal structure with a stoichiometry relative to Formula (1) that is approximately equivalent to a monohydrate. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide gentisate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide gentisate Form A is characterized by an X-ray powder diffraction pattern comprising peaks at 4.6, 9.0, 12.9, 13.8, and 19.6° 2θ±0.2° 2θ. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide gentisate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide gentisate Form A is characterized by an X-ray powder diffraction pattern substantially in agreement with the X-ray powder diffraction pattern of FIG. 60. In an embodiment, the X-ray powder diffraction pattern of any of the foregoing embodiments is measured in transmission mode. In an embodiment, the X-ray powder diffraction pattern of any of the foregoing embodiments is measured in reflection mode.

In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide oxalate. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide oxalate, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide oxalate is characterized by at least one of: (a) an X-ray powder diffraction pattern with at least five peaks selected from the group consisting of 5.5, 5.8, 7.4, 9.3, 11.0, 11.5, 12.7, 15.2, 16.5, 17.3, 18.5, 18.7, 19.1, 19.7, 20.2, 20.8, 22.0, 22.3, 23.3, 23.6, 24.8, 27.4, 28.6, 29.3, 29.6, 31.2, 33.1, and any combination thereof, with peak positions measured in ° 2θ±0.2° 2θ; (b) a Raman spectrum with at least five peaks selected from the group consisting of 3073, 2992, 2950, 2922, 2247, 1671, 1612, 1584, 1552, 1504, 1469, 1440, 1336, 1311, 1273, 1235, 1191, 1162, 1095, 1012, 897, 718, 633, 409, 370, 263, and any combination thereof, with peak positions measured in $cm^{-1} \pm 4\ cm^{-1}$; (c) an IR spectrum with at least five peaks selected from the group consisting 3419, 2249, 1670, 1615, 1544, 1503, 1438, 1391, 1334, 1304, 1262, 1195, 1151, 1126, 1093, 1013, 894, 877, 823, 783, 765, 738, 652, and any combination thereof, with peak positions measured in cm$^{-1}$±4 cm$^{-1}$; and (d) the presence of water in the crystal structure at a concentration between about 0% to about 9% by weight. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide oxalate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide oxalate Form A is characterized by an X-ray powder diffraction pattern comprising peaks at 5.5, 5.8, 9.3, 11.5, and 12.7° 2θ±0.2° 2θ. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide oxalate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide oxalate Form A is characterized by an X-ray powder diffraction pattern substantially in agreement with the X-ray powder diffraction pattern of FIG. 61. In an embodiment, the X-ray powder diffraction pattern of any of the foregoing embodiments is measured in transmission mode. In an embodiment, the X-ray powder diffraction pattern of any of the foregoing embodiments is measured in reflection mode.

In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide sulfate. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide sulfate, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide sulfate is characterized by at least one of: (a) an X-ray powder diffraction pattern with at least five peaks selected from the group consisting of 4.6, 5.0, 8.0, 9.0, 9.8, 12.0, 12.7, 13.2, 14.6, 15.0, 15.6, 16.2, 17.5, 17.9, 19.8, 20.2, 21.9, 23.8, 24.4, 24.9, 25.7, 26.0, 27.2, 29.5, 30.4, 31.6, 32.5, and any combination thereof, with peak positions measured in ° 2θ±0.2° 2θ; (b) a Raman spectrum with at least five peaks selected from the group consisting of 3115, 2977, 2926, 2224, 1675, 1611, 1537, 1498, 1449, 1409, 1361, 1327, 1310, 1288, 1243, 1198, 1155, 1042, 1009, 978, 948, 906, 849, 771, 713, 652, 632, 464, 370, 254, and any combination thereof, with peak positions measured in cm$^{-1}$±4 cm$^{-1}$; (c) an IR spectrum with at least five peaks selected from the group consisting 3430, 3101, 3029, 2225, 1667, 1633, 1615, 1598, 1563, 1557, 1508, 1428, 1350, 1328, 1308, 1276, 1225, 1088, 1036, 1018, 925, 891, 848, 816, 783, 736, 723, 694, 612, and any combination thereof, with peak positions measured in cm$^{-1}$±4 cm$^{-1}$; and (d) the presence of water in the crystal structure at a concentration between about 2.5% to about 12.5% by weight. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide sulfate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide sulfate Form A is characterized by an X-ray powder diffraction pattern comprising peaks at 4.6, 9.0, 9.8, 17.5, and 18.0° 2θ±0.2° 2θ. In an embodiment, the invention provides a composition comprising crystalline (S)-4-(8-amino-3-(1-(but-2-ynoyl)pyrrolidin-2-yl)imidazo[1,5-a]pyrazin-1-yl)-N-(pyridin-2-yl)benzamide sulfate Form A, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide sulfate Form A is characterized by an X-ray powder diffraction pattern substantially in agreement with the X-ray powder diffraction pattern of FIG. 66. In an embodiment, the X-ray powder diffraction pattern of any of the foregoing embodiments is measured in transmission mode. In an embodiment, the X-ray powder diffraction pattern of any of the foregoing embodiments is measured in reflection mode.

In an embodiment, the invention provides a composition comprising a cocrystal of (S)-4-(8-amino-3-(1-(but-2-ynoyl)pyrrolidin-2-yl)imidazo[1,5-a]pyrazin-1-yl)-N-(pyridin-2-yl)benzamide and L-arabitol. In an embodiment, the invention provides a composition comprising a cocrystal of (S)-4-(8-amino-3-(1-(but-2-ynoyl)pyrrolidin-2-yl)imidazo[1,5-a]pyrazin-1-yl)-N-(pyridin-2-yl)benzamide and L-arabitol, wherein the cocrystal of (S)-4-(8-amino-3-(1-(but-2-ynoyl)pyrrolidin-2-yl)imidazo[1,5-a]pyrazin-1-yl)-N-(pyridin-2-yl)benzamide L-arabitol is characterized by at least one of: (a) an X-ray powder diffraction pattern with at least five peaks selected from the group consisting of 5.6, 7.0, 9.2, 11.2, 12.9, 13.5, 14.0, 14.8, 15.3, 16.8, 17.9, 18.2, 18.4, 21.1, 21.4, 22.5, 22.9, 23.9, 24.8, 25.5, 26.0, 26.6, 27.7, 28.2, 28.8, 29.4, and any combination thereof, with peak positions measured in ° 2θ±0.2° 2θ; (b) a Raman spectrum with at least five peaks selected from the group consisting of 2917, 2241, 1674, 1610, 1581, 1565, 1529, 1494, 1455, 1348, 1325, 1309, 1264, 1242, 1189, 1164, 999, 872, 279, and any combination thereof, with peak positions measured in cm$^{-1}$±4 cm$^{-1}$; (c) an IR spectrum with at least five peaks selected from the group consisting 3471, 3188, 2924, 2239, 1670, 1637, 1621, 1603, 1579, 1524, 1505, 1435, 1346, 1306, 1274, 1242, 1203, 1135, 1090, 1049, 1009, 998, 950, 902, 892, 862, 821, 783, 739, 726, 711, 694, 637, 621, and any combination thereof, with peak positions measured in cm$^{-1}$±4 cm$^{-1}$; and (d) the presence of water in the crystal structure at a concentration between about 0% to about 5% by weight. In an embodiment, the X-ray powder diffraction pattern of any of the foregoing embodiments is measured in transmission mode. In an embodiment, the X-ray powder diffraction pattern of any of the foregoing embodiments is measured in reflection mode.

In an embodiment, the invention provides a composition comprising a cocrystal of (S)-4-(8-amino-3-(1-(but-2-ynoyl)pyrrolidin-2-yl)imidazo[1,5-a]pyrazin-1-yl)-N-(pyridin-2-yl)benzamide and L-proline. In an embodiment, the invention provides a composition comprising a cocrystal of (S)-4-(8-amino-3-(1-(but-2-ynoyl)pyrrolidin-2-yl)imidazo[1,5-c]pyrazin-1-yl)-N-(pyridin-2-yl)benzamide and L-proline, wherein the cocrystal of (S)-4-(8-amino-3-(1-(but-2-ynoyl)pyrrolidin-2-yl)imidazo[1,5-a]pyrazin-1-yl)-N-(pyridin-2-yl)benzamide L-proline is characterized by at least one of: (a) an X-ray powder diffraction pattern with at least five peaks selected from the group consisting of 7.0, 10.5, 14.0, 14.8, 17.1, 17.6, 21.1, 22.1, and any combination thereof, with peak positions measured in ° 2θ±0.2° 2θ; (b) a Raman spectrum with at least five peaks selected from the group consisting of 3064, 2971, 2919, 2881, 2242, 1675, 1607, 1577, 1530, 1484, 1454, 1434, 1344, 1323, 1311, 1264, 1243, 1185, 1157, 1035, 1020, 993, 370, 275, 190, 153, and any combination thereof, with peak positions measured in cm$^{-1}$±4 cm$^{-1}$; (c) an IR spectrum with at least five peaks selected from the group consisting 3471, 3310, 3108, 2358, 1672, 1615, 1526, 1495, 1452, 1431, 1399, 1342, 1305, 1262, 1241, 1184, 1148, 1091, 1038, 1014, 991, 944, 890, 872, 837, 816, 775, 756, 737, 713, 668, and any combination thereof, with peak positions measured in cm$^{-1}$±4 cm$^{-1}$; and (d) the absence of water in the crystal structure. In an embodiment, the X-ray powder diffraction pattern of any of the foregoing embodiments is measured in transmission mode. In an embodiment, the X-ray powder diffraction pattern of any of the foregoing embodiments is measured in reflection mode.

In an embodiment, the invention provides a composition comprising a cocrystal of (S)-4-(8-amino-3-(1-(but-2-ynoyl)pyrrolidin-2-yl)imidazo[1,5-a]pyrazin-1-yl)-N-(pyridin-2-yl)benzamide and D-sorbitol. In an embodiment, the invention provides a composition comprising a cocrystal of (S)-4-(8-amino-3-(1-(but-2-ynoyl)pyrrolidin-2-yl)imidazo[1,5-a]pyrazin-1-yl)-N-(pyridin-2-yl)benzamide and D-sorbitol, wherein the cocrystal of (S)-4-(8-amino-3-(1-(but-2-ynoyl)pyrrolidin-2-yl)imidazo[1,5-a]pyrazin-1-yl)-N-(pyridin-2-yl)benzamide D-sorbitol is characterized by at least one of: (a) an X-ray powder diffraction pattern with at least five peaks selected from the group consisting of 3.0, 4.4, 5.1, 6.0, 7.3, 8.3, 8.6, 10.1, 12.3, 12.7, 13.4, 13.0, 14.3, 14.5, 15.6, 16.5, 17.1, 18.0, 18.5, 18.9, 19.4, 19.8, 20.5, 21.2, 21.8, 22.3, 22.6, 24.4, 25.5, 27.3, 28.0, 32.9, and any combination thereof, with peak positions measured in ° 2θ±0.2° 2θ; (b) a Raman spectrum with at least five peaks selected from the group consisting of 3071, 2921, 2246, 1682, 1610, 1579, 1531, 1493, 1453, 1437, 1343, 1311, 1246, 1183, 1162, 1039, 1000, 950, 646, and any combination thereof, with peak positions measured in $cm^{-1}±4\ cm^{-1}$; (c) an IR spectrum with at least five peaks selected from the group consisting 3207, 2244, 1681, 1666, 1651, 1615, 1578, 1548, 1531, 1504, 1463, 1434, 1418, 1398, 1311, 1243, 1207, 1149, 1112, 1093, 1052, 1017, 1004, 948, 891, 867, 821, 777, 735, 724, 707, 643, 618, and any combination thereof, with peak positions measured in $cm^{-1}±4\ cm^{-1}$; and (d) the presence of water in the crystal structure at a concentration between about 0% to about 13% by weight. In an embodiment, the X-ray powder diffraction pattern of any of the foregoing embodiments is measured in transmission mode. In an embodiment, the X-ray powder diffraction pattern of any of the foregoing embodiments is measured in reflection mode.

In an embodiment, the invention provides a composition comprising a cocrystal of (S)-4-(8-amino-3-(1-(but-2-ynoyl)pyrrolidin-2-yl)imidazo[1,5-a]pyrazin-1-yl)-N-(pyridin-2-yl)benzamide and succinic acid. In an embodiment, the invention provides a composition comprising a cocrystal of (S)-4-(8-amino-3-(1-(but-2-ynoyl)pyrrolidin-2-yl)imidazo[1,5-a]pyrazin-1-yl)-N-(pyridin-2-yl)benzamide and succinic acid, wherein the crystalline (S)-4-(8-amino-3-(1-(but-2-ynoyl)pyrrolidin-2-yl)imidazo[1,5-a]pyrazin-1-yl)-N-(pyridin-2-yl)benzamide succinic acid is characterized by at least one of: (a) an X-ray powder diffraction pattern with at least five peaks selected from the group consisting of 5.2, 7.5, 8.0, 8.4, 10.3, 12.1, 13.3, 14.2, 14.7, 15.5, 16.0, 17.1, 17.5, 18.1, 18.6, 19.2, 19.6, 20.5, 21.2, 22.5, 22.8, 23.2, 23.6, 25.5, 26.2, 27.4, 28.2, 28.7, 29.4, 30.3, 31.0, 31.6, 32.2, 33.2, 35.5, and any combination thereof, with peak positions measured in ° 2θ±0.2° 2θ; (b) a Raman spectrum with at least five peaks selected from the group consisting of 2973, 2922, 2252, 1670, 1613, 1580, 1566, 1545, 1529, 1496, 1450, 1347, 1330, 1307, 1270, 1244, 1190, 1160, 1036, 1010, 844, 728, 634, 411, 237, 200, 138, and any combination thereof, with peak positions measured in $cm^{-1}±4\ cm^{-1}$; (c) an IR spectrum with at least five peaks selected from the group consisting 2359, 1712, 1668, 1620, 1603, 1578, 1526, 1494, 1432, 1417, 1403, 1367, 1346, 1304, 1246, 1220, 1174, 1162, 1130, 1096, 1035, 1009, 993, 965, 950, 896, 863, 851, 838, 778, 754, 734, 726, 712, 672, 636, 624, 606, and any combination thereof, with peak positions measured in $cm^{-1}±4\ cm^{-1}$. In an embodiment, the X-ray powder diffraction pattern of any of the foregoing embodiments is measured in transmission mode. In an embodiment, the X-ray powder diffraction pattern of any of the foregoing embodiments is measured in reflection mode.

Amorphous Forms

In an embodiment, the invention provides a composition comprising an amorphous solid dispersion of (S)-4-(8-amino-3-(1-(but-2-ynoyl)pyrrolidin-2-yl)imidazo[1,5-a]pyrazin-1-yl)-N-(pyridin-2-yl)benzamide (Formula (1)) and a polymer, wherein the polymer is selected from the group consisting of hydroxypropylmethylcellulose acetate succinate, polyvinylpyrrolidone, vinylpyrrolidone-vinyl acetate copolymer, methacrylic acid-ethyl acrylate copolymer, methacrylic acid-methyl methacrylate copolymer, and a mixture of vinylpyrrolidone-vinyl acetate copolymer and hydroxypropylmethylcellulose, wherein the concentration of the polymer is between about 20% and about 95% by weight of the composition, and wherein the (S)-4-(8-amino-3-(1-(but-2-ynoyl)pyrrolidin-2-yl)imidazo[1,5-a]pyrazin-1-yl)-N-(pyridin-2-yl)benzamide and polymer are molecularly dispersed in each other. Such a composition may be referred to as an amorphous solid dispersion of Formula (1). In an embodiment, the concentration of the polymer is selected from the group consisting of about 30% by weight of the composition, about 35% by weight of the composition, about 40% by weight of the composition, about 45% by weight of the composition, about 50% by weight of the composition, about 55% by weight of the composition, about 60% by weight of the composition, about 65% by weight of the composition, about 70% by weight of the composition, about 75% by weight of the composition, about 80% by weight of the composition, about 85% by weight of the composition, about 90% by weight of the composition, and about 95% by weight of the composition. In an embodiment, the concentration of the polymer is between about 30% and about 95% by weight of the composition. In an embodiment, the concentration of the polymer is between about 40% and about 95% by weight of the composition. In an embodiment, the concentration of the polymer is between about 50% and about 95% by weight of the composition. In an embodiment, the concentration of the polymer is between about 60% and about 95% by weight of the composition. In an embodiment, the concentration of the polymer is between about 70% and about 95% by weight of the composition. In an embodiment, the concentration of the polymer is between about 80% and about 95% by weight of the composition. In any of the foregoing embodiments, the amorphous solid dispersion is an amorphous solid molecular dispersion. In any of the foregoing embodiments, the amorphous solid dispersion is characterized by a single glass transition temperature ($T_g$) when analyzed by differential scanning calorimetry, including modulated differential scanning calorimetry or temperature-modulated differential scanning calorimetry. In any of the foregoing embodiments, the amorphous solid dispersion is characterized by domains containing high concentrations of Formula (1) that are of the order of 30 nm or less in approximate size. In any of the foregoing embodiments, the amorphous solid dispersion is an intimate mixture of Formula (1) and a polymer.

In an embodiment, an amorphous solid dispersion of Formula (1) further comprises an extragranular acidulant. In an embodiment, an amorphous solid dispersion of Formula (1) further comprises an extragranular acidulant, wherein the extragranular acidulant is selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, Protacid F 120 NM, Protacid AR 1112 (also known as Kelacid NF), Carbopol 971P (carboxypolymethylene), and Carbomer 941 (polyacrylic acid), and combinations thereof. In an embodiment, an amorphous solid dispersion of Formula (1) further comprises an extragranular acidulant, wherein the extragranular acidulant is fumaric acid at a concentration of between about 15% to about 33% by weight. In an embodiment, an amorphous solid dispersion of Formula (1) further comprises an extragranular acidulant, wherein the extragranular acidulant is alginic acid at a concentration of between about 5% to about 33% by weight. In an embodiment, an amorphous solid dispersion of Formula (1) further comprises an extragranular acidulant, wherein the extragranular acidulant is L-tartaric acid at a concentration of between about 25% to about 33% by weight. In an embodiment, an amorphous solid dispersion of Formula (1) further comprises an extragranular acidulant, wherein the extragranular acidulant is ascorbic acid at a concentration of between about 20% to about 50% by weight and Carbomer 941 (polyacrylic acid) at a concentration of between about 2.5% to about 10% by weight. In an embodiment, an amorphous solid dispersion of Formula (1) further comprises an extragranular acidulant, wherein the extragranular acidulant is ascorbic acid at a concentration of between about 20% to about 50% by weight and Carbopol 971P (carboxypolymethylene) at a concentration of between about 2.5% to about 10% by weight. In an embodiment, an amorphous solid dispersion of Formula (1) further comprises an extragranular acidulant, wherein the extragranular acidulant is fumaric acid at a concentration of between about 5% to about 15% by weight and alginic acid at a concentration of about 15% to about 33% by weight. In an embodiment, an amorphous solid dispersion of Formula (1) further comprises an extragranular acidulant, wherein the extragranular acidulant is L-tartaric acid at a concentration of between about 5% to 15% by weight and alginic acid at a concentration of between about 15% to about 33% by weight.

In an embodiment, the invention provides for preparation of any of the foregoing amorphous solid dispersions comprising a step selected from the group consisting of spray drying, hot melt extrusion, lyophilization, co-grinding, co-milling, evaporation, and combinations thereof. Suitable methods for preparation of any of the foregoing amorphous solid dispersions may also be found in U.S. Pat. Nos. 6,548,555; 8,173,142; 8,236,328; and 8,263,128, the disclosures of which are incorporated by reference herein.

Pharmaceutical Compositions

In an embodiment, the invention provides a pharmaceutical composition comprising a crystalline polymorphic form of the free base of the BTK inhibitor of Formula (1). In an embodiment, the invention provides a pharmaceutical composition comprising a crystalline solvate of the free base of Formula (1). In an embodiment, the invention provides a pharmaceutical composition comprising a crystalline hydrate of the free base of the BTK inhibitor of Formula (1). In an embodiment, the invention provides a pharmaceutical composition comprising a crystalline salt of Formula (1). In an embodiment, the invention provides a pharmaceutical composition comprising an amorphous form of the BTK inhibitor of Formula (1).

The pharmaceutical compositions are typically formulated to provide a therapeutically effective amount o of a solid form of the BTK inhibitor of Formula (1), as the active ingredient, or a pharmaceutically acceptable salt, ester, prodrug, solvate, hydrate or derivative thereof. Where desired, the pharmaceutical compositions contain a pharmaceutically acceptable salt thereof, and one or more pharmaceutically acceptable excipients, carriers, including inert solid diluents and fillers, diluents, permeation enhancers, solubilizers, or adjuvants. The pharmaceutical compositions may also contain an acidulant, as described herein, for reducing or overcoming the effects of acid reducing agents on the exposure of BTK inhibitor of Formula (1).

In some embodiments, the concentration of a solid form of the BTK inhibitor of Formula (1), provided in the pharmaceutical compositions of the invention is independently less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, or 0.001%, w/w, w/v, or v/v, relative to the total mass or volume of the pharmaceutical composition.

In some embodiments, the concentration of a solid forms of the BTK inhibitor of Formula (1), provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v, relative to the total mass or volume of the pharmaceutical composition.

In some embodiments, the concentration of a solid form of the BTK inhibitor of Formula (1), of the invention is independently in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12% or approximately 1% to approximately 10% w/w, w/v or v/v, relative to the total mass or volume of the pharmaceutical composition.

In some embodiments, the concentration of a solid form of the BTK inhibitor of Formula (1), of the invention is independently in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v, or v/v, relative to the total mass or volume of the pharmaceutical composition.

In some embodiments, the amount of a solid form of the BTK inhibitor of Formula (1), of the invention is independently equal to or less than 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g or 0.0001 g.

In some embodiments, the amount of a solid form of the BTK inhibitor of Formula (1), of the invention is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, or 3 g.

Each of the solid forms of the BTK inhibitor of Formula (1), according to the invention is effective over a wide dosage range. For example, in the treatment of adult humans, dosages independently range from 0.01 to 1000 mg, from 0.5 to 100 mg, from 1 to 50 mg per day, from 2 to 40 mg per day, and from 5 to 25 mg per day are examples of dosages that may be used. The exact dosage will depend upon the route of administration, the form in which the compound is administered, the gender and age of the subject to be treated, the body weight of the subject to be treated, and the preference and experience of the attending physician.

In selected embodiments, the invention provides a pharmaceutical composition for oral administration containing the BTK inhibitor of Formula (1), and a pharmaceutical excipient suitable for oral administration.

In selected embodiments, the invention provides a solid pharmaceutical composition for oral administration containing: (i) an effective amount of the BTK inhibitor of Formula (1), and (ii) a pharmaceutical excipient suitable for oral administration. In selected embodiments, the composition further contains (iii) an effective amount of another active pharmaceutical ingredient.

In selected embodiments, the pharmaceutical composition may be a liquid pharmaceutical composition suitable for oral consumption. Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil emulsion. Pharmaceutical compositions of the invention also include powder for reconstitution, powders for oral consumptions, bottles (such as powder or liquid in bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the solid forms of the BTK inhibitor of Formula (1), can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, glidants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a SYLOID® silica gel, a coagulated aerosol of synthetic silica, silicified microcrystalline cellulose, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

An empirical parameter used to characterize the relative hydrophilicity and hydrophobicity of non-ionic amphiphilic compounds is the hydrophilic-lipophilic balance ("HLB" value). A suitable hydrophilic surfactant may generally have an HLB value of at least 10, while suitable lipophilic surfactants may generally have an HLB value of or less than about 10. Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols, glycerol fatty acid esters, acetylated glycerol fatty acid esters, lower alcohol fatty acids esters, propylene glycol fatty acid esters, sorbitan fatty acid esters, polyethylene glycol sorbitan fatty acid esters, sterols and sterol derivatives, polyoxyethylated sterols and sterol derivatives, polyethylene glycol alkyl ethers, sugar esters, sugar ethers, lactic acid derivatives of mono- and di-glycerides, and hydrophobic transesterification products of a polyol with at least one member of the group consisting of glycerides, vegetable oils, hydrogenated vegetable oils, fatty acids and sterols, oil-soluble vitamins/vitamin derivatives, and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, xylitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, epsilon-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but are not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Dosages and Dosing Regimens

In an embodiment, the invention provides a pharmaceutical composition comprising a crystalline form of the free base of Formula (1). In an embodiment, the invention provides a pharmaceutical composition comprising a crystalline solvate of the free base of Formula (1). In an embodiment, the invention provides a pharmaceutical composition comprising a crystalline hydrate of the free base of Formula (1). In an embodiment, the invention provides a pharmaceutical composition comprising a crystalline salt of Formula (1). In an embodiment, the invention provides a pharmaceutical composition comprising an amorphous form of Formula (1).

The amounts of the solid form of the BTK inhibitor of Formula (1), will be dependent on the mammal being treated, the severity of the disorder or condition, the rate of administration, the disposition of the compounds and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect, for example by dividing such larger doses into several small doses for administration throughout the day.

In selected embodiments, a solid form of the BTK inhibitor of Formula (1) is administered in a single dose. Typically, such administration will be by injection, for example by intravenous injection, in order to introduce the active pharmaceutical ingredients quickly. However, other routes may be used as appropriate. A single dose of a solid form of the BTK inhibitor of Formula (1) may also be used for treatment of an acute condition.

In selected embodiments, a solid form of the BTK inhibitor of Formula (1) is administered in multiple doses. Dosing may be about once, twice, three times, four times, five times, six times, or more than six times per day. Dosing may be about once a month, once every two weeks, once a week, or once every other day. In other embodiments, a solid form of the BTK inhibitor of Formula (1) is administered about once per day to about 6 times per day. In another embodiment the administration of the BTK inhibitor of Formula (1), continues for less than about 7 days. In yet another embodiment the administration continues for more than about 6, 10, 14, 28 days, two months, six months, or one year. In some cases, continuous dosing is achieved and maintained as long as necessary.

Administration of the active pharmaceutical ingredients of the invention may continue as long as necessary. In selected embodiments, a solid form of the BTK inhibitor of Formula (1), are administered for more than 1, 2, 3, 4, 5, 6, 7, 14, or 28 days. In some embodiments, the solid forms of the BTK inhibitor of Formula (1) are administered for less than 28, 14, 7, 6, 5, 4, 3, 2, or 1 day. In selected embodiments, a solid form of the BTK inhibitor of Formula (1) is administered chronically on an ongoing basis—e.g., for the treatment of chronic effects.

In some embodiments, an effective dosage of a solid form of the BTK inhibitor of Formula (1) is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of a solid form of the BTK inhibitor of Formula (1) is about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In some embodiments, an effective dosage of a solid form of the BTK inhibitor of Formula (1) is 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg.

In some embodiments, an effective dosage of a solid form of the BTK inhibitor of Formula (1) is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a solid form of the BTK inhibitor of Formula (1) is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, a solid form of the BTK inhibitor of Formula (1) is adminstered at a dosage of 10 to 400 mg once daily (QD), including a dosage of 5 mg, 10 mg, 12.5 mg, 25 mg, 50 mg, 75 mg, 100 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg once daily (QD).

In some embodiments, a solid form of the BTK inhibitor of Formula (1) is adminstered at a dosage of 10 to 400 mg BID, including a dosage of 5 mg, 10 mg, 12.5 mg, 25 mg, 50 mg, 75 mg, 100 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg BID.

In some embodiments, a solid form of the BTK inhibitor of Formula (1) is administered at a dosage of 10 to 400 mg TID, including a dosage of 5 mg, 10 mg, 12.5 mg, 25 mg, 50 mg, 75 mg, 100 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg TID.

An effective amount of a solid form of the BTK inhibitors may be administered in either single or multiple doses by any of the accepted modes of administration of active pharmaceutical ingredients having similar utilities, including rectal, buccal, intranasal and transdermal routes, by intra-arterial injection, intravenously, intraperitoneally, parenterally, intramuscularly, subcutaneously, orally, topically, or as an inhalant.

Pharmaceutical Compositions for Overcoming the Effects of Acid Reducing Agents

The compositions and methods described herein can be used to overcome the effects of acid reducing agents. Acid-reducing agents can greatly limit the exposure of weakly acidic drugs (such as Formula (1) free base) in mammals. Smelick, et al., *Mol. Pharmaceutics* 2013, 10, 4055-4062. Acid reducing agents include proton pump inhibitors, such as omeprazole, esomeprazole, lansoprazole, dexlansoprazole, pantoprazole, rabeprazole, and ilaprazole; $H_2$ receptor antagonists, such as cimetidine, ranitidine, and famotidine; and antacids such as bicarbonates, carbonates, and hydroxides of aluminium, calcium, magnesium, potassium, and sodium, as well as mixtures of antacids with agents targeting mechanisms of gastric secretion. Overcoming the effects of acid reducing agents is a significant issue in the treatment of patients with cancer, inflammatory diseases, immune diseases, and autoimmune diseases, since these patients are commonly co-administered acid reducing agents for gastric irritation that often accompanies their conditions. Acid reducing agents are the most commonly prescribed medications in North America and Western Europe. Most recently approved oral cancer therapeutics have pH-dependent solubility and thus a potential drug-drug interaction with regards to acid reducing agents. In cancer patients, it is estimated that 20-33% of all patients are using some form of acid-reducing agent. In particular cancers, such as pancreatic cancer or gastrointestinal cancers, acid reducing agent use is as high as 60-80% of patients. Smelick, et al., *Mol. Pharmaceutics* 2013, 10, 4055-4062.

In an embodiment, a pharmaceutical composition comprises a BTK inhibitor according to Formula (1) and an acidulant. In an embodiment, a pharmaceutical composition comprises a BTK inhibitor according to Formula (1) and an acidulant selected from the group consisting of fumaric acid, tartaric acid, ascorbic acid, alginic acid, sodium alginate, potassium alginate, and Carbopol 971P (carboxypolymethylene). In an embodiment, a pharmaceutical composition comprises a BTK inhibitor according to Formula (1) and an acidulant selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, Protacid F 120 NM, Protacid AR 1112 (also known as Kelacid NF), Carbomer 941 (polyacrylic acid), and Carbopol 971P (carboxypolymethylene). In an embodiment, the solid form of Formula (1) in any of the foregoing embodiments is Form I of the free base. In an embodiment, the acidulant is extragranular. In an embodiment, the acidulant is intragranular.

Alginic acid is a polysaccharide copolymer, β-D-mannuronic acid (M) and α-L-guluronic acid (G) linked by 1-4 glycosidic bonds. In an embodiment, a pharmaceutical composition comprises a BTK inhibitor according to Formula (1) and an acidulant that is an alginic acid, or a salt thereof, wherein the alginic acid, or a salt thereof, exhibits an M/G ratio selected from the group consisting of between 0.1 and 0.5, between 0.2 and 0.6, between 0.3 and 0.7, between 0.4 and 0.8, between 0.5 and 0.9, between 0.6 and 1.0, between 0.7 and 1.1, between 0.8 and 1.2, between 0.9 and 1.3, between 1.0 and 1.4, between 1.1 and 1.5, between 1.2 and 1.6, between 1.3 and 1.7, between 1.4 and 1.8, between 1.5 and 1.9, between 1.6 and 2.0, between 1.7 and 2.1, between 1.8 and 2.2, between 1.9 and 2.3, between 2.0 and 2.4, and between 2.1 and 2.5. In an embodiment, a pharmaceutical composition comprises a BTK inhibitor according to Formula (1) and an acidulant that is an alginic acid, or a salt thereof, wherein the alginic acid, or a salt thereof, exhibits an M/G ratio selected from the group consisting of less than 0.5, less than 1.0, less than 1.5, less than 2.0, and less than 2.5. In an embodiment, a pharmaceutical composition comprises a BTK inhibitor according to Formula (1) and an acidulant that is an alginic acid, or a salt thereof, wherein the alginic acid, or a salt thereof, exhibits an M/G ratio selected from the group consisting of greater than 0.5, greater than 1.0, greater than 1.5, greater than 2.0, and greater than 2.5. In an embodiment, a pharmaceutical composition comprises a BTK inhibitor according to Formula (1) and an acidulant that is an alginic acid, or a salt thereof, wherein the alginic acid, or a salt thereof, exhibits an M/G ratio selected from the group consisting of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, and 2.5. In an embodiment, the solid form of Formula (1) in any of the foregoing embodiments is Form I of the free base. M/G ratio, as well as the fraction of M and G groups, the fractions of MM and GG "diads," the fractions of "triads" (e.g., MGG), and the fractions of larger sequences of M and G groups, may be determined by methods known to those of ordinary skill in the art, including nuclear magnetic resonance (NMR) spectroscopy (with or without digestion) and mass spectrometry. Larsen, et al., *Carbohydr. Res.*, 2003, 338, 2325-2336.

In an embodiment, a pharmaceutical composition comprises a BTK inhibitor according to Formula (1) and an acidulant in a concentration (% mass) selected from the group consisting of between 1% and 5%, between 5% and 10%, between 10% and 15%, between 15% and 20%, between 20% and 25%, between 25% and 30%, and between 30% and 35%. In an embodiment, a pharmaceutical composition comprises a BTK inhibitor according to Formula (1) and an acidulant in a concentration (% mass) selected from the group consisting of between 1% and 5%, between 5% and 10%, between 10% and 15%, between 15% and 20%, between 20% and 25%, between 25% and 30%, and between 30% and 35%, wherein the acidulant is selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, sodium alginate, potassium alginate, Protacid F 120 NM, Protacid AR 1112 (also known as Kelacid NF), and Carbopol 971P (carboxypolymethylene). In an embodiment, the solid form of Formula (1) in any of the foregoing embodiments is Form I of the free base.

In an embodiment, a pharmaceutical composition comprises a BTK inhibitor according to Formula (1) and an acidulant in a concentration (% mass) selected from the group consisting of less than 1%, less than 5%, less than 10%, less than 15%, less than 20%, less than 25%, less than 30%, and less than 35%. In an embodiment, a pharmaceutical composition comprises a BTK inhibitor according to Formula (1) and an acidulant in a concentration (% mass) selected from the group consisting of less than 1%, less than 5%, less than 10%, less than 15%, less than 20%, less than 25%, less than 30%, and less than 35%, wherein the acidulant is selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, sodium alginate, potassium alginate, Protacid F 120 NM, Protacid AR 1112 (also known as Kelacid NF), and Carbopol 971P (carboxypolymethylene). In an embodiment, the solid form of Formula (1) in any of the foregoing embodiments is Form I of the free base.

In an embodiment, a pharmaceutical composition comprises a BTK inhibitor according to Formula (1) and an acidulant in a concentration (% mass) selected from the group consisting of greater than 1%, greater than 5%, greater than 10%, greater than 15%, greater than 20%, greater than 25%, greater than 30%, and greater than 35%. In an embodiment, a pharmaceutical composition comprises a BTK inhibitor according to Formula (1) and an acidulant in a concentration (% mass) selected from the group consisting of greater than 1%, greater than 5%, greater than 10%, greater than 15%, greater than 20%, greater than 25%, greater than 30%, and greater than 35%, wherein the acidulant is selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, sodium alginate, potassium alginate, Protacid F 120 NM, Protacid AR 1112 (also known as Kelacid NF), and Carbopol 971P (carboxypolymethylene). In an embodiment, the solid form of Formula (1) in any of the foregoing embodiments is Form I of the free base.

In an embodiment, a pharmaceutical composition comprises a BTK inhibitor according to Formula (1) and an acidulant in a concentration (% mass) selected from the group consisting of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, and about 40%. In an embodiment, a pharmaceutical composition comprises a BTK inhibitor according to Formula (1) and an acidulant in a concentration (% mass) selected from the group consisting of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, and about 40%, wherein the acidulant is selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, sodium alginate, potassium alginate, Protacid F 120 NM, Protacid AR 1112 (also known as Kelacid NF), and Carbopol 971P (carboxypolymethylene). In an embodiment, the solid form of Formula (1) in any of the foregoing embodiments is Form I of the free base.

In an embodiment, a pharmaceutical composition comprises a BTK inhibitor according to Formula (1) and an extragranular acidulant, wherein the extragranular acidulant is selected from the group consisting of fumaric acid, succinic acid, D-tartaric acid, L-tartaric acid, racemic tartaric acid, ascorbic acid, isoascorbic acid (also known as erythorbic acid and D-araboascorbic acid), alginic acid, sodium alginate, potassium alginate, Protacid F 120 NM, Protacid AR 1112 (also known as Kelacid NF), and Carbopol 971P (carboxypolymethylene), and combinations thereof. In an embodiment, a pharmaceutical composition comprises a BTK inhibitor according to Formula (1) and an extragranular acidulant, wherein the extragranular acidulant is fumaric acid at a concentration of between about 15% to about 33% by weight. In an embodiment, a pharmaceutical composition comprises a BTK inhibitor according to Formula (1) and an extragranular acidulant, wherein the extragranular acidulant is alginic acid or a salt thereof (such as sodium alginate or potassium alginate) at a concentration of between about 5% to about 33% by weight. In an embodiment, a pharmaceutical composition comprises a BTK inhibitor according to Formula (1) and an extragranular acidulant, wherein the extragranular acidulant is L-tartaric acid at a concentration of between about 25% to about 33% by weight. In an embodiment, a pharmaceutical composition comprises a BTK inhibitor according to Formula (1) and an extragranular acidulant, wherein the extragranular acidulant is ascorbic acid at a concentration of between about 20% to about 50% by weight and Carbopol 971P (carboxypolymethylene) at a concentration of between about 2.5% to about 10% by weight. In an embodiment, a pharmaceutical composition comprises a BTK inhibitor according to Formula (1) and an extragranular acidulant, wherein the extragranular acidulant is fumaric acid at a concentration of between about 5% to about 15% by weight and alginic acid or a salt thereof at a concentration of about 15% to about 33% by weight. In an embodiment, a pharmaceutical composition comprises a BTK inhibitor according to Formula (1) and an extragranular acidulant, wherein the extragranular acidulant is L-tartaric acid at a concentration of between about 5% to 15% by weight and alginic acid at a concentration of between about 15% to about 33% by weight.

In an embodiment, a pharmaceutical composition comprises a BTK inhibitor according to Formula (1) and an acidulant, wherein the acidulent is selected from the group consisting of fumaric acid, maleic acid, phosphoric acid, L-tartaric acid, citric acid, gentisic acid, oxalic acid, and sulfuric acid. In an embodiment, a pharmaceutical composition comprises a BTK inhibitor according to Formula (1) and an acidulant, wherein the acidulent is selected from the group consisting of fumaric acid, maleic acid, phosphoric acid, L-tartaric acid, citric acid, gentisic acid, oxalic acid, and sulfuric acid, and wherein the acidulant is a salt counterion included in a single crystalline phase with Formula (1).

In an embodiment, in addition to an acidulant, a pharmaceutical composition includes an excipient to prolong the exposure of Formula (1) to the acidic microenvironment. In an embodiment, this excipient is a polymer of natural, synthetic or semisynthetic origins. The polymer may contain acidic, anionic, or non-ionic monomers, oligomers or polymers or a mixture of acidic, anionic and non-ionic monomers or copolymers. In one version the excipient is selected from the group consisting of hydroxypropylmethylcellulose, low substituted hydroxypropylcellulose, hydroxypropylcellulose, tocopherol polyethyleneoxide succinate (D-α-tocopherol polyethylene glycol succinate, TPGS, or vitamin E TPGS), methylcellulose, comboxymethylcellulose, sodium carboxymethylcellulose, methylacrylate, ethylacrylate, copolymers of methyl and ethyl acrylate, hydroxypropylmethylcellulose acetate succinate, gelatin, maize starch, pea starch, modified maize starch, potato starch, modified potato starch, sodium starch glycolate, croscarmellose, crospovidone, copovidone, polyethylene glycol, polypropylene glycol, polyethylene and polypropylene glycol copolymers, polyvinylalcohol, polyvinylalcohol and polyethylene oxide copolymers. Copolymers of the foregoing polymers, where applicable, may also be used. Copolymers may be block, branched or terminal copolymers. In an embodiment, the polymer exhibits swelling, binding, or gelling properties that inhibit the disintegration, dissolution, and erosion of the pharmaceutical composition in order to prolong dissolution or to increase total dissolution. In an embodiment, the inclusion of the polymer increases dissolution rate and extent of dissolution over the use of an acidulant alone. The swelling, binding or gelling properties are pH-dependent in one embodiment, wherein the polymer swells, binds, or gels at one pH or range of pH in a different manner than at another pH. In one embodiment this may decrease dissolution at a lower pH than at a higher pH or vice versa. In another embodiment this leads to similar dissolution of Formula I in acidic, neutral or basic pH. This leads to similar plasma exposure independent of stomach pH.

The dissolution profile of a formulation containing one or more swelling, gelling, or binding excipients may exhibit a zero, first, or second differential rate order at one or more pH value or a mixture of different rate orders at different pH values. In an embodiment, a pharmaceutical composition will provide a constant level of drug into the gastrointestinal tract of a mammal by dissolution. Where the Formula (1) is absorbed, this leads to a sustained plasma level of drug over a period, delays the $t_{max}$, and reduces the $c_{max}$ of an equivalent dose of an immediate release formulation of Formula (1). In another embodiment this leads to similar exposure in a mammal regardless of stomach pH.

Methods of Treating Solid Tumor Cancers, Hematological Malignancies, Inflammatory Diseases, Autoimmune Disorders, Immune Disorders, and Other Diseases The pharmaceutical compositions described herein can be used in a method for treating diseases. In preferred embodiments, they are for use in treating hyperproliferative disorders. They may also be used in treating other disorders as described herein and in the following paragraphs.

In some embodiments, the invention provides a method of treating a hyperproliferative disorder in a mammal that comprises administering to the mammal a therapeutically effective amount of a crystalline or amorphous solid form of Formula (1), or a pharmaceutical composition comprising a crystalline or amorphous solid form of Formula (1), as described herein each including Form I of the free base of Formula (1). In some embodiments, the hyperproliferative disorder is cancer. In preferred embodiments, the cancer is selected from the group consisting of chronic lymphocytic leukemia, non-Hodgkin's lymphoma, diffuse large B-cell lymphoma, mantle cell lymphoma, follicular lymphoma, and Waldenström's macroglobulinemia. In preferred embodiments, the cancer is selected from the group consisting of non-Hodgkin's lymphomas (such as diffuse large B-cell lymphoma), acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, bone (e.g., metastatic bone), esophageal, testicular, gynecological, thyroid, CNS, PNS, AIDS-related (e.g., lymphoma and Kaposi's sarcoma), viral-induced cancers such as cervical carcinoma (human papillomavirus), B-cell lymphoproliferative disease and nasopharyngeal carcinoma (Epstein-Barr virus), Kaposi's sarcoma and primary effusion lymphomas (Kaposi's sarcoma herpesvirus), hepatocellular carcinoma (hepatitis B and hepatitis C viruses), and T-cell leukemias (Human T-cell leukemia virus-1), B cell acute lymphoblastic leukemia, Burkitt's leukemia, juvenile myelomonocytic leukemia, hairy cell leukemia, Hodgkin's disease, multiple myeloma, mast cell leukemia, and mastocytosis. In selected embodiments, the method relates to the treatment of a non-cancerous hyperproliferative disorder such as benign hyperplasia of the skin (e.g., psoriasis), restenosis, or prostate conditions (e.g., benign prostatic hypertrophy (BPH)). In some embodiments, the hyperproliferative disorder is an inflammatory, immune, or autoimmune disorder. In some embodiments, the hyperproliferative disorder is selected from the group consisting of tumor angiogenesis, chronic inflammatory disease, rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma and melanoma, ulcerative colitis, atopic dermatitis, pouchitis, spondylarthritis, uveitis, Behcet's disease, polymyalgia rheumatica, giant-cell arteritis, sarcoidosis, Kawasaki disease, juvenile idiopathic arthritis, hidratenitis suppurativa, Sjögren's syndrome, psoriatic arthritis, juvenile rheumatoid arthritis, ankylosing spondylitis, Crohn's disease, lupus, and lupus nephritis. In an embodiment, the solid form of Formula (1) in any of the foregoing embodiments is Form I of the free base. In an embodiment, the method of any of the foregoing embodiments further includes the step of administering an acid reducing agent to the mammal. In an embodiment, the acid reducing agent is selected from the group consisting of proton pump inhibitors, such as omeprazole, esomeprazole, lansoprazole, dexlansoprazole, pantoprazole, rabeprazole, and ilaprazole; $H_2$ receptor antagonists, such as cimetidine, ranitidine, and famotidine; and antacids such as bicarbonates, carbonates, and hydroxides of aluminium, calcium, magnesium, potassium, and sodium.

In some embodiments, the invention provides pharmaceutical compositions of a solid form of Formula (1) described herein for use in the treatment of cancers such as thymus cancer, brain cancer (e.g., glioma), lung cancer, squamous cell cancer, skin cancer (e.g., melanoma), eye cancer, retinoblastoma cancer, intraocular melanoma cancer, oral cavity cancer, oropharyngeal cancer, bladder cancer, gastric cancer, stomach cancer, pancreatic cancer, bladder cancer, breast cancer, cervical cancer, head and neck cancer, renal cancer, kidney cancer, liver cancer, ovarian cancer, prostate cancer, colorectal cancer, colon cancer, esophageal cancer, testicular cancer, gynecological cancer, ovarian cancer, thyroid cancer, CNS cancer, PNS cancer, AIDS-related cancer (e.g., lymphoma and Kaposi's sarcoma), viral-induced cancer, and epidermoid cancer. In some embodiments, the invention provides pharmaceutical compositions of a solid form of Formula (1) described herein for the treatment of a non-cancerous hyperproliferative disorder such as benign hyperplasia of the skin (e.g., psoriasis), restenosis, or prostate (e.g., benign prostatic hypertrophy (BPH)). In some embodiments, the invention provides pharmaceutical compositions of a solid form of Formula (1) described herein for use in the treatment of disorders such as myeloproliferative disorders (MPDs), myeloproliferative neoplasms, polycythemia vera (PV), essential thrombocythemia (ET), primary myelofibrosis (PMF), myelodysplastic syndrome, chronic myelogenous leukemia (BCR-ABL1-positive), chronic neutrophilic leukemia, chronic eosinophilic leukemia, or mastocytosis. The invention also provides compositions for use in treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, and hemangioma.

In selected embodiments, the invention provides a method of treating a solid tumor cancer with a composition including a solid form of Formula (1) described herein, wherein the dose is effective to inhibit signaling between the solid tumor cells and at least one microenvironment selected from the group consisting of macrophages, monocytes, mast cells, helper T cells, cytotoxic T cells, regulatory T cells, natural killer cells, myeloid-derived suppressor cells, regulatory B cells, neutrophils, dendritic cells, and fibroblasts. In selected embodiments, the invention provides a method of treating pancreatic cancer, breast cancer, ovarian cancer, melanoma, lung cancer, squamous cell carcinoma including head and neck cancer, and colorectal cancer using a solid form of Formula (1) described herein, wherein the dose is effective to inhibit signaling between the solid tumor cells and at least one microenvironment selected from the group consisting of macrophages, monocytes, mast cells, helper T cells, cytotoxic T cells, regulatory T cells, natural killer cells, myeloid-derived suppressor cells, regulatory B cells, neutrophils, dendritic cells, and fibroblasts. In an embodiment, the invention provides a method for treating pancreatic cancer, breast cancer, ovarian cancer, melanoma, lung cancer, head and neck cancer, and colorectal cancer using a combination of a solid form of Formula (1) described herein and a second agent selected from the group consisting of bendamustine, venetoclax, gemcitabine, albumin-bound paclitaxel, rituximab, obinutuzumab, ofatumumab, pembrolizumab, nivolumab, durvalumab, avelumab, and atezolizumab. wherein the BTK inhibitor is a solid form of Formula (1) described herein. In an embodiment, the solid form of Formula (1) in any of the foregoing embodiments is Form I of the free base.

In some embodiments, the invention relates to a method of treating an inflammatory, immune, or autoimmune disorder in a mammal with a composition including a solid form of Formula (1) described herein. In selected embodiments, the invention also relates to a method of treating a disease with a composition including a solid form of Formula (1) described herein, wherein the disease is selected from the group consisting of tumor angiogenesis, chronic inflammatory disease, rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma and melanoma, ulcerative colitis, atopic dermatitis, pouchitis, spondylarthritis, uveitis, Behcets disease, polymyalgia rheumatica, giant-cell arteritis, sarcoidosis, Kawasaki disease, juvenile idiopathic arthritis, hidratenitis suppurativa, Sjögren's syndrome, psoriatic arthritis, juvenile rheumatoid arthritis, ankylosing spoldylitis, Crohn's Disease, lupus, and lupus nephritis.

In some embodiments, the invention relates to a method of treating a hyperproliferative disorder in a mammal with a composition including a solid form of Formula (1) described herein, wherein the hyperproliferative disorder is a B cell hematological malignancy selected from the group consisting of chronic lymphocytic leukemia (CLL), small lymphocytic leukemia (SLL), non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, myelodysplatic syndromes, or myelofibrosis. In some embodiments, the invention relates to a method of treating a hyperproliferative disorder in a mammal with a composition including a solid form of Formula (1) described herein, wherein the hyperproliferative disorder is selected from the group consisting of chronic myelocytic leukemia, acute myeloid leukemia, DLBCL (including activated B-cell (ABC) and germinal center B-cell (GCB) subtypes), follicle center lymphoma, Hodgkin's disease, multiple myeloma, indolent non-Hodgkin's lymphoma, and mature B-cell ALL.

In some embodiments, the hyperproliferative disorder is a subtype of CLL. A number of subtypes of CLL have been characterized. CLL is often classified for immunoglobulin heavy-chain variable-region ($IgV_H$) mutational status in leukemic cells. R. N. Damle, et al., *Blood* 1999, 94, 1840-47; T. J. Hamblin, et al., *Blood* 1999, 94, 1848-54. Patients with $IgV_H$ mutations generally survive longer than patients without $IgV_H$ mutations. ZAP70 expression (positive or negative) is also used to characterize CLL. L. Z. Rassenti, et al., *N. Engl. J. Med.* 2004, 351, 893-901. The methylation of ZAP-70 at CpG3 is also used to characterize CLL, for example by pyrosequencing. R. Claus, et al., *J. Clin. Oncol.* 2012, 30, 2483-91; J. A. Woyach, et al., *Blood* 2014, 123, 1810-17. CLL is also classified by stage of disease under the Binet or Rai criteria. J. L. Binet, et al., *Cancer* 1977, 40, 855-64; K. R. Rai, T. Han, *Hematol. Oncol. Clin. North Am.* 1990, 4, 447-56. Other common mutations, such as 11q deletion, 13q deletion, and 17p deletion can be assessed using well-known techniques such as fluorescence in situ hybridization (FISH). In an embodiment, the invention relates to a method of treating a CLL in a human, wherein the CLL is selected from the group consisting of IgV$_H$ mutation negative CLL, ZAP-70 positive CLL, ZAP-70 methylated at CpG3 CLL, CD38 positive CLL, chronic lymphocytic leukemia characterized by a 17p13.1 (17p) deletion, and CLL characterized by a 11q22.3 (11q) deletion.

In some embodiments, the hyperproliferative disorder is a CLL wherein the CLL has undergone a Richter's transformation. Methods of assessing Richter's transformation, which is also known as Richter's syndrome, are described in P. Jain and S. O'Brien, Oncology, 2012, 26, 1146-52. Richter's transformation is a subtype of CLL that is observed in 5-10% of patients. It involves the development of aggressive lymphoma from CLL and has a generally poor prognosis.

In some embodiments, the hyperproliferative disorder is a CLL or SLL in a patient, wherein the patient is sensitive to lymphocytosis. In an embodiment, the invention relates to a method of treating CLL or SLL in a patient, wherein the patient exhibits lymphocytosis caused by a disorder selected from the group consisting of a viral infection, a bacterial infection, a protozoal infection, or a post-splenectomy state. In an embodiment, the viral infection in any of the foregoing embodiments is selected from the group consisting of infectious mononucleosis, hepatitis, and cytomegalovirus. In an embodiment, the bacterial infection in any of the foregoing embodiments is selected from the group consisting of pertussis, tuberculosis, and brucellosis.

Efficacy of the compounds and combinations of compounds described herein in treating, preventing and/or managing other indicated diseases or disorders described here can also be tested using various models known in the art. Efficacy in treating, preventing and/or managing asthma can be assessed using the ova induced asthma model described, for example, in Lee, et al., J. Allergy Clin. Immunol. 2006, 118, 403-9. Efficacy in treating, preventing and/or managing arthritis (e.g., rheumatoid or psoriatic arthritis) can be assessed using the autoimmune animal models described in, for example, Williams, et al., Chem. Biol. 2010, 17, 123-34, WO 2009/088986, WO 2009/088880, and WO 2011/008302. Efficacy in treating, preventing and/or managing psoriasis can be assessed using transgenic or knockout mouse model with targeted mutations in epidermis, vasculature or immune cells, mouse model resulting from spontaneous mutations, and immuno-deficient mouse model with xenotransplantation of human skin or immune cells, all of which are described, for example, in Boehncke, et al., Clinics in Dermatology, 2007, 25, 596-605. Efficacy in treating, preventing and/or managing fibrosis or fibrotic conditions can be assessed using the unilateral ureteral obstruction model of renal fibrosis, which is described, for example, in Chevalier, et al., Kidney International 2009, 75, 1145-1152; the bleomycin induced model of pulmonary fibrosis described in, for example, Moore, et al., Am. J. Physiol. Lung. Cell. Mol. Physiol. 2008, 294, L152-L160; a variety of liver/biliary fibrosis models described in, for example, Chuang, et al., Clin. Liver Dis. 2008, 12, 333-347 and Omenetti, et al., Laboratory Investigation, 2007, 87, 499-514 (biliary duct-ligated model); or any of a number of myelofibrosis mouse models such as described in Varicchio, et al., Expert Rev. Hematol. 2009, 2, 315-334. Efficacy in treating, preventing and/or managing scleroderma can be assessed using a mouse model induced by repeated local injections of bleomycin described, for example, in Yamamoto, et al., J. Invest. Dermatol. 1999, 112, 456-462. Efficacy in treating, preventing and/or managing dermatomyositis can be assessed using a myositis mouse model induced by immunization with rabbit myosin as described, for example, in Phyanagi, et al., Arthritis & Rheumatism, 2009, 60(10), 3118-3127. Efficacy in treating, preventing and/or managing lupus can be assessed using various animal models described, for example, in Ghoreishi, et al., Lupus, 2009, 19, 1029-1035; Ohl, et al., J. Biomed. & Biotechnol., Article ID 432595 (2011); Xia, et al., Rheumatology, 2011, 50, 2187-2196; Pau, et al., PLoS ONE, 2012, 7(5), e36761; Mustafa, et al., Toxicology, 2011, 90, 156-168; Ichikawa et al., Arthritis & Rheumatism, 2012, 62(2), 493-503; Rankin, et al., J. Immunology, 2012, 188, 1656-1667. Efficacy in treating, preventing and/or managing Sjögren's syndrome can be assessed using various mouse models described, for example, in Chiorini, et al., J. Autoimmunity, 2009, 33, 190-196.

Efficacy of the compounds and combinations of compounds described herein in treating, preventing and/or managing the indicated diseases or disorders can be tested using various models known in the art. For example, models for determining efficacy of treatments for pancreatic cancer are described in Herreros-Villanueva, et al., World J. Gastroenterol. 2012, 18, 1286-1294. Models for determining efficacy of treatments for breast cancer are described, e.g., in Fantozzi, Breast Cancer Res. 2006, 8, 212. Models for determining efficacy of treatments for ovarian cancer are described, e.g., in Mullany, et al., Endocrinology 2012, 153, 1585-92; and Fong, et al., J. Ovarian Res. 2009, 2, 12. Models for determining efficacy of treatments for melanoma are described, e.g., in Damsky, et al., Pigment Cell & Melanoma Res. 2010, 23, 853-859. Models for determining efficacy of treatments for lung cancer are described, e.g., in Meuwissen, et al., Genes & Development, 2005, 19, 643-664. Models for determining efficacy of treatments for lung cancer are described, e.g., in Kim, Clin. Exp. Otorhinolaryngol. 2009, 2, 55-60; and Sano, Head Neck Oncol. 2009, 1, 32. Models for determining efficacy of treatments for colorectal cancer, including the CT26 model, are described in Castle, et al., BMC Genomics, 2013, 15, 190; Endo, et al., Cancer Gene Therapy, 2002, 9, 142-148; Roth et al., Adv. Immunol. 1994, 57, 281-351; Fearon, et al., Cancer Res. 1988, 48, 2975-2980.

Models for determining efficacy of treatments in hematological malignancies, including B cell cancers, may also be used. For example, efficacy in diffuse large B cell lymphoma (DLBCL) may be assessed using the PiBCL1 murine model and BALB/c (haplotype H-2d) mice. Illidge, et al., Cancer Biother. & Radiopharm. 2000, 15, 571-80. Efficacy in non-Hodgkin's lymphoma (NHL) may be assessed using the 38C13 murine model with C3H/HeN (haplotype 2-Hk) mice or alternatively the 38C13 Her2/neu model. Timmerman, et al., Blood 2001, 97, 1370-77; Penichet, et al., Cancer Immunolog. Immunother. 2000, 49, 649-662. Efficacy in CLL may be assessed using the BCL1 model using BALB/c (haplotype H-2d) mice. Dutt, et al., Blood, 2011, 117, 3230-29.

EXAMPLES

Example 1. Form I of (S)-4-(8-Amino-3-(1-(but-2-ynoyl)pyrrolidin-2-yl)imidazo[1,5-a]pyrazin-1-yl)-N-(pyridin-2-yl)benzamide (Free Base) Crystalline Anhydrate Example 1.1. Preparation of Form I Crystalline Anhydrate A crystallization study was performed using amorphous (S)-4-(8-amino-3-(1-(but-2-ynoyl)pyrrolidin-2-yl)imidazo

[1,5-a]pyrazin-1-yl)-N-(pyridin-2-yl)benzamide as input. The amorphous character of this batch was confirmed by PXRD. For cooling crystallization experiments, 25 mg of amorphous Formula (1) was dissolved in 300 µL solvent, heated to 60° C. at a rate of 5° C./hour, held for 1 hour at that temperature, and then cooled down to 5° C. at the same rate. For slurry experiments, 25 mg of amorphous Formula (1) was suspended in 150 µL solvent at 20° C. for 3 days. All solids were isolated for PXRD analysis. The solvents were evaporated under vacuum (200 mbar) when a clear solution was obtained. The results are summarized in Table 1. The results indicate that, when solids are obtained, the amorphous form of Formula (1) is obtained from most solvents, and that Form I is difficult to crystallize but may be prepared from a very limited set of solvents, in particular certain mixtures with n-heptane (e.g., with acetone). Form I may also be crystallized or recrystallized from ethanol at larger scales, including at 60 g scale.

TABLE 1

Results of crystallization and slurry experiments for (S)-4-(8-amino-3-(1-(but-2-ynoyl)pyrrolidin-2-yl)imidazo[1,5-a]pyrazin-1-yl)-N-(pyridin-2-yl)benzamide.

| Sample | Solvent | Type | Appearance | Appearance after evaporation | PXRD | DSC | TGA |
|---|---|---|---|---|---|---|---|
| 1 | methanol | Cooling crystallization | Dissolved | Solid | Amorphous | — | — |
| 2 | ethanol | Cooling crystallization | Dissolved | Gel | — | — | — |
| 3 | 2-propanol | Cooling crystallization | Gel | Gel | — | — | — |
| 4 | N,N-dimethylacetamide | Cooling crystallization | Dissolved | Gel | — | — | — |
| 5 | acetone | Cooling crystallization | Dissolved | Solid | Amorphous | — | — |
| 6 | 2-butanone | Cooling crystallization | Dissolved | Gel | — | — | — |
| 7 | cyclohexanone | Cooling crystallization | Dissolved | Gel | — | — | — |
| 8 | dimethyl sulfoxide | Cooling crystallization | Dissolved | Gel | — | — | — |
| 9 | chlorobenzene | Cooling crystallization | Solid | — | Amorphous | — | — |
| 10 | dichloromethane | Cooling crystallization | Dissolved | Solid | Amorphous | — | — |
| 11 | methanol - water 3:1 | Cooling crystallization | Dissolved | Solid | Amorphous | — | — |
| 12 | methanol - water 1:1 | Cooling crystallization | Gel | Gel | — | — | — |
| 13 | methanol - water 1:3 | Cooling crystallization | Gel | Gel | — | — | — |
| 14 | ethanol - water 3:1 | Cooling crystallization | Dissolved | Solid | Amorphous | — | — |
| 15 | ethanol - water 1:1 | Cooling crystallization | Gel | Gel | — | — | — |
| 16 | ethanol - water 1:3 | Cooling crystallization | Gel | Gel | — | — | — |
| 17 | 2-propanol - water 3:1 | Cooling crystallization | Dissolved | Solid | Amorphous | — | — |
| 18 | 2-propanol - water 1:1 | Cooling crystallization | Dissolved | Solid | Amorphous | — | — |
| 19 | 2-propanol - water 1:3 | Cooling crystallization | Gel | Gel | — | — | — |
| 20 | N,N-dimethylacetamide - water 3:1 | Cooling crystallization | Dissolved | Gel | — | — | — |
| 21 | N,N-dimethylacetamide - water 1:1 | Cooling crystallization | Dissolved | Gel | — | — | — |
| 22 | N,N-dimethylacetamide - water 1:3 | Cooling crystallization | Gel | Gel | — | — | — |
| 23 | acetone - heptane 3:1 | Cooling crystallization | Solid | — | Form I | — | — |
| 24 | acetone - heptane 1:1 | Cooling crystallization | Solid | — | Form I | — | — |
| 25 | acetone - heptane 1:3 | Cooling crystallization | Gel | Gel | — | — | — |
| 26 | 2-butanone - heptane 3:1 | Cooling crystallization | Gel | Gel | — | — | — |
| 27 | 2-butanone - heptane 1:1 | Cooling crystallization | Gel | Gel | — | — | — |
| 28 | 2-butanone - heptane 1:3 | Cooling crystallization | Solid | — | Amorphous | — | — |
| 29 | cyclohexanone - heptane 3:1 | Cooling crystallization | Dissolved | Gel | — | — | — |
| 30 | cyclohexanone - heptane 1:1 | Cooling crystallization | Gel | Gel | — | — | — |
| 31 | cyclohexanone - heptane 1:3 | Cooling crystallization | Gel | Gel | — | — | — |
| 32 | dimethyl sulfoxide - water 3:1 | Cooling crystallization | Gel | Gel | — | — | — |
| 33 | dimethyl sulfoxide - water 1:1 | Cooling crystallization | Gel | Gel | — | — | — |
| 34 | dimethyl sulfoxide - water 1:3 | Cooling crystallization | Solid | — | Amorphous | — | — |
| 35 | chlorobenzene - heptane 3:1 | Cooling crystallization | Solid | — | Amorphous | — | — |
| 36 | chlorobenzene - heptane 1:1 | Cooling crystallization | Solid | — | Amorphous | — | — |
| 37 | chlorobenzene - heptane 1:3 | Cooling crystallization | Solid | — | Amorphous | — | — |
| 38 | dichloromethane - heptane 3:1 | Cooling crystallization | Dissolved | Solid | Amorphous | — | — |
| 39 | dichloromethane - heptane 1:1 | Cooling crystallization | Solid | — | Form I | 207° C. (−161 J/g) | −1.6% (40-140° C.) −1.2% (150-240° C.) |
| 40 | dichloromethane - heptane 1:3 | Cooling crystallization | Gel | Gel | — | — | — |
| 41 | methyl tert-butyl ether | Slurry (20° C. for 3 days) | Solid | — | Amorphous | — | — |
| 42 | tetrahydrofuran | Slurry (20° C. for 3 days) | Dissolved | Solid | Amorphous | — | — |
| 43 | diisopropyl ether | Slurry (20° C. for 3 days) | Solid | — | Amorphous | — | — |
| 44 | 2-methyltetrahydrofuran | Slurry (20° C. for 3 days) | Solid | — | Amorphous | — | — |
| 45 | cyclopentyl methyl ether | Slurry (20° C. for 3 days) | Solid | — | Amorphous | — | — |
| 46 | methanol - water 3:1 | Slurry (20° C. for 3 days) | Dissolved | Solid | Amorphous | — | — |
| 47 | methanol - water 1:1 | Slurry (20° C. for 3 days) | Gel | Gel | — | — | — |
| 48 | methanol - water 1:3 | Slurry (20° C. for 3 days) | Gel | Gel | — | — | — |
| 49 | ethanol - water 3:1 | Slurry (20° C. for 3 days) | Dissolved | Solid | Amorphous | — | — |
| 50 | ethanol - water 1:1 | Slurry (20° C. for 3 days) | Gel | Gel | — | — | — |
| 51 | ethanol - water 1:3 | Slurry (20° C. for 3 days) | Gel | Gel | — | — | — |
| 52 | 2-propanol - water 3:1 | Slurry (20° C. for 3 days) | Dissolved | Solid | Amorphous | — | — |
| 53 | 2-propanol - water 1:1 | Slurry (20° C. for 3 days) | Solid | — | Form II | ~150° C. ~150° C. ~220° C. | −9.7% (40-120° C.) |
| 54 | 2-propanol - water 1:3 | Slurry (20° C. for 3 days) | Gel | Gel | — | — | — |
| 55 | N,N-dimethylacetamide - water 3:1 | Slurry (20° C. for 3 days) | Dissolved | Gel | — | — | — |
| 56 | N,N-dimethylacetamide - water 1:1 | Slurry (20° C. for 3 days) | Dissolved | Gel | — | — | — |
| 57 | N,N-dimethylacetamide - water 1:3 | Slurry (20° C. for 3 days) | Gel | Gel | — | — | — |
| 58 | acetone - heptane 3:1 | Slurry (20° C. for 3 days) | Solid | — | Form I | — | — |

TABLE 1-continued

Results of crystallization and slurry experiments for (S)-4-(8-amino-3-(1-(but-2-ynoyl)pyrrolidin-2-yl)imidazo[1,5-a]pyrazin-1-yl)-N-(pyridin-2-yl)benzamide.

| Sample | Solvent | Type | Appearance | Appearance after evaporation | PXRD | DSC | TGA |
|---|---|---|---|---|---|---|---|
| 59 | acetone - heptane 1:1 | Slurry (20° C. for 3 days) | Gel | Gel | — | — | — |
| 60 | acetone - heptane 1:3 | Slurry (20° C. for 3 days) | Solid | — | Amorphous | — | — |
| 61 | 2-butanone - heptane 3:1 | Slurry (20° C. for 3 days) | Gel | Gel | — | — | — |
| 62 | 2-butanone - heptane 1:1 | Slurry (20° C. for 3 days) | Solid | — | Amorphous | — | — |
| 63 | 2-butanone - heptane 1:3 | Slurry (20° C. for 3 days) | Solid | — | Amorphous | — | — |
| 64 | cyclohexanone - heptane 3:1 | Slurry (20° C. for 3 days) | Dissolved | Gel | — | — | — |
| 65 | cyclohexanone - heptane 1:1 | Slurry (20° C. for 3 days) | Gel | Gel | — | — | — |
| 66 | cyclohexanone - heptane 1:3 | Slurry (20° C. for 3 days) | Solid | — | Amorphous | — | — |
| 67 | dimethyl sulfoxide - water 3:1 | Slurry (20° C. for 3 days) | Solid | — | Poorly cystalline | — | — |
| 68 | dimethyl sulfoxide - water 1:1 | Slurry (20° C. for 3 days) | Solid | — | Amorphous | — | — |
| 69 | dimethyl sulfoxide - water 1:3 | Slurry (20° C. for 3 days) | Solid | — | Form II | — | — |
| 70 | chlorobenzene - heptane 3:1 | Slurry (20° C. for 3 days) | Solid | — | Amorphous | — | — |
| 71 | chlorobenzene - heptane 1:1 | Slurry (20° C. for 3 days) | Solid | — | Amorphous | — | — |
| 72 | chlorobenzene - heptane 1:3 | Slurry (20° C. for 3 days) | Solid | — | Amorphous | — | — |
| 73 | dichloromethane - heptane 3:1 | Slurry (20° C. for 3 days) | Dissolved | Solid | Amorphous | — | — |
| 74 | dichloromethane - heptane 1:1 | Slurry (20° C. for 3 days) | Gel | Gel | — | — | — |
| 75 | dichloromethane - heptane 1:3 | Slurry (20° C. for 3 days) | Solid | — | Amorphous | — | — |

Anti-solvent addition experiments were performed by stepwise addition of anti-solvent until crystallization, to a clear solution of Formula (1) in the solvent shown in Table 2. The results again highlight the difficulty in preparing crystalline Formula (1).

TABLE 2

Results of anti-solvent addition experiments for (S)-4-(8-amino-3-(1-(but-2-ynoyl)pyrrolidin-2-yl)imidazo[1,5-a]pyrazin-1-yl)-N-(pyridin-2-yl)benzamide.

| Sample | Solvent | Type | Anti-solvent | Appearance[1] | PXRD |
|---|---|---|---|---|---|
| 76 | methanol | Anti-solvent | Water | FFP | Amorphous |
| 77 | ethanol | Anti-solvent | Water | FFP | Amorphous |
| 78 | 2-propanol | Anti-solvent | Water | No solids | — |
| 79 | N,N- | Anti-solvent | Water | FFP | Amorphous |
| 80 | acetone | Anti-solvent | Heptane | Sticky solids | Amorphous |
| 81 | 2-butanone | Anti-solvent | Heptane | Sticky solids | Amorphous |
| 82 | cyclohexanone | Anti-solvent | Heptane | FFP | Amorphous |
| 83 | dimethyl sulfoxide | Anti-solvent | Water | FFP + sticky solids | Amorphous |
| 84 | chlorobenzene | Anti-solvent | Heptane | FFP + sticky solids | Amorphous |
| 85 | dichloromethane | Anti-solvent | Heptane | FFP | Amorphous |

[1]FFP refers to free flowing powder.

Example 1.2. Physical Characterization of Form I Crystalline Anhydrate

Figure 9:
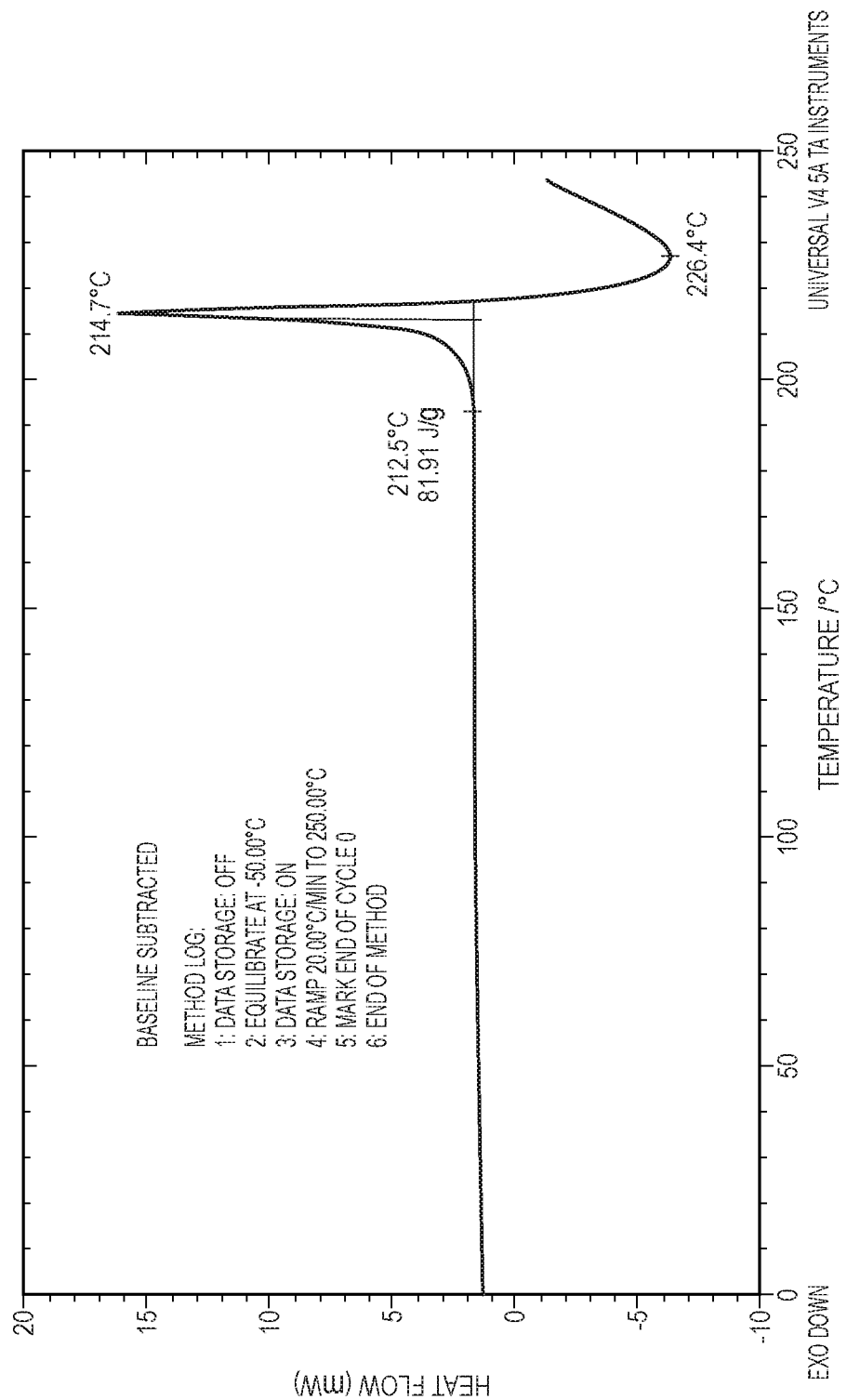
FIG. 9 illustrates a thermogram from differential scanning calorimetry (DSC) analysis of Form I of the free base of Formula (1) (PP502-P1).
Figure 10:
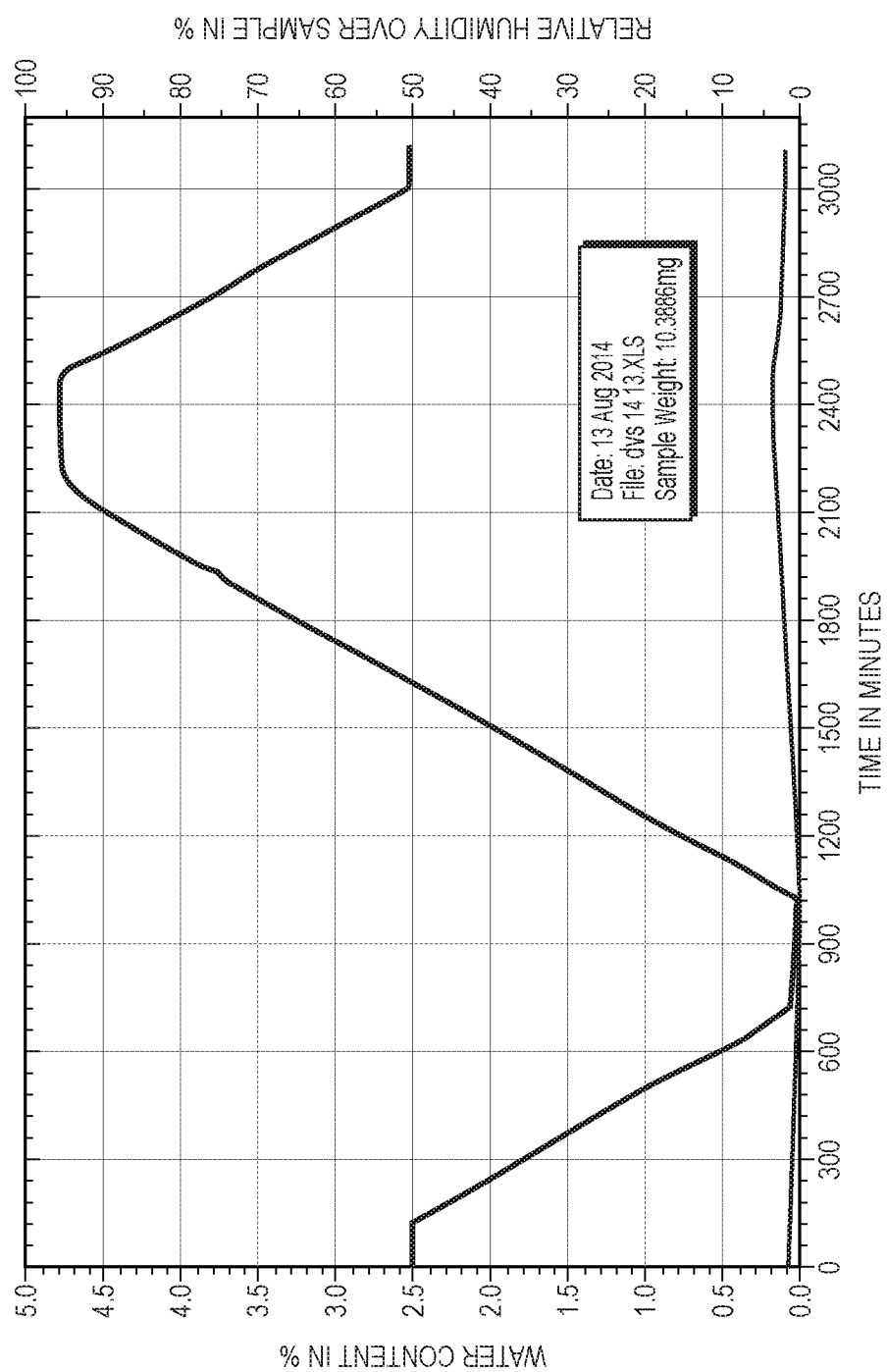
FIG. 10 illustrates a plot of the water content vs. time and relative humidity (RH) for Form I of the free base of Formula (1). The red line is the water content (left y-axis) and the blue line reflects the measurement program to which the sample was exposed (right y-axis).
Figure 11:
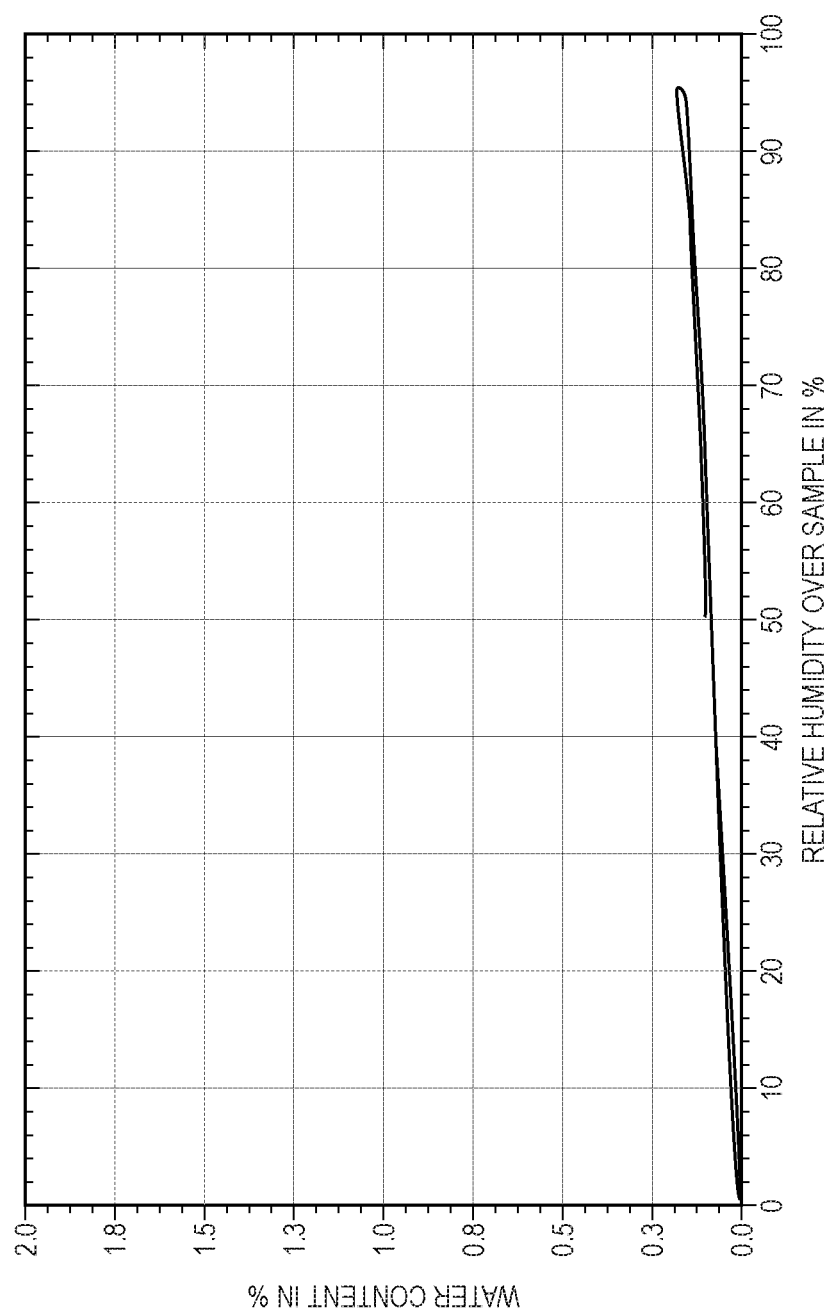
FIG. 11 illustrates a dynamic vapor sorption (DVS) isotherm plot with water content versus RH for Form I of the free base of Formula (1).

Characterization of Form I of the free base of Formula (1) produced by crystallization from acetone in the presence of methanol (referred to as sample PP502-P1 herein) was carried out using various techniques including: PXRD (FIG. 1 and FIG. 2), optical microscopy (FIG. 3), Raman (FIG. 4) and IR spectroscopy (FIG. 5 and FIG. 6), solution-state NMR spectroscopy after dissolution of Form I (FIG. 7), TG-FTIR (FIG. 8), differential scanning calorimetry (DSC) (FIG. 9), semi-quantitative solubility testing, and dynamic vapor sorption (DVS; also known as gravimetric vapor sorption or GVS) (FIGS. 10 and 11).

The transmission PXRD pattern of Form I was acquired using a Stoe Stadi P high-precision two circle goniometer instrument equipped with a Mythen 1K Detector and a Cu-K$_{\alpha 1}$ radiation source operating at standard measurement conditions of: 40 kV tube voltage and 40 mA tube current; curved Ge monochromator; 0.02° 2θ step size; 48 seconds step time, 1.5-50.5° 2θ scanning range; and detector mode including a step scan at 1° 2θ detector step. Samples were prepared by placing 10 to 20 mg of material between two acetate foils in the Stoe transmission sample holder which was rotated during measurement. The measurements using the Stoe Stadi diffractometer were taken in transmission (Debye-Scherrer) mode. This instrument can also be operated in reflection (Bragg-Brentano) mode.

Reflection PXRD measurements were also performed using a second instrument, a Bruker D8 Advance powder X-ray diffractometer equipped with a LynxEye detector and operating in Bragg-Brentano reflection geometry. 2θ values are generally accurate to within an error of ±0.2°. The samples were generally prepared without any special treatment other than the application of slight pressure to get a flat surface. Samples were measured uncovered unless otherwise noted. Operating conditions included a tube voltage of 40 kV and current of 40 mA. A variable divergence slit was used with a 3° window. The step size was 0.02° 2θ with a step time of 37 seconds. The sample was rotated at 0.5 rps during the measurement. When calibrated, the reflection mode PXRD pattern of Form I may be compared to the transmission mode PXRD pattern of Form I, although the person of skill in the art will appreciate that the diffraction patterns may vary, particularly with respect to peak intensities, as described herein.

FIG. 1 shows the PXRD pattern for Form I of Formula (1) measured using reflection geometry. The following peaks were identified in the PXRD pattern of FIG. 1: 6.4, 8.6, 10.5, 10.9, 11.3, 11.6, 12.7, 13.4, 14.3, 14.9, 15.1, 15.7, 16.1, 17.3, 18.2, 19.2, 19.4, 19.8, 20.7, 21.1, 21.4, 21.6, 21.9, 22.6, 23.3, 23.6, 24.9, 25.2, 25.4, 25.7, 26.1, 26.4, 26.8, 26.9, 27.7, 28.6, 29.1, 29.4, 30.1, 30.5, 31.7, 31.9, 32.2, 32.6, 33.1, 33.4, 34.5, 35.9, 36.1, 36.8, 37.4, 38.1, 38.9, and 39.5° 2θ±0.2° 2θ.

Figure 2:
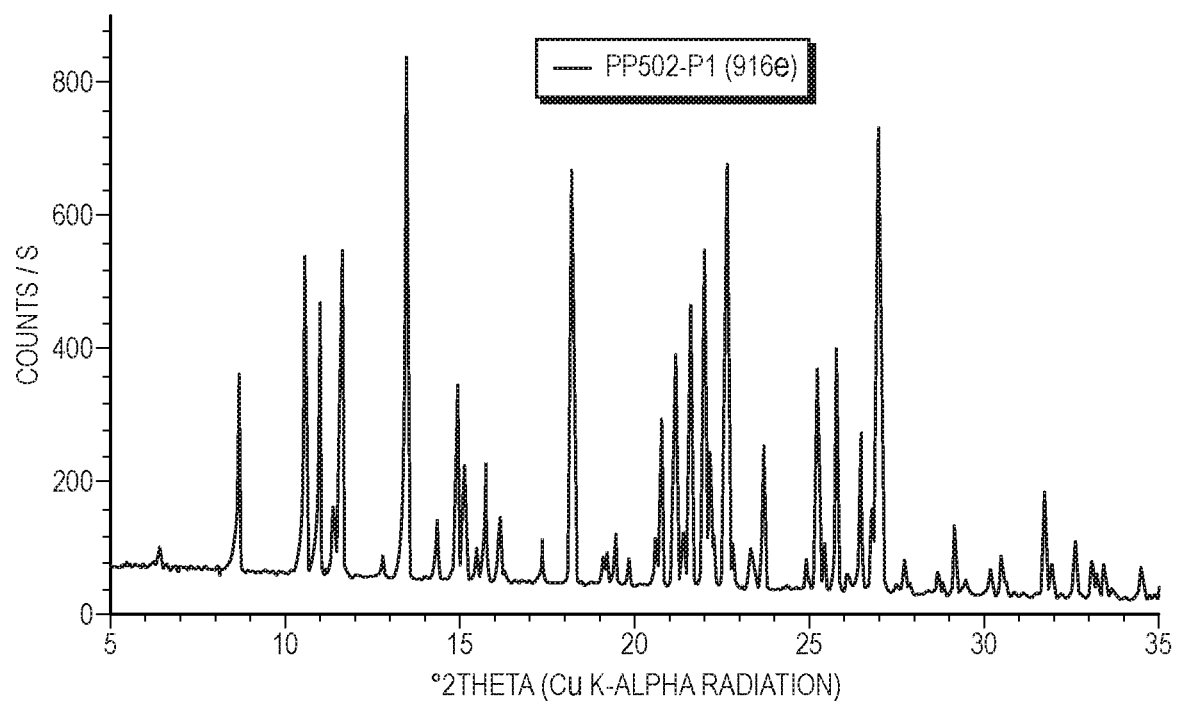
FIG. 2 illustrates a PXRD pattern of Form I (sample PP502-P1) of the free base of Formula (1) measured in transmission mode.

FIG. 2 shows the PXRD pattern for Form I measured using transmission geometry. The following peaks were identified in the PXRD pattern of FIG. 2: 6.4, 8.7, 10.5, 11.0, 11.4, 11.6, 12.8, 13.5, 14.3, 14.9, 15.1, 15.5, 15.7, 16.1, 17.3, 18.2, 19.1, 19.2, 19.5, 19.8, 20.6, 20.8, 21.2, 21.4, 21.6, 22.0, 22.2, 22.3, 22.6, 22.8, 23.3, 23.7, 24.9, 25.2, 25.4, 25.8, 26.1, 26.5, 26.8, 27.0, 27.0, 27.7, 28.7, 29.2, 29.9, 30.5, 31.7, 32.0, 32.6, 33.1, 33.2, 33.5, 34.5, and 35.1°2θ±0.2° 2θ. Form I shows distinctive peaks (relative to the other forms) at 6.4, 8.6, 10.5, 11.6, and 15.7° 2θ±0.2° 2θ, and shows further distinctive peaks (relative to the other forms) at 10.9, 12.7, 13.4, 14.3, 14.9, and 18.2° 2θ±0.2° 2θ.

Figure 3:
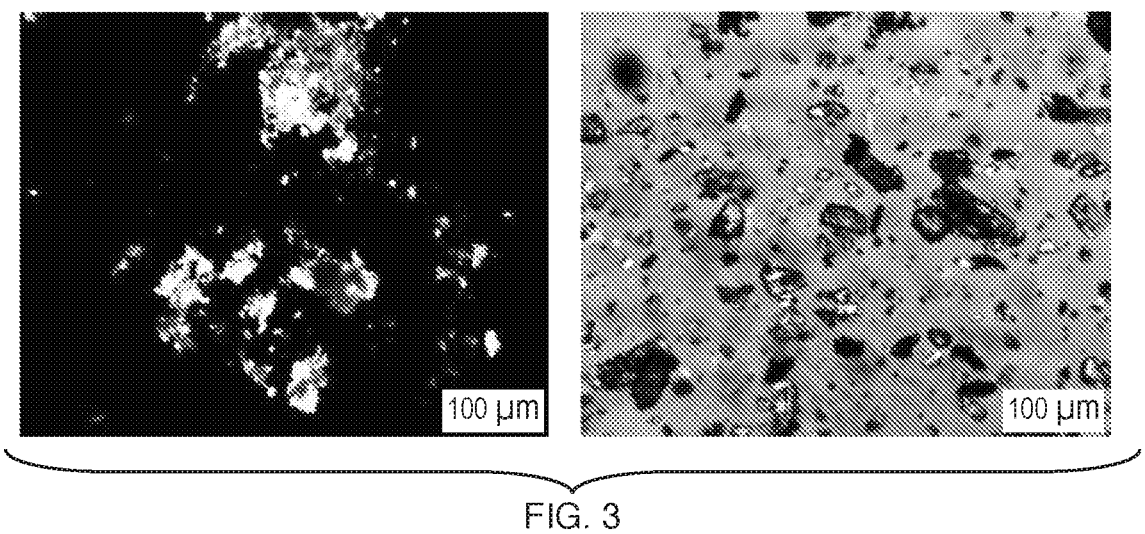
FIG. 3 illustrates optical polarized microscope images of Form I (sample PP502-P1) of the free base of Formula (1). The left image shows undispersed crystals. The right image shows crystals dispersed with paraffin oil.

Both the PXRD patterns of FIG. 1 and FIG. 2, along with the birefringence observed in the polarized optical microscopy images of FIG. 3, show that the anhydrate of Form I of Formula (1) is crystalline.

Figure 4:
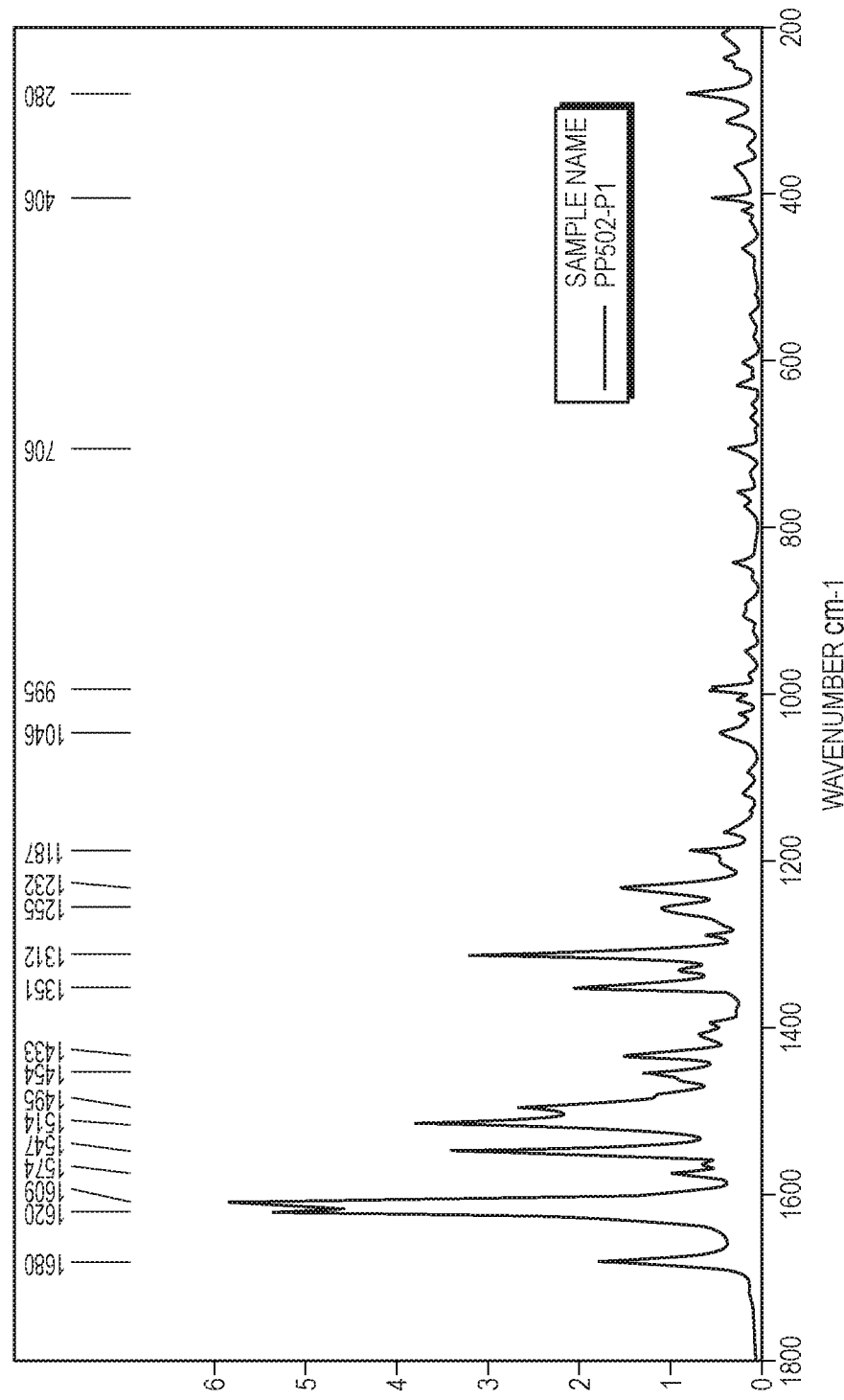
FIG. 4 illustrates a Raman spectrum of Form I of the free base of Formula (1) in the spectral range from 200 to 1800 $cm^{-1}$.

The Fourier-transform (FT) Raman spectrum of Form I was acquired using a Bruker RFS 100 FT-Raman spectrophotometer equipped with a liquid nitrogen-cooled germanium detector and a near IR Nd:YAG laser operating at 1064 nm with a power setting of 100 mW. Spectra were the result of 64 scans collected with a resolution of 2 cm$^{-1}$ in the range between 3500 and 50 cm$^{-1}$. The FT-Raman spectrum of Form I in the relevant fingerprint region is shown in FIG. 4, and has peaks at 1680, 1620, 1609, 1574, 1547, 1514, 1495, 1454, 1433, 1351, 1312, 1255, 1232, 1187, 1046, 995, 706, 406, and 280 (Raman shift, cm$^{-1}$±2 cm$^{-1}$).

Figure 5:
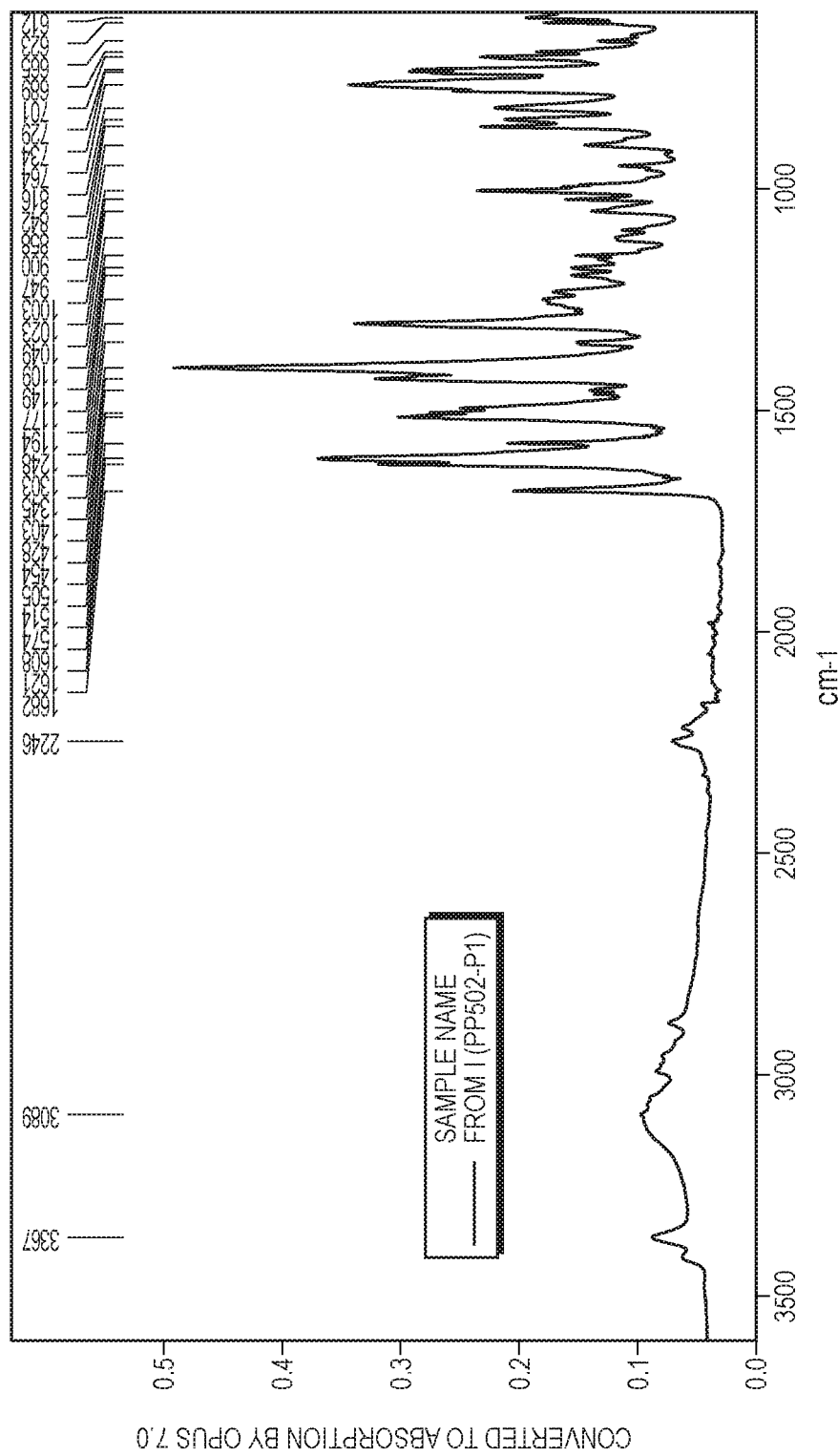
FIG. 5 illustrates an infrared (IR) spectrum of Form I of the free base of Formula (1).
Figure 6:
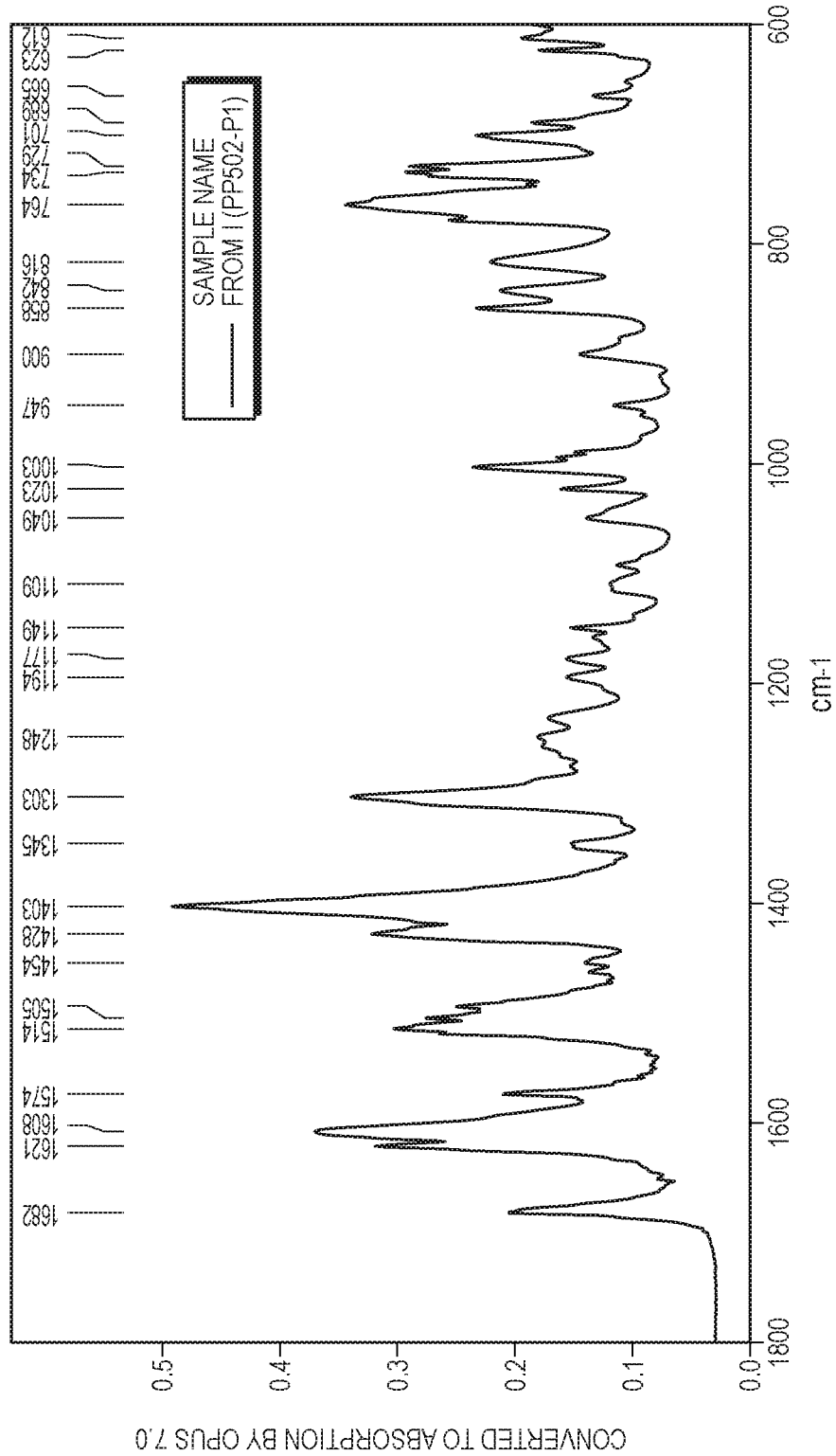
FIG. 6 illustrates an IR spectrum of Form I of the free base of Formula (1).

The IR spectrum of Form I (sample PP502-P1) was obtained using IR spectroscopy. The spectra were obtained by recording 32 scans using attenuated total reflectance (ATR) sampling and a Perkin Elmer BXII IR spectrometer at a resolution of 2 wavenumbers (cm$^{-1}$). For the spectrum shown here, the original spectra in transmission mode were converted to absorption mode using the OPUS 7.0 software from Bruker and peak tables were generated. The IR spectrum of Form I is illustrated in FIG. 5, and an expansion of the region from 1800 to 600 cm$^{-1}$ is shown in FIG. 6. The characteristic peaks for Form I are given in Table 3.

TABLE 3

Characteristic peaks for Form I as determined by ATR IR spectroscopy (+/−4 cm$^{-1}$).

| Wavenumber (cm$^{-1}$) | Intensity (arbitrary units) |
|---|---|
| 3367 | 0.088 |
| 3089 | 0.098 |
| 2246 | 0.071 |
| 1682 | 0.208 |
| 1621 | 0.319 |
| 1608 | 0.371 |
| 1574 | 0.212 |
| 1514 | 0.304 |
| 1504 | 0.278 |
| 1454 | 0.141 |
| 1428 | 0.322 |
| 1403 | 0.493 |
| 1345 | 0.152 |
| 1303 | 0.340 |
| 1248 | 0.181 |
| 1194 | 0.156 |
| 1177 | 0.156 |
| 1149 | 0.153 |
| 1109 | 0.119 |
| 1049 | 0.139 |
| 1023 | 0.162 |
| 1003 | 0.236 |
| 947 | 0.116 |
| 900 | 0.145 |
| 858 | 0.233 |
| 842 | 0.213 |
| 816 | 0.221 |
| 764 | 0.345 |
| 734 | 0.295 |
| 729 | 0.290 |
| 701 | 0.234 |
| 689 | 0.186 |
| 665 | 0.134 |
| 623 | 0.181 |
| 612 | 0.195 |

Figure 7:
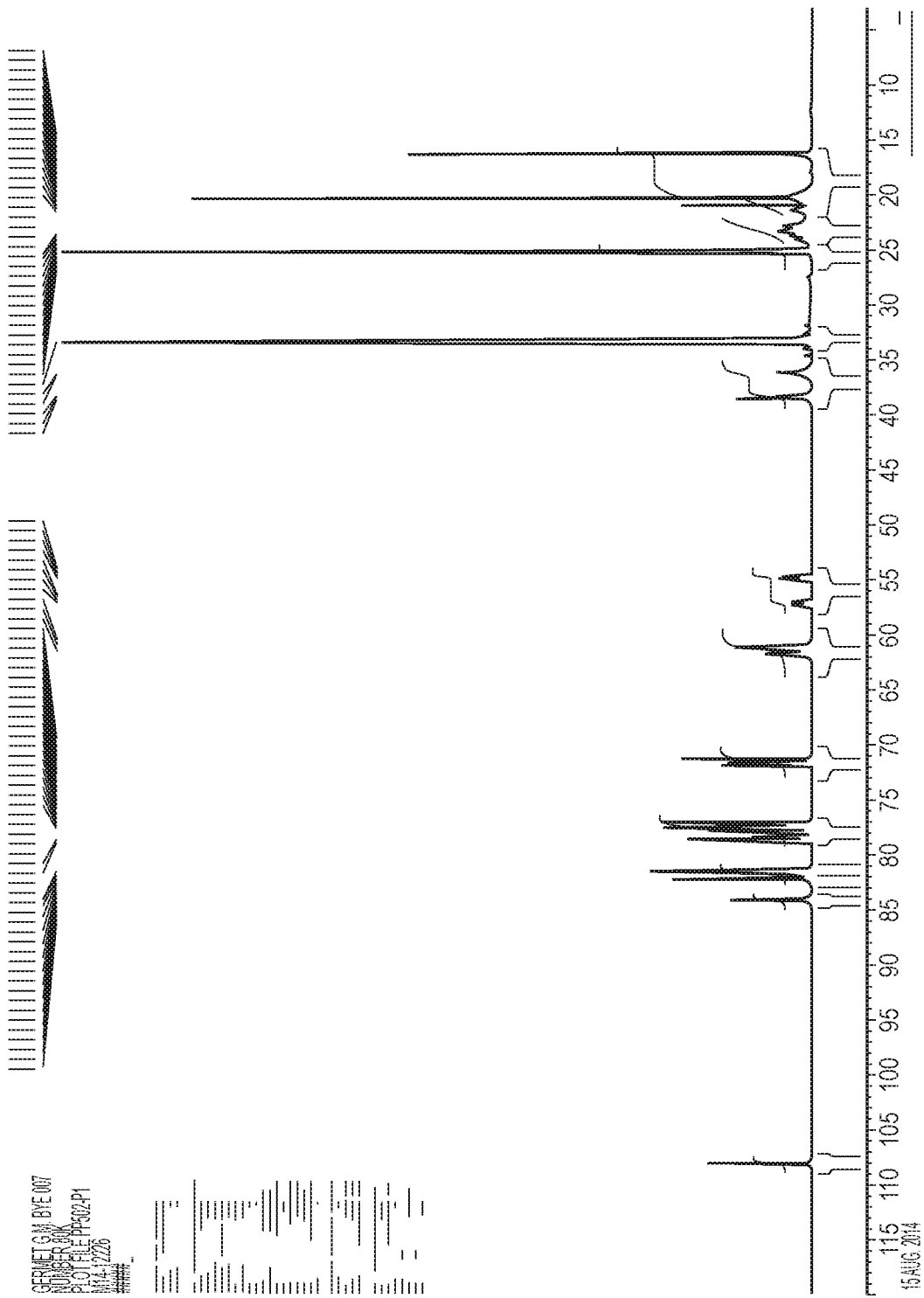
FIG. 7 illustrates a $^1$H nuclear magnetic resonance (NMR) spectrum of Form I of the free base of Formula after dissolution in $d_6$-DMSO.

The $^1$H NMR spectrum of Form I recorded in deuterated dimethyl sulfoxide (d$_6$-DMSO) is illustrated in FIG. 7 and confirms the molecular structure of (S)-4-(8-amino-3-(1-(but-2-ynoyl)pyrrolidin-2-yl)imidazo[1,5-a]pyrazin-1-yl)-N-(pyridin-2-yl)benzamide present in this crystalline anhydrate.

Figure 8:
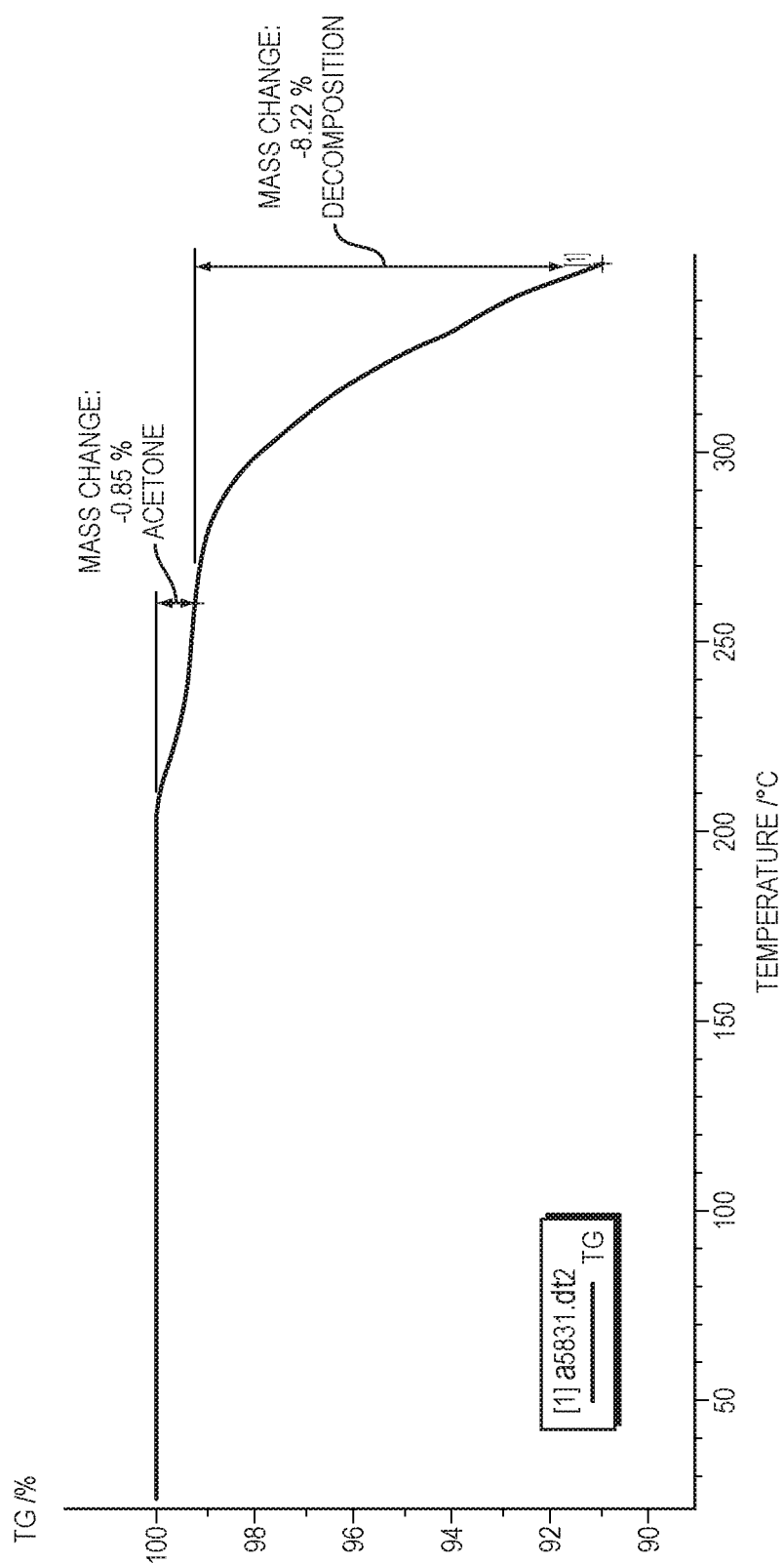
FIG. 8 illustrates a thermogram from thermogravimetric analysis (TGA) with Fourier transform IR spectroscopy (TG-FTIR) of Form I of the free base of Formula (1) (PP502-P1).

TGA and TG-FTIR analysis was carried out using a Netzsch Thermo-Microbalance TG 209 coupled to a Bruker FTIR spectrometer (instrument model Vector 22). The sample pans having a pinhole were tared before the sample was introduced and then and heated to 350° C. at a ramp rate of 10° C./minute under a constant flow of a nitrogen. TG-FTIR analysis of the sample of Form I revealed a mass loss of about 0.8% upon heating to 250° C. TG-FTIR spectroscopy showed that the observed mass loss up to 250° C. is essentially attributable to acetone solvent, which appears to be tightly bound to the Form I crystal since the mass loss occurs above 200° C. Weight loss above 250° C. is mostly attributable to decomposition. The TGA thermogram obtained from the TG-FTIR experiment is depicted in FIG. 8.

Differential scanning calorimetry was carried out with a Perkin Elmer DSC-7 or with a TA Instruments Q2000 instrument. Samples were prepared in a closed gold sample pan at temperature ramp rates of 10° C./minute or 20° C./minute up to approximately 250° C. Melting begins at about 200° C. and a peak is observed near 215° C. with a heat flow of approximately 16 mW for the melting endotherm; however, it appears that melting is concurrent with thermal decomposition and the enthalpy of fusion cannot be evaluated. Nevertheless, the temperature range of the mass loss observed in the TGA analysis of FIG. 8 suggests that Form I must be molten in order to release the residual solvent. The DSC thermogram is shown in FIG. 9, where endothermic events are plotted in the upward direction. After the melting event, exothermic degradation occurs at 226.4° C.

Form I was also tested with respect to solubilities in various water-solvent mixtures and non-aqueous solvents. Solubility studies were conducted by a stepwise dilution of a suspension of about 10 mg of Form I in 0.1 mL of analytical grade solvent. Results of the approximate solubilities are shown in Table 4. Solubility values are estimated approximations and are subject to variable experimental error.

TABLE 4

Approximate solubility measurements for Form I.

| Pure Solvent | Solubility [S, mg/mL] | Solvent mixture | Solubility [S, mg/mL] |
| --- | --- | --- | --- |
| acetic acid | 102 < S < 204 | acetic acid:water 1:1 | 104 < S < 208 |
| acetone | S~2 | acetic acid:ethyl acetate 1:1 | 92 < S < 184 |
| acetonitrile | S < 1 | acetic acid:ethyl acetate 1:9 | 60 < S < 90 |
| dichloromethane, DCM | 36 < S < 43 | acetic acid:MEK 1:9 | 63 < S < 95 |
| N,N-dimethylformamide, DMF | 49 < S < 65 | acetic acid:isopropanol 1:9 | S~4 |
| dimethyl sulfoxide, DMSO | 39 < S < 49 | acetone:water 4:1 | 26 < S < 31 |
| ethyl acetate | S < 1 | ethanol:water 1:1 | S~6 |
| ethanol | S~3 | ethanol:water 9:1 at 60° C. | S > 60 |
| formic acid | 97 < S < 194 | ethanol:water 95:5 | S~8 |
| 2-butanone, MEK | S < 1 | MEK saturated with water | 26 < S < 30 |
| methanol | S~14 | methanol :MEK 1:1 at reflux | S > 90 |
| N-methyl-2-pyrrolidone, NMP | 39 < S < 49 | methanol:water 9:1 | S~15 |
| 2-propanol | S < 1 | THF:water 9:1 | S > 50 |
| tetrahydrofuran, THF | S~5 | | |
| trifluoroethane | 97 < S < 194 | | |

The aqueous solubility of Form I was determined after equilibrating at 25° C. for three days. High-performance liquid chromatography (HPLC) was used to determine the concentration in filtered solution, which resulted in S~68 µg/mL. PXRD of the solid residue confirmed that Form I was retained.

A gravimetric vapor sorption study was run using a standard procedure. Samples were run using a dynamic vapor sorption (DVS) analyzer. Sample sizes were approximately 10 mg. A moisture adsorption-desorption isotherm was performed as outlined below. Samples were exposed to a starting 50% RH, decreasing humidity to 0% RH, increasing humidity to 95% RH, and finally decreasing humidity back to the starting 50% RH. The DVS results, including sorption and desorption isotherm curves, shown in FIG. 10 and FIG. 11, show the total weight gain observed between 0% RH and 80% RH to be about 0.17%, which indicates that Form I is non-hygroscopic according to the European Pharmacopoeia (EP) classification (non-hygroscopic: <0.2%; slightly hygroscopic: ≥0.2% and <2%; hygroscopic: ≥2% and <15%; very hygroscopic: ≥15%; deliquescent: sufficient water is absorbed to form a liquid; all values measured as weight increase at 80% RH and 25° C.). The desorption curve indicates that Form I lost moisture at a similar rate to the moisture gained during sorption, with limited hysteresis. Almost all of the adsorbed water was removed by the end of the DVS experiment. No form change was observed by PXRD after the DVS experiment.

Example 2. Form II of (S)-4-(8-Amino-3-(1-(but-2-ynoyl)pyrrolidin-2-yl)imidazo[1,5-a]pyrazin-1-yl)-N-(pyridin-2-yl)benzamide (Free Base) Trihydrate Example 2.1. Preparation of Form II Crystalline Trihydrate The crystallization study described above and reported in Table 1 also yielded Form II in a very limited set of solvents.

Form II (sample PP502-P21) of the free base of Formula (1) was also produced by dissolving Form I in an acetone-water (8:2) mixture at reflux temperature followed by cooling of the solution and removing 50% of the solvent volume under a slight nitrogen purge. The obtained samples were dried at room temperature in air and under ambient conditions (at about 45% RH). A mass loss of about 9.7% was observed after drying, corresponding to approximately 2.7 water molecules per molecule of Formula (1) (i.e., a trihydrate).

Example 2.2. Physical Characterization of Form II Crystalline Trihydrate

Characterization of Form II of the free base of Formula (1) was carried out using various techniques including PXRD (FIG. 12), optical microscopy (FIG. 13), Raman spectroscopy (FIG. 14), IR spectroscopy (FIG. 15 and FIG. 16), TG-FTIR (FIG. 17), DSC (FIG. 18), DVS (FIG. 19 and FIG. 20), and semi-quantitative solubility testing. Characterization methods used for Form II were performed as described previously for the characterization of Form I.

Figure 12:
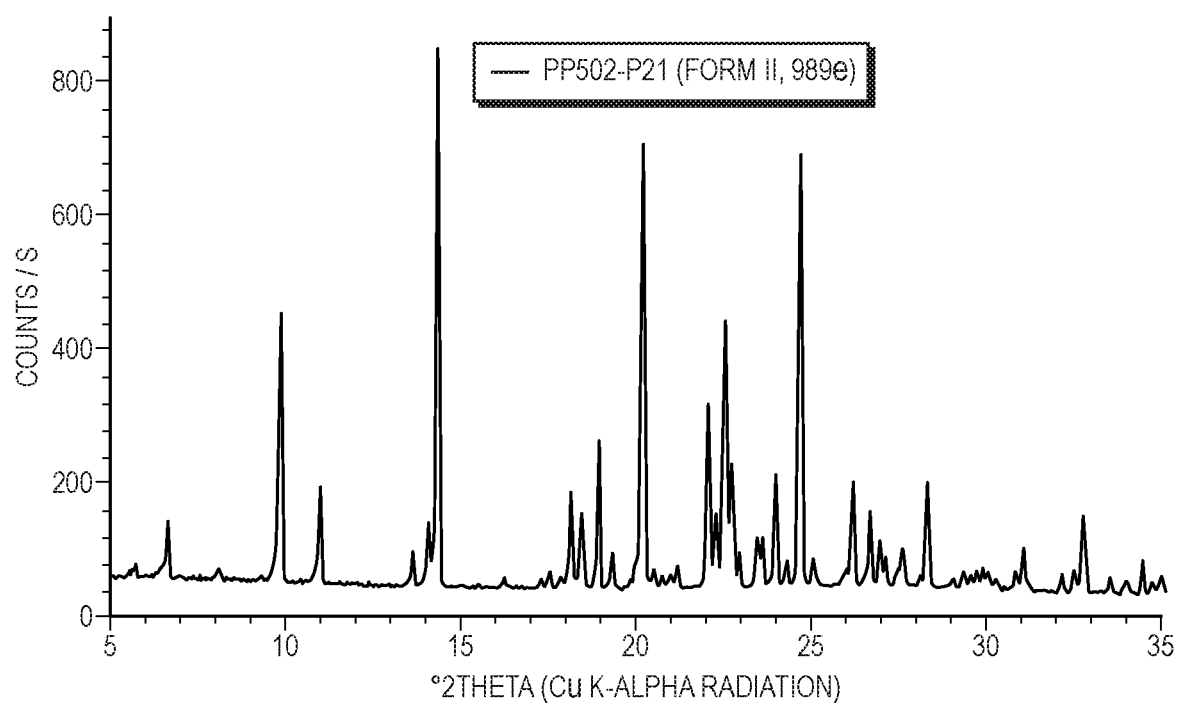
FIG. 12 illustrates a PXRD pattern of Form II of the free base of Formula (1).
Figure 13:
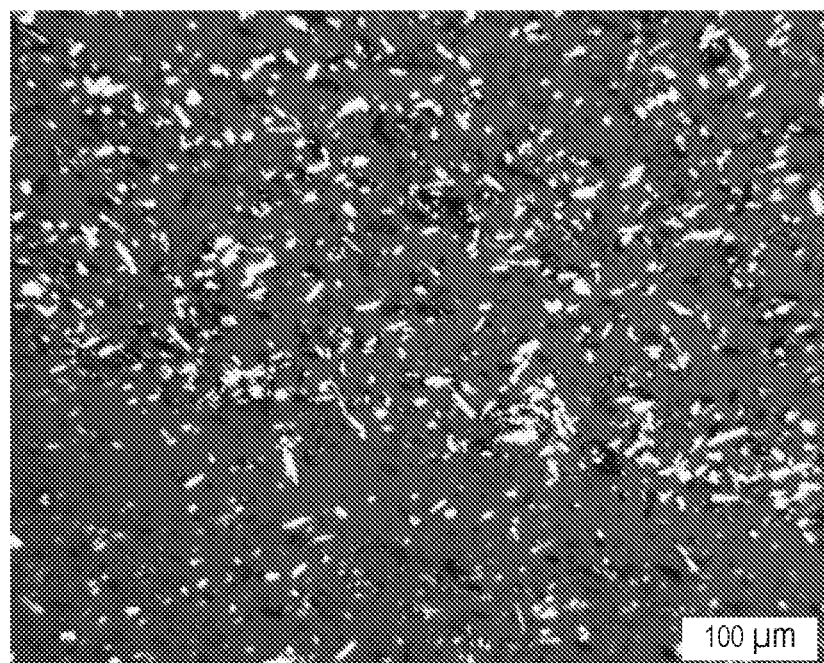
FIG. 13 illustrates a polarized microscope image of Form II of the free base of Formula (1) dispersed in paraffin oil.

FIG. 12 shows the PXRD pattern for Form II of Formula (1) measured in transmission mode. The following characteristic peaks were identified in the PXRD pattern of FIG. 12: 6.6, 9.9, 11.0, 13.6, 14.0, 14.3, 18.1, 18.4, 18.9, 19.3, 20.2, 21.1, 22.0, 22.2, 22.5, 22.7, 22.9, 23.4, 23.5, 23.9, 24.2, 24.6, 25.0, 26.1, 26.6, 26.9, 27.5, 28.2, 31.0, 32.1, 32.4, 32.7, 33.4, 33.9, and 34.4° 2θ±0.2° 2θ. An optical microscopic image of Form II in FIG. 13 shows that the Form II sample (PP502-P21) exhibits rod-shaped particles with lengths up to about 50 µm.

Figure 14:
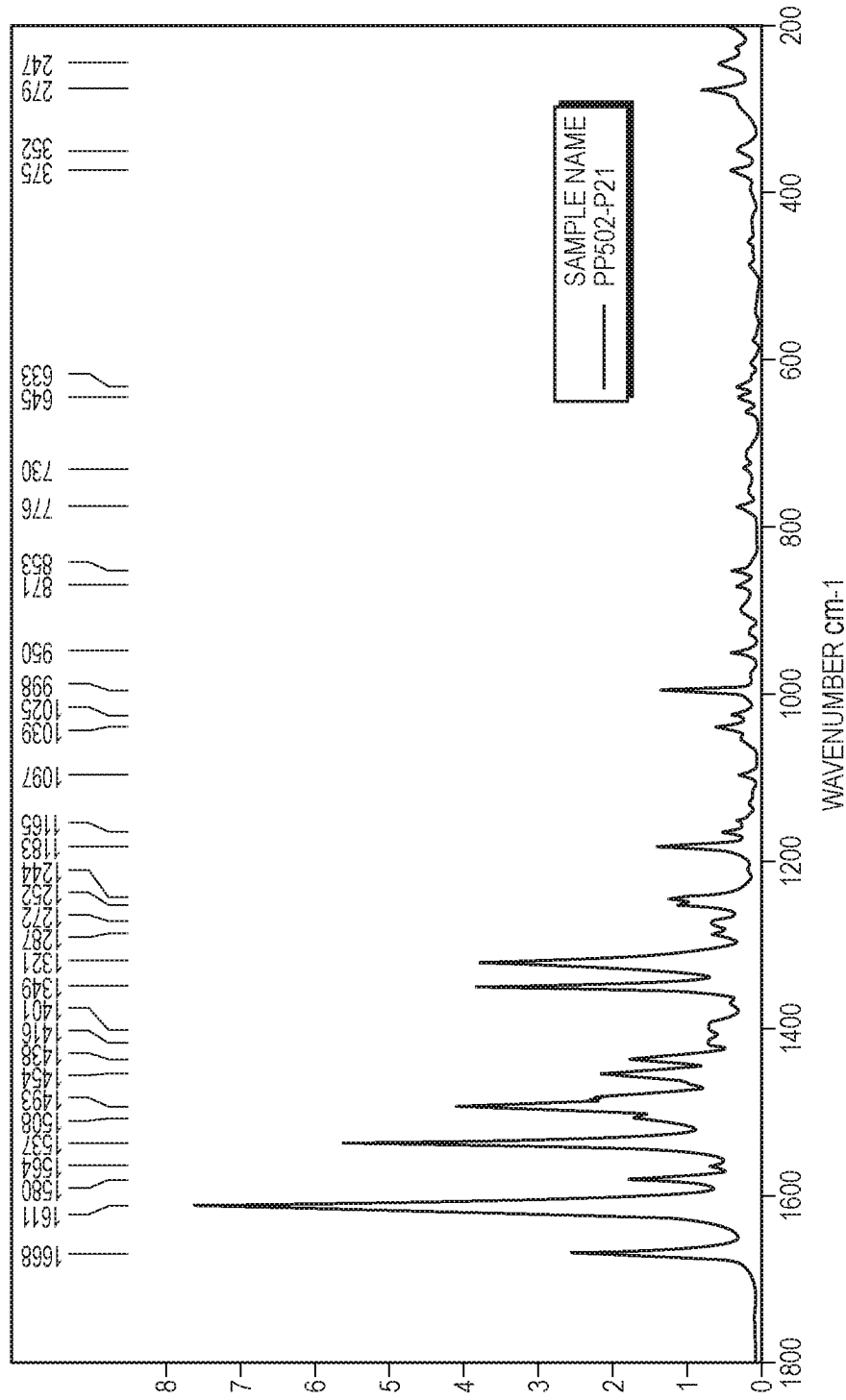
FIG. 14 illustrates a Raman spectrum of Form II of the free base of Formula (1) in the spectral range from 200 to 1800 $cm^{-1}$.

The FT-Raman spectrum of Form II in the relevant fingerprint region (200 cm$^{-1}$ to 1800 cm$^{-1}$) is shown in FIG. 14 and exhibits peaks (Raman shift, cm$^{-1}$±2 cm$^{-1}$) at 1668, 1611, 1580, 1564, 1537, 1506, 1493, 1454, 1436, 1416, 1401, 1349, 1321, 1287, 1272, 1252, 1244, 1183, 1165, 1097, 1039, 1025, 996, 950, 871, 853, 776, 730, 645, 633, 375, 352, 279, and 247.

Figure 15:
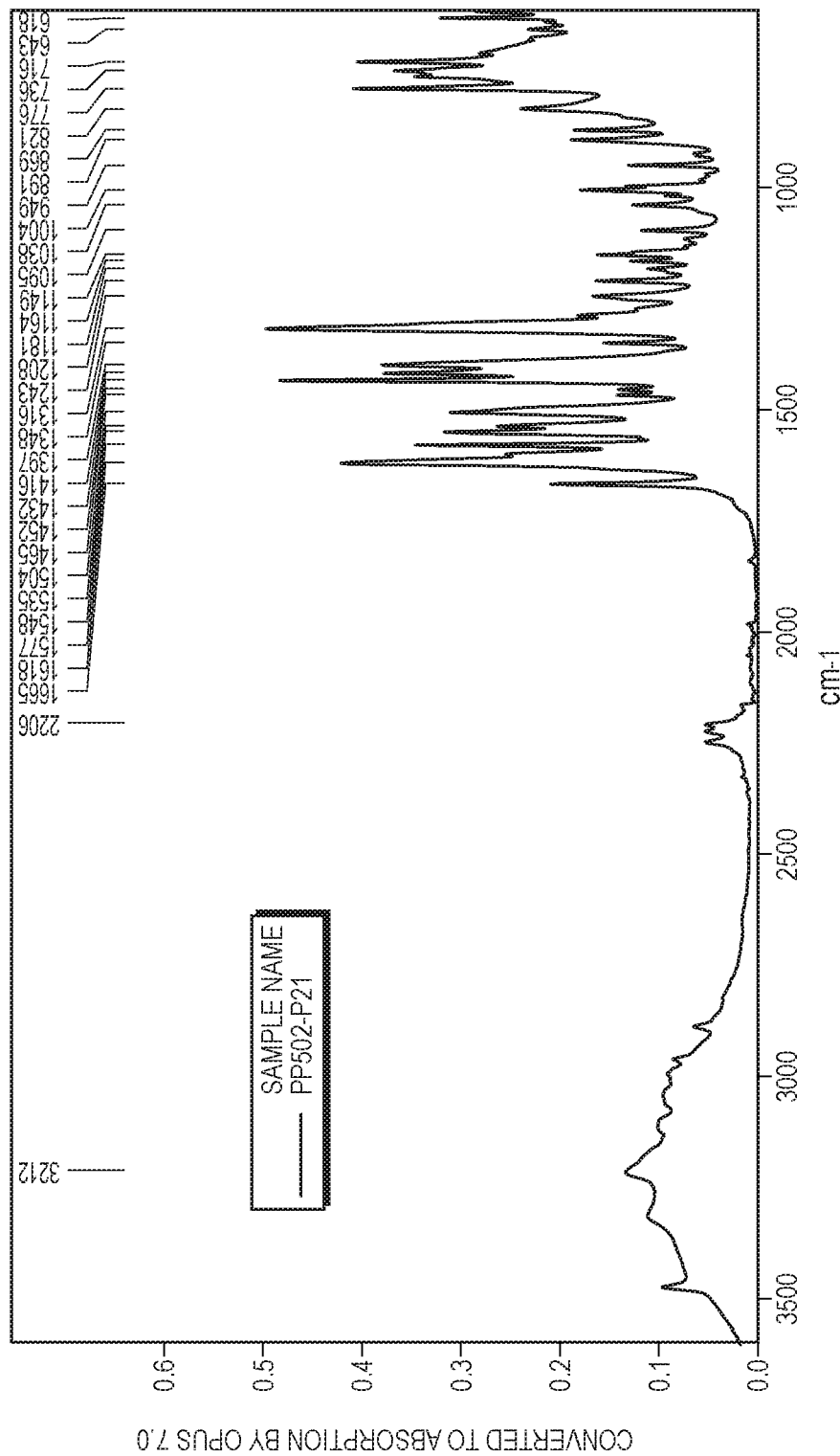
FIG. 15 illustrates an IR spectrum of Form II of the free base of Formula (1).
Figure 16:
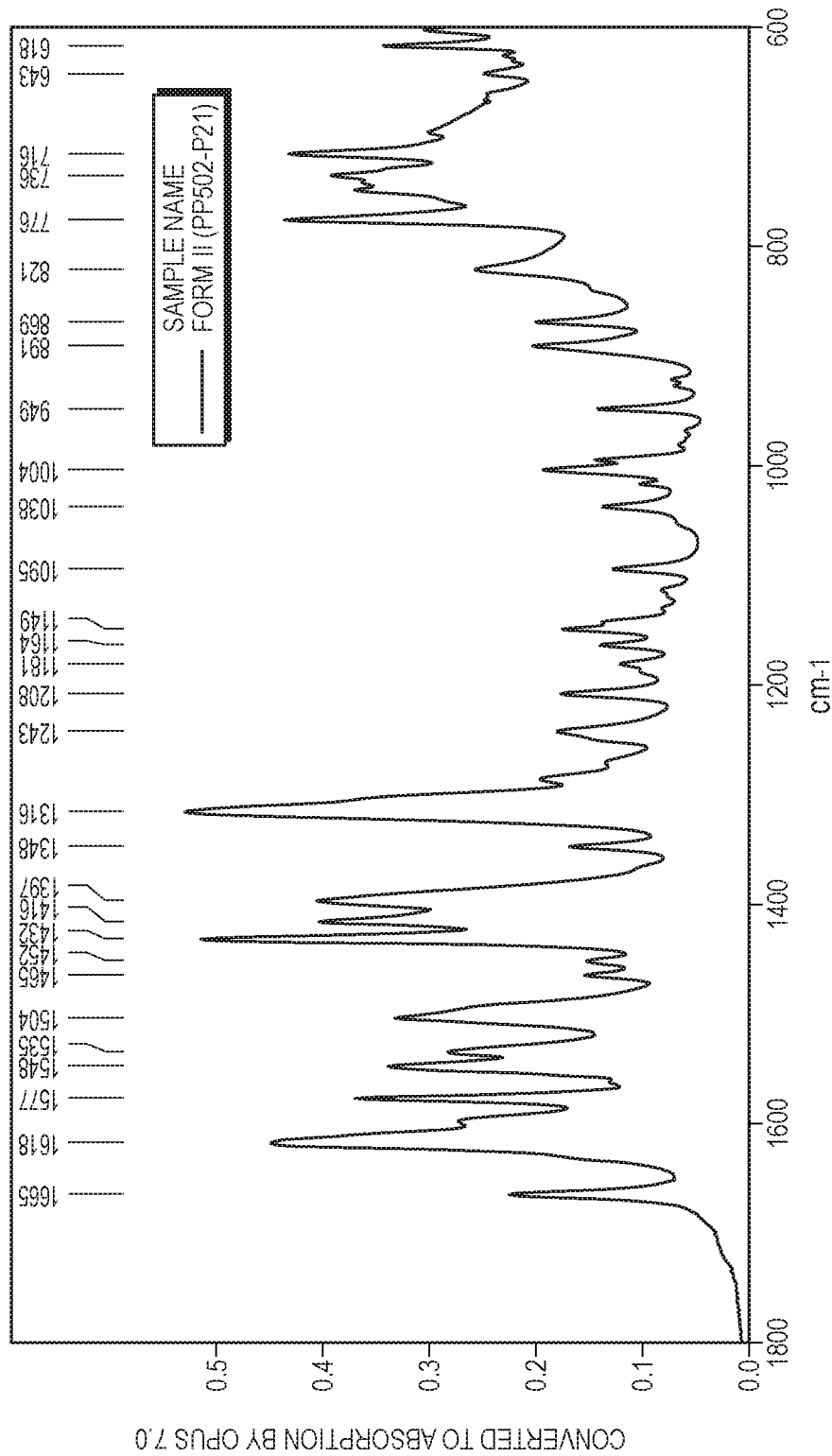
FIG. 16 illustrates an IR spectrum of Form II of the free base of Formula (1).
Figure 17:
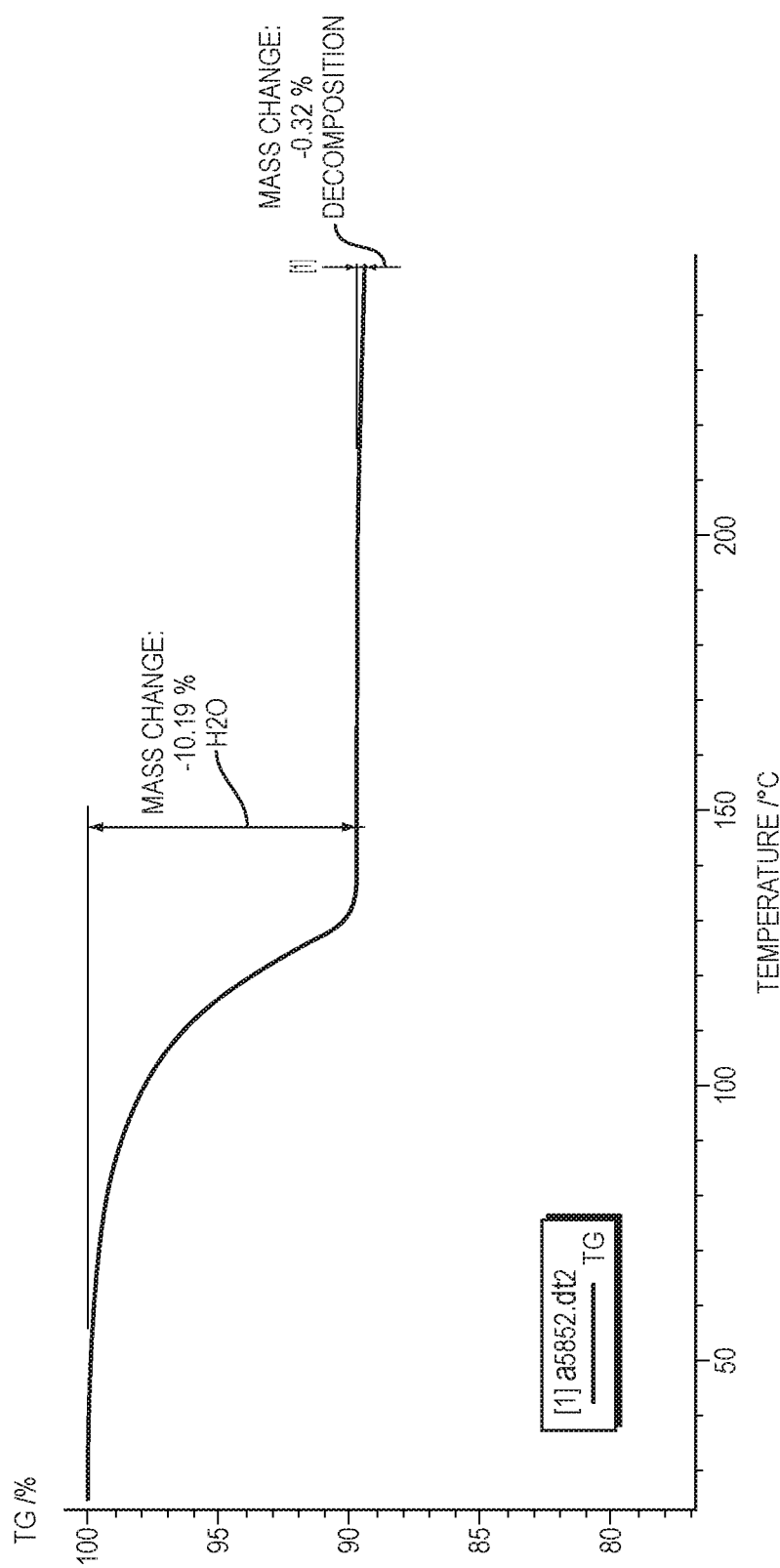
FIG. 17 illustrates a TGA thermogram from TG-FTIR analysis of Form II of the free base of Formula (1).

FIG. 15 shows the IR spectrum of Form II (sample PP502-P21), and an expansion of the region from 1800 to 600 cm$^{-1}$ is shown in FIG. 16. The characteristic peaks observed for Form II are provided in Table 5.

TABLE 5

Characteristic peaks for Form II as determined by ATR IR spectroscopy (+/−4 cm$^{-1}$).

| Wavenumber (cm$^{-1}$) | Intensity (arbitrary units) |
| --- | --- |
| 3212 | 0.146 |
| 2206 | 0.061 |

TABLE 5-continued

Characteristic peaks for Form II as determined by ATR IR spectroscopy (+/−4 cm$^{-1}$).

| Wavenumber (cm$^{-1}$) | Intensity (arbitrary units) |
|---|---|
| 1665 | 0.225 |
| 1618 | 0.449 |
| 1577 | 0.370 |
| 1548 | 0.339 |
| 1535 | 0.283 |
| 1504 | 0.332 |
| 1465 | 0.155 |
| 1452 | 0.153 |
| 1432 | 0.515 |
| 1416 | 0.404 |
| 1397 | 0.406 |
| 1348 | 0.169 |
| 1316 | 0.529 |
| 1243 | 0.181 |
| 1208 | 0.178 |
| 1181 | 0.122 |
| 1164 | 0.141 |
| 1149 | 0.177 |
| 1095 | 0.129 |
| 1038 | 0.139 |
| 1004 | 0.194 |
| 948 | 0.144 |
| 891 | 0.204 |
| 869 | 0.201 |
| 821 | 0.257 |
| 776 | 0.436 |
| 736 | 0.393 |
| 716 | 0.432 |
| 643 | 0.250 |
| 617 | 0.346 |

TG-FTIR preparation of Form II samples consisted of exposing two samples (PP502-P14 and PP502-P21) to 60% RH for about three days at which point both contained identical amounts of water. TG-FTIR analysis of the samples of Form II, shown in FIG. 17, revealed a mass loss of about 10.2% upon heating to approximately 130° C. This decrease is essentially attributable to release of water and agrees well with the theoretical water content for a trihydrate of 10.4%. Mass loss of about 0.3% upon heating thereafter to approximately 250° C. was due primarily to decomposition.

Figure 18:
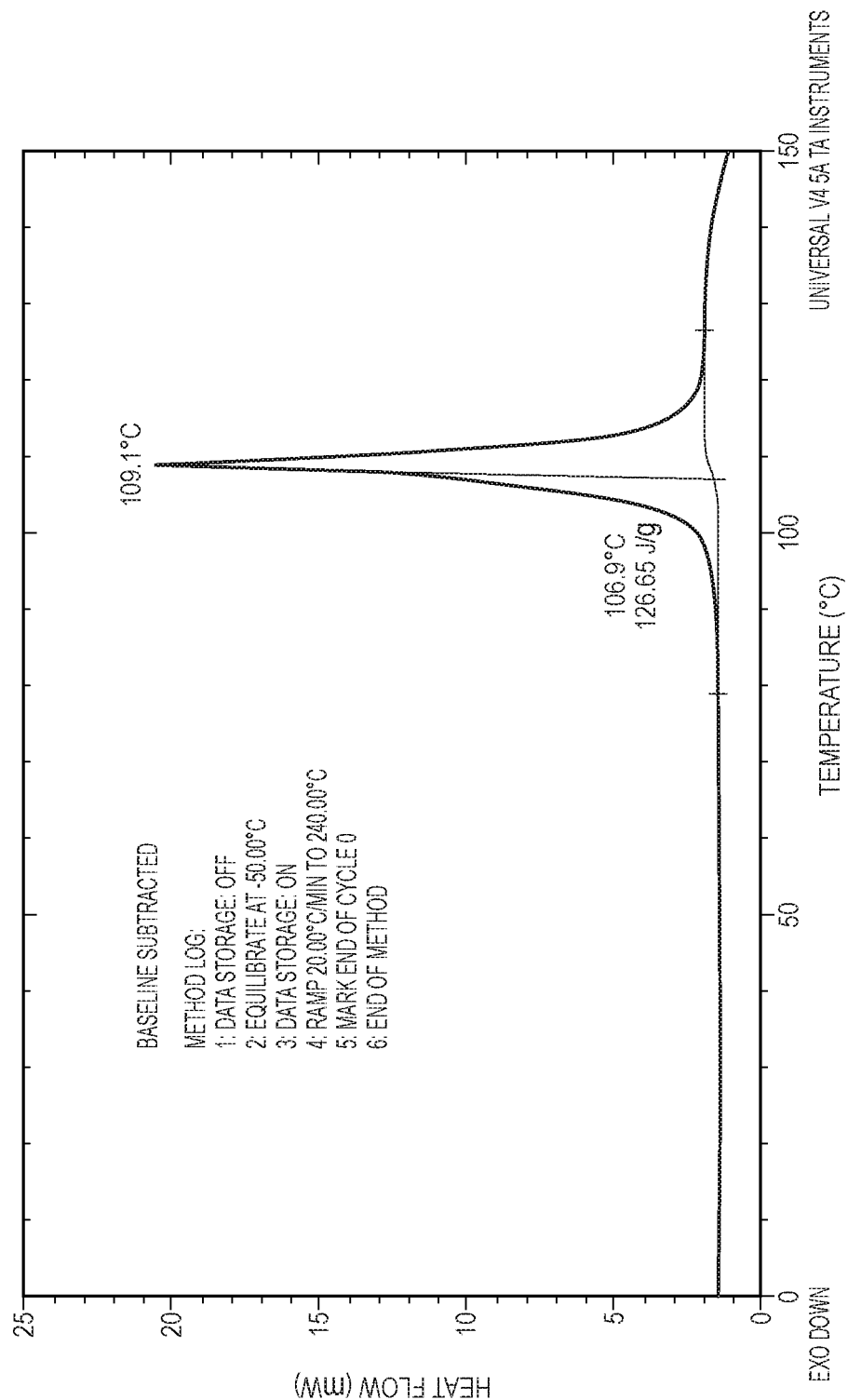
FIG. 18 illustrates a DSC thermogram of Form II of the free base of Formula (1).

A representative DSC analysis of a Form II sample is shown in FIG. 18. The sample was stabilized at equilibrium under approximately 62% RH before analysis using temperature ramp rates of 10° C./minute or 20° C./minute up to approximately 150° C. Melting begins at about 75° C. and a peak is observed near about 109° C. with an enthalpy of fusion of about 127 J/g. The DSC thermogram shows a slight shoulder on the left side of the peak that suggests that some of the hydrate water might have been released from the sample into the residual volume of the hermetically sealed sample pan.

Figure 19:
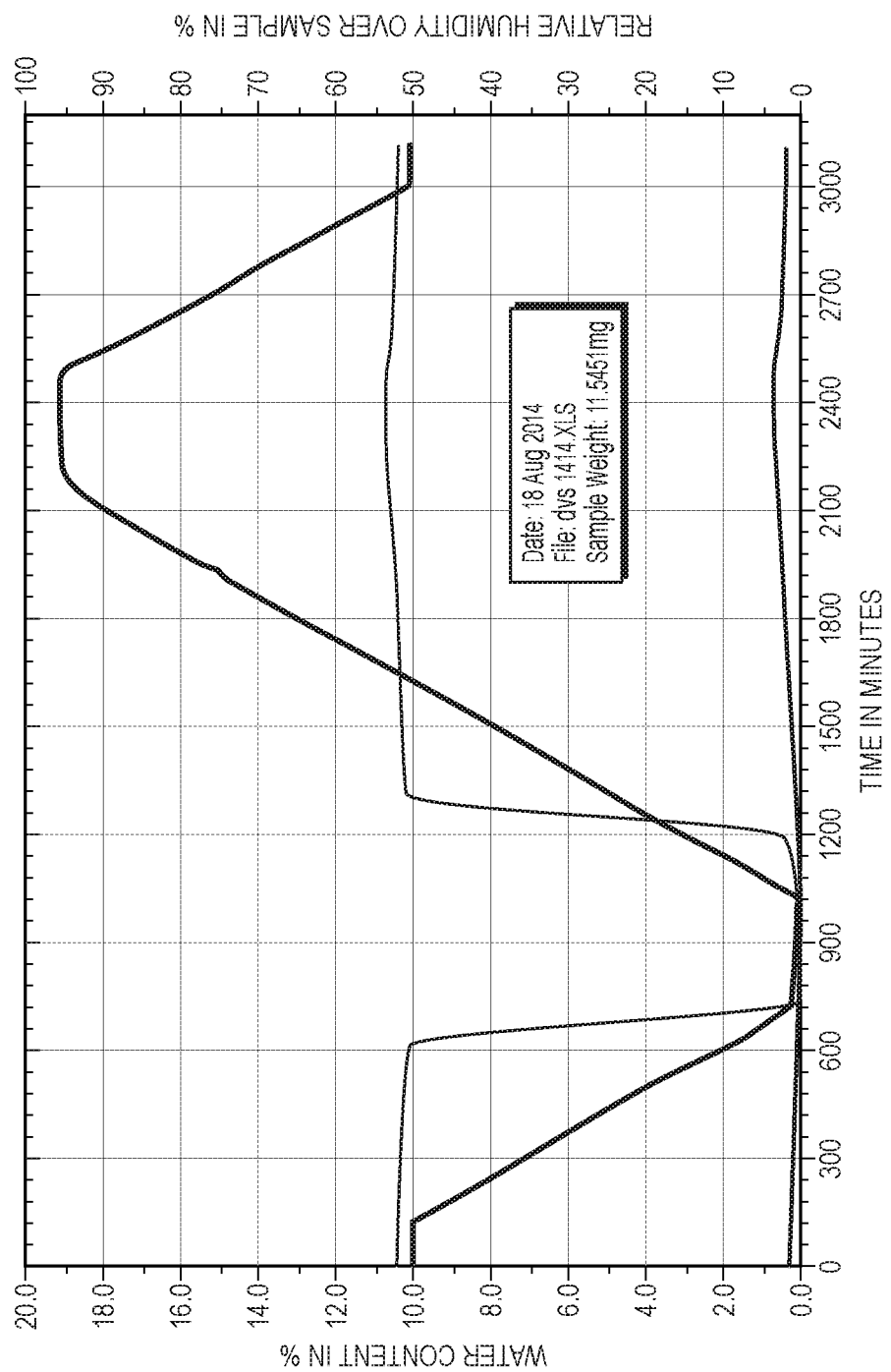
FIG. 19 illustrates a plot of the water content versus time and RH for Form II of the free base of Formula (1).
Figure 20:
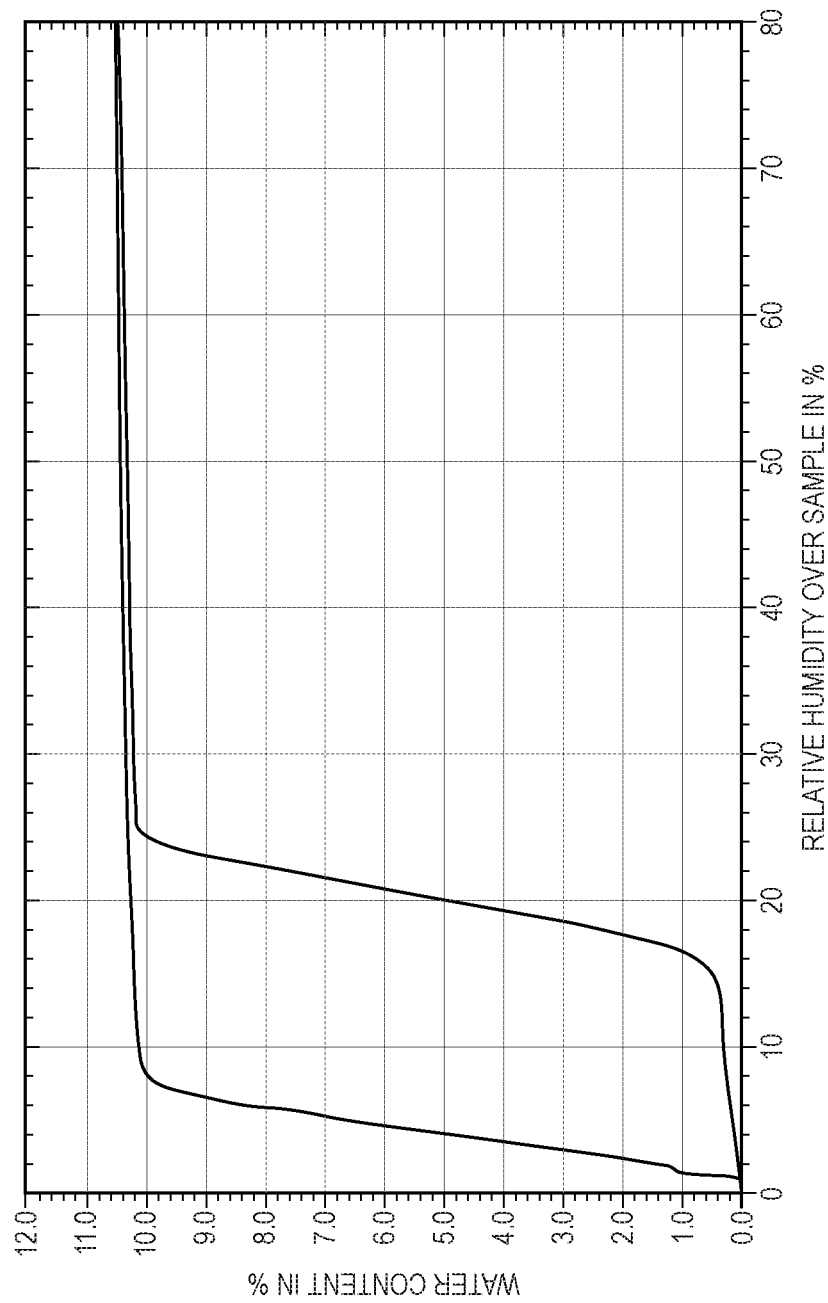
FIG. 20 illustrates an isotherm plot of the DVS analysis for Form II of the free base of Formula (1).

DVS analysis of the Form II (sample PP502-P14) was performed by exposing samples to a starting 50% RH, decreasing humidity to 0% RH, increasing humidity to 95% RH, and finally decreasing humidity back to the starting 50% RH. The DVS results, including sorption and desorption curves, are shown in FIG. 19 and FIG. 20. The results show that significant water loss occurs below about 10% RH, when the trihydrate water content rapidly decreases from approximately 10% to approximately 0%. This result is consistent with the mass loss in the TGA analysis. Upon increasing the RH to 95%, water was re-adsorbed to achieve a maximum water content of about 10.4%, which corresponds to the expected water content for a trihydrate. Hysteresis was also observed between the sorption and desorption curves. Form II thus behaves as a variable hydrate. The DVS results, including sorption and desorption isotherm curves, show the total weight gain observed between 0% RH and 80% RH to be about 10%, which indicates that Form II is hygroscopic according to the EP classification (see Example 1.2

Finally, Form II was tested with respect to solubilities in various water-solvent mixtures and non-aqueous solvents. The aqueous solubility of Form II was determined after equilibrating at 25° C. for three days. High-performance liquid chromatography (HPLC) was used to determine the concentration of Form II in the filtered solution at approximately 14 μg/mL, which translates into a critical water activity ($a_w$) of about 0.59. In comparison, the aqueous solubility for Form I is about 68 μg/mL.

Critical water activity is a measure of the relative thermodynamic stability of Form I in comparison to the trihydrate Form II. Below an $a_w$ of about 0.59, Form I is more stable at room temperature while above this value Form II is more stable. Suspension equilibration experiments in ethanol-water mixtures, each having a different water activity, affirmed this conclusion. Water activities included in the experiments were maintained at: about 0.35 (ethanol-water ratio of 95:5, PP502-P32), about 0.53 (ethanol-water ratio of 9:1, PP502-P33) and about 0.77 (ethanol-water ratio of 7:3, PP502-P34). At an $a_w$ of about 0.53, suspension experiments having mixtures of Form I and Form II resulted in pure Form I and at an $a_w$ of about 0.77, the result was pure Form II.

Example 3. Form III of (S)-4-(8-Amino-3-(1-(but-2-ynoyl)pyrrolidin-2-yl)imidazo[1,5-a]pyrazin-1-yl)-N-(pyridin-2-yl)benzamide (Free Base) Dihydrate Example 3.1. Preparation of Form III Crystalline Dihydrate Form III of the free base of Formula (1) was prepared from seeded crystallization experiments using Form I seeds. Saturated solutions of Formula (1) were prepared at 60° C. The solutions were cooled and seeds of Form I were added before spontaneous crystallization occurred. The results are summarized in Table 6.

TABLE 6

Results of seeded crystallization experiments for (S)-4-(8-amino-3-(1-(but-2-ynoyl)pyrrolidin-2-yl)imidazo[1,5-a]pyrazin-1-yl)-N-(pyridin-2-yl)benzamide.

| Sample | Solvent | Type | Appearance | PXRD | DSC | TGA |
|---|---|---|---|---|---|---|
| 86 | methanol - water 1:1 | Seeding | Solid | Form III | 147° C. (−23.7 J/g) 215° C. (141 J/g) | −4.8% (40-130° C.) |
| 87 | ethanol - water 1:3 | Seeding | Solid | Form III | — | — |
| 88 | 2-propanol - water 1:3 | Seeding | Solid | Form III | — | — |

TABLE 6-continued

Results of seeded crystallization experiments for (S)-4-(8-amino-3-(1-(but-2-ynoyl)pyrrolidin-2-yl)imidazo[1,5-a]pyrazin-1-yl)-N-(pyridin-2-yl)benzamide.

| Sample | Solvent | Type | Appearance | PXRD | DSC | TGA |
|---|---|---|---|---|---|---|
| 89 | N,N-dimethylacetamide - water 1:2 | Seeding | Solid | Poorly crystalline | — | — |
| 90 | Acetone - heptane 1:1 | Seeding | Solid | Form I | — | — |
| 91 | 2-butanone - heptane 1:1 | Seeding | Gel | — | — | — |
| 92 | cyclohexanone - heptane 1:1 | Seeding | Solid | Form I | — | — |
| 93 | dimethyl sulfoxide - water 1:3 | Seeding | Solid | Poorly crystalline | — | — |
| 94 | methyl tert-butyl ether | Seeding | Solid | Amorphous | — | — |
| 95 | tetrahydrofuran - water 1:6 | Seeding | Solid | Form III | — | — |
| 96 | diisopropyl ether | Seeding | Solid | Amorphous | — | — |
| 97 | 2-methyltetrahydrofuran | Seeding | Solid | Poorly crystalline | — | — |
| 98 | cyclopentyl methyl ether | Seeding | Solid | Poorly crystalline | — | — |
| 99 | chlorobenzene | Seeding | Solid | Poorly crystalline | — | — |
| 100 | dichloromethane - water 1:3 | Seeding | Gel | — | — | — |

Form III may be prepared by crystallization of amorphous Formula (1) free base in pure water. For instance, sample PP502-P120 was the results of a slurry of amorphous Formula (1) free base (sample PP502-P107A) in water. After one day, Form III was found in the suspension, and after an extended stirring period of three days, Form III was still retained. However, because Form II may also be obtained in other experiments under similar conditions, additional procedures to prepare Form III were development.

Form III may also been prepared from amorphous Formula (1) suspended in water. To about 160 mg of amorphous Formula (1), 5.0 mL of water is added and the resulting suspension is stirred at ambient temperature. Investigation of the solid after about 24 hours of equilibration at room temperature led to crystallization of Form III.

Form III may also be prepared by direct precipitation via pH adjustment. 940 mg of Formula (1) Form I is dissolved in 4.0 mL of 1 N aqueous hydrochloric acid solution. The solution neutralized with the same amount of 1 N aqueous sodium hydroxide solution. Further dilution with 8.0 mL of water leads to a thick suspension from which the solid is separated by filtration. The glass bottle is rinsed with 16 mL of water and the wash liquid is poured onto the glass frit filter and pulled through the filtration unit by application of vacuum. The obtained solid material is dried in an air dryer at 40° C. for about 24 hours. Powder X-ray diffraction confirms that Formula (1) Form III is obtained and thermogravimetry coupled with infrared spectroscopy shows that the sample contains about 6% water, which suggests that the material was slightly overdried. The water content found is still consistent with the result from the DVS testing as this water content is found near 40% RH.

Example 3.2. Physical Characterization of Form III Crystalline Dihydrate

The PXRD, TGA, and DSC characterization methods used for Form III of the free base of Formula (1) were performed as follows. The PXRD studies were performed using a Bruker AXS D2 PHASER operating in the Bragg-Brentano configuration. Data was collected using a Cu anode at 30 kV and 10 mA with the sample rotating. Monochromatisation was performed using a Kj3-filter (0.5% Ni). Fixed divergence slits were set at 1.0 mm (0.61°), the primary axial Soller slit was set at 2.5°, and the secondary axial Soller slit was set at 2.5°. The detector was a linear LYNXEYE detector with a receiving slit 5° detector opening. The standard sample holder (0.1 mm cavity in (510) silicon wafer) has a minimal contribution to the background signal. Measurement conditions were as follows: scan range 5-45° 2θ, sample rotation 5 rpm, 0.5 s/step, 0.010°/step, 3.0 mm detector slit; and all measuring conditions are logged in the instrument control file. As a check of system suitability, a corundum sample A26-B26-S(NIST standard) is measured daily. The software used for PXRD data collection is Diffrac.Commander v3.3.35. Data analysis was performed using Diffrac.Eva V3.0 software. No background correction or smoothing was applied to the patterns. The contribution of the Cu-Kα2 peak was stripped off using the Diffrac.Eva software. TGA and DSC studies were performed using a Mettler Toledo TGA/DSC1 STARe System with a 34-position auto sampler. The samples were prepared using aluminium crucibles (40 µL; pierced). Typically, 5-10 mg of sample was loaded into a pre-weighed aluminium crucible and was kept at 30° C. for 5 minutes, after which it was heated at 10° C./min from 30° C. to 300° C. A nitrogen purge of 40 mL/min was maintained over the sample. As system suitability check, indium and zinc are used as references. The software used for data collection and evaluation is STARe Software v10.00 build 2480. No corrections are applied to the thermogram.

Figure 21:
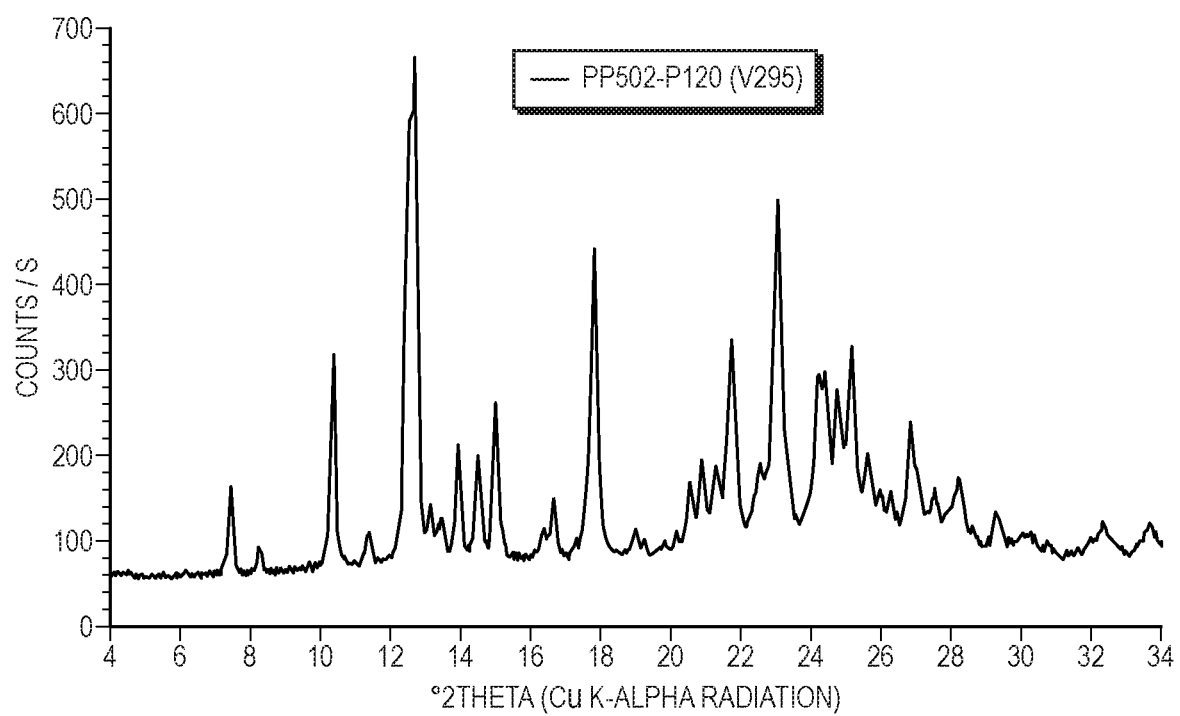
FIG. 21 illustrates a PXRD pattern of Form III of the free base of Formula (1).

Additional PXRD characterization of Form III was obtained in a similar manner as described in Example 1.2 for Form I. This PXRD pattern, which was obtained from sample PP502-P120 (prepared as described above), is shown in FIG. 21. The following peaks were identified in the PXRD pattern of FIG. 6: 10.4, 12.6, 12.8, 17.9, 21.3, 21.7, 23.1, 24.2, 25.2, and 27.0° 2θ±0.2° 2θ. Form III shows distinctive peaks (relative to the other forms) at 7.6, 8.5, 12.6, 12.8, 14.6, 16.8, and 23.2° 2θ±0.2° 2θ. The weak nature of the PXRD pattern indicates that Form III is poorly crystalline. An image obtained by optical microscopy of Form III showed the presence of some crystalline material with an irregular habit.

Figure 22:
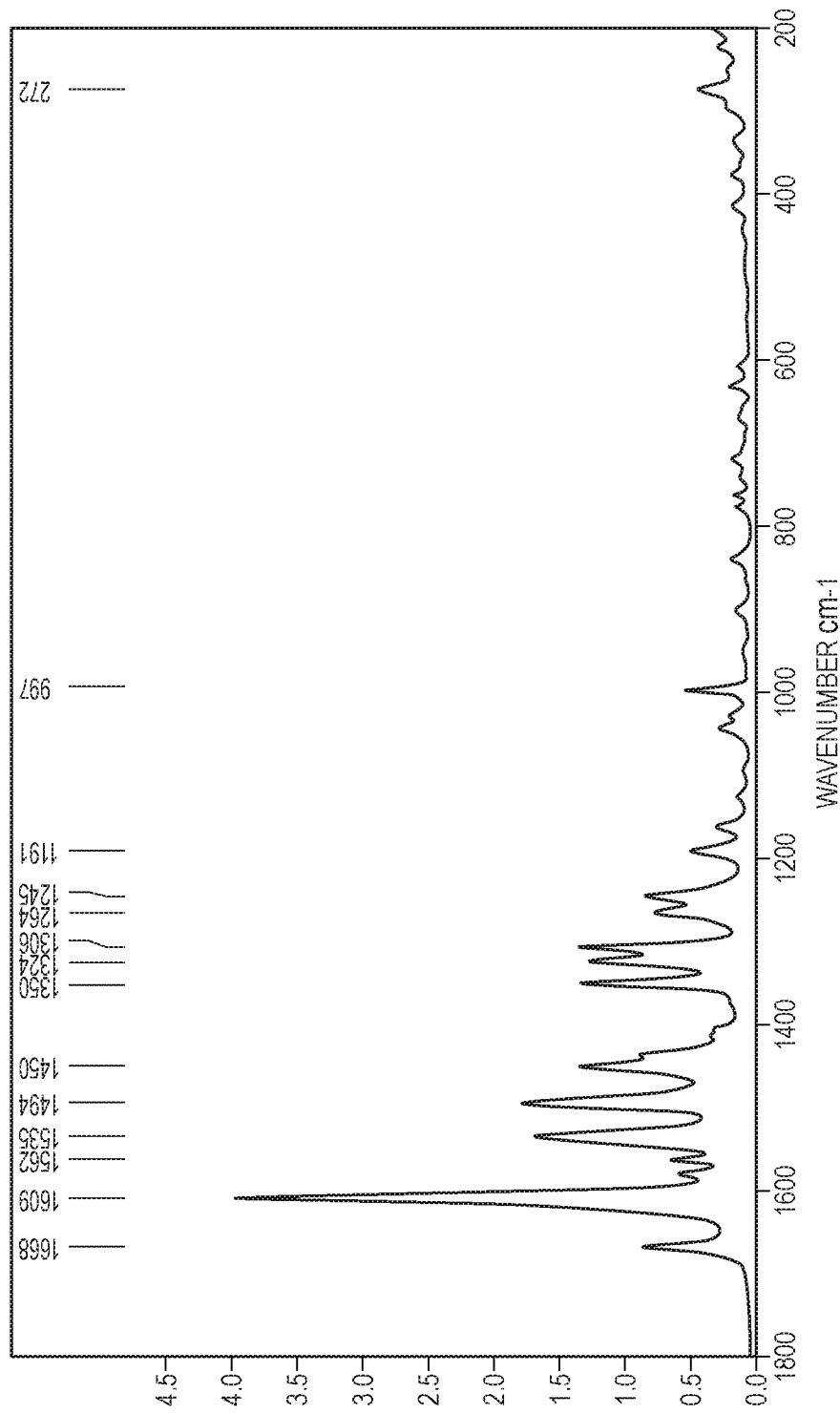
FIG. 22 illustrates a Raman spectrum of Form III.

The Raman spectrum of Form III was obtained in a similar manner as described in Example 1.2 for Form I. An expanded region of the Raman spectrum of Form III (sample PP502-P120) is shown in FIG. 22 and exhibits peaks (Raman shift, cm$^{-1}$±2 cm$^{-1}$) at 1668, 1609, 1562, 1535, 1494, 1450, 1350, 1324, 1306, 1264, 1245, 1190, 997, and 272.

Figure 23:
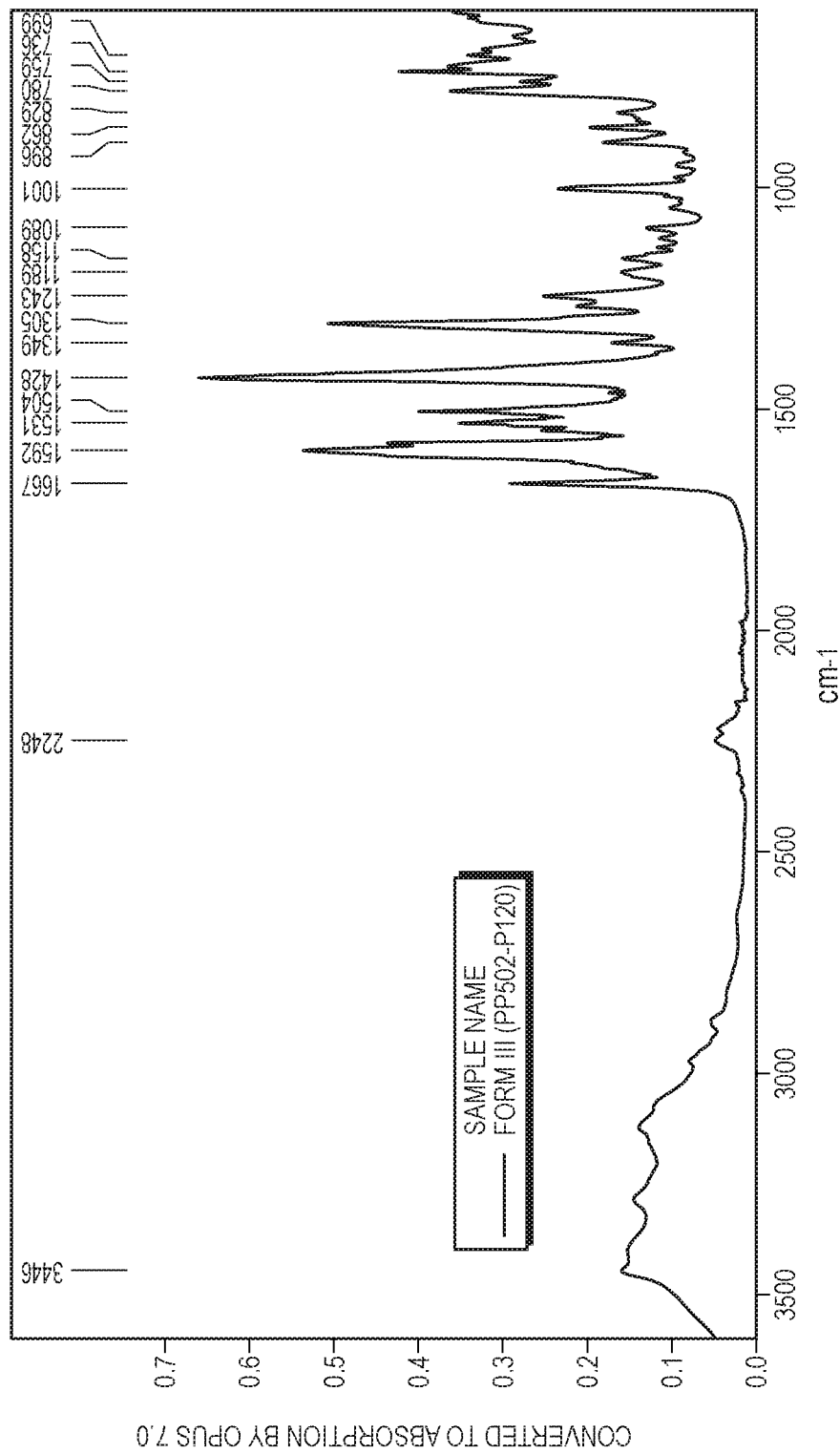
FIG. 23 illustrates an IR spectrum of Form III of the free base of Formula (1).
Figure 24:
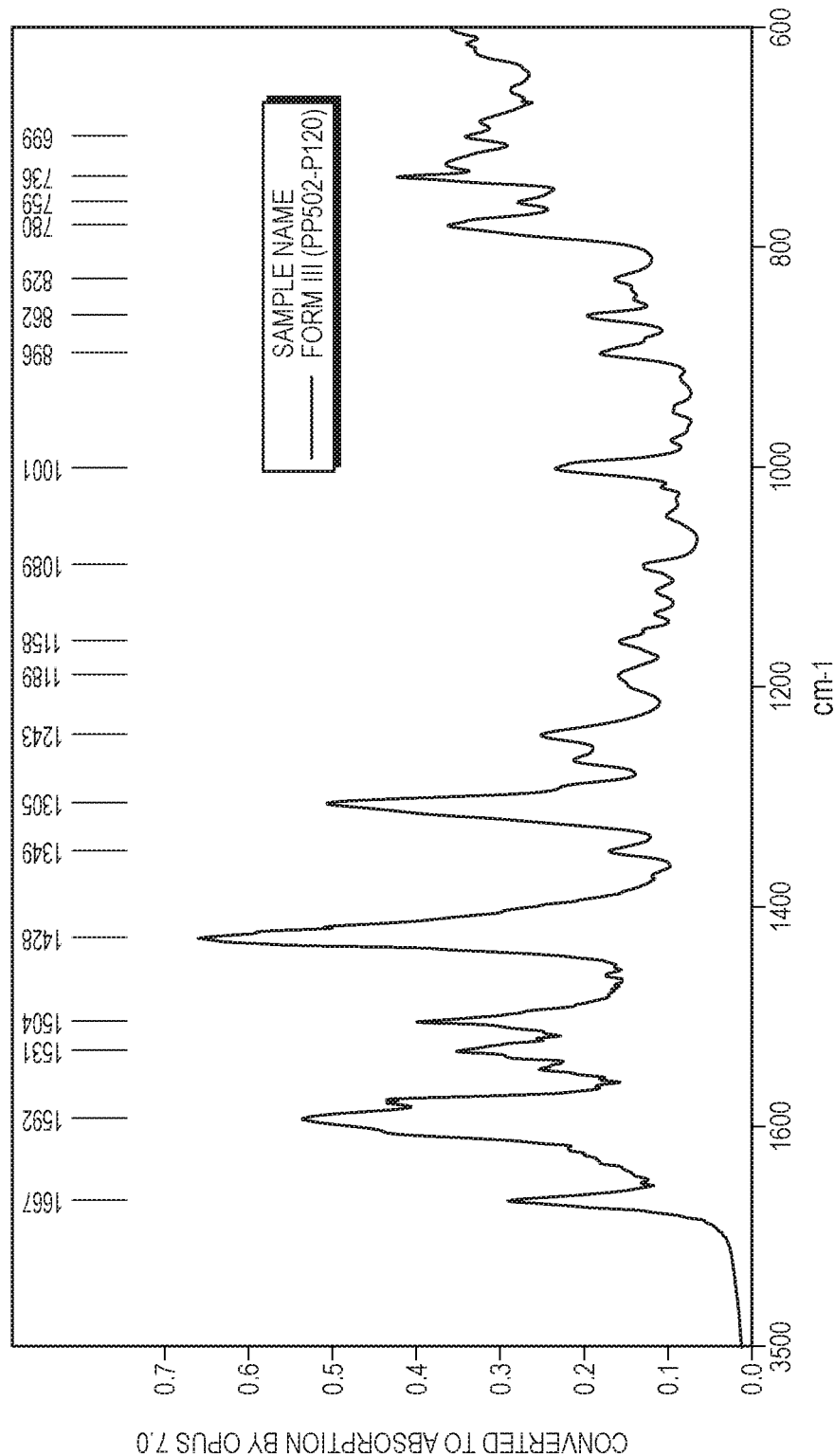
FIG. 24 illustrates an IR spectrum of Form III of the free base of Formula (1).

The IR spectrum of Form III was obtained using the same method as described in Example 1.2 for Form I. FIG. 23 shows the IR spectrum of Form III (sample PP502-P120), and an expansion of the spectral region from 1800 to 600 cm$^{-1}$ is shown in FIG. 24. The characteristic peaks observed for Form III are provided in Table 7.

TABLE 7

Characteristic peaks for Form III determined by ATR IR spectroscopy (+/−4 cm$^{-1}$).

| Wavenumber (cm$^{-1}$) | Intensity (arbitrary units) |
|---|---|
| 3446 | 0.159 |
| 2248 | 0.048 |
| 1667 | 0.292 |
| 1592 | 0.536 |
| 1531 | 0.352 |
| 1504 | 0.400 |
| 1428 | 0.659 |
| 1349 | 0.171 |
| 1305 | 0.507 |
| 1243 | 0.252 |
| 1189 | 0.160 |
| 1158 | 0.159 |
| 1089 | 0.130 |
| 1001 | 0.235 |
| 896 | 0.181 |
| 862 | 0.197 |
| 829 | 0.164 |
| 780 | 0.362 |
| 759 | 0.280 |
| 736 | 0.424 |
| 699 | 0.342 |

Figure 25:
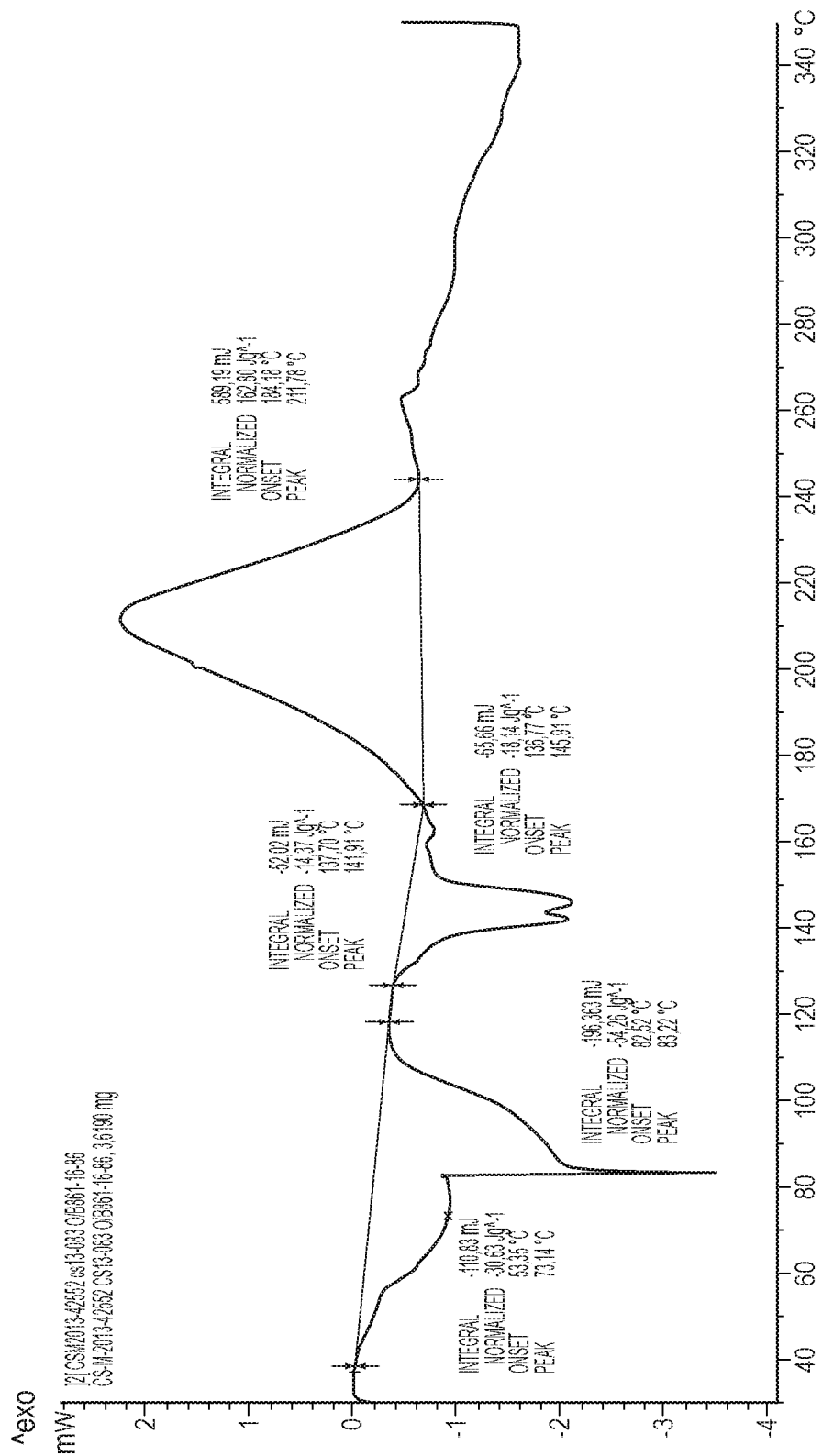
FIG. 25 illustrates a DSC thermogram of Form III of the free base of Formula (1).

The DSC thermogram of Form III is shown in FIG. 25, with events at 147° C. (−23.7 J/g) and 215° C. (141 J/g) assigned to solvent loss and melting, respectively. By TGA, Form III was observed to lose 4.8% mass over the temperature range of 40-130° C.

Because it was known that Form III is a metastable hydrate, the DVS analysis of Form III (sample PP502-P120) was programmed to begin with increasing relative humidity instead of decreasing relative humidity. The experiment began at 50% RH, which was increased to 95% RH, decreased to 0% RH, and finally increased back to the starting 50% RH. The resulting DVS shows a maximum water content of about 8.5% at 95% RH and nearly all of the water is removed at 0% RH. The DVS results, including sorption and desorption isotherm curves, show the total weight gain observed between 0% RH and 80% RH to be about 8%, which indicates that Form III is hygroscopic according to the EP classification (see Example 1.2). Little hysteresis is observed between the sorption and desorption curves. The DVS results, combined with PXRD data taken before and after the DVS experiments, indicates that Form III is a non-stoichiometric channel hydrate, rather than a dihydrate, because the water content can vary continuously over the whole relative humidity range. Like Form II, Form III thus also behaves as a variable hydrate.

Example 4. Forms Prepared From Form II (Forms IV-VIII of the Free Base of Formula (1))

In addition to Form II, which is a trihydrate with a typical water content of about 10%, several other derivatives of Form II were also investigated. For example, when Form II is dehydrated below about 20% relative humidity (RH), another non-solvated form is obtained. This form is designated as Form IV. Characterization of Form IV was carried out using various techniques including PXRD and DSC, which were performed as described previously for the characterization of Forms I and II.

Figure 26:
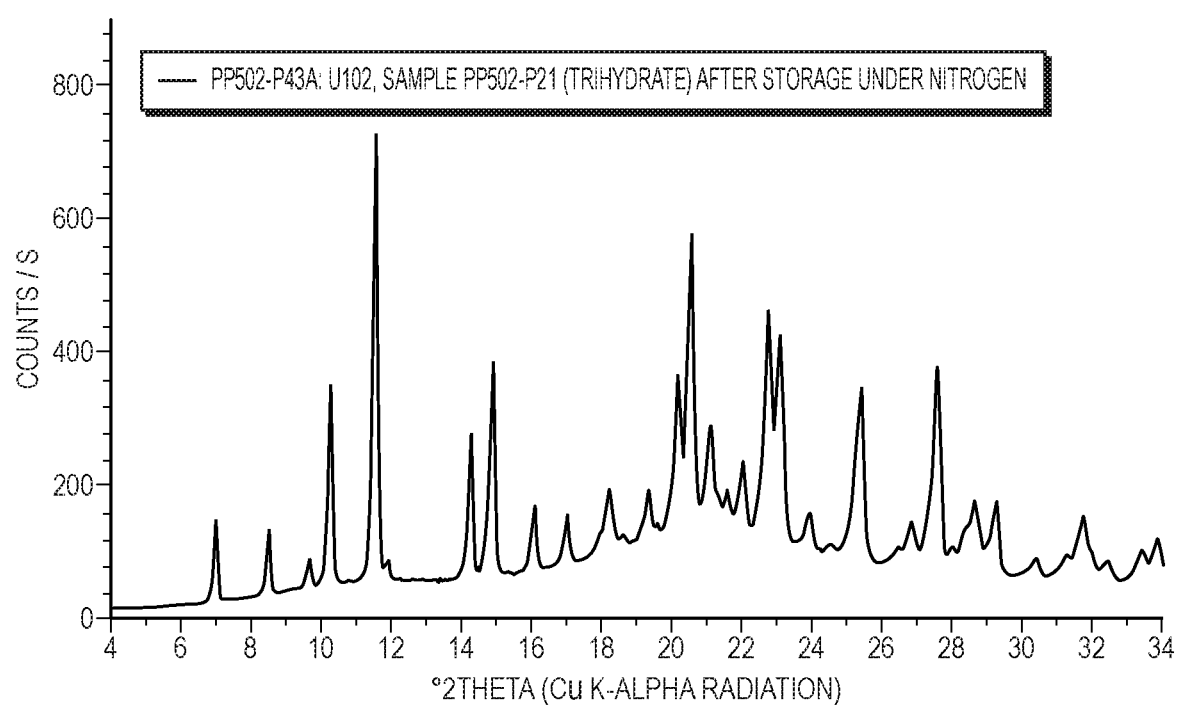
FIG. 26 illustrates a PXRD pattern of Form IV of the free base of Formula (1) (Form II after dehydration under nitrogen).

In order to evaluate the state of dehydrated Form II, a sample of the trihydrate (Form II) was placed into a 1.0 mm PXRD sample holder and kept under dry nitrogen overnight. After 24 hours, the sample holder was covered with a PMMA dome to keep the sample under nitrogen, and a PXRD pattern was recorded. FIG. 26 depicts the PXRD pattern for Form IV. The following peaks were identified in the PXRD pattern of FIG. 26: 7.0, 8.5, 9.6, 10.3, 11.5, 11.9, 14.3, 14.9, 16.1, 17.0, 18.2, 19.3, 20.2, 20.6, 21.1, 21.6, 22.1, 22.8, 23.1, 24.0, 25.4, 26.9, 27.6, 28.4, 28.7, 29.3, 30.4, 31.8, 32.5, 33.5, 33.9, and 34.9° 2θ±0.2° 2θ.

Because the DVS results of Form II indicate reversible moisture sorption-desorption behavior (see above), tests were performed to confirm that storage of the dehydrated Form II sample (i.e., Form IV) at about 60% RH would again lead to the trihydrate form (Form II). Reexamination by PXRD confirms that dehydrated Form IV does revert to Form II after storage at 60% RH for three days.

DSC analysis of Form IV was performed after the sample was equilibrated under dry nitrogen for about 60 hours. The dehydrated sample was exposed to temperature ramp rates of 10° C./minute or 20° C./minute up to approximately 240° C. The DSC thermogram illustrates a melting peak at approximately 159° C. with an enthalpy of fusion of about 57 J/g. Thermal decomposition begins immediately after melting.

Another dehydrated form was obtained when Form II was dried at 100° C. under vacuum for 2 hours. This form is designated as Form V. From DVS analysis of Form II (see above), it is known that Form II loses water when kept under dry nitrogen. Form V was identified while studying the behavior of Form II after exposure to elevated temperatures. Characterization of Form V was carried out using various techniques including: PXRD (FIG. 27); and Raman spectroscopy (FIG. 28). Form V shows a distinct PXRD pattern and a new Raman spectrum, which were performed as described previously for the characterization of Forms I and II. $^1$H NMR spectroscopy confirmed the chemical integrity of the compound.

Figure 27:
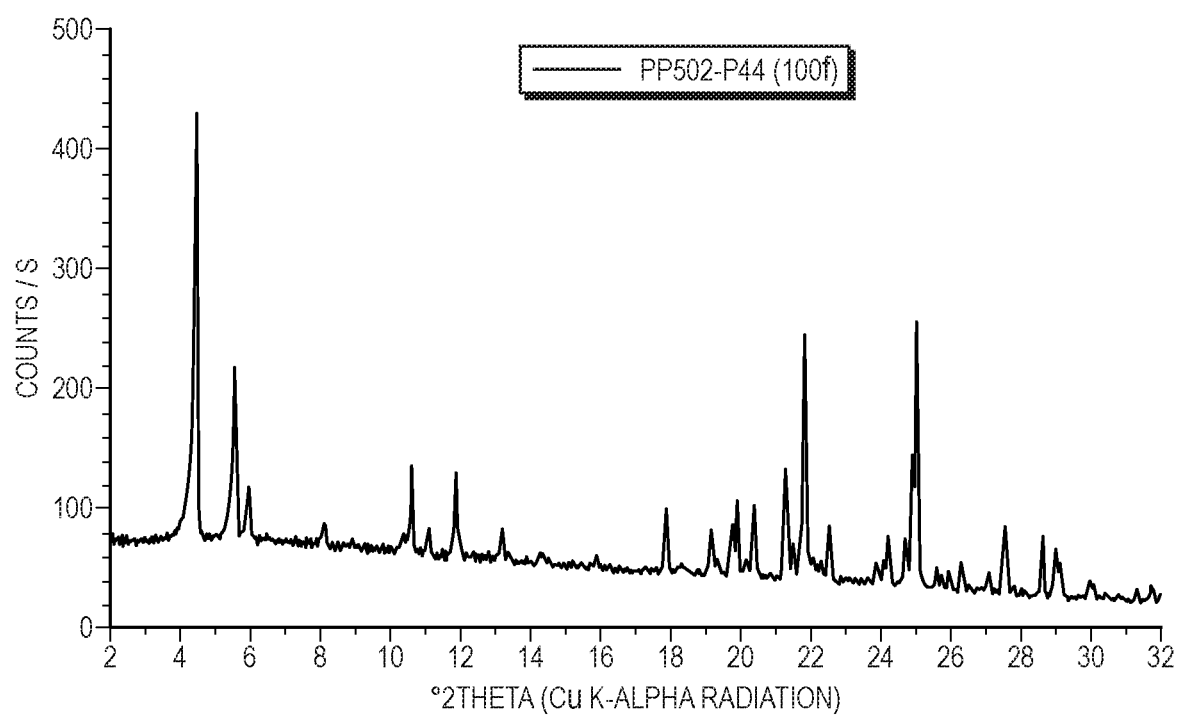
FIG. 27 illustrates a PXRD pattern of Form V of the free base of Formula (1).
Figure 28:
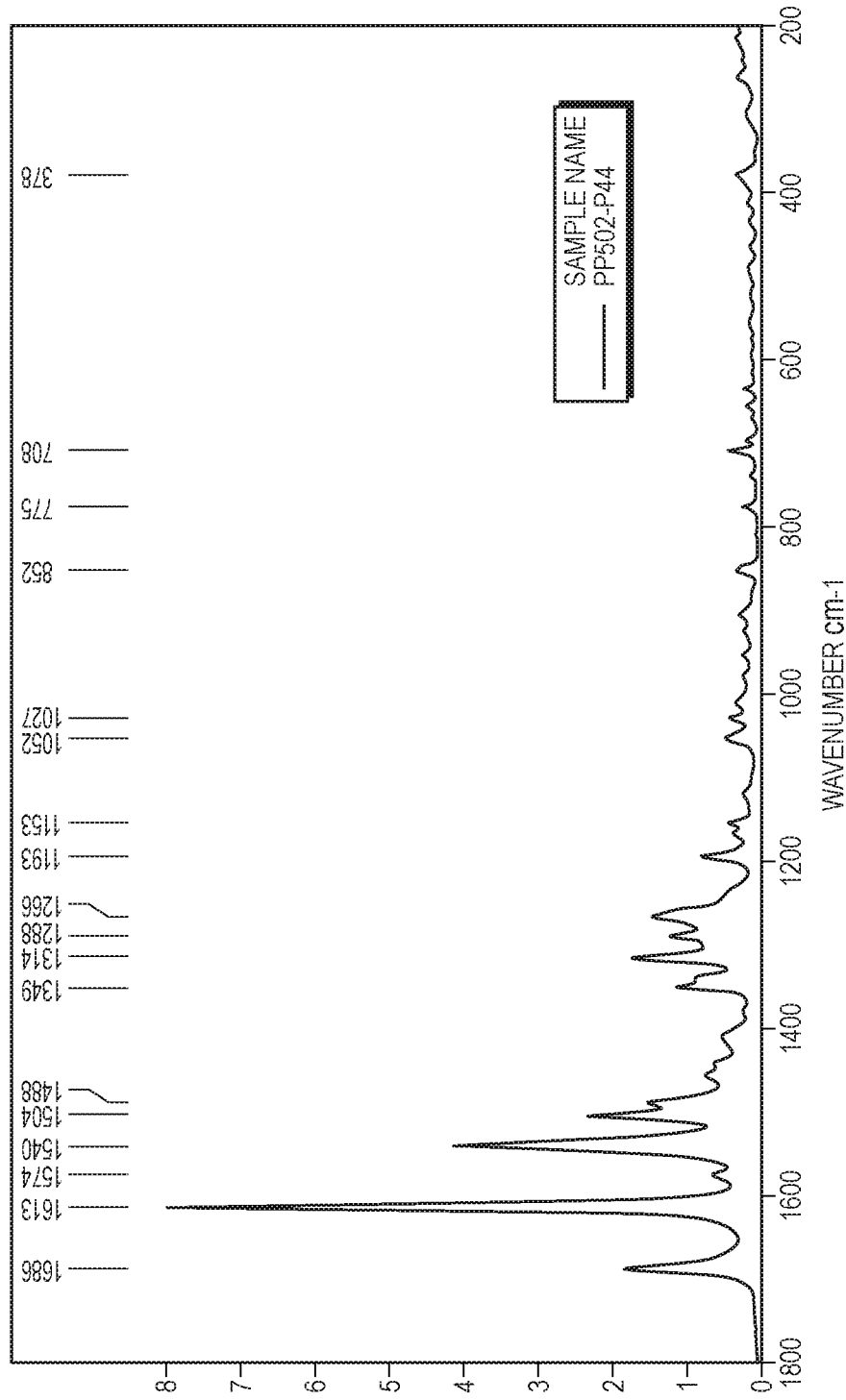
FIG. 28 illustrates a Raman spectrum of Form V of the free base of Formula (1) in the spectral range from 200 to 1800 $cm^{-1}$.

FIG. 27 shows the PXRD pattern for Form V, and specifically, sample PP502-P44. The following peaks were identified in the PXRD pattern of FIG. 27: 4.5, 5.5, 5.9, 8.1, 10.6, 11.1, 11.9, 13.2, 17.9, 19.2, 19.9, 20.4, 21.3, 21.8, 22.6, 23.7, 24.3, 24.7, 25.0, 26.0, 26.3, 27.6, 28.6, and 30° 2θ±0.2° 2θ. Comparisons between the PXRD pattern for Form II (FIG. 12) and the PXRD pattern for Form V show overlapping peaks at 11.0, 19.3, 22.0, 22.5, 22.7, 23.9, 24.2, 24.6, 25.0, 26.1, 27.5° 2θ±0.2° 2θ for Form II and 11.1, 19.2, 21.8, 22.6, 23.9, 24.3, 24.7, 25.0, 26.0, 27.6° 2θ±0.2° 2θ for Form V with the following peaks of Form II either disappearing entirely or decreasing in intensity: 9.9, 11.0, 14.3, 18.1, 18.4, 18.9, 20.2, 22.0, 22.2, 22.5, 22.7, 22.9, 23.9, 24.6, 26.1, 26.6, 28.2, and 32.7° 2θ.

Thermoanalytical characterization of Form V was carried out using TG-FTIR and DSC analytical techniques. The TG-FTIR thermogram shows that the sample immediately loses about 5% of its water mass upon heating at a rate of 10° C. per minute to about 100° C. to 120° C. The sample remains stable till approximately 200° C., at which point an additional mass change of about 17% is seen due to sample decomposition upon continued heating up to approximately 340° C. to 350° C.

DSC of a Form V sample was carried out in a sample pan sealed under ambient conditions. The DSC thermogram shows a very broad endotherm with a peak at about 125° C. A substantial part of this endothermic signal corresponds to release of water from the sample into the void volume of the hermetically sealed sample pan since the TG-FTIR thermogram shows that the release of water commences just above ambient temperature, indicating that the water is likely to be loosely bound in the crystal structure.

The FT-Raman spectrum of Form V in the relevant fingerprint region (200 cm$^{-1}$ to 1800 cm$^{-1}$) is shown in FIG. 28 and exhibits peaks (Raman shift, cm$^{-1}$±2 cm$^{-1}$) at 1686, 1613, 1574, 1540, 1504, 1488, 1349, 1314, 1288, 1266, 1193, 1153, 1052, 1027, 852, 775, 708, and 378. Differences in the Raman spectra of Form V and Form II are highlighted by peaks at 1686, 1574, 1488, 1314, 1266, 1193, 1153, 1052, and 708 cm$^{-1}$ of the Form V spectra, all of which do not appear in the Form II spectrum (see FIG. 15). Furthermore, peaks appearing at 1668, 1580, 1564, 1493, 1454, 1436, 1416, 1401, 1321, 1272, 1252, 1244, 1183, 1165, 1097, 1039, 996, 950, 871, 730, 645, 633, 352, 279, and 247 cm$^{-1}$ of the Form II spectrum are not present in the Form V spectra, indicating the presence of distinct phases.

A comparison of the Raman spectra of Forms I, II and V, as shown in FIGS. 4, 14 and 28, respectively, illustrates that all three forms may be readily distinguished by Raman spectroscopy.

Figure 29:
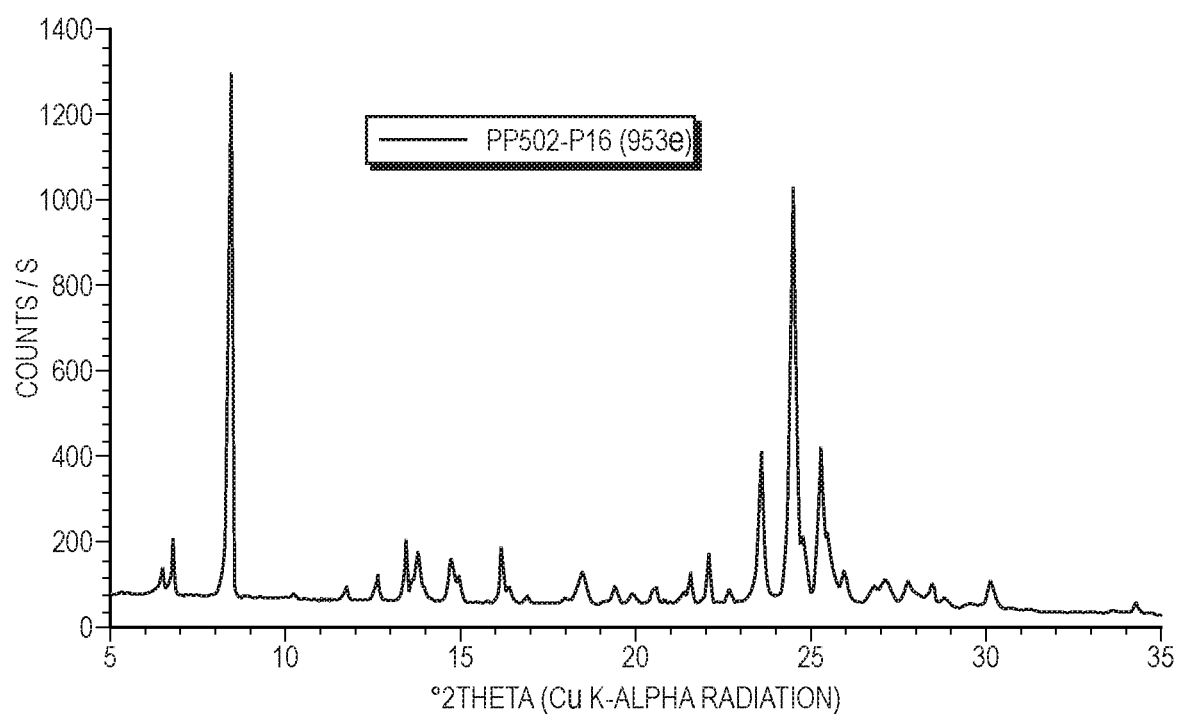
FIG. 29 illustrates a PXRD pattern of Form VI.
Figure 30:
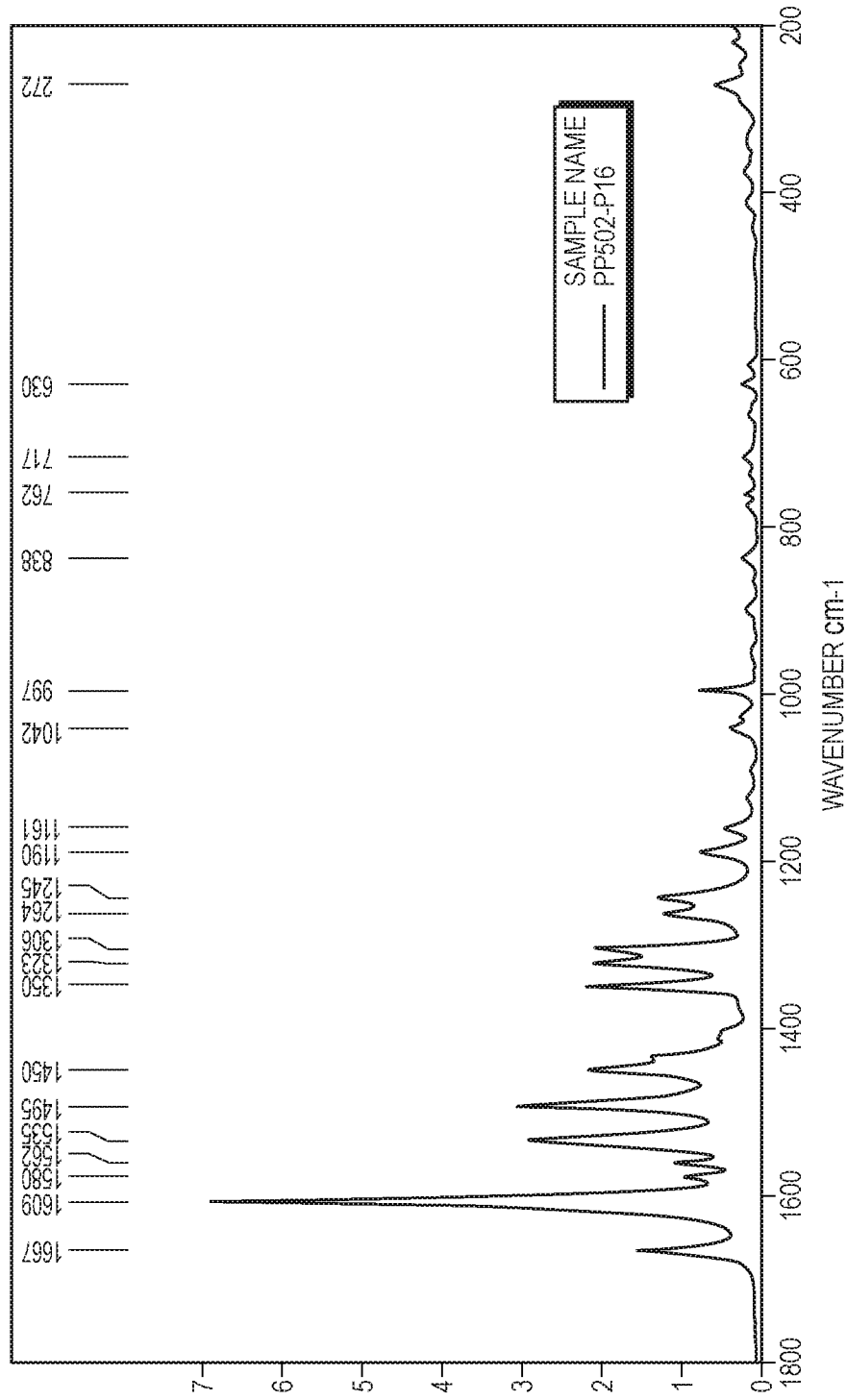
FIG. 30 illustrates a Raman spectrum of Form VI in the spectral range from 200 to 1800 $cm^{-1}$.
Figure 31:
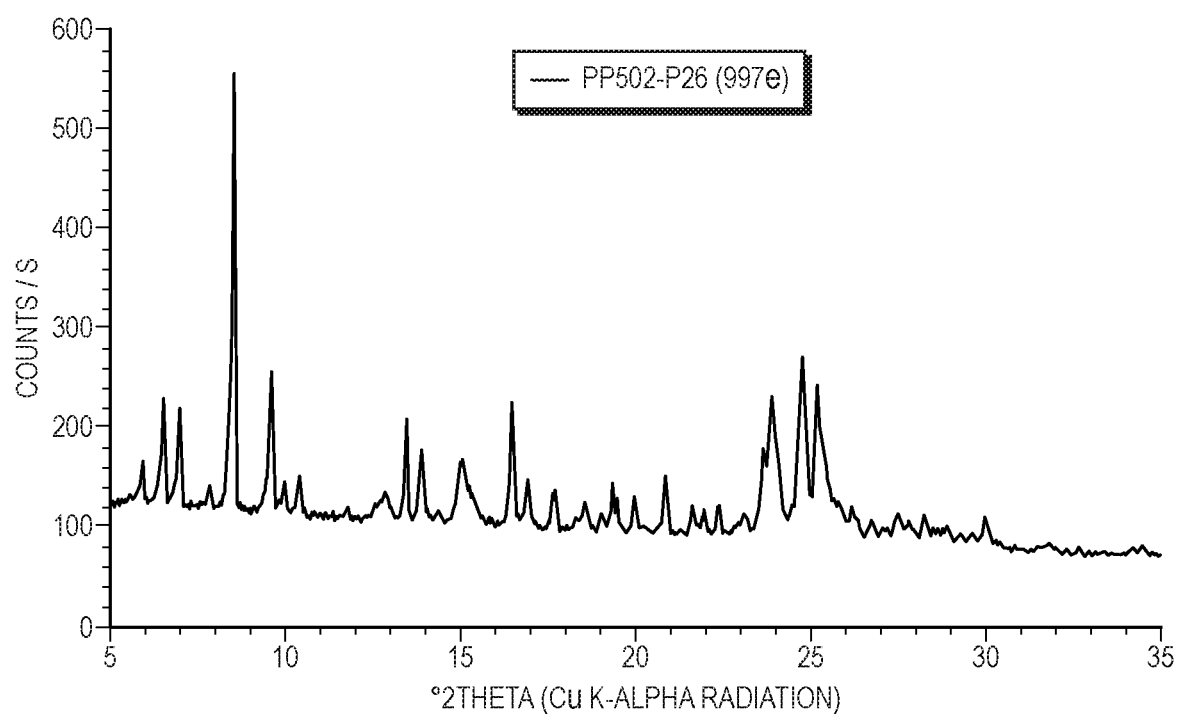
FIG. 31 illustrates a PXRD pattern of Form VII.

Crystallization of Formula (1) in methanol and methanol-water mixtures (95:5) led to samples with new PXRD patterns (samples P502-P26 and PP502-P16, respectively). Form VI was the product from a crystallization experiment conducted in a methanol-water mixture (95:5) at 5° C. (sample PP502-P16). Form VI exhibits a unique PXRD pattern (FIG. 29) and Raman spectrum (FIG. 30). Comparison of the PXRD pattern for Form VI (FIG. 29) with those of Form I (FIG. 1) and Form II (FIG. 12) shows that neither Form I nor Form II is present in sample PP502-P16. The following characteristic peaks were identified in the PXRD pattern of Form VI: 6.5, 6.8, 8.5, 11.8, 12.6, 13.5, 13.8, 14.8, 15.0, 16.2, 16.4, 16.9, 18.5, 19.4, 19.9, 20.6, 21.6, 22.1, 22.7, 23.6, 24.5, 24.8, 25.3, 26.0, 27.2, 27.8, 28.5, 28.9, 30.2, and 34.3° 2θ±0.2° 2θ. Characteristic peaks for Form VI in FIG. 31 are observed at 1667, 1609, 1580, 1562, 1535, 1495, 1450, 1350, 1323, 1306, 1264, 1245, 1190, 1161, 1042, 997, 838, 762, 717, 630, and 272 cm$^{-1}$±2 cm$^{-1}$.

Figure 32:
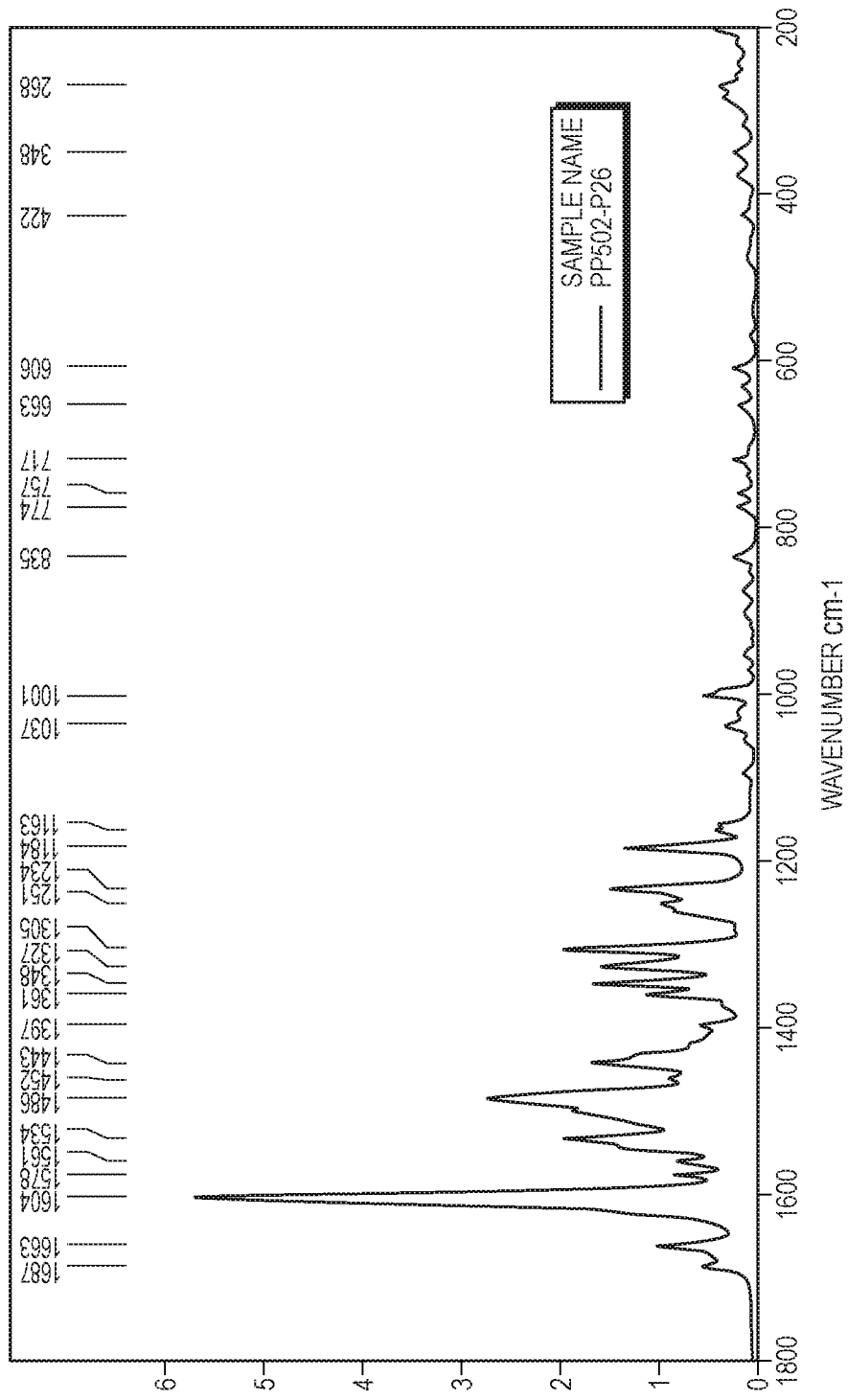
FIG. 32 illustrates a Raman spectrum of Form VII in the spectral range from 200 to 1800 $cm^{-1}$.

Form VII was obtained from the crystallization experiment conducted in pure methanol where the obtained solid sample PP502-P26 precipitated out when stored at 4° C. Form VII exhibits a unique PXRD pattern (FIG. 31) and Raman spectrum (FIG. 32). Comparison of the PXRD pattern for Form VII with those of Form I and Form II (FIG. 31, FIG. 1 and FIG. 12, respectively) shows that neither Form I nor Form II is present in sample PP502-P26. The following characteristic peaks were identified in the PXRD pattern of Form VII: 5.9, 6.5, 7.0, 7.8, 8.5, 9.6, 10.0, 10.4, 13.4, 13.9, 15.0, 16.5, 16.9, 17.7, 18.5, 19.0, 19.9, 20.8, 21.6, 22.4, 23.7, 23.9, 24.8, 25.2, 27.5, 28.3, and 30.0° 2θ±0.2° 2θ. Characteristic Raman peaks for Form VII in FIG. 32 are observed at 1687, 1663, 1604, 1578, 1561, 1534, 1486, 1462, 1443, 1397, 1361, 1348, 1327, 1305, 1251, 1234, 1184, 1163, 1037, 1001, 835, 774, 757, 717, 653, 606, 422, 348, and 268 cm$^{-1}$±2 cm$^{-1}$.

$^1$H NMR spectroscopy shows that both Form VI and VII contain about 0.7 equivalents of methanol, and according to TG-FTIR, both forms also contain substantial amounts of water. Forms VI and VII are likely to be metastable methanol solvates or mixed solvate-hydrates (i.e., methanolate-hydrate). Suspension equilibration experiments conducted at 5° C. in methanol with a mixture of Forms (I), VI, and VII show that pure Form I was recovered after five days, suggesting that even in pure methanol, Form I is likely to be more stable than either Form VI or Form VII.

Figure 33:
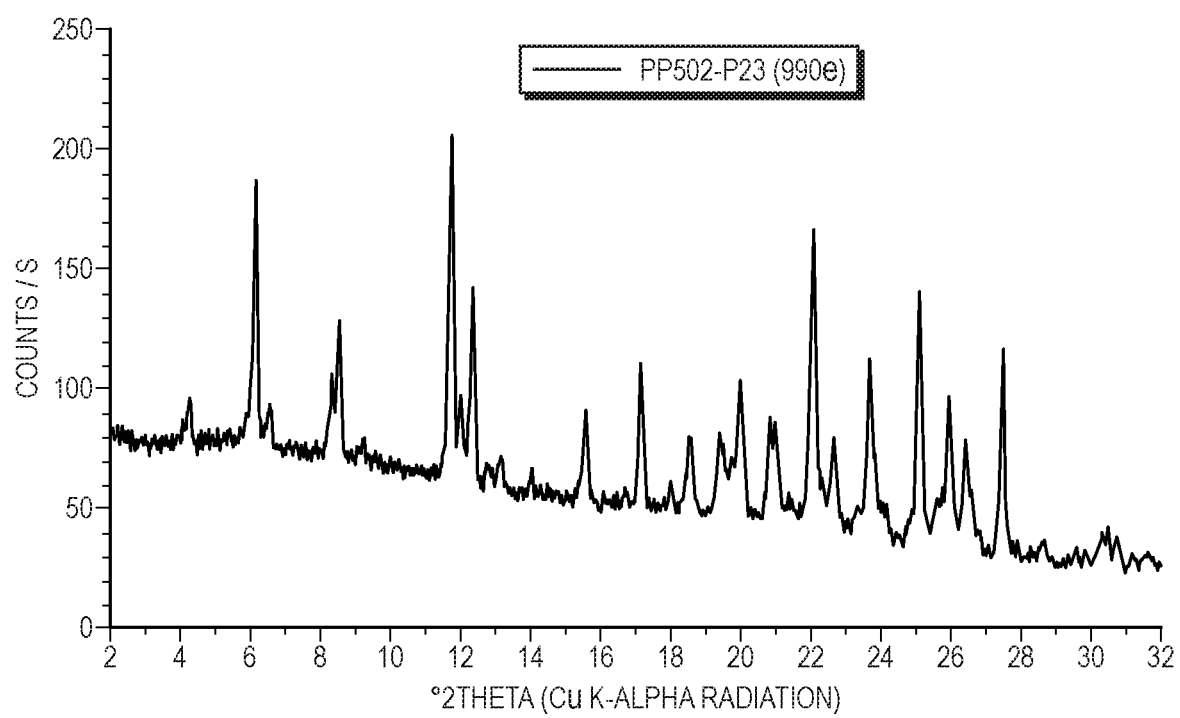
FIG. 33 illustrates a PXRD pattern of Form VIII.
Figure 34:
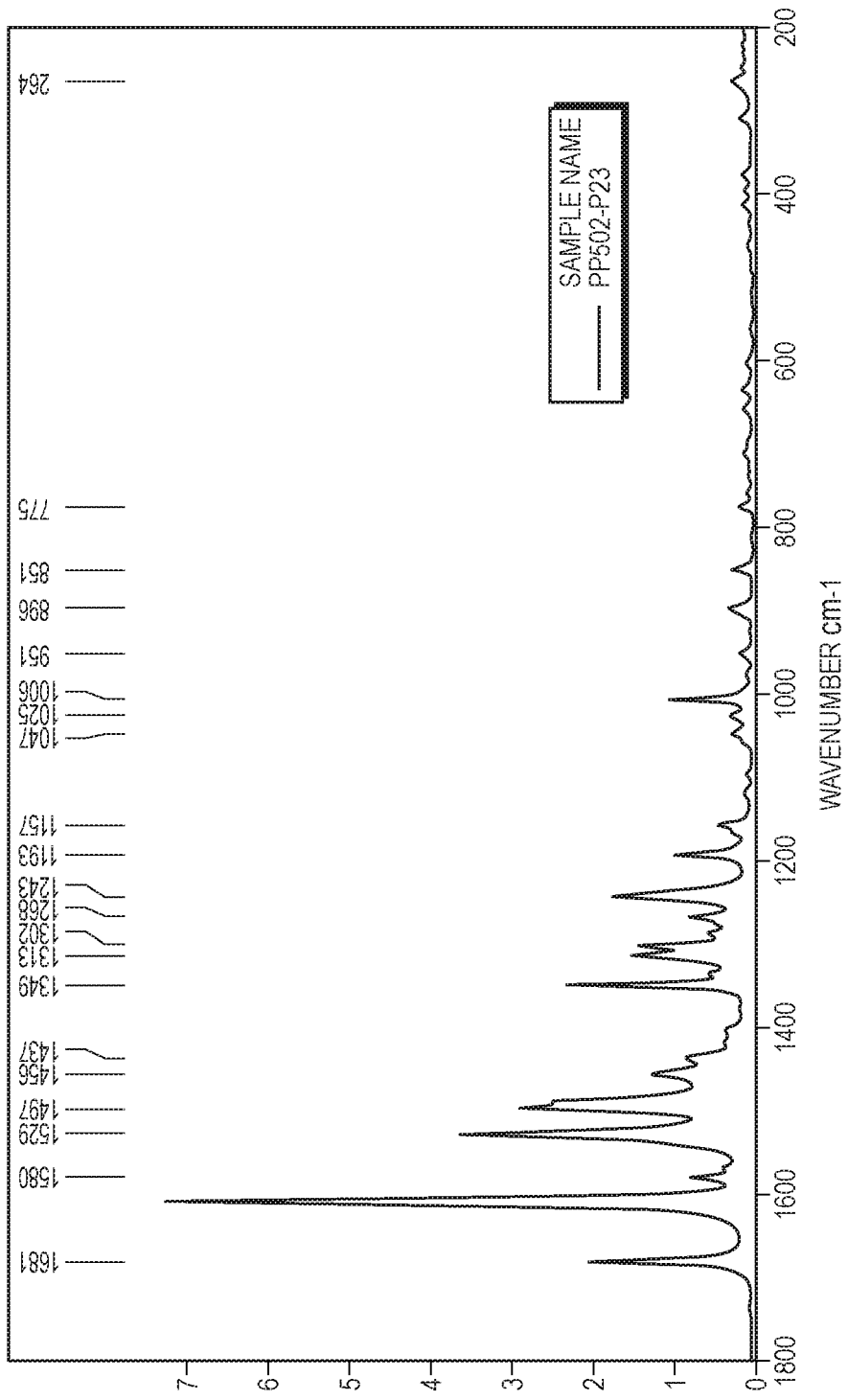
FIG. 34 illustrates a Raman spectrum of Form VIII in the spectral range from 200 to 1800 $cm^{-1}$.

Form VIII (sample PP502-P23) is a putative acetic acid disolvate. The PXRD pattern of Form VIII is shown in FIG. 33. The following peaks were identified in the PXRD pattern of Form VIII: 4.28, 6.18, 6.59, 8.57, 11.75, 12.03, 12.38, 15.61, 17.16, 18.02, 18.58, 19.43, 20.02, 20.85, 22.07, 22.68, 23.69, 25.13, 25.96, 26.43, and 27.49° 2θ±0.2° 2θ. The Raman spectrum of Form VIII is shown in FIG. 34. Characteristic Raman peaks for Form VIII are observed at 1681, 1580, 1529, 1497, 1456, 1437, 1349, 1313, 1302, 1268, 1243, 1193, 1157, 1047, 1025, 1006, 951, 896, 851, 775, and 264 cm$^{-1}$±2 cm$^{-1}$.

An overview of the forms is presented in Table 8.

TABLE 8

Overview of crystalline forms of the free base of Formula (1).

| Form | Description | Stability at Room Temperature | Comments |
|---|---|---|---|
| Form I | anhydrous, non-solvated | stable relative to Form II below $a_w = 0.6$ | Stability at lower aw enables isolation of Form I from organic solvents |
| Form II | trihydrate | stable relative to Form I above $a_w = 0.6$ | Variable hydrate; contains up to about 10% water at variable levels |
| Form III | dihydrate | metastable | Higher energy variable hydrate; contains up to about 8% water at variable levels |
| Form IV | anhydrous, non-solvated | metastable | Form II dehydrated by low moisture |
| Form V | anhydrous, non-solvated | metastable | Form II dehydrated by heat |
| Form VI | methanol solvate | metastable | Organic solvate |
| Form VII | methanol solvate | metastable | Organic solvate |
| Form VIII | acetic acid disolvate | metastable | Organic solvate |

Figure 35:
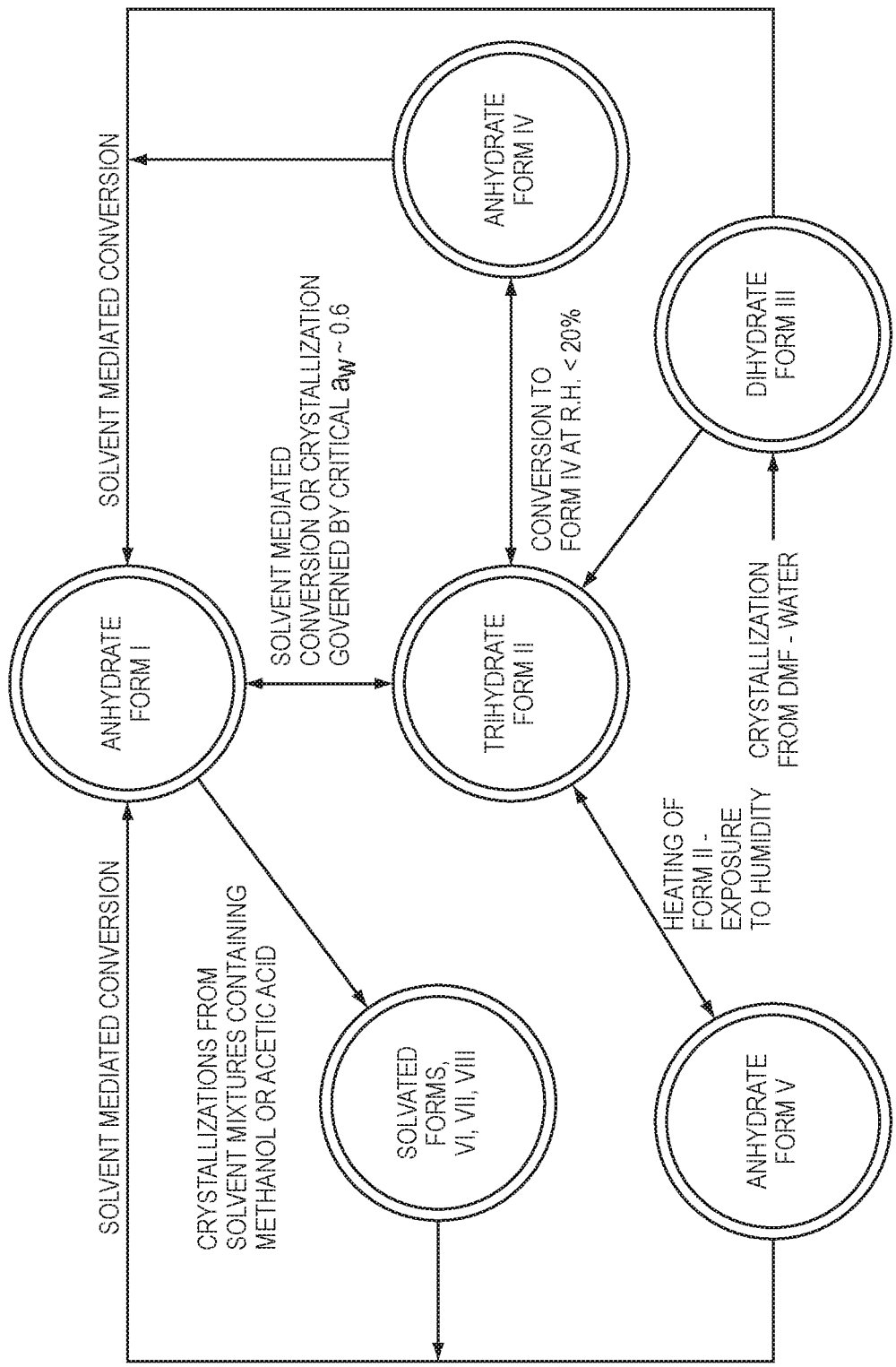
FIG. 35 illustrates the interrelationship between several forms of Formula (1).

A diagram showing the transformation scheme between the forms is given in FIG. 35. In FIG. 35, black arrows indicate that the transformation has been established by experiments, while blue arrows indicate that the transformation may occur.

Example 5. Preparation and Characterization of Amorphous (S)-4-(8-Amino-3-(1-(but-2-ynoyl)pyrrolidin-2-yl)imidazo[1,5-a]pyrazin-1-yl)-N-(pyridin-2-yl)benzamide Amorphous (S)-4-(8-amino-3-(1-(but-2-ynoyl)pyrrolidin-2-yl)imidazo[1,5-a]pyrazin-1-yl)-N-(pyridin-2-yl)benzamide can be prepared by various methods, including the procedure described in Example 6 of U.S. Patent Application Publication No US 2014/0155385 A1 and International Patent Application Publication No. WO 2013/010868 A1, the disclosure of which is incorporated herein by reference. Fast evaporation of the solvent from a solution in dichloromethane or in a mixture of dichloromethane with a co-solvent, e.g., acetone or an alcohol, can be used to prepare the amorphous form. In addition, the amorphous form can be produced by freeze drying of an aqueous solution that contains a small amount of an acid, e.g., formic acid or acetic acid, to solubilize the free base form I.

Figure 36:
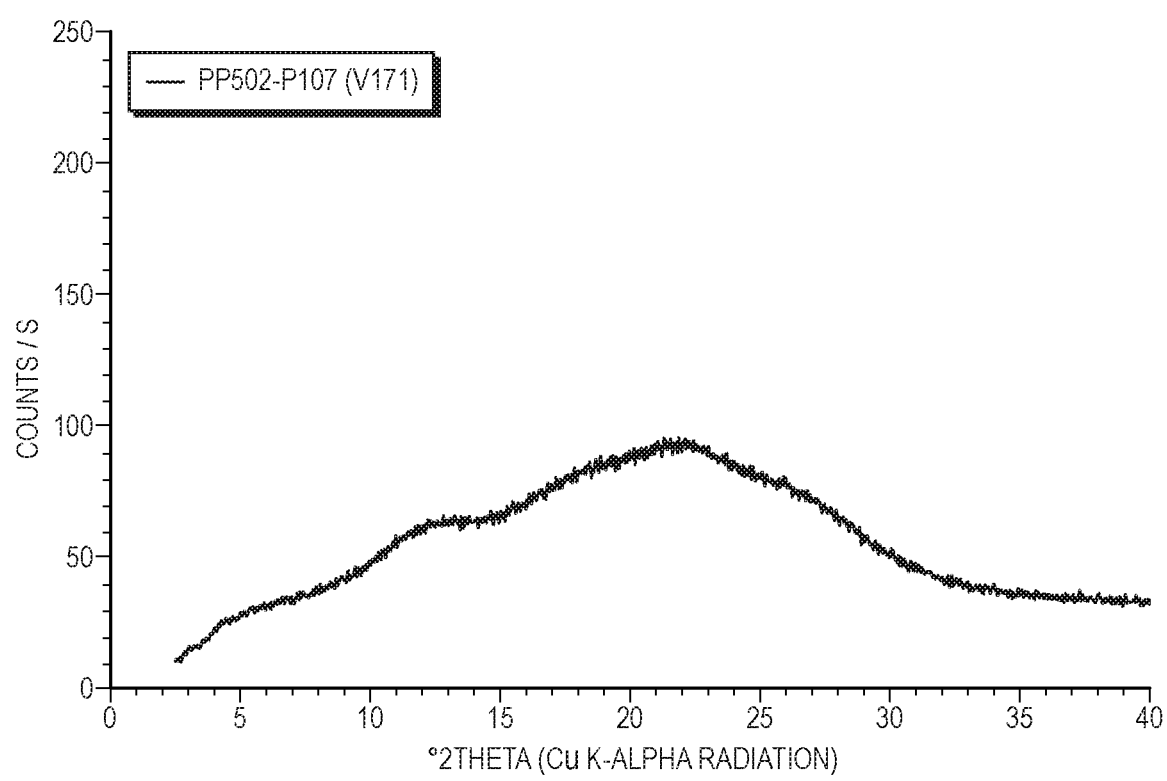
FIG. 36 illustrates the PXRD pattern of a sample of amorphous Formula (1).

Amorphous (S)-4-(8-amino-3-(1-(but-2-ynoyl)pyrrolidin-2-yl)imidazo[1,5-a]pyrazin-1-yl)-N-(pyridin-2-yl)benzamide can be prepared by adding 3.0 mL of water to 200 mg of crystalline Form I. Formic acid is then added dropwise until dissolution of the solid is complete. About 50 microliter of formic acid is typically sufficient to achieve complete dissolution of the form I. The clear solution is filtered into a 100 mL round flask through a 0.22 μm micropore polytetrafluoroethylene (PTFE) filter (for instance using a syringe) and the solution in the round flask is freeze dried. The resulting product (sample PP502-P107) is the amorphous form. Characterization of the product after freeze drying by powder X-ray diffraction reveals that the amorphous form is obtained. The resulting PXRD pattern is shown in FIG. 36. No Bragg reflections are observed, and the PXRD pattern is characterized by diffuse scattering typical of an amorphous material.

Figure 37:
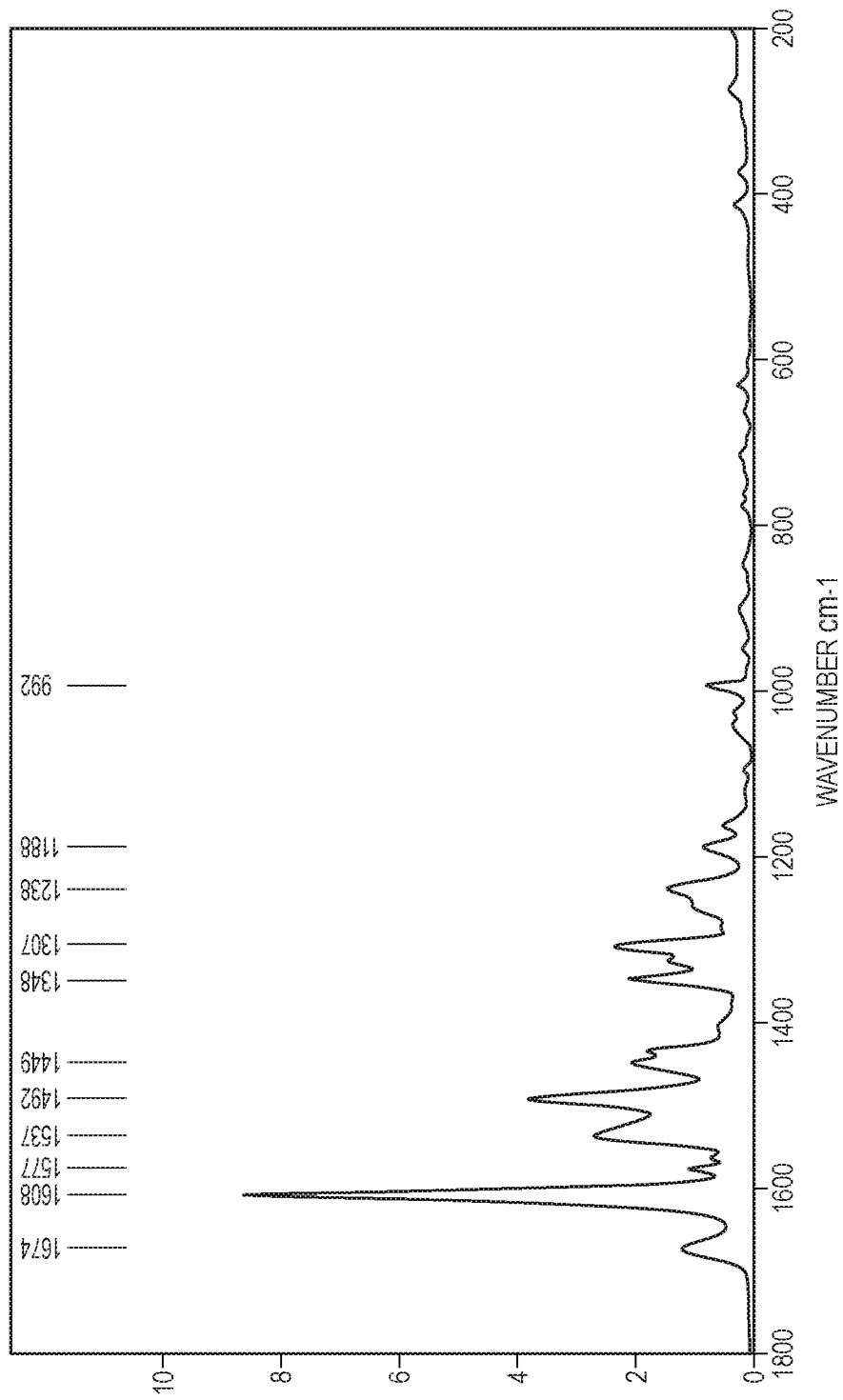
FIG. 37 illustrates the Raman spectrum of a sample of amorphous Formula (1).

An expanded region of the Raman spectrum of a similarly-prepared sample of amorphous Formula (1) (sample PP502-P118) is shown in FIG. 37. Characteristic Raman peaks are observed at 1674, 1608, 1577, 1537, 1492, 1449, 1348, 1307, 1238, 1188, and 992+/−4 cm$^{-1}$.

Figure 38:
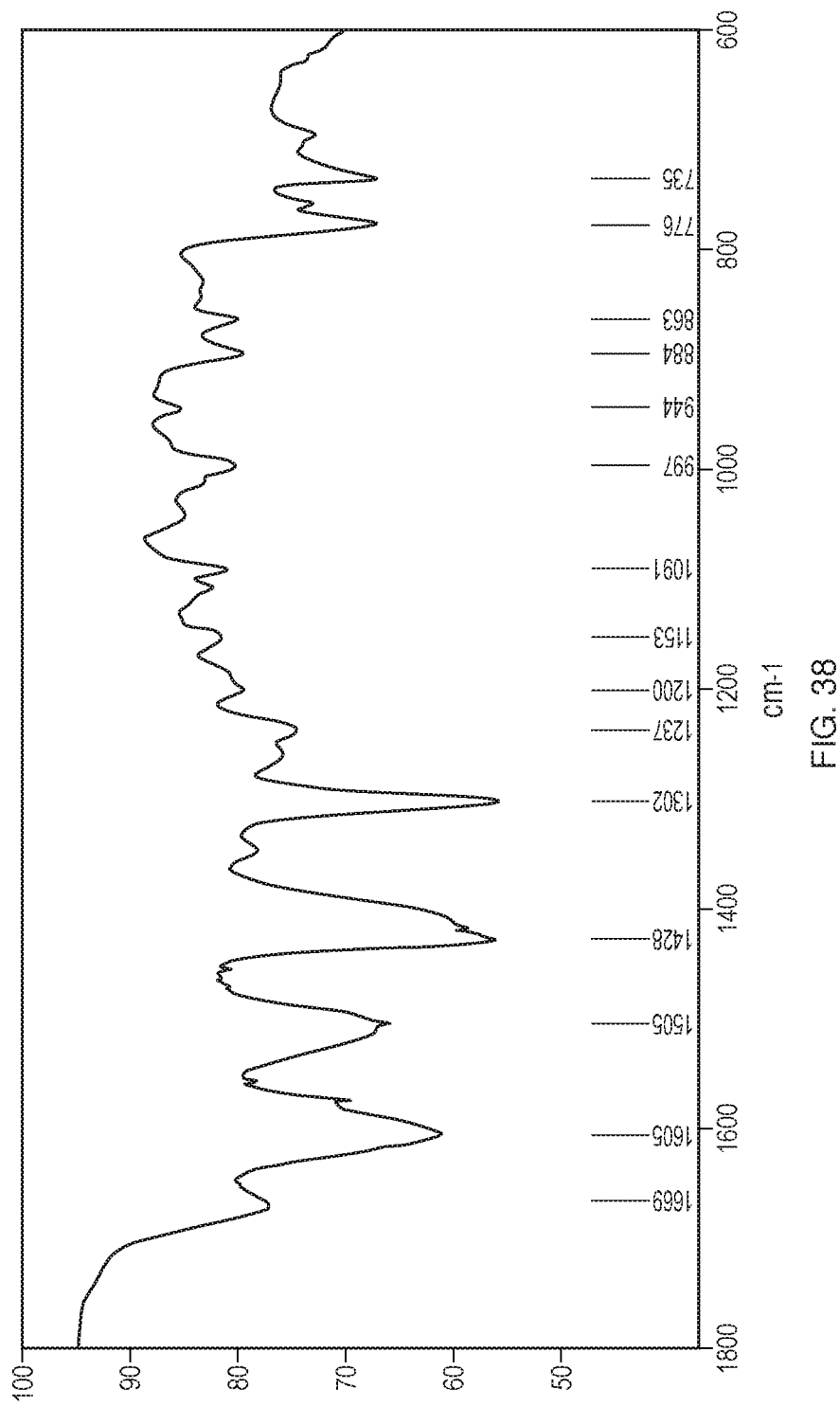
FIG. 38 illustrates the IR spectrum of a sample of amorphous Formula (1).

An expanded region of the IR spectrum of a similarly-prepared sample of amorphous Formula (1) (sample P502-P148) obtained with ATR sampling is shown in FIG. 38. The y-axis is shown in arbitrary units with a transmittance scale. Characteristic IR peaks are observed at 1668, 1605, 1505, 1428, 1302, 1237, 1200, 1153, 1091, 997, 944, 894, 863, 776, and 735+/−4 cm$^{-1}$ which are distinct from the spectra of other crystalline forms of Formula (1).

Figure 39:
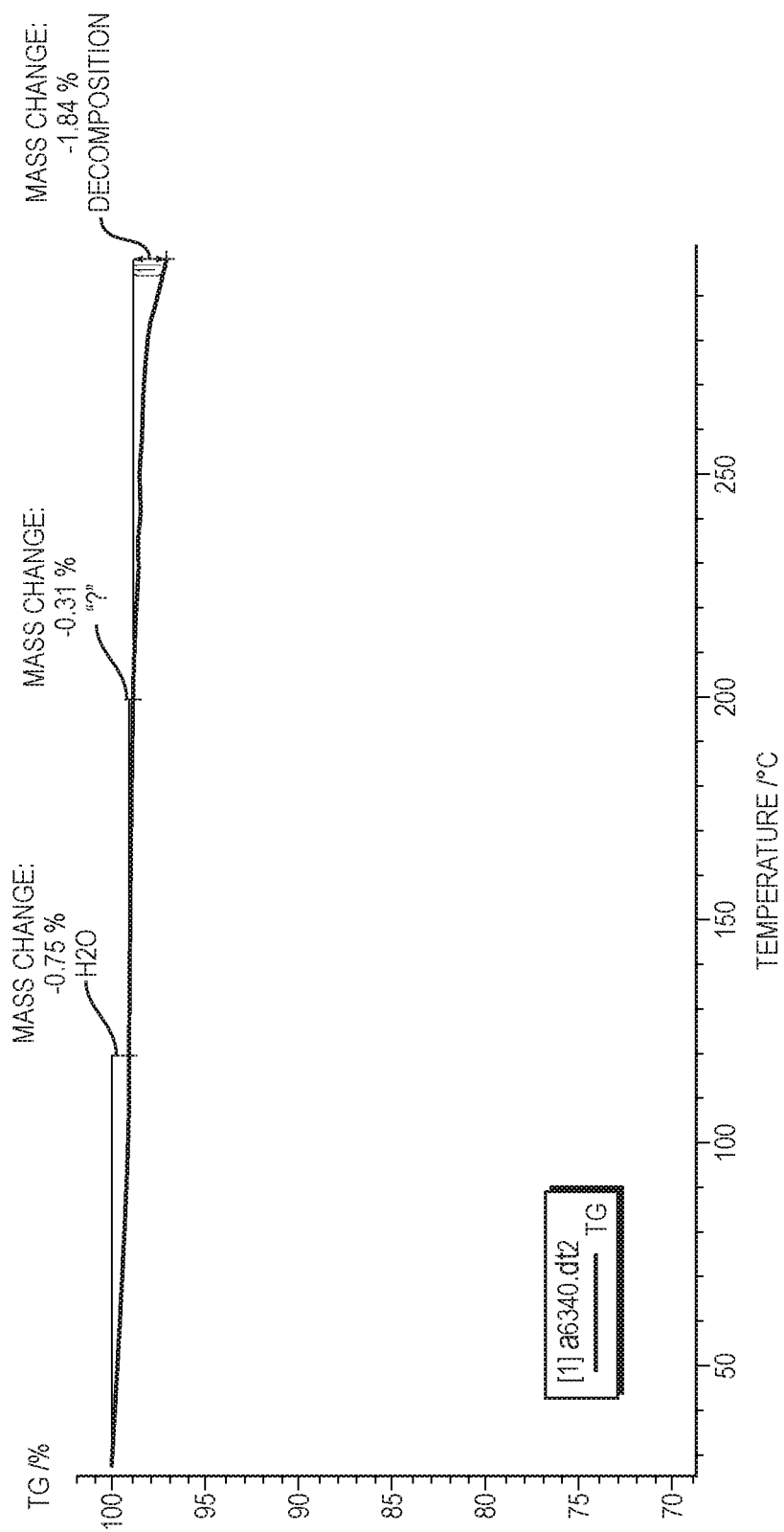
FIG. 39 illustrates a FTIR thermogram of a sample of amorphous Formula (1).
Figure 40:
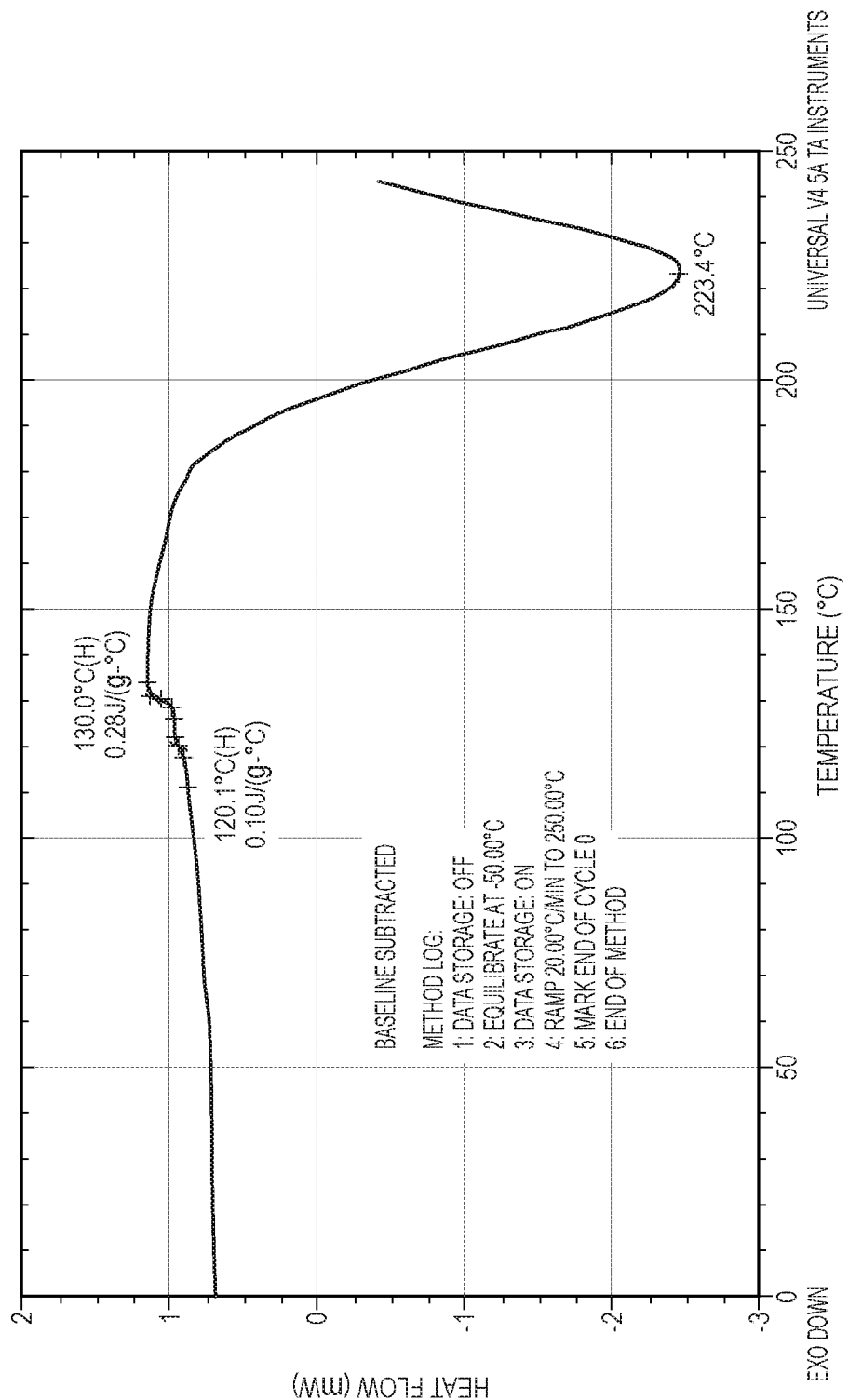
FIG. 40 illustrates a DSC thermogram of a sample of amorphous (Formula) (1).

Further characterization of the product after freeze drying by TG-FTIR revealed that a small amount of formic acid is present. Therefore, the obtained amorphous sample was further dried under vacuum at 80° C. for about 20 hours and retested by TG-FTIR and DSC. The TG-FTIR and DSC thermograms of sample PP502-P107A are shown in FIG. 39 and FIG. 40, respectively. TG-FTIR of the dried sample showed that only very little water and residual solvent was present. DSC of the essentially solvent-free amorphous form shows a glass transition temperature at about 130° C. with a $\Delta C_p$ of about 0.3 J/(g·K). A smaller change of the heat capacity at about 120° C. might be due to another fraction of amorphous material that might contain traces of solvents, thus showing a reduced glass transition temperature. Thermal degradation begins above about 160° C.

The DVS results for a similarly-prepared sample of amorphous Formula (1) (sample P502-P148), including sorption and desorption curves, was performed by exposing samples to a starting 50% RH, decreasing humidity to 0% RH, increasing humidity to 95% RH, and finally decreasing humidity back to the starting 50% RH. The DVS results, including sorption and desorption curves, show that significant water gain occurs during sorption starting at about 20% RH. The total water gain observed between 0% RH and 80% RH is about 6% by weight, which indicates that Form II is hygroscopic according to the EP classification (see Example 1.2). Furthermore, the total mass gained up to 95% RH is approximately 13%, and the mass is irreveribily gained after sorption (with the final decrease to 50% RH only removing 5% of the 10% moisture gained in the 50 to 95% RH range). The results illustrate the hygroscopic nature of the amorphous form, including the irreversible uptake of a large amount of water upon exposure to high RH.

Example 6. Crystalline Salts of (S)-4-(8-Amino-3-(1-(but-2-ynoyl)pyrrolidin-2-yl)imidazo[1,5-a]pyrazin-1-yl)-N-(pyridin-2-yl)benzamide A salt screening with (S)-4-(8-amino-3-(1-(but-2-ynoyl)pyrrolidin-2-yl)imidazo[1,5-a]pyrazin-1-yl)-N-(pyridin-2-yl)benzamide free base (sample PP502-P1, prepared as described above, comprised crystallization experiments with 11 different acids, including: benzoic acid, benzenesulfonic acid, citric acid, fumaric acid, hydrochloric acid, maleic acid, nicotinic acid, phosphoric acid, saccharin, succinic acid, and L-tartaric acid. Of these, crystalline samples were obtained with citric acid, fumaric acid, maleic acid, phosphoric acid, succinic acid and L-tartaric acid.

A summary of the starting materials for the salt preparations is provided in Table 9. Each prepared product was given a sample identifier as follows: SP221-XXX-Pn (XXX=salt identification code, and n=experiment/sample number).

TABLE 9

Summary of starting materials for salt preparation.

| Compound | pK$_a$ | m [g/mol] | Source/ Number | Sample Designation |
|---|---|---|---|---|
| Free base | ~5.7 | 465.5 | Formula (1)/ CML1476, Lot CS13-083 HB873-98 | PP502-P1 |
| Fumaric acid | 3.0 (4.4) | 116.07 | Sigma # 240745 | SP221-FUM-Pn |
| Maleic acid | 1.9 (6.2) | 116.1 | Fluka # 63180 | SP221-MLE-Pn |
| Phosphoric acid | 2.0 (7.1) | 98.0 | Fluka # 79606 | SP221-PO4-Pn |
| L-Tartaric acid | 3.0 (4.4) | 150.09 | Fluka # 95310 | SP221-LTA-Pn |

Characterization of fumarate salt, maleate salt, phosphate salt and L-tartrate salt was conducted using $^1$H NMR spectroscopy, TG-FTIR, DSC, dynamic vapor sorption, optical microscopy, high-performance liquid chromatography (HPLC) purity, laser diffraction, approximate bulk and tapped density, and aqueous solubility analytical techniques.

Once seeding crystals were obtained, the formation of crystalline salts was shown to be reproducible, with the various salts showing a good tendency towards crystallization. A summary of salt properties is detailed in Table 10.

TABLE 10

Summary of Formula (1) salt properties in comparison to free base.

| Salt | Solubility (3 hours) | Melting Pt./ Thermal Stability (Decomposition Pt.) | Behavior in DVS | Solid Form Assessment |
|---|---|---|---|---|
| Free base | S < 1 mg/mL | 215° C., (Form I) | Form I is not hygroscopic; higher melting point | Anhydrate Form I and trihydrate Form II |
| Fumarate | ~1.8 mg/mL | ~170° C./ 170° C. | Reversible anhydrate-hydrate formation, $\Delta$m~0.8% (20-80% RH) | Sesquihydrate, possibly multiple forms |
| Maleate | 2.2 mg/mL | ~161° C./ 170° C. | Water more strongly bound than in the fumarate, $\Delta$m~0.7% (20-80% RH) | Possibly sesquihydrate, multiple forms |
| Phosphate | 9.8 mg/mL | ~15° C./ 180° C. | Reversible anhydrate-hydrate formation, $\Delta$m~0.7% (20-80% RH) | At least two forms, anhydrate and hydrate |
| L-Tartrate | 5.3 mg/mL | ~158° C./ 165° C. | Does not completely dehydrate at 0% RH, $\Delta$m~0.7% (20-80% RH) | Possibly sesquihydrate, possibly multiple forms |

Because the solubility was measured after an equilibration time of only three hours and without adjustment of pH, the solubility of all salts is dramatically increased in comparison to the free base. Whereas the free base is a poor water soluble drug, the salts were well soluble in water.

All of the salts described above appear to form hydrates. Preliminary test experiments consisted of one to three suspension equilibration experiments for each salt. Results show that all four salts can exist in multiple solid forms including polymorphic forms.

Example 6.1. Form A of the Fumarate Salt of Formula (1)

Crystalline Form A of the fumarate salt of Formula (1) was prepared by dissolving 16.294 g of PP502-P1 free base and 4.065 g fumaric acid in 500 mL acetone. The mixture was subsequently heated to 50° C., whereby 50 mL of water was added. The water addition led to a clear solution at which time, the solution was allowed to cool to room temperature while stirring at about 300 rpm. At room temperature, the clear solution was seeded with about 20 mg of SP221-FUM-P5 and after about 48 hours, the suspension was filtered to obtain a solid which was dried in air at 40° C. for about 24 hours. Initial characterization of the obtained solid resulted in a yield of approximately 13.6 grams (about 64%) at about 99.9% purity, as measured by high-performance liquid chromatography (HPLC).

Form A of the fumarate salt was characterized by $^1$H NMR spectroscopy; optical microscopy, Fraunhofer laser diffraction, reflection PXRD (FIG. 41), TG-FTIR, DSC and dynamic vapor sorption (DVS).

The $^1$H NMR spectrum of the fumarate salt (sample SP221-FUM-P9) was recorded in acetone solvent and confirmed the composition is consistent with a 1:1 fumarate salt. A peak near 2.1 ppm indicates a trace of acetone as residual solvent that is still present after drying.

The fumarate salt was obtained as small particles. Because the obtained salt was clumpy, the dried material was sieved through a 500 µm sieve prior to further characterization. Examination by polarized light optical microscopy was conducted by dispersing the compound in heptane and thereafter sonicating for short period of time sufficient to disperse the crystals. Optical microscopy revealed very small crystalline particles that, after sieving and dispersion, are still largely agglomerated.

Particle size distribution testing was conducted using Fraunhofer laser diffraction with values for the maximum particle size for a given percentage volume of the sample shown in Table 11 below. For example, the size dimension at ×50 (42 µm) represents the maximum particle diameter below which 50% of the sample volume exists. This parameter is also known as the median particle size by volume.

TABLE 11

Particle size distribution results for the fumarate salt.

| Sample | 10 | x50 (median) | x90 |
|---|---|---|---|
| SP221-FUM-P9a | 3.6 µm | 42 µm | 329 µm |

By monitoring these three parameters (×10, ×50, ×90), it is possible to determine if there are significant changes in the main particle size, as well as changes at the extremes of the distribution, possibly due to the presence of fines or oversized particles or agglomerates in the particle size distribution. Static light scattering techniques such as laser diffraction give a volume weighted distribution wherein the contribution of each particle in the distribution relates to the volume of that particle (equivalent to mass if the density is uniform). This is extremely useful since the distribution represents the composition of the sample in terms of its volume/mass.

Figure 41:
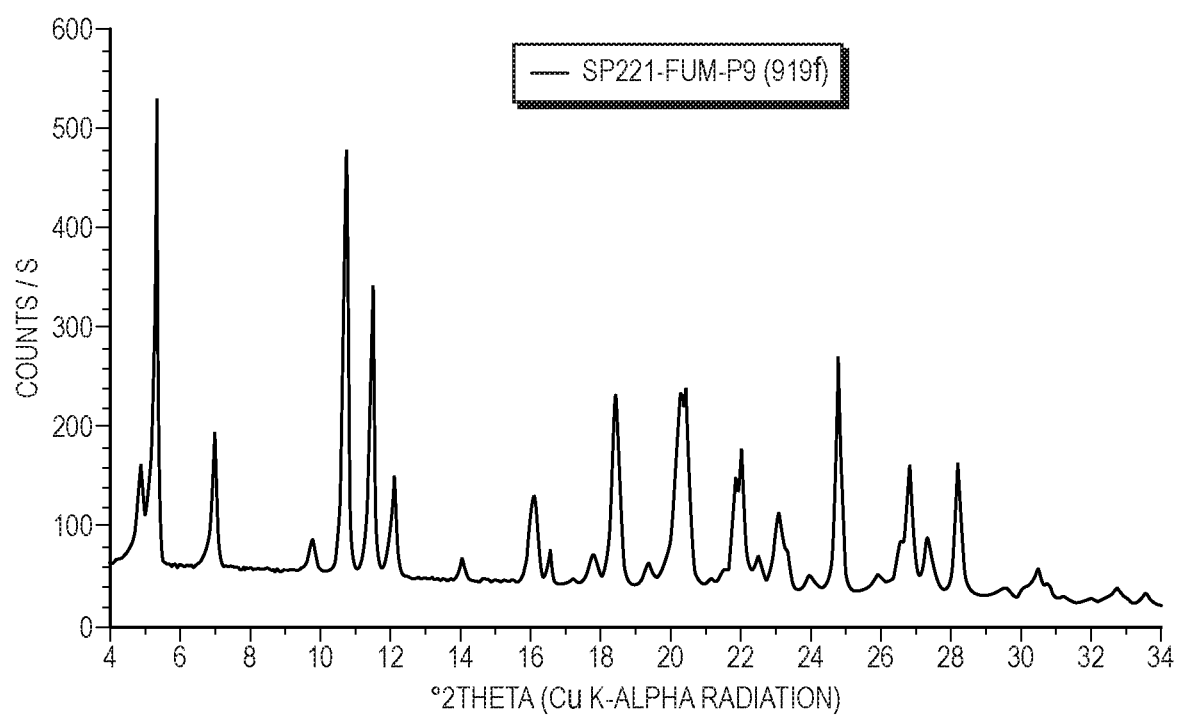
FIG. 41 illustrates PXRD patterns of the fumarate salt of Formula (1).

PXRD, along with the optical microscopy images, confirmed the crystalline nature of the salt. The reflection PXRD pattern of fumarate salt sample SP221-FUM-P9 is depicted in FIG. 41 and shows the following representative peaks at: 4.9, 5.4, 7.0, 9.8, 10.8, 11.5, 12.1, 14.1, 16.1, 16.6, 17.8, 18.5, 19.4, 20.3, 2056, 21.9, 22.1, 22.5, 23.1, 24.0, 24.8, 26.6, 26.8, 27.3, and 28.2±0.2° 2θ.

Thermoanalytical characterization of Form A of the fumarate salt was carried out using TG-FTIR and DSC. TG-FTIR analysis of a representative crystalline Formula (1) fumarate sample revealed a mass loss of about 4.5%; this is essentially attributable to water loss. The amount of water attributed to the loss in mass closely matches the theoretical water content of a sesquihydrate at 4.6%. Mass loss of about 12.75% upon heating thereafter to approximately 300° C. was due primarily to decomposition. DSC of the same sample shows an endothermic peak near 162° C. that deviates from the baseline above about 120° C. and increases slowly. However, because of an exothermic degradation beginning at around 170° C., the enthalpy of fusion cannot be evaluated reliably.

Hygroscopic behavior of the fumarate salt (sample SP221-FUM-P9a) was measured using dynamic vapor sorption. The DVS sorption and desorption results indicate that the salt loses nearly all water content at low humidity conditions while reaching a maximum saturation of approximately 6% at a RH of about 95%. The water content change between 20% and 80% RH is about 0.8%. Similar to previously described moisture adsorption-desorption isotherms, samples were exposed to a starting 50% RH, decreasing humidity to 0% RH, increasing humidity to 95% RH, and finally decreasing humidity back to the starting 50% RH.

Example 6.2. Form A of the Maleate Salt of Formula (1)

Crystalline Form A maleate salt (sample SP221-MLE-P9) was prepared by dissolving 16.296 g of PP502-P1 free base in a 350 mL of acetone and 35 mL of water mixture. The mixture was subsequently heated to 50° C., which led to a clear solution. Thereafter, 20 mL of an aqueous solution containing 4.043 g of maleic acid was added. Moreover, the vessel and pipette holding the aqueous maleic acid solution were washed with 1.0 mL of water and the wash solution was also included in the mixture. The solution was allowed to cool while stirring at about 300 rpm. At about 45° C., the solution was seeded with about 20 mg of SP221-MLE-8 and further cooled to approximately 20° C. After about 24 hours, the suspension was filtered to obtain a solid which was dried in air at 40° C. for about 20 hours. Initial characterization of the obtained solid resulted in a yield of approximately 14.1 grams (about 66%).

The maleate salt was characterized by $^1$H NMR spectroscopy, optical microscopy, Fraunhofer laser diffraction, reflection PXRD (FIG. 42), TG-FTIR, DSC, and DVS.

The $^1$H NMR spectrum of the maleate salt (sample SP221-MLE-P9), recorded in acetone solvent, confirmed the composition and is consistent with a 1:1 maleate salt. Similar to the $^1$H NMR analysis of the fumarate salt of Formula (1), a minute trace (0.7%) of acetone as residual solvent is also present in the spectra.

Examination by polarized optical microscopy revealed that the maleate salt consists of small crystalline particles ranging in size from about 10 μm to about 100 μm. The prepared maleate salt was substantially larger than the particles of the fumarate salt (discussed above), the phosphate salt and the L-tartrate salt (latter two discussed below). The fine powder showed favorable flow properties and no sieving was necessary after drying.

Particle size distribution testing was conducted using Fraunhofer laser diffraction with values for the maximum particle size for a given percentage volume of the sample shown in Table 12 below.

TABLE 12

Particle size distribution results for the maleate salt.

| Sample | x10 | x50 (median) | x90 |
|---|---|---|---|
| SP221-MLE-P9 | 10.7 μm | 38 μm | 73 μm |

Particle size distribution function for the maleate salt and optical microscopy images confirm a particle size distribution ranging roughly between 10 μm and 100 μm.

Figure 42:
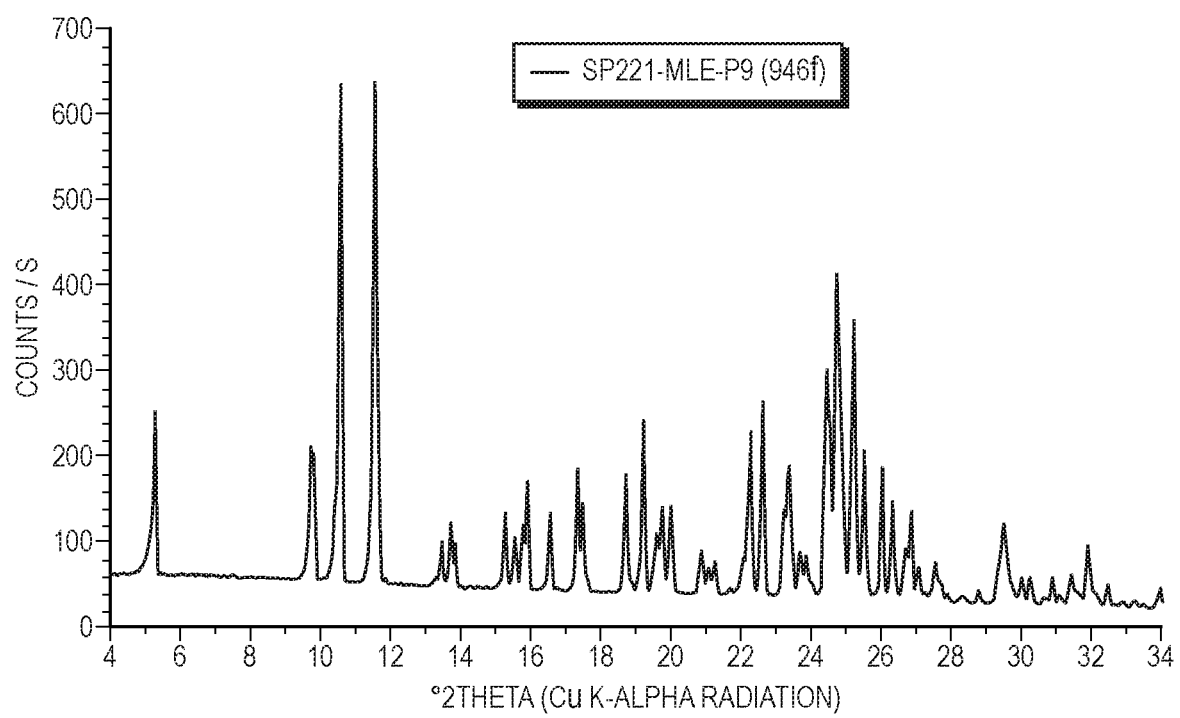
FIG. 42 illustrates a PXRD pattern of Formula (1) maleate salt of Formula (1).

Powder X-ray diffraction, along with the optical microscopy, confirmed the crystalline nature of the salt. The reflection PXRD pattern of maleate salt sample SP221-MLE-P9 is depicted in FIG. 42 and shows the following representative peaks at: 5.3, 9.8, 10.6, 11.6, 13.5, 13.8, 13.9, 14.3, 15.3, 15.6, 15.8, 15.9, 16.6, 17.4, 17.5, 18.7, 19.3, 19.6, 19.8, 20.0, 20.9, 21.3, 22.0, 22.3, 22.7, 23.2, 23.4, 23.7, 23.9, 24.5, 24.8, 25.2, 25.6, 26.1, 26.4, 26.7, 26.9, 27.1, 27.6, 28.8, 29.5, 30.0, 30.3, 30.9, 31.5, 31.9, 32.5, 34.0, and 35.1° 2θ±0.2° 2θ.

Thermoanalytical characterization of the maleate salt was carried out using TG-FTIR, and DSC. TG-FTIR analysis of the representative crystalline Formula (1) maleate sample revealed a mass loss of about 5.3%; this is essentially attributable to water loss. The amount of water attributed to the loss in mass closely matches the theoretical water content of sesquihydrates at 4.6%. However, no acetone was detected. Mass loss of about 10.1% upon heating thereafter to approximately 300° C. was due primarily to decomposition. DSC of the same sample shows an endothermic peak near 174° C., followed by decomposition.

Hygroscopic behavior of the maleate salt (sample SP221-MLE-P9) was measured using dynamic vapor sorption. The DVS sorption and desorption results indicate that the salt loses very little water at 0% RH. The sample reaches a maximum saturation of approximately 5.8% at a RH of about 95%. The water content change between 20% and 80% RH is about 0.5%. Samples were exposed to a starting 50% RH, decreasing humidity to 0% RH, increasing humidity to 95% RH, and finally decreasing humidity back to the starting 50% RH.

Example 6.3. Form A of the Phosphate Salt of Formula (1)

Preparation of Form A of the phosphate salt of Formula (1) was accomplished as follows. First, 350 mL of acetone and 35 mL of water were added to 16.2998 grams (35 mmol) of Formula (1) free base PP502-P1. Upon heating to 50° C., a clear solution was obtained. To this solution was slowly added 2.5 mL of 85-90% phosphoric acid (35 mmol). The solution was allowed to cool while stirring at about 300 rpm. At about 38° C., crystallization was observed without seeding. After about 80 hours the suspension was filtered and the obtained solid was dried in air at 40° C. for about 24 hours. The yield was approximately 20.48 grams (97%). The phosphate salt was obtained as small particles. After drying the material was clumpy and very strongly agglomerated particles were observed. In order to obtain a free flowing powder for the tapped density test and particle size analysis, the dried material was sieved through a 500 μm sieve. The sample after drying was termed SP221-PO4-P5 and the sample after sieving was termed SP221-PO4-P5a.

Initial characterization of the obtained solid resulted in a purity of about 99.9%, as measured by HPLC. Based on DVS and TG-FTIR, the phosphate salt form produced is likely to be a dihydrate having a theoretical phosphorus content of about 5.2%. The phosphorus content was examined by inductively-coupled plasma optical emission spectrometry (ICP-OES) and was determined to be approximately 4.7%, which is slightly below the required content for a 1:1 salt.

The phosphate salt was characterized by $^1$H NMR spectroscopy, optical microscopy, Fraunhofer laser diffraction, reflection PXRD (FIG. 43), TG-FTIR, DSC, and DVS.

$^1$H NMR spectroscopy confirmed the composition was consistent with the structure of a crystalline phosphate salt. Examination by polarized optical microscopy revealed that the phosphate salt was a crystalline material that consisted of very small particles, most of which were less than about 10 μm in diameter. Sample SP221-PO4-P4 shows needle-shaped particles. While needles are not clearly visible for sample SP221-PO4-P5, one reason might be because of the small size of the particles.

Particle size distribution testing was conducted using Fraunhofer laser diffraction with values for the maximum particle size for a given percentage volume of the sample shown in Table 13 below.

TABLE 13

Particle size distribution results for the phosphate salt.

| Sample | x10 | x50 (median) | x90 |
|---|---|---|---|
| S13221-PO4-P5 | 2.8 μm | 29 μm | 191 μm |

Figure 43:
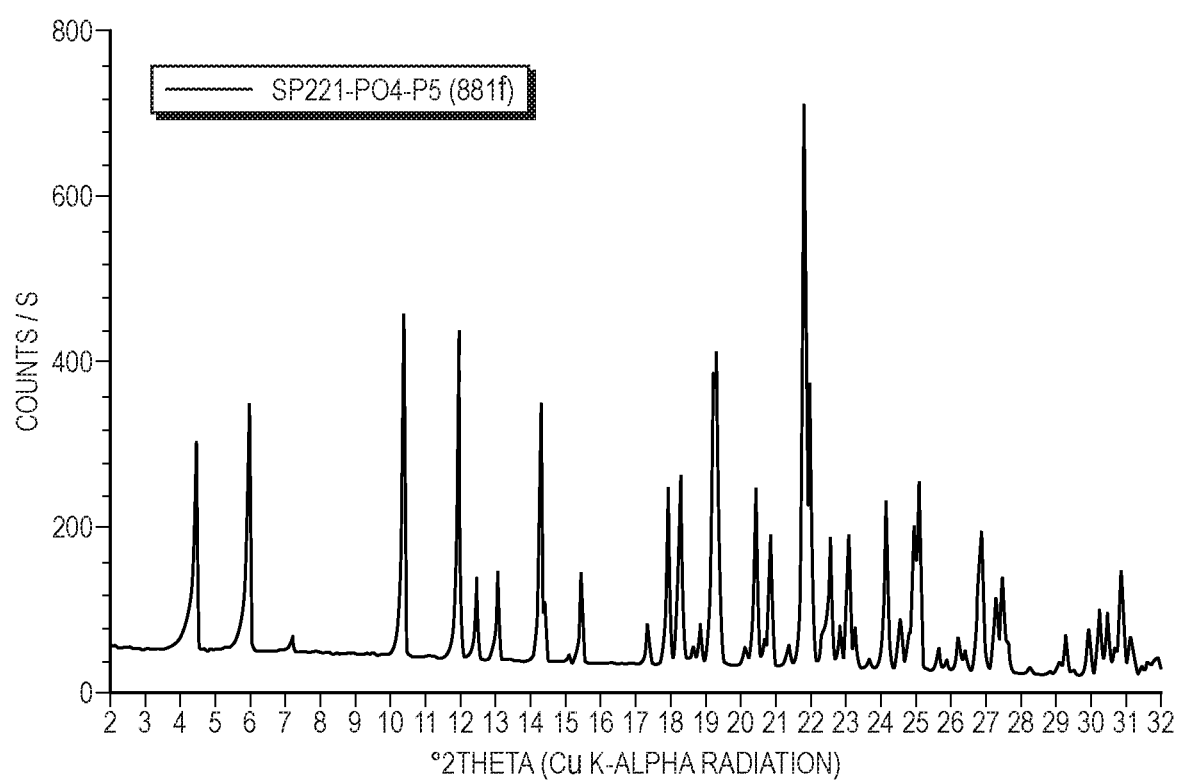
FIG. 43 illustrates a PXRD pattern of the phosphate salt of Formula (1).

PXRD confirmed the crystalline nature of the salt. The reflection PXRD pattern of a sample taken from a 20 gram batch of sample SP221-PO4-P5 phosphate salt is depicted in FIG. 43 and shows the following representative peaks at: 4.5, 6.0, 7.2, 10.4, 12.0, 12.5, 13.1, 14.3, 15.5, 17.4, 18.0, 18.3, 18.9, 19.3, 20.2, 20.5, 20.9, 21.4, 21.9, 22.0, 22.6, 22.9, 23.1, 23.3, 24.2, 24.6, 25.0, 25.7, 26.2, 26.4, 26.9, 27.3, 27.5, 29.3, 30.0, 30.3, 30.5, 30.9, 31.2, 31.9, and 35.7° 2θ±0.2° 2θ. The phosphate salt exists in at least two different crystalline forms, an anhydrous form of the crystalline structure and a hydrate form of the crystalline structure, with each form exhibiting unique PXRD patterns. The peaks of FIG. 44 correspond to the hydrate form of the crystalline phosphate salt.

Thermoanalytical characterization of the phosphate salt was carried out using TG-FTIR and DSC. TG-FTIR analysis of the crystalline Formula (1) phosphate salt (sample SP221-PO4-P1) revealed a mass loss of about 5.9%; this is essentially attributable to water loss. This result suggests that the obtained crystalline form of the phosphate is a dihydrate since the 5.9% water content of the phosphate sample is close to the expected content for a dihydrate (6.0%). Additional mass losses upon heating thereafter to approximately 250° C. were due primarily to decomposition. DSC of the same sample shows a broad endothermic peak near 138° C. The enthalpy of fusion is estimated to about 134 J/g.

Hygroscopic behavior of the phosphate salt (sample SP221-PO4-P1) was measured using DVS. The DVS sorption and desorption results indicate that the salt loses nearly all water content at low RH conditions while reaching a reaching a maximum saturation of approximately 6.6% at a RH of about 95%. DVS analysis suggests that the phosphate salt forms a dihydrate with a water content of about 6.0%. Samples were exposed to a starting 50% RH, decreasing humidity to 0% RH, increasing humidity to 95% RH, and finally decreasing humidity back to the starting 50% RH.

Example 6.4. Form A of the L-Tartrate Salt of Formula (1)

Crystalline Form A of Formula (1) L-tartrate salt was prepared by dissolving 16.298 g of PP502-P1 free base in a 350 mL of acetone and 35 mL of water mixture. The mixture was subsequently heated to 50° C., which led to a clear solution. Thereafter, 20 mL of an aqueous solution containing 5.257 g of L-tartaric acid was added to the clear solution. The solution was allowed to cool to approximately 20° C. while stirring at about 300 rpm. After about 24 hours, the suspension was filtered to obtain a solid which was dried in air at 40° C. for about 20 hours. Initial characterization of the obtained solid resulted in a yield of approximately 20.1 grams (about 89%) at about a 99.78% purity, as measured by HPLC.

The L-tartrate salt was characterized by $^1$H NMR spectroscopy, optical microscopy, Fraunhofer laser diffraction, reflection PXRD (FIG. 44), TG-FTIR, DSC, and DVS.

$^1$H NMR spectroscopy confirmed the composition was consistent with the structure of a 1:1 crystalline L-tartrate salt. The L-tartrate salt was obtained as a crystalline material; examination by polarized optical microscopy revealed that the material consists of partially agglomerated fine needles varying in length from about 2 to about 40 μm and widths on the order of a few μm.

Particle size distribution testing was conducted using Fraunhofer laser diffraction with values for the maximum particle size for a given percentage volume of the sample shown in Table 14 below.

TABLE 14

Particle size distribution results for the L-tartrate salt.

| Sample | ×10 | ×50 (median) | ×90 |
| --- | --- | --- | --- |
| SP221-LTA-P8a | 1.7 μm | 17 μm | 59 μm |

PXRD, along with the optical microscopy, confirmed the crystalline nature of the salt. The reflection PXRD pattern of L-tartrate salt sample SP221-LTA-P8 is depicted in FIG. 80 and shows the following representative peaks at: 4.6, 5.5, 7.2, 9.3, 10.7, 10.9, 11.8, 14.3, 14.9, 16.4, 17.0, 17.7, 19.2, 19.4, 19.5, 20.3, 21.6, 22.4, 23.3, 23.8, 24.3, 24.5, 24.7, 25.1, 25.6, 26.8, 27.2, 27.8, 28.4, 28.7, 29.0, 29.5, 30.0, 30.9, 31.6, 32.1, 32.4, 33.0, 33.5, and 33.9° 2θ±0.2° 2θ.

Thermoanalytical characterization of the L-tartrate salt was carried out using TG-FTIR and DSC. TG-FTIR analysis of the crystalline Formula (1) L-tartrate salt (sample SP221-LTA-P8) revealed a mass loss of about 4.8%; this is essentially attributable to water loss. This amount of water is near the theoretical amount of water for a sesquihydrate which is 4.3%. Additional mass loss of about 20% upon heating thereafter to approximately 300° C. was due primarily to decomposition. DSC of the same sample shows an endothermic peak near 156.5° C. with an enthalpy of fusion of about 40.70 J/g.

Hygroscopic behavior of the L-tartrate salt (sample SP221-LTA-P8a) was measured using dynamic vapor sorption. The DVS sorption and desorption results indicate that the salt loses water at low humidity conditions while reaching a maximum saturation of approximately 5.4% at a RH of about 95%. Moreover, from an initial water content of about 4.8% at 50% RH (confirmed by TG-FTIR), the DVS analysis suggests that about 30% of this water was removed within the timescale of the measurement. The water content change between 20% and 80% RH is about 0.7%. Moisture adsorption-desorption isotherms were prepared in a similar manner as described above.

Example 7. Solubility as a Function of pH

Example 7.1. Free Base Solubility

The aqueous solubility of Formula (1) free base was examined as a function of pH. Experiments were conducted in aqueous HCl solution and buffer solutions at pHs of 1, 3, 5, 6.8, 7.4 and 9. It was determined that at low pH values of 1 and 3, the solid completely dissolved over the equilibration time while the pH in the system stabilized to approximately 3 in both experiments. It was found that the solubility in HCl solution having a pH of about 1 is at least 150 mg/mL. Solubility of the free base Form I (PP502-P1) at various pH values greater than 3 is presented in Table 15.

TABLE 15

Solubility data for Formula (1) free base.

| Effective pH at the end of the test | Solubility (mg/mL) |
| --- | --- |
| 5.0 | 0.69 |
| 6.7 | 0.056 |
| 7.3 | 0.049 |
| 8.9 | 0.051 |

Figure 45:
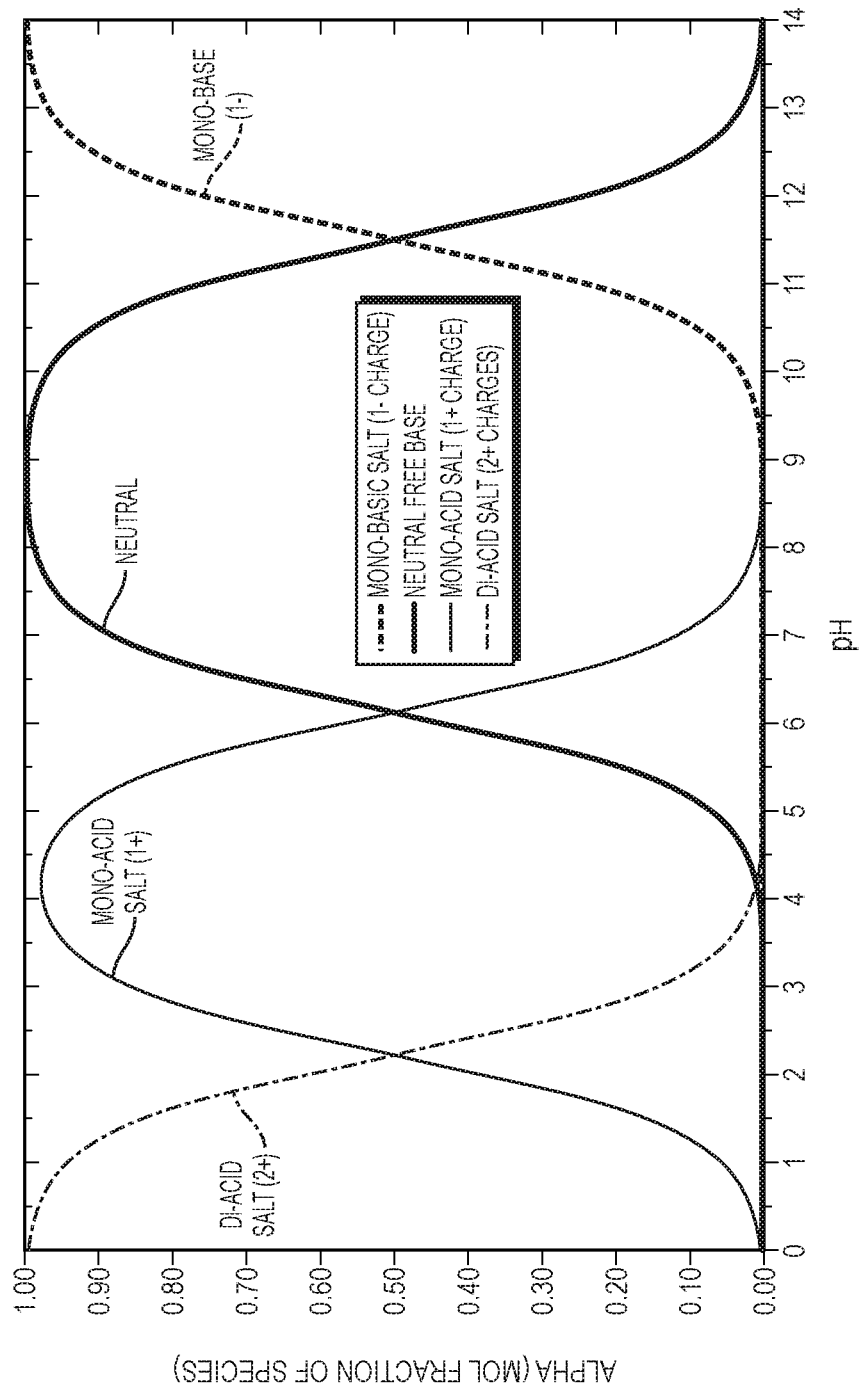
FIG. 45 illustrates a species distribution for Formula (1) based on calculated pH values: 2.2, 6.1 and 11.5.

Data shows that aqueous solubility of Formula (1) free base (sample PP502-P1) stabilizes at approximately 50 μg/mL at about pH 6.7. FIG. 45 displays the possible species of Formula (1) based on the calculated p$K_a$ values ranging from 2.2 (basic) to 6.1 (basic) to 11.5 (acidic). Therefore, a doubly-positive charged molecule is highly soluble in water, whereas the singly positive and the neutral forms are poorly soluble. This highlights the challenges in successful delivery of Formula (1) through the stomach into the higher pH environment of the duodenum.

Figure 46:
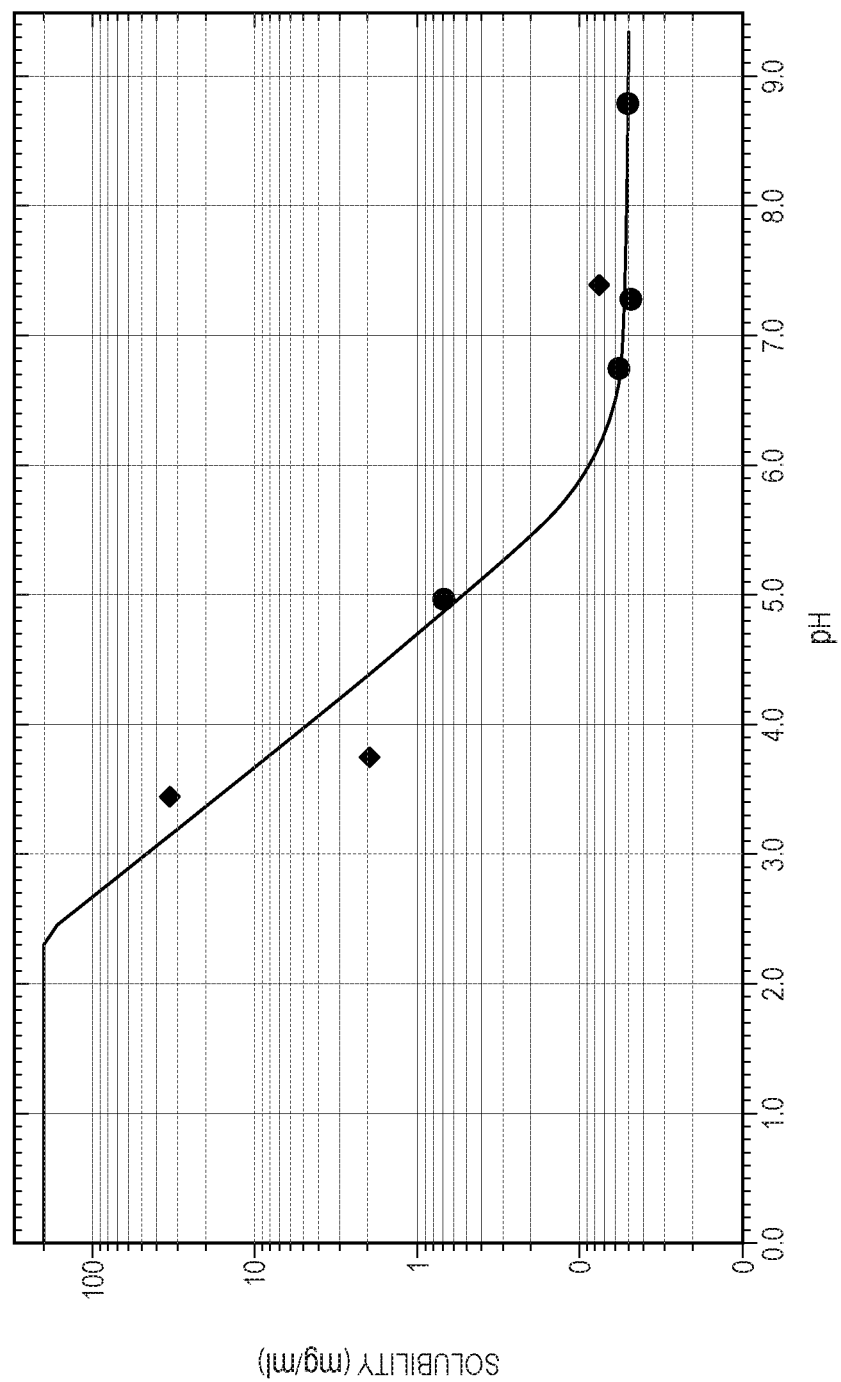
FIG. 46 illustrates the pH-dependent solubility of the free base of Formula (1) with HCl and buffer solutions as the solvent media.

The equilibrium pH-solubility relationship calculated for the free base of Formula (1) is shown in FIG. 46 in comparison to experimental measurements at selected intervals. At pH 6.7 and greater, the aqueous solubility reaches a constant level of about 50 μg/mL, further illustrates the challenges of delivery of Formula (1).

Figure 47:
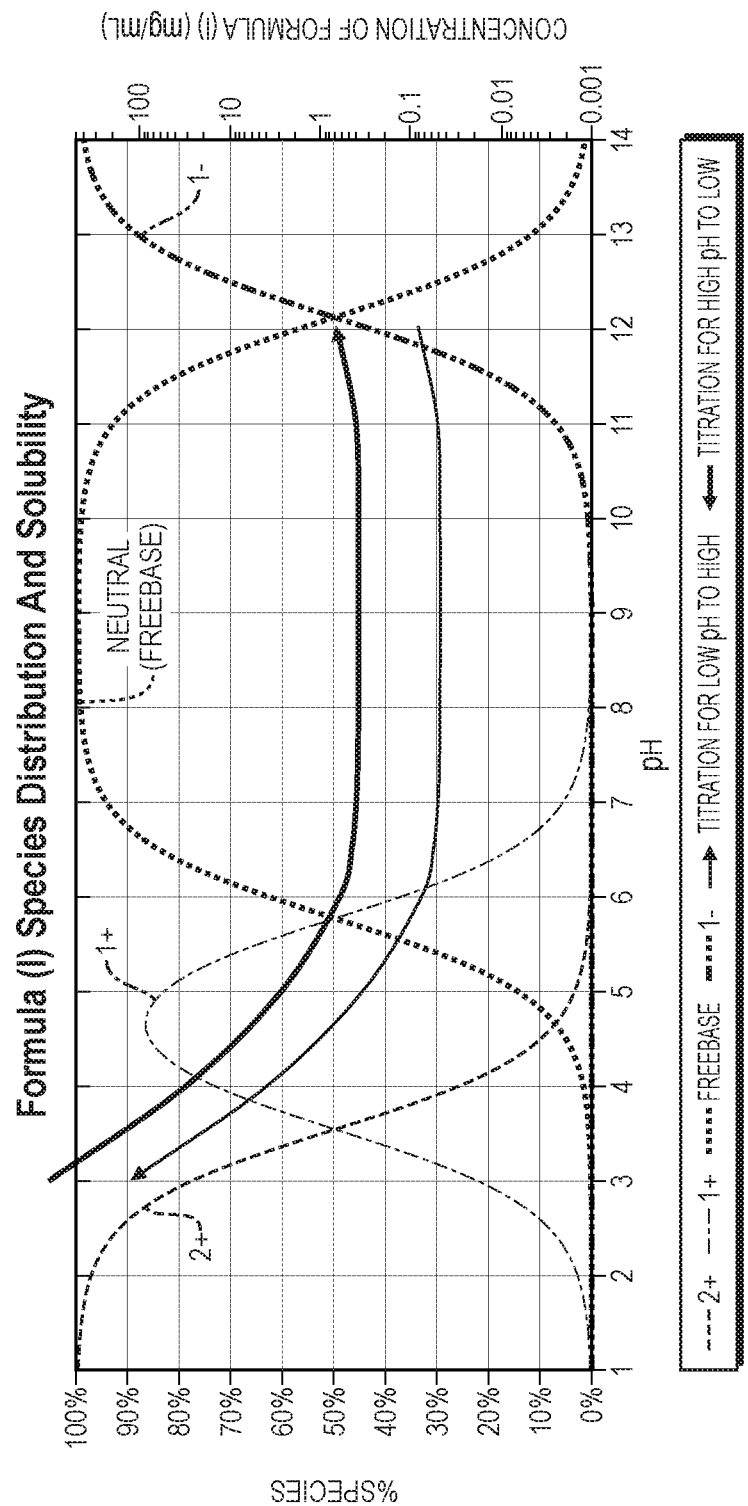
FIG. 47 illustrates the species distribution and solubility as a function of pH for Formula (1).

The p$K_a$ values for Formula (1) free base were determined and used to create the speciation plot shown in FIG. 47 to illustrate the species present as the Formula (1) passes through the gastrointestinal tract. The sample p$K_a$ values were determined using an ultraviolet (UV) spectrometric technique. The sample was initially titrated in a fast-UV triple titration between pH 2-12 at concentrations of 31-19 μM, under aqueous conditions. Three p$K_a$ values, with average values of ~3.6, ~5.8 and ~12.0, were determined.

The sample was subsequently titrated in six titrations, under aqueous conditions over a total range of pH 1.5-12.5 at concentrations of 30-18 μM. Three $pK_a$ values for Formula (1), with average values of 3.54±0.01, 5.77±0.01 and 12.12±0.03, were determined from the spectroscopic data collected.

The log P of Formula (1) free base was determined using the potentiometric (pH-metric) technique. The sample was titrated in various ratios of octanol/water from pH 1.9-12.1 at concentrations of 1.1-0.5 mM at 25° C. in an ionic environment of 0.15 M KCl. The potentiometric data collected were used to calculate the log P of the neutral (2.03±0.01) and the cationic (−0.31±0.06) species.

Example 7.2. Salt Solubility

Tests were directed to determine the aqueous solubility of the maleate salt as a function of pH. Experiments were conducted in aqueous HCl solution and buffer solutions at pHs of 1, 3, 5, 6.8, 7.4 and 9. It was determined that at low pH values of 1 and 3, the solid completely dissolved over the equilibration time while the pH in the system stabilized to approximately 3 in both experiments. In parallel, aqueous solubilities of the fumarate, maleate, phosphate, and L-tartrate was determined in pure water. Solubility data for the fumarate, maleate, phosphate, and L-tartrate salts in pure water are presented in Table 16, with the phosphate salt showing the highest apparent solubility after 24 hours. The solubility data for the maleate salt as a function of pH in various aqueous media is presented in Table 17.

TABLE 16

Solubility data for selected salts in pure water at 25° C..

| Salt | Sample name | pH | Solubility (mg/mL) after 24 hours equilibration |
|---|---|---|---|
| Fumarate | SP221-FUM-P9a | 4.0 | 2.1 |
| Maleate | SP221-MILE-P9 | 4.1 | 2.3 |
| Phosphate | SP221-PO4-P5 | 3.6 | 15.0 |
| L-tartrate | SP221-LTA-P8 | 3.8 | 3.7 |

TABLE 17

Solubility data for the maleate salt as a function of pH in aqueous media.

| Sample name | Description | pH after 24 hours | Solubility (mg/mL) |
|---|---|---|---|
| SP221-MLE-P8_pH1 | 0.1N HCl, Sigma # 71763 | 1.8 | 37.0 |
| SP221-MLE-P8_pH3 | citrate buffer pH 3, VWR #109434 | 3.2 | 8.0 |
| SP221-MLE-P8_pH5 | buffer pH 5, Sigma # 33544 | 4.8 | 4.3 |
| SP221-MLE-P8_pH6.8 | phosphate buffer pH 7, KH2PO4 | 4.8 | 1.2 |
| SP221-MLE-P8_pH7.4 | phosphate buffer pH 7, KH2PO4 | 5.0 | 0.8 |
| SP221-MLE-P8_pH9 | borate buffer, VWR # 109408 | 4.7 | 1.2 |

Example 7.3. Bulk and Tapped Density of Salts

The bulk and tapped density of the fumarate, maleate, phosphate, and L-tartrate salts were estimated by conducting experiments on four 10 gram samples. The results are presented in Table 18.

TABLE 18

Bulk and tapped density measurements for selected salts.

| Salt | Sample name | Bulk density (g/mL) | Tapped density (g/mL) |
|---|---|---|---|
| Fumarate | SP221-FUM-P9a | 0.45 | 0.57 |
| Maleate | SP221-MLE-P9 | 0.35 | 0.45 |
| Phosphate | SP221-PO4-P5a | 0.33 | 0.48 |
| L-Tartrate | SP221-LTA-P8a | 0.29 | 0.50 |

Example 8. Analytical Characterization of Form I Recrystallized from Ethanol (Sample P502-P99)

About 60 g of Formula (1) batch CS13-083 HB873-98 was recrystallized from ethanol. The product was characterized by PXRD (FIG. 49), DSC, TG-FTIR, $^1$H NMR spectroscopy, high-performance liquid chromatography purity analysis, Fraunhofer laser diffraction, DVS, and optical microscopy.

Figure 49:
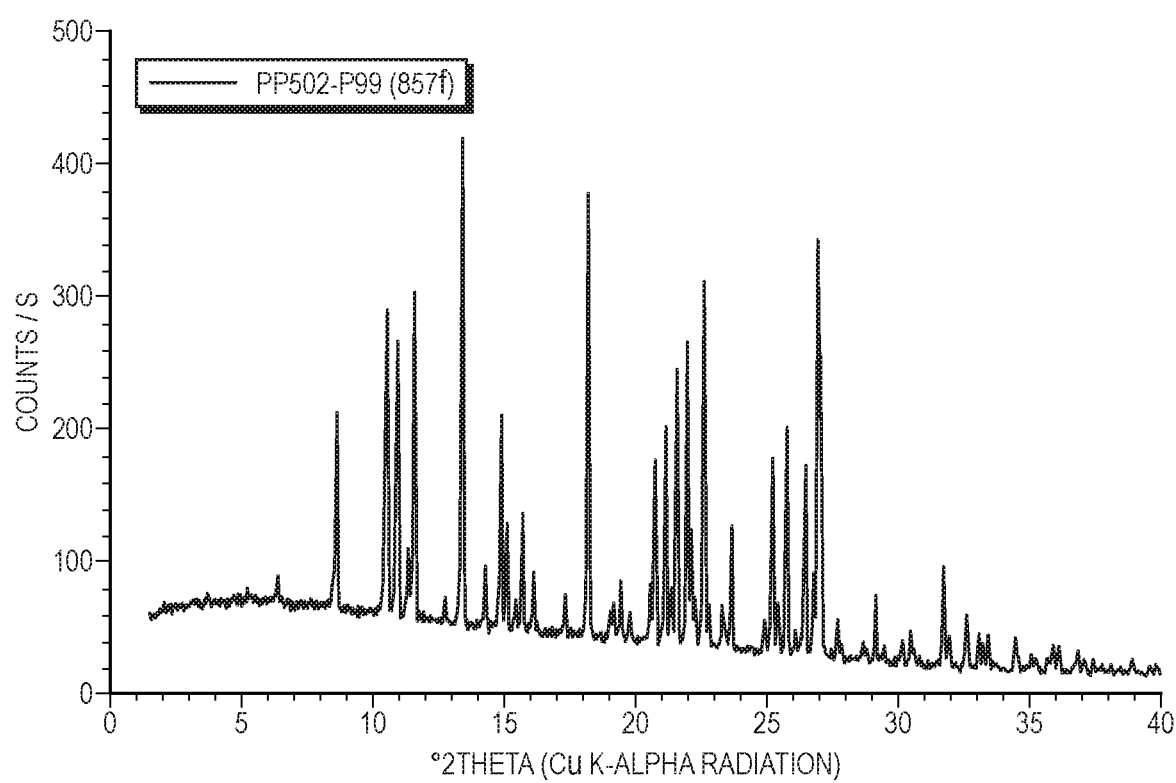
FIG. 49 illustrates a PXRD pattern of Form I of the free base of Formula (1) recrystallized from ethanol.

PXRD analysis confirmed that the structure of sample PP502-P99 corresponds to Form I. The PXRD pattern of recrystallized Formula (1) from ethanol is depicted in FIG. 49. DSC of sample PP502-P99 revealed a melting onset at about 211° C. and an endothermic peak near 213° C. (with an enthalpy of fusion of 61.57 J/g) followed immediately by an exothermic degradation event.

TG-FTIR analysis of sample PP502-P99 revealed a mass loss of about 0.2% due to water loss and an additional mass loss of about 0.6% at 220° C. attributable to ethanol. A small amount of water and possibly a very minor part of thermal degradation products is observed to begin upon melting as heating continues thereafter to approximately 300° C.

The chemical identity and integrity of the recrystallized Formula (1) was confirmed by $^1$H NMR spectroscopy. The triplet signal around 1.06 ppm is due to ethanol, and based on the integration of the split single proton at 5.50/5.71 ppm, the ethanol content is calculated to be about 0.054 equivalent which corresponds to 0.54%. No other residual solvent appears to be present. The purity of the recrystallized Form I of Formula (1) was confirmed by HPLC.

Particle size distribution testing was conducted using Fraunhofer laser diffraction technique in n-heptane using a Malvern Mastersizer 2000. Values for the maximum particle size for a given percentage volume of the sample shown in Table 19 below. Furthermore, the particle size distribution function for the recrystallized base form indicates a peak at approximately 20 μm.

TABLE 19

Particle size distribution for recrystallized Form I free base.

| Sample | x10 | x50 (median) | x90 |
|---|---|---|---|
| P502-P99 | 3 μm | 15 μm | 37 μm |

Hygroscopic behavior of the recrystallized Formula (1) (sample P502-P99) was measured using dynamic vapor sorption. The DVS results indicate that the recrystallized Formula (1) starts with an initial water content of approximately 0.25% at 50% RH, decreasing to about 0% at 0% RH, and reaching a maximum saturation of approximately 0.5% at a RH of about 95%. DVS confirms that Formula (1) is not hygroscopic and the water absorption within the timeframe of the test is less than about 0.3% at 95% RH. Moisture adsorption-desorption isotherms were prepared in a similar manner as described above.

The recrystallized Formula (1) from ethanol was obtained as a crystalline material; examination by polarized optical microscopy revealed that the material consists of particles ranging in sizes from a few microns, for the smaller particles, to about 100 μm for the largest particles.

Example 9. Crystallization Optimization for Formula (1) Free Base Form I

Crystallization experiments were performed towards optimized production of Formula (1) free base Form I. The starting material for the crystallization experiments was recrystallized Formula (1) Form I. The study was supplemented with additional crystallizations of the free base from a sample of crude oil.

The obtained products were characterized using powder X-ray diffraction (PXRD) or Raman spectroscopy to investigate crystalline form and by TG-FTIR or $^1$H NMR or both to investigate residual solvent contents. Polarized microscopy images were recorded to determine particle size.

Acetone, ethanol, and 1-propanol are the most promising solvents for the recrystallization of Form I. Since crystalline Form I has a low solubility in many ICH class 3 solvents, the addition of potentially useful co-solvents was explored. For example, ethanol, water, and acetic acid are solvents that may be used to increase the solubility of Form I, which is important in the design of a crystallization process that maximizes volume efficiency and yield.

Solubility data was collected for several solvent systems. Temperature dependence of the Form I solubility was estimated for acetone, ethanol, ethanol-water 94:4 (v/v) and 1-propanol. Linear and non-linear cooling profiles and various temperature cycling strategies were applied in order to improve the quality of crystalline nature of Form I.

One method is based on crystallization of the maleate salt from a crude oil wherein the crystalline maleate salt is neutralized with base and the free base is extracted (presumably in amorphous form). Thereafter, the free base is crystallized from acetone and crystalline Form I (anhydrous form) is obtained. The resultant crystalline Form I consistently contain substantial amounts of residual solvent even when PXRD patterns of all produced samples are identical.

For example, a sample of recrystallized Form I (sample PP502-P1) contains about 0.9% of acetone as determined by TG-FTIR. No mass loss is observable below about 200° C.; however, heating thereafter results in a release of acetone solvent along with melting of the solid form (melting point of the solid form is approximately 215° C.). Prolonged drying at conventional drying temperatures does not necessarily efficiently reduce the residual solvents. However, recrystallization from other solvents (e.g., ethanol) have been shown to remove residual solvent from Form I.

Crystallization of an amorphous material after conversion of a salt to the free base is fundamentally different from the process of recrystallization of a stable polymorphic form such as Form I. Form I is much less soluble than the amorphous form since it is typically recovered after the extraction and evaporation of the solvent; however, solubility can change if the free base crystallizes spontaneously after the extraction step. Thought the specific difference in solubility between the amorphous form and the stable crystalline form is not known, it ranges from a factor of 10 to 100.

In the current methodology, 100 mg/mL of stable Form I is preferably mixed into an ICH class 3 solvent or solvent mixture for the purposes of recrystallization. Solvent possibilities were narrowed by collecting detailed solubility data for the most common solvents. Formula (1) is not known to crystallize in different polymorphs, i.e., no other non-solvated form was obtained from a crystallization experiment from a saturated solution.

The polymorphism study showed that Form I is stable and that this form is obtained consistently when the water activity was below the critical limit for hydrate formation. A seeded process is recommended because seeding allows a better control of the crystallization process to obtain a more reproducible form, particle size and shape distribution. The samples in Table 20 were used in this study.

TABLE 20

Samples used in the optimization of the crystallization process for Formula (1) free base Form I study.

| Sample name | Batch No. | Sample code | Form |
|---|---|---|---|
| Formula (1), recrystallized | CS13-083 HB873-98 | PP502-P1 | Form I |
| Formula (1), crude oil | CS13-083 HB933-54-4 | PP502-P61 | Oil |
| Formula (1), (CML 1476) maleate salt | CS13-083 HB933-54-5 | PP502-P67 | Crystalline |
| Formula (1), recrystallized | CS13-083, Am-1406 | PP502-P62 | Form I |

Example 9.1. Solubility by HPLC

The solubility of recrystallized Formula (1) Form I was tested in various water-solvent mixtures and non-aqueous solvents. Complete solubility data generated for these and other solvent systems is presented in Table 21 below.

TABLE 21

Solubility data for Form I. MEK refers to methyl ethyl ketone and THF refers to tetrahydrofuran.

| Pure solvent | Solubility (S, mg/mL) | Solvent mixture | Solubility (S, mg/mL) |
|---|---|---|---|
| acetone, 25° C. | 4.1 | ethanol – water 96:4, 0° C. | 6.7 |
| acetone at RFT | 10.0 | ethanol – water 96:4, 25° C. | 10.0 |
| ethyl acetate, 25° C. | 1.5 | ethanol – water 96:4, 60° C. | 24.7 |
| ethanol, 5° C. | 3.6 | ethanol – water 9:1, 25° C. | 23.7 |
| ethanol, 25° C. | 4.4 | | |
| ethanol, 50° C. | 10.2 | | |
| MEK, 25° C. | 3.7 | | |
| methanol, 25° C. | 19.9 | | |
| 1-propanol, 5° C. | 3.4 | | |
| 1-propanol, r.t. | 4.7 | | |
| 1-propanol, 25° C. | 4.0 | | |
| 1-propanol, 60° C. | 14.4 | | |
| 2-propanol, 25° C. | 1.3 | | |
| THF, 25° C. | 20.4 | | |

Acetone, ethanol, 96%-ethanol and 1-propanol were considered as the most promising solvent systems. Solubility in 96% ethanol is rather high at room temperature (approximately 22° C.) and cooling to low temperature would be necessary to obtain good yields. Cooling below 0° C. was not explored during the polymorphism study as crystallization at sub-zero temperatures leads to hydrate formation. Though the presence of water in high-temperature co-solvent mixtures might lead to deteriorating Formula (1)

stability (indicated by a red discoloration), water still serves as a useful co-solvent at low concentration levels from about 0.5 to 4%.

Example 9.2. Multimax Solubility Tests

Metastable zone width experiments were conducted in a Mettler-Toledo Multimax crystallization process optimization system equipped with turbidity probes, in order to demonstrate control of crystallization for Form I.

Figure 48:
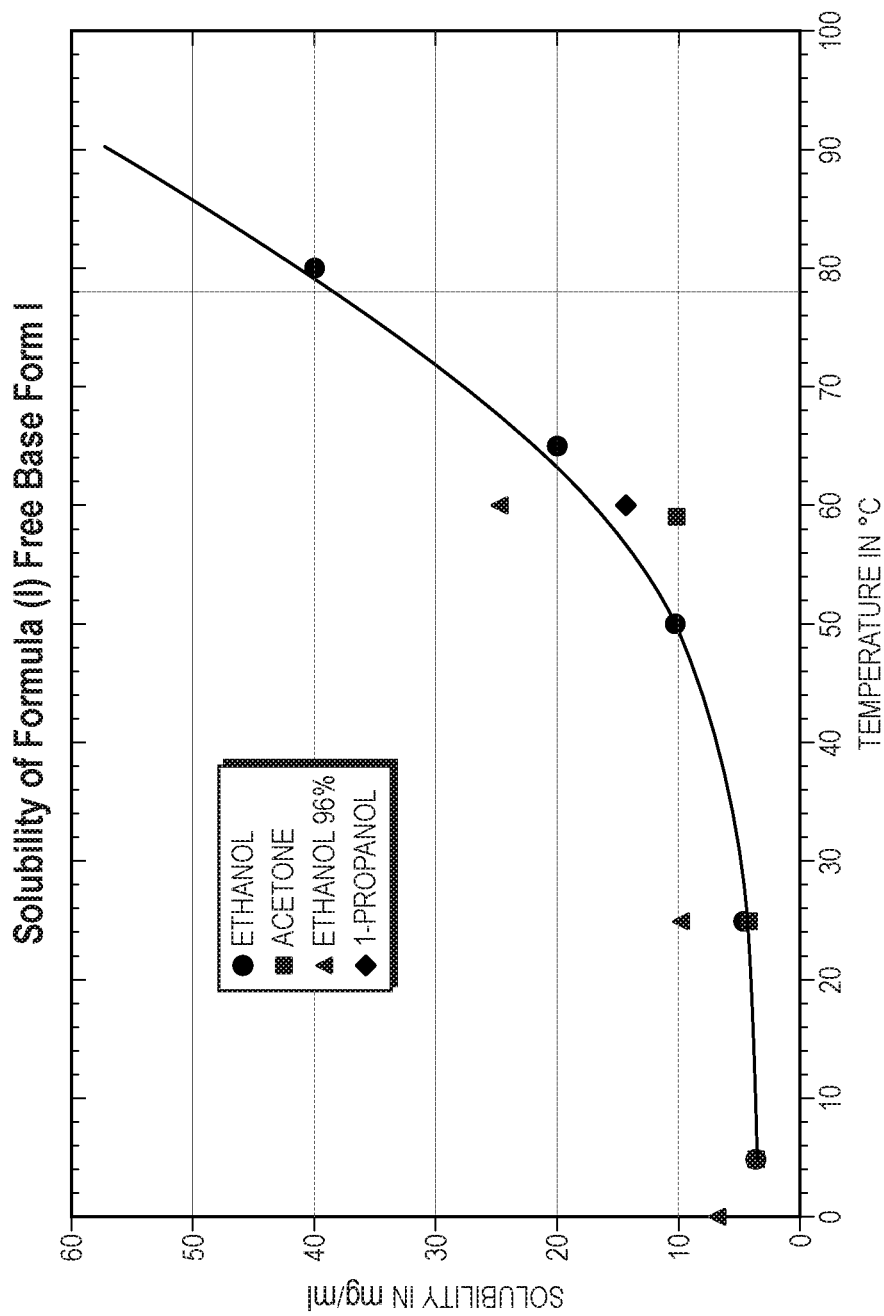
FIG. 48 illustrates the temperature dependent solubility of Formula (1).

Acetone, ethanol, and ethanol-water (96:4) were selected as the solvent systems. Three different concentrations were selected for acetone and ethanol; two different concentrations were selected for the ethanol-water (96:4) solvent system. Solubility data obtained from the Multimax experiments were in agreement with previously obtained data; however, values from the Multimax experiment are slightly lower than the actual value due to the kinetic nature of the Multimax experiment. The temperature dependence of the solubility of the Formula (1) free base Form I in ethanol and acetone is depicted in FIG. 48.

Ethanol and 1-propanol display similar solubility characteristics given that data points for the 1-propanol solvent appear to align well with the curve fit for the ethanol data points. Moreover, because the boiling point of 1-propanol is 97° C. as compared to a boiling point of 78° C. for ethanol, 1-propanol is considered a viable alternative to ethanol resulting in a substantial increase of the volume efficiency and yield.

Without seeding, the crystallization experiments from cooling of supersaturated solutions did not lead to crystallization in any of the examined solvents. As a consequence, the metastable zones in all tested solvents are very wide. Therefore, seeding is mandatory to control the crystallization process and is applied soon after oversaturation has been achieved.

Example 9.3. Experimental Approach to Reduction of Residual Solvents

Example 9.3.1. Temperature Cycling Experiments—Part One

Figure 50:
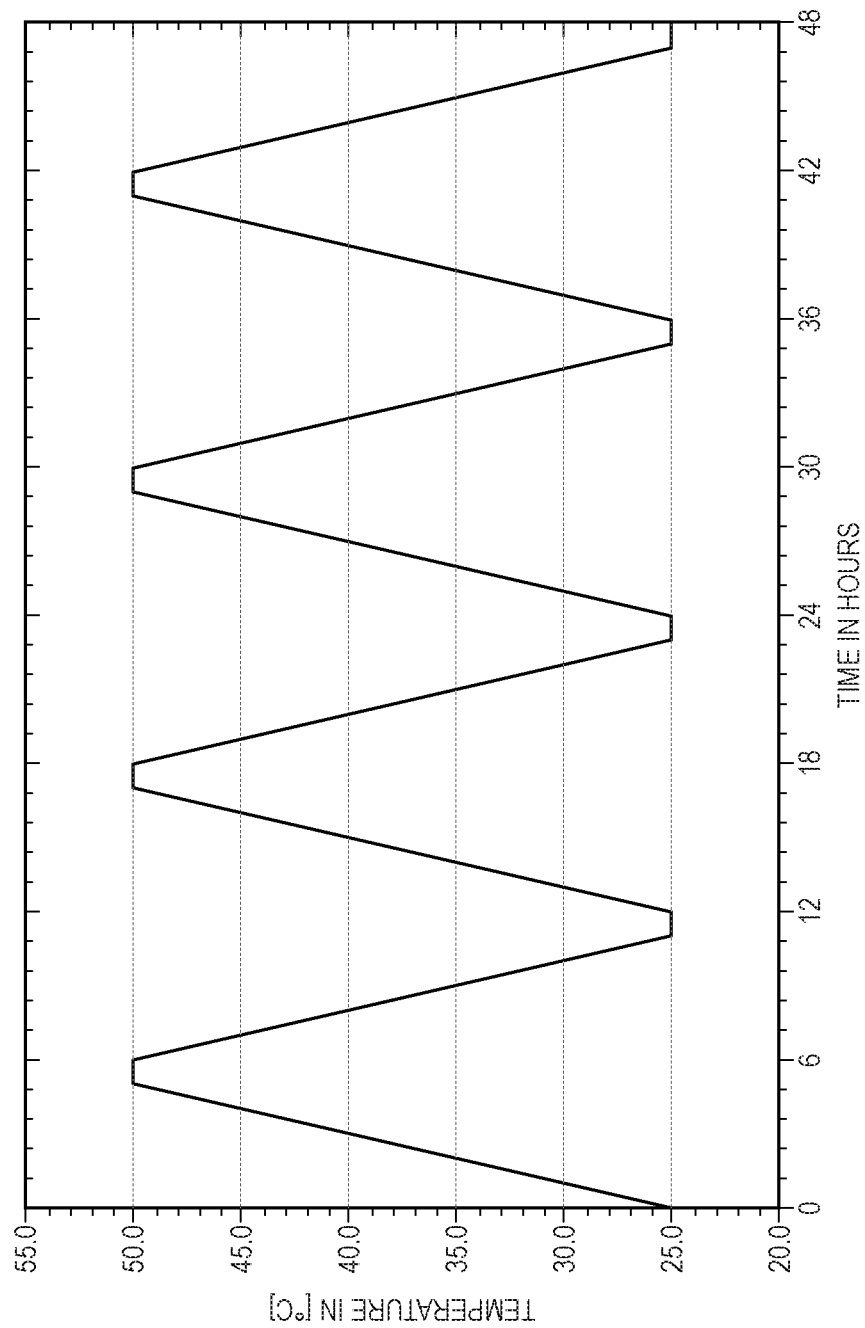
FIG. 50 illustrates a temperature cycling profile for suspension equilibration experiments PP502-P55 through PP502-P58.

Temperature cycling experiments were carried out to investigate the origin of high residual solvent contents, which are hypothesized to be due to solvate formation, or due to an inherent property of the free base Form I to form "solvent inclusion" complexes, or due to crystal defects that allow solvent inclusion. Polymorphism studies did not offer any positive proof for solvate formation for acetone, ethanol, ethyl acetate and 1-propanol, though solvated forms were found with methanol and acetic acid. However, substantial amounts of residual solvent were found for all of the mentioned solvents. Specifically, temperature cycling experiments were conducted to test whether high residual solvent contents are due to crystal defects. The experiments were carried out in four different solvent systems: acetone, ethanol, 1-propanol and a 1:1 mixture of methanol and TBME. Experiments with a T-cycling profile as shown in FIG. 50 were run between 25° C. and 50° C. for two days.

Figure 51:
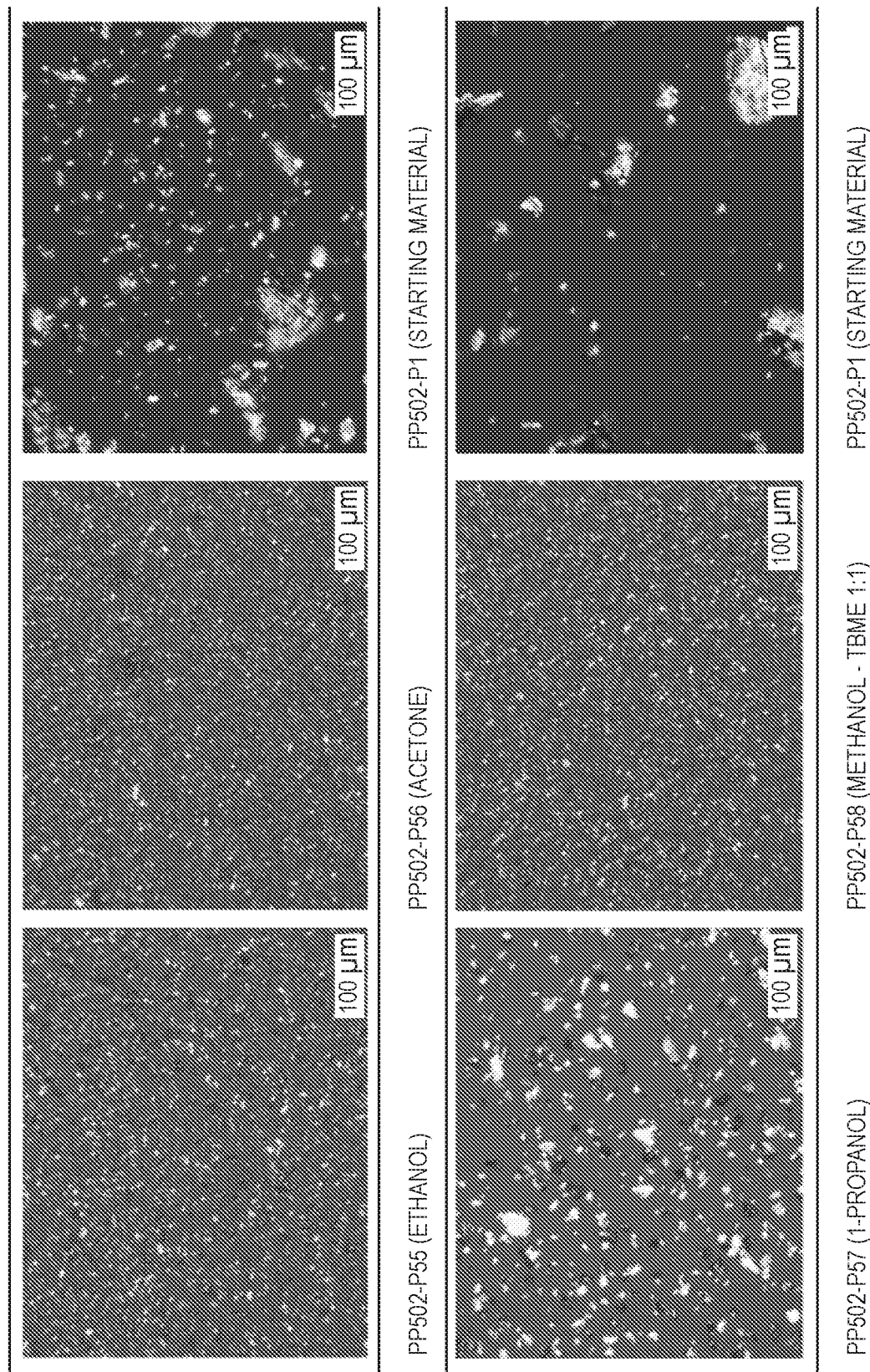
FIG. 51 illustrates light microscope images from samples of experiments PP502-P55 through PP502-P58 (left two columns) and the starting material (sample PP502-P1, right column). Recorded with crossed polarizers and dispersed in paraffin oil.

After 48 hours the suspensions were filtered, the obtained solids were dried under vacuum at 60° C. and tested by TG-FTIR and optical microscopy. The TG-FTIR results are summarized in Table 22 and the optical microscopy results are presented in FIG. 51. In all experiments, the solvent content was slightly reduced. In experiments with ethanol solvent and methanol-TBME mixture, no acetone could be found by TG-FTIR. Optical microscopy shows that in the ethanol, acetone, and methanol-TBME mixture experiments, (the exception is 1-propanol) very small particles were obtained. Compared to the starting material of sample PP502-P1, particle size distribution shifts to smaller particles. The particles of samples PP502-P55 (in ethanol), PP502-P56 (in acetone) and PP502-P58 (in the methanol-TBME mixture) have sizes of a few μm which border the limit of microscopic resolution. Stirring with a magnet bar might possibly have led to a milling effect over the two day cycling period. The exception of sample PP502-P57 in 1-propanol might be due to irregular rotation of the magnet bars in the temperature controlled apparatus.

TABLE 22

TG-FTIR results from the temperature cycling experiments with Formula (1) free base Form I (containing approximately 0.8% of acetone at the beginning of the experiment).

| Sample | Summarized Conditions | TG-FTIR result |
| --- | --- | --- |
| PP502-P55 | Form T in ethanol | Mass loss 0.69%; likely water, but not clearly attributable |
| PP502-P56 | Form T in acetone | Mass loss 0.58%; attributable to acetone |
| PP502-P57 | Form T in 1-propanol | Mass loss 0.55%; attributable to acetone |
| PP502-P58 | Form T in methanol-TBME 1:1 | Mass loss 0.43%; likely water, but not clearly attributable |

The results shown in Table 22 suggest a residual solvent reduction of about 30%; though this may be attributed to a milling effect rather than to elimination of defect sites in crystalline particles. Therefore, wet-milling might be one way to reduce residual solvent content and ethanol might be a good solvent in the wet-milling process.

Example 9.3.2. Temperature Cycling Experiments—Part Two

Additional temperature cycling experiments were carried out in acetone and ethanol using two different temperature cycling programs. Different from the previous experiments, these experiments were carried out in the Multimax crystallization system. The first program consisted of four cycles with a duration of 12 hours each (cooling rate of 4 K/h) and the second program consisted of eight cycles with a duration of 6 hours each (cooling rate of 7.5 K/h). Both temperature cycling programs covered a temperature range of from about 23° C. to about 53° C. and ran for 48 hours and subsequently a cooling to 3° C. at the end of the experiment. Turbidity in the system was recorded with a turbidity probe (not shown). In all experiments, concentration of solid was about 50 mg/mL of solvent, i.e., based on the solubility results for ethanol, about 10% of the solid is dissolved at the beginning of the cycle and about 20% of the solid is dissolved at the high temperature end of the cycle.

Aliquots were taken and analyzed by PXRD and TG-FTIR after 24 hours and after 48 hours. After the samples were cooled to 3° C., the samples were again isolated and analyzed by PXRD, optical microscopy, and TG-FTIR. A summary of the results from the TG-FTIR is given in Table 23. PXRD showed that all samples were obtained as Form I. Although a slight reduction in the acetone content is observable, TG-FTIR mass losses still suggest an acetone content of about 0.7%.

TABLE 23

Results of equilibration experiments with temperature cycling.

| Sample | Solvent | Temperature Program | TG-FTIR result |
|---|---|---|---|
| PP502-P71 | ethanol | 4 cycles, 12 hours each | PP502-P71A ~0.78% acetone. PP502-P71B ~0.66% acetone. PP502-P71 (end) ~0.68% acetone. |
| PP502-P72 | acetone | 4 cycles, 12 hours each | PP502-P72A ~0.68% acetone. PP502-P72B ~0.67% acetone. PP502-P72 ~0.71% acetone. |
| PP502-P73 | ethanol | 8 cycles, 6 hours each | PP502-P73A ~0.65% acetone. PP502-P73B ~0.77% acetone. PP502-P73 ~0.75% acetone. |
| PP502-P74 | acetone | 8 cycles, 6 hours each | PP502-P74A ~0.67% acetone. PP502-P74B ~0.70% acetone. PP502-P72 ~0.72% acetone. |

Example 9.3.3. Crystallization by Slow Cooling of Saturated Solutions

Two preliminary experiments were carried out in ethanol-water 96:4 (v/v) and in 1-propanol. Optical microscopy of samples PP502-P59 and PP502-P60 (not shown) revealed that particle sizes were small and the residual solvent content was slightly reduced with respect to the starting material for sample PP502-P60 in 96% ethanol, but not for sample PP502-P59 in 1-propanol.

Additional slow cooling crystallization experiments starting from clear solutions were carried out in a Multimax apparatus with a 1-propanol/$H_2O$ 98:2 mixture and an ethanol/$H_2O$~97:3 mixture using two different cooling profiles. For both profiles, Form I was dissolved at 85° C.; the solution was cooled to 75° C., seeded with Form I, and then cooled down to 6° C. for the 1-propanol/$H_2O$ mixture or 4° C. for the ethanol/$H_2O$ mixture. The first program (for samples PP502-P75 and PP502-P76) consisted of a stepwise cooling with integrated temperature cycling (cooling rate of 5 K/h) while the second program (for samples PP502-P77 and PP502-P78) consisted of a continuous, non-linear cooling profile (starting cooling rate of 0.5 K/h and stepwise increase at lower temperatures to a final cooling rate of 16 K/h). The cooling phase of both crystallization experiments was about 22 hours.

The turbidity of the samples was measured in-situ in order to monitor the crystallization process. With the exception of PP502-P78, a slow and gradual increase of turbidity was observed during the cooling process, which is an indication of a controlled crystallization process. Turbidity analysis for sample PP502-P78 reflected that seed crystals were dissolved because the solution was not saturated when seed crystals were added. The samples were worked up and examined by PXRD, optical microscopy and TG-FTIR. Powder X-ray diffraction of sample PP502-P78 resulted in a pattern similar to the pattern for the amorphous form and showed that the PP502-P78 sample did not crystallize. The PXRD patterns of all other samples (PP502-P75 to PP502-P77) correspond to Form I.

Figure 52:
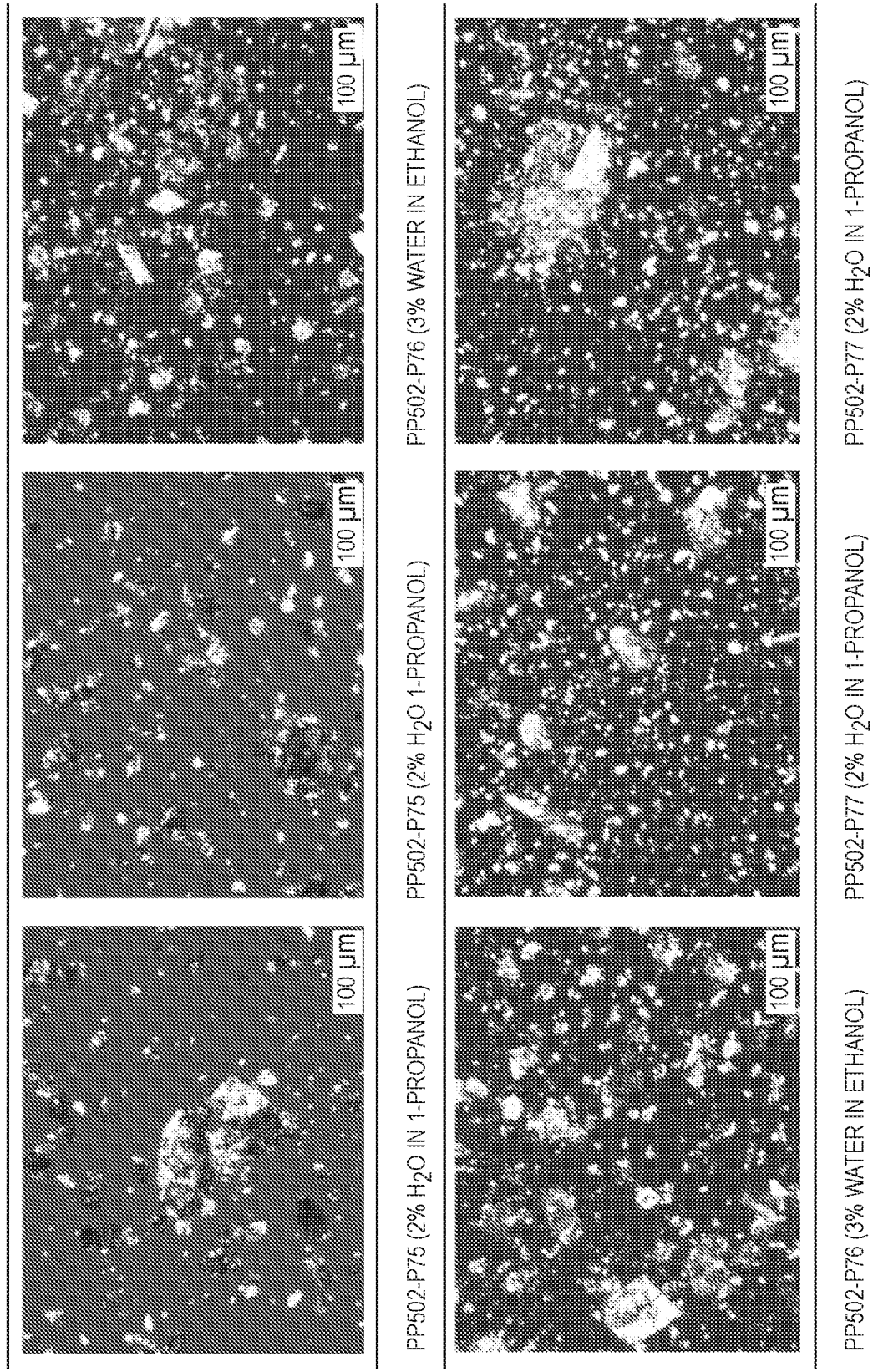
FIG. 52 illustrates optical microscopy images from samples of experiments PP502-P75 through PP502-P77. The images were recorded with crossed polarizers dispersed in paraffin oil.

The optical microscopy images are presented in FIG. 52 and a summary of the TG-FTIR results are shown in Table 24. Whereas optical microscopy showed that highly crystalline materials were obtained with particle sizes of up to about 100 μm, TG-FTIR results reflect that even a slow, gradual cooling crystallization does not result in solid material without enclosed solvent residues, where solvent contents were typically about 1% or slightly higher.

TABLE 24

Results of cooling crystallization experiments.

| Sample | Solvent | Cooling profile | TG-FTIR result |
|---|---|---|---|
| PP502-P75 | 2% $H_2O$ in 1-propano | Stepwise cooling with temperature cycling | 1.09% 1-propanol |
| PP502-P76 | 3% $H_2O$ in ethanol | Stepwise cooling with temperature cycling | 0.94% ethanol |
| PP502-P77 | 2% $H_2O$ in 1-propanol | Slow continuous, non-linear cooling | 1.34% 1-propanol |
| PP502-P78 | 3% $H_2O$ in ethanol | Slow continuous, non-linear cooling | ~3% mass loss due to water |

Example 9.3.4. The Effect of Wet-Milling

Whereas the results from the first series of temperature cycling experiments (example 8.3.1 above) suggested that the solvent contents can potentially be reduced by crystal ripening in suspension experiments, results from the second series of temperature cycling experiments (example 8.3.2 above) failed to confirm this result. Because optical microscopy showed that particles in experiments PP502-P55 through PP502-P58 were generally small and particles from experiments PP502-P71 through PP502-P74 were large crystals, it was suspected that the use of different magnetic stir bars had caused a milling effect in the former case while more gentle stirring (and slower cooling rates) in the latter case allowed the formation of larger crystals.

Here, a suspension of sample PP502-P77 containing about 1.3% of 1-propanol (see Table 24 above) was stirred with a fairly large magnetic stirrer at about 1000 rpm for four days at room temperature. Optical microscopy images showing the comparison between stirring processes revealed that particle size distribution changes with stirring conditions. Whereas sample PP502-P77 contained particles having sizes up to about 100 μm, the slurried sample PP502-P88 does not appear to contain any particles greater than 10 μm.

Due to small particle sizes, filtration of sample PP502-P88 was slow. Investigation of PP502-P88 by $^1$H NMR showed that the sample contains 0.32% 1-propanol and 0.07% ethanol after drying at 60° C. under vacuum for several hours. This experiment confirms that the residual solvents in samples with small particle sizes below about 10 μm may be reduced to below the ICH limits. The result also suggests that 1-propanol was partially replaced by ethanol. As a consequence, if wet-milling is considered, a milling-solvent screen can be employed if ethanol is not suitable. Where water leads to a partial formation of the hydrate, dry milling is not recommended because this leads to partial amorphization of the compound.

Example 10. Crystal Structure of Form I of the Formula (1) Free Base

A study of the crystal structure of Formula (1) free base Form I was performed. Intensity data were collected at 173 K, using Cu radiation (λ=1.54184 Å), on an Oxford Diffraction Gemini-R Ultra diffractometer operated by the CrysAlis software (Agilent Technologies, 2012, Yarnton, England; CrysAlis CCD and CrysAlis RED, 2003). The data were corrected for absorption effects by means of comparison of equivalent reflections. The structures were solved with the direct methods procedure implemented in SHELXT and refined by full-matrix least squares on $F^2$ using SHELXL-2014, as described in Sheldrick, *Acta Cryst.* 2008, A64, 112-122.

Non-hydrogen atoms were located in difference maps and refined anisotropically. Hydrogen atoms of the main component were located in difference maps and those bonded to carbon atoms were fixed in idealized positions and their thermal displacement parameters were set to $1.2U_{eq}$ (CH and $CH_2$) or $1.5U_{eq}$ ($CH_3$ groups) of the parent C atom. The positions of NH hydrogen atoms were refined with N—H distances restrained to 0.86(2) Å and the $U_{iso}$ parameters were refined freely.

The results of the crystallographic experiments are summarized in Table 25.

TABLE 25

Crystal data and structure refinement for Form I.

| | |
|---|---|
| Identification code | 14thg420_PP502-P703 |
| Empirical formula | $C_{26}H_{23}N_7O_2$ |
| Formula weight | 465.51 |
| Temperature | 173(2) K |
| Wavelength | 1.54184 Å (Cu radiation) |
| Crystal system | Triclinic |
| Space group | P1 |
| Unit cell dimensions | a = 8.0630(6) Å    α = 85.841(5)° |
| | b = 10.2949(6) Å    β = 75.798(6)° |
| | c = 14.2825(8) Å    γ = 82.331(5)° |
| Volume | 1138.07(13) Å$^3$ |
| Z | 2 |
| Density (calculated) | 1.358 Mg/m$^3$ |
| Absorption coefficient | 0.733 mm$^{-1}$ |
| F(000) | 488 |
| Crystal | block; colorless |
| Crystal size | 0.150 × 0.100 × 0.050 mm$^3$ |
| Theta range for data collection | 3.2-68.2° |
| Index ranges | −9 ≤ h ≤ 9, −12 ≤ k ≤ 12, −17 ≤ l ≤ 17 |
| Reflections collected | 20885 |
| Independent reflections | 7763 [$R_{int}$ = 0.0559] |
| Completeness to theta = 67.7° | 99.1 % |
| Absorption correction | Semi-empirical from equivalents |
| Max. and min. transmission | 1.00000 and 0.80527 |
| Refinement method | Full-matrix least-squares on F$^2$ |
| Data/restraints/parameters | 7763/9/657 |
| Goodness-of-fit on F$^2$ | 1.024 |
| Final R indices [F$^2$ > 2σ(F$^2$)] | R1 = 0.0530, wR2 = 0.1351 |
| R indices (all data) | R1 = 0.0645, wR2 = 0.1477 |
| Absolute structure parameter (Flack) | −0.1(3) |
| Extinction coefficient | none |
| Largest cliff peak and hole | 0.380 and −0.227 e Å$^{-3}$ |

Figure 53:
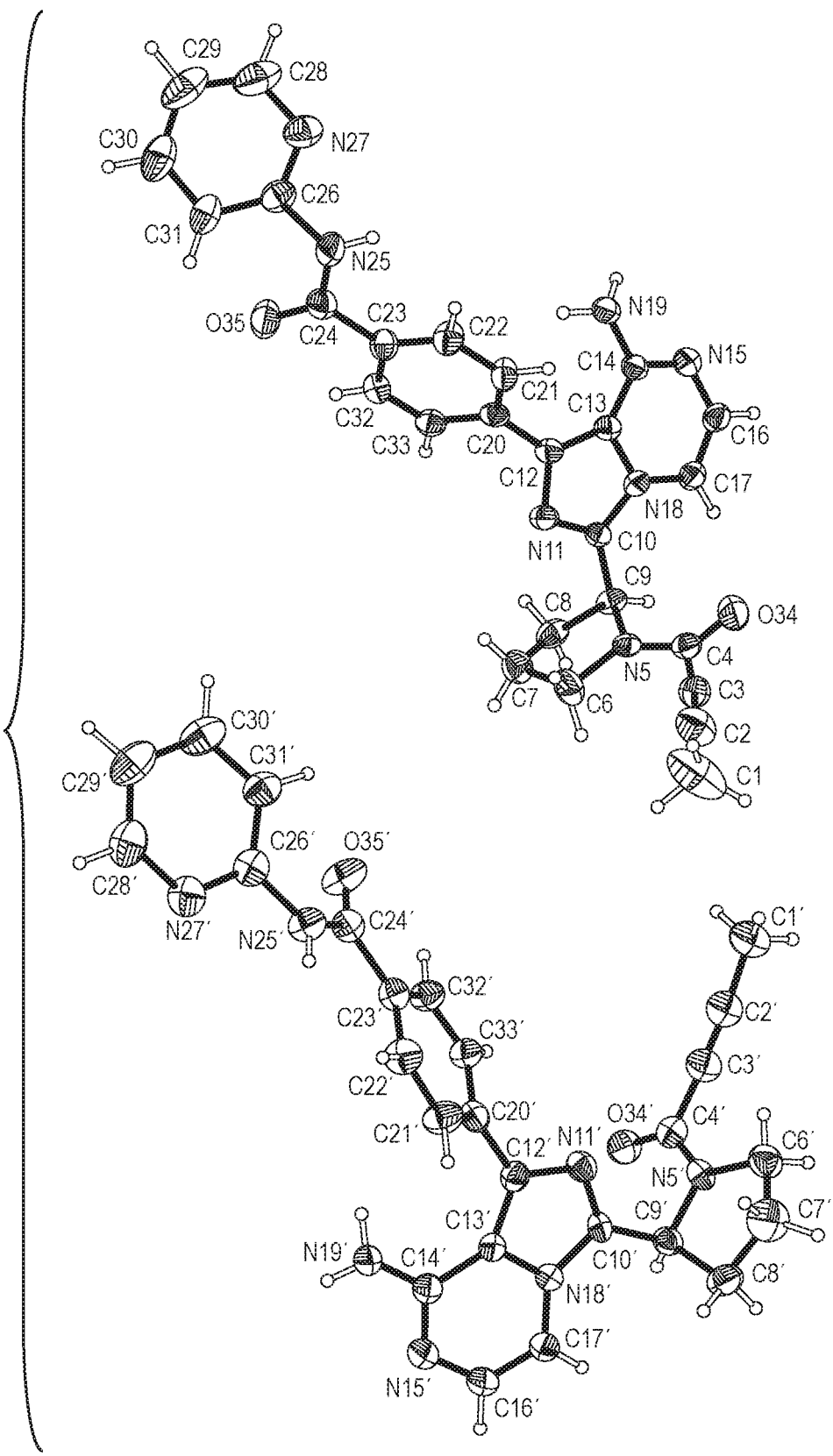
FIG. 53 illustrates the labeling scheme and molecular conformation obtained from the single-crystal X-ray diffraction (SCXRD) study of Form I for molecules A (top) and B (bottom), with non-hydrogen atoms represented as thermal ellipsoids drawn at the 50% probability level. Hydrogen atoms are shown as spheres of arbitrary size.

The asymmetric unit of the Form I crystal structure contains two molecules, denoted A and B (FIG. 53), which differ fundamentally in their conformation. The absolute configuration at both C9 and C9' was established as the (S)-configuration by anomalous-dispersion effects. The Flack x parameters, −0.1(3), was determined using 2602 quotients [(I+)−(I−)]/[(I+)+(I−)], as described in Parsons, et al., *Acta Cryst.* 2013, B69, 249-259). The hydrogen atoms of the NH$_2$ and NH groups were located in difference maps. They were refined with the N—H distances being restrained to 0.86(2) Å (which results in nine distance restraints), and their $U_{iso}$ parameters were refined freely. The crystal structure contains classical N—H•••O and N—H•••N bonds (listed in Table 26) which involve the NH$_2$ groups of N19 and N19' as H-bond donor sites. By contrast, neither of the NH groups (N25 and N25') is engaged in a classical N—H•••A interaction.

TABLE 26

Hydrogen bonds in the Form I crystal structure.

| D—H•••A | d(D—H) (Å) | d(H•••A) (Å) | d(D•••A) (Å) | DHA angle (Å) |
|---|---|---|---|---|
| N(19)-H(19A)•••N(15')#1 | 0.88(3) | 2.23(3) | 3.082(7) | 163(5) |
| N(19)-H(19B)•••O(35') | 0.88(3) | 2.34(5) | 2.997(6) | 132(5) |
| N(19')-H(19C)•••N(15)#2 | 0.88(3) | 2.19(3) | 3.051(7) | 168(5) |
| N(19')-H(19D)•••O(35) | 0.86(3) | 2.31(4) | 2.961(6) | 133(4) |

Symmetry transformations used to generate equivalent atoms:
1 x − 1, y + 1, z  #2 x + 1, y − 1, z Additional results, including atomic coordinates for the Form I crystal structure, are given in Table 27, Table 28, and Table 29.

TABLE 27

Atomic coordinates (× 10$^4$), equivalent isotropic displacement parameters (Å$^2$ × 10$^3$) and site occupancy factors for heavy atoms in the Form I crystal structure. $U_{eq}$ is defined as one third of the trace of the orthogonalized $U_{ij}$ tensor.

| Atom | x | y | z | $U_{eq}$ | s.o.f. |
|---|---|---|---|---|---|
| C(1) | −5031(12) | 4749(10) | 11713(8) | 102(4) | 1 |
| C(2) | −4155(7) | 5851(6) | 11213(5) | 55(1) | 1 |
| C(3) | −3457(6) | 6761(5) | 10816(4) | 44(1) | 1 |
| C(4) | −2490(6) | 7774(5) | 10254(4) | 38(1) | 1 |
| N(5) | −815(5) | 7611(4) | 10249(3) | 34(1) | 1 |
| C(6) | 48(7) | 6576(5) | 10786(5) | 47(1) | 1 |
| C(7) | 1914(7) | 6819(6) | 10537(5) | 50(1) | 1 |
| C(8) | 1921(6) | 8234(5) | 10125(4) | 42(1) | 1 |
| C(9) | 384(6) | 8486(5) | 9660(4) | 35(1) | 1 |
| C(10) | 869(6) | 8113(4) | 8620(4) | 32(1) | 1 |
| N(11) | 1834(5) | 7013(4) | 8313(3) | 34(1) | 1 |
| C(12) | 1941(6) | 6994(4) | 7340(4) | 32(1) | 1 |
| C(13) | 1042(6) | 8128(5) | 7044(4) | 31(1) | 1 |
| C(14) | 864(6) | 8767(4) | 6143(4) | 32(1) | 1 |
| N(15) | 42(5) | 9955(4) | 6099(3) | 40(1) | 1 |
| C(16) | −699(7) | 10570(5) | 6961(4) | 41(1) | 1 |
| C(17) | −566(6) | 10076(5) | 7829(4) | 36(1) | 1 |
| N(18) | 349(5) | 8832(4) | 7882(3) | 31(1) | 1 |
| N(19) | 1578(6) | 8135(4) | 5299(3) | 37(1) | 1 |
| C(20) | 2983(6) | 5898(4) | 6779(4) | 32(1) | 1 |
| C(21) | 2317(6) | 5168(5) | 6203(4) | 39(1) | 1 |
| C(22) | 3348(7) | 4157(5) | 5677(4) | 42(1) | 1 |
| C(23) | 5067(6) | 3866(4) | 5712(4) | 34(1) | 1 |
| C(24) | 6328(7) | 2859(5) | 5117(4) | 37(1) | 1 |
| N(25) | 5808(6) | 2362(4) | 4391(4) | 42(1) | 1 |
| C(26) | 6841(7) | 1525(5) | 3677(4) | 39(1) | 1 |
| N(27) | 6489(6) | 1771(5) | 2817(4) | 49(1) | 1 |
| C(28) | 7406(8) | 1006(7) | 2100(5) | 62(2) | 1 |
| C(29) | 8617(8) | −12(8) | 2228(6) | 68(2) | 1 |
| C(30) | 8947(8) | −248(6) | 3131(6) | 60(2) | 1 |
| C(31) | 8054(6) | 530(5) | 3885(5) | 45(1) | 1 |
| C(32) | 5713(6) | 4562(5) | 6308(4) | 36(1) | 1 |
| C(33) | 4676(6) | 5560(5) | 6840(4) | 35(1) | 1 |
| O(34) | −3169(5) | 8677(4) | 9817(3) | 50(1) | 1 |
| O(35) | 7747(5) | 2531(4) | 5270(3) | 56(1) | 1 |
| C(1') | 8013(7) | 5676(6) | −1723(5) | 54(2) | 1 |
| C(2') | 8922(7) | 4542(5) | −1320(5) | 48(1) | 1 |
| C(3') | 9675(6) | 3596(5) | −994(4) | 44(1) | 1 |
| C(4') | 10504(6) | 2521(5) | −495(4) | 38(1) | 1 |
| N(5') | 12205(5) | 2548(4) | −578(3) | 34(1) | 1 |
| C(6') | 13250(7) | 3509(5) | −1178(5) | 46(1) | 1 |
| C(7') | 14868(8) | 3325(6) | −838(6) | 63(2) | 1 |
| C(8') | 15030(7) | 1917(5) | −430(4) | 46(1) | 1 |
| C(9') | 13158(6) | 1680(5) | 19(4) | 35(1) | 1 |
| C(10') | 12527(6) | 2046(4) | 1057(3) | 30(1) | 1 |
| N(11') | 11591(5) | 3147(4) | 1374(3) | 34(1) | 1 |
| C(12') | 11338(6) | 3088(5) | 2362(4) | 32(1) | 1 |
| C(13') | 12134(5) | 1901(4) | 2658(4) | 29(1) | 1 |
| C(14') | 12207(6) | 1197(5) | 3554(4) | 33(1) | 1 |
| N(15') | 12982(5) | 0(4) | 3586(3) | 39(1) | 1 |
| C(16') | 13775(7) | −571(5) | 2716(4) | 40(1) | 1 |
| C(17') | 13765(6) | −14(5) | 1835(4) | 34(1) | 1 |
| N(18') | 12895(5) | 1245(4) | 1806(3) | 31(1) | 1 |

TABLE 27-continued

Atomic coordinates (× 10⁴), equivalent isotropic displacement parameters (Å² × 10³) and site occupancy factors for heavy atoms in the Form I crystal structure. $U_{eq}$ is defined as one third of the trace of the orthogonalized $U_{ij}$ tensor.

| Atom | x | y | z | $U_{eq}$ | s.o.f. |
|---|---|---|---|---|---|
| N(19') | 11457(6) | 1795(4) | 4404(3) | 38(1) | 1 |
| C(20') | 10255(6) | 4156(5) | 2948(4) | 32(1) | 1 |
| C(21') | 10816(7) | 4799(5) | 3611(5) | 43(1) | 1 |
| C(22') | 9761(7) | 5791(5) | 4148(4) | 42(1) | 1 |
| C(23') | 8077(6) | 6141(5) | 4049(4) | 35(1) | 1 |
| C(24') | 6789(6) | 7134(5) | 4630(4) | 36(1) | 1 |
| N(25') | 7299(5) | 7695(4) | 5342(3) | 39(1) | 1 |
| C(26') | 6224(6) | 8530(5) | 6041(4) | 36(1) | 1 |
| N(27') | 6563(6) | 8331(4) | 6920(4) | 43(1) | 1 |
| C(28') | 5595(7) | 9096(6) | 7612(5) | 48(1) | 1 |
| C(29') | 4311(7) | 10047(6) | 7481(5) | 51(2) | 1 |
| C(30') | 3991(7) | 10254(5) | 6562(5) | 47(1) | 1 |
| C(31') | 4960(6) | 9479(5) | 5821(5) | 41(1) | 1 |
| C(32') | 7535(7) | 5502(5) | 3372(4) | 39(1) | 1 |
| C(33') | 8588(6) | 4532(5) | 2832(4) | 35(1) | 1 |
| O(34') | 9721(5) | 1648(3) | −30(3) | 49(1) | 1 |
| O(35') | 5357(5) | 7389(4) | 4493(3) | 52(1) | 1 |

TABLE 28

Bond lengths (Å) and angles (°) for the Form I crystal structure.

| | |
|---|---|
| C(1)-C(2) | 1.465(9) |
| C(1)-H(1A) | 0.98 |
| C(1)-H(1B) | 0.98 |
| C(1)-H(1C) | 0.98 |
| C(2)-C(3) | 1.193(8) |
| C(3)-C(4) | 1.459(8) |
| C(4)-O(34) | 1.225(6) |
| C(4)-N(5) | 1.337(6) |
| N(5)-C(6) | 1.468(7) |
| N(5)-C(9) | 1.475(6) |
| C(6)-C(7) | 1.509(8) |
| C(6)-H(6A) | 0.99 |
| C(6)-H(6B) | 0.99 |
| C(7)-C(8) | 1.532(8) |
| C(7)-H(7A) | 0.99 |
| C(7)-H(7B) | 0.99 |
| C(8)-C(9) | 1.528(7) |
| C(8)-H(8A) | 0.99 |
| C(8)-H(8B) | 0.99 |
| C(9)-C(10) | 1.505(7) |
| C(9)-H(9) | 1 |
| C(10)-N(11) | 1.323(6) |
| C(10)-N(18) | 1.363(7) |
| N(11)-C(12) | 1.372(7) |
| C(12)-C(13) | 1.386(7) |
| C(12)-C(20) | 1.472(7) |
| C(13)-N(18) | 1.399(6) |
| C(13)-C(14) | 1.432(7) |
| C(14)-N(15) | 1.316(6) |
| C(14)-N(19) | 1.372(7) |
| N(15)-C(16) | 1.386(7) |
| C(16)-C(17) | 1.330(8) |
| C(16)-H(16) | 0.95 |
| C(17)-N(18) | 1.397(6) |
| C(17)-H(17) | 0.95 |
| N(19)-H(19A) | 0.88(3) |
| N(19)-H(19B) | 0.88(3) |
| C(20)-C(33) | 1.385(7) |
| C(20)-C(21) | 1.395(7) |
| C(21)-C(22) | 1.384(7) |
| C(21)-H(21) | 0.95 |
| C(22)-C(23) | 1.390(7) |
| C(22)-H(22) | 0.95 |
| C(23)-C(32) | 1.385(7) |
| C(23)-C(24) | 1.501(7) |
| C(24)-O(35) | 1.217(6) |
| C(24)-N(25) | 1.363(7) |
| N(25)-C(26) | 1.413(7) |
| N(25)-H(25) | 0.86(3) |
| C(26)-N(27) | 1.327(8) |
| C(26)-C(31) | 1.387(8) |
| N(27)-C(28) | 1.343(8) |
| C(28)-C(29) | 1.368(11) |
| C(28)-H(28) | 0.95 |
| C(29)-C(30) | 1.377(11) |
| C(29)-H(29) | 0.95 |
| C(30)-C(31) | 1.383(8) |
| C(30)-H(30) | 0.95 |
| C(31)-H(31) | 0.95 |
| C(32)-C(33) | 1.380(7) |
| C(32)-H(32) | 0.95 |
| C(33)-H(33) | 0.95 |
| C(1')-C(2') | 1.453(8) |
| C(1')-H(1'1) | 0.98 |
| C(1')-H(1'2) | 0.98 |
| C(1')-H(1'3) | 0.98 |
| C(2')-C(3') | 1.204(8) |
| C(3')-C(4') | 1.449(8) |
| C(4')-O(34') | 1.228(6) |
| C(4')-N(5') | 1.351(6) |
| N(5')-C(9') | 1.465(6) |
| N(5')-C(6') | 1.472(7) |
| C(6')-C(7') | 1.485(9) |
| C(6')-H(6'1) | 0.99 |
| C(6')-H(6'2) | 0.99 |
| C(7')-C(8') | 1.523(9) |
| C(7')-H(7'1) | 0.99 |
| C(7')-H(7'2) | 0.99 |
| C(8')-C(9') | 1.532(7) |
| C(8')-H(8'1) | 0.99 |
| C(8')-H(8'2) | 0.99 |
| C(9')-C(10') | 1.502(7) |
| C(9')-H(9') | 1 |
| C(10')-N(11') | 1.318(6) |
| C(10')-N(18') | 1.370(6) |
| N(11')-C(12') | 1.373(7) |
| C(12')-C(13') | 1.390(7) |
| C(12')-C(20') | 1.480(7) |
| C(13')-N(18') | 1.398(6) |
| C(13')-C(14') | 1.434(7) |
| C(14')-N(15') | 1.308(6) |
| C(14')-N(19') | 1.366(7) |
| N(15')-C(16') | 1.383(7) |
| C(16')-C(17') | 1.346(8) |
| C(16')-H(16') | 0.95 |
| C(17')-N(18') | 1.392(6) |
| C(17')-H(17') | 0.95 |
| N(19')-H(19'C) | 0.88(3) |
| N(19')-H(19'D) | 0.86(3) |
| C(20')-C(21') | 1.386(7) |
| C(20')-C(33') | 1.394(7) |
| C(21')-C(22') | 1.385(8) |
| C(21')-H(21') | 0.95 |
| C(22')-C(23') | 1.396(7) |
| C(22')-H(22') | 0.95 |
| C(23')-C(32') | 1.391(7) |
| C(23')-C(24') | 1.493(7) |
| C(24')-O(35') | 1.209(6) |
| C(24')-N(25') | 1.376(7) |
| N(25')-C(26') | 1.409(7) |
| N(25')-H(25') | 0.85(3) |
| C(26')-N(27') | 1.345(7) |
| C(26')-C(31') | 1.392(7) |
| N(27')-C(28') | 1.334(7) |
| C(28')-C(29') | 1.366(9) |
| C(28')-H(28') | 0.95 |
| C(29')-C(30') | 1.395(10) |
| C(29')-H(29') | 0.95 |
| C(30')-C(31') | 1.385(8) |
| C(30')-H(30') | 0.95 |
| C(31')-H(31') | 0.95 |
| C(32')-C(33') | 1.370(7) |
| C(32')-H(32') | 0.95 |
| C(33')-H(33') | 0.95 |

TABLE 28-continued

Bond lengths (Å) and angles (°) for the Form I crystal structure.

| | |
|---|---|
| C(2)-C(1)-H(1A) | 109.5 |
| C(2)-C(1)-H(1B) | 109.5 |
| H(1A)-C(1)-H(1B) | 109.5 |
| C(2)-C(1)-H(1C) | 109.5 |
| H(1A)-C(1)-H(1C) | 109.5 |
| H(1B)-C(1)-H(1C) | 109.5 |
| C(3)-C(2)-C(1) | 179.0(9) |
| C(2)-C(3)-C(4) | 173.8(6) |
| O(34)-C(4)-N(5) | 123.7(5) |
| O(34)-C(4)-C(3) | 122.1(4) |
| N(5)-C(4)-C(3) | 114.1(4) |
| C(4)-N(5)-C(6) | 125.8(4) |
| C(4)-N(5)-C(9) | 121.5(4) |
| C(6)-N(5)-C(9) | 112.6(4) |
| N(5)-C(6)-C(7) | 105.2(5) |
| N(5)-C(6)-H(6A) | 110.7 |
| C(7)-C(6)-H(6A) | 110.7 |
| N(5)-C(6)-H(6B) | 110.7 |
| C(7)-C(6)-H(6B) | 110.7 |
| H(6A)-C(6)-H(6B) | 108.8 |
| C(6)-C(7)-C(8) | 105.3(4) |
| C(6)-C(7)-H(7A) | 110.7 |
| C(8)-C(7)-H(7A) | 110.7 |
| C(6)-C(7)-H(7B) | 110.7 |
| C(8)-C(7)-H(7B) | 110.7 |
| H(7A)-C(7)-H(7B) | 108.8 |
| C(9)-C(8)-C(7) | 105.3(4) |
| C(9)-C(8)-H(8A) | 110.7 |
| C(7)-C(8)-H(8A) | 110.7 |
| C(9)-C(8)-H(8B) | 110.7 |
| C(7)-C(8)-H(8B) | 110.7 |
| H(8A)-C(8)-H(8B) | 108.8 |
| N(5)-C(9)-C(10) | 110.3(4) |
| N(5)-C(9)-C(8) | 102.4(4) |
| C(10)-C(9)-C(8) | 111.9(4) |
| N(5)-C(9)-H(9) | 110.7 |
| C(10)-C(9)-H(9) | 110.7 |
| C(8)-C(9)-H(9) | 110.7 |
| N(11)-C(10)-N(18) | 111.2(4) |
| N(11)-C(10)-C(9) | 123.6(5) |
| N(18)-C(10)-C(9) | 125.1(4) |
| C(10)-N(11)-C(12) | 106.8(4) |
| N(11)-C(12)-C(13) | 109.6(4) |
| N(11)-C(12)-C(20) | 119.8(4) |
| C(13)-C(12)-C(20) | 130.5(5) |
| C(12)-C(13)-N(18) | 105.4(4) |
| C(12)-C(13)-C(14) | 136.7(5) |
| N(18)-C(13)-C(14) | 117.4(4) |
| N(15)-C(14)-N(19) | 118.7(5) |
| N(15)-C(14)-C(13) | 121.8(5) |
| N(19)-C(14)-C(13) | 119.5(4) |
| C(14)-N(15)-C(16) | 117.9(5) |
| C(17)-C(16)-N(15) | 124.8(5) |
| C(17)-C(16)-H(16) | 117.6 |
| N(15)-C(16)-H(16) | 117.6 |
| C(16)-C(17)-N(18) | 117.7(5) |
| C(16)-C(17)-H(17) | 121.1 |
| N(18)-C(17)-H(17) | 121.1 |
| C(10)-N(18)-C(17) | 132.6(4) |
| C(10)-N(18)-C(13) | 107.0(4) |
| C(17)-N(18)-C(13) | 120.2(4) |
| C(14)-N(19)-H(19A) | 109(4) |
| C(14)-N(19)-H(19B) | 115(4) |
| H(19A)-N(19)-H(19B) | 116(6) |
| C(33)-C(20)-C(21) | 118.6(4) |
| C(33)-C(20)-C(12) | 119.0(4) |
| C(21)-C(20)-C(12) | 122.3(4) |
| C(22)-C(21)-C(20) | 120.5(4) |
| C(22)-C(21)-H(21) | 119.8 |
| C(20)-C(21)-H(21) | 119.8 |
| C(21)-C(22)-C(23) | 120.2(5) |
| C(21)-C(22)-H(22) | 119.9 |
| C(23)-C(22)-H(22) | 119.9 |
| C(32)-C(23)-C(22) | 119.3(4) |
| C(32)-C(23)-C(24) | 116.1(4) |
| C(22)-C(23)-C(24) | 124.5(4) |
| O(35)-C(24)-N(25) | 122.5(5) |
| O(35)-C(24)-C(23) | 121.1(4) |
| N(25)-C(24)-C(23) | 116.4(4) |
| C(24)-N(25)-C(26) | 126.1(4) |
| C(24)-N(25)-H(25) | 114(4) |
| C(26)-N(25)-H(25) | 117(4) |
| N(27)-C(26)-C(31) | 124.8(5) |
| N(27)-C(26)-N(25) | 113.2(5) |
| C(31)-C(26)-N(25) | 122.1(5) |
| C(26)-N(27)-C(28) | 116.7(6) |
| N(27)-C(28)-C(29) | 123.4(7) |
| N(27)-C(28)-H(28) | 118.3 |
| C(29)-C(28)-H(28) | 118.3 |
| C(28)-C(29)-C(30) | 118.5(6) |
| C(28)-C(29)-H(29) | 120.7 |
| C(30)-C(29)-H(29) | 120.7 |
| C(29)-C(30)-C(31) | 120.0(6) |
| C(29)-C(30)-H(30) | 120 |
| C(31)-C(30)-H(30) | 120 |
| C(30)-C(31)-C(26) | 116.6(6) |
| C(30)-C(31)-H(31) | 121.7 |
| C(26)-C(31)-H(31) | 121.7 |
| C(33)-C(32)-C(23) | 120.3(4) |
| C(33)-C(32)-H(32) | 119.9 |
| C(23)-C(32)-H(32) | 119.9 |
| C(32)-C(33)-C(20) | 121.0(4) |
| C(32)-C(33)-H(33) | 119.5 |
| C(20)-C(33)-H(33) | 119.5 |
| C(2')-C(1')-H(1'1) | 109.5 |
| C(2')-C(1')-H(1'2) | 109.5 |
| H(1'1)-C(1')-H(1'2) | 109.5 |
| C(2')-C(1')-H(1'3) | 109.5 |
| H(1'1)-C(1')-H(1'3) | 109.5 |
| H(1'2)-C(1')-H(1'3) | 109.5 |
| C(3')-C(2')-C(1') | 179.4(6) |
| C(2')-C(3')-C(4') | 173.5(6) |
| O(34')-C(4')-N(5') | 122.3(5) |
| O(34')-C(4')-C(3') | 122.6(4) |
| N(5')-C(4')-C(3') | 115.1(5) |
| C(4')-N(5')-C(6') | 121.7(4) |
| C(4')-N(5')-C(6') | 125.2(4) |
| C(9')-N(5')-C(6') | 112.8(4) |
| N(5')-C(6')-C(7') | 103.7(5) |
| N(5')-C(6')-H(6'1) | 111 |
| C(7')-C(6')-H(6'1) | 111 |
| N(5')-C(6')-H(6'2) | 111 |
| C(7')-C(6')-H(6'2) | 111 |
| H(6'1)-C(6')-H(6'2) | 109 |
| C(6')-C(7')-C(8') | 105.8(5) |
| C(6')-C(7')-H(7'1) | 110.6 |
| C(8')-C(7')-H(7'1) | 110.6 |
| C(6')-C(7')-H(7'2) | 110.6 |
| C(8')-C(7')-H(7'2) | 110.6 |
| H(7'1)-C(7')-H(7'2) | 108.7 |
| C(7')-C(8')-C(9') | 103.5(4) |
| C(7')-C(8')-H(8'1) | 111.1 |
| C(9')-C(8')-H(8'1) | 111.1 |
| C(7')-C(8')-H(8'2) | 111.1 |
| C(9')-C(8')-H(8'2) | 111.1 |
| H(8'1)-C(8')-H(8'2) | 109 |
| N(5')-C(9')-C(10') | 109.5(4) |
| N(5')-C(9')-C(8') | 102.6(4) |
| C(10')-C(9')-C(8') | 113.8(4) |
| N(5')-C(9')-H(9') | 110.2 |
| C(10')-C(9')-H(9') | 110.2 |
| C(8')-C(9')-H(9') | 110.2 |
| N(11')-C(10')-N(18') | 111.1(4) |
| N(11')-C(10')-C(9') | 126.2(4) |
| N(18')-C(10')-C(9') | 122.6(4) |
| C(10')-N(11')-C(12') | 107.0(4) |
| N(11')-C(12')-C(13') | 109.7(4) |
| N(11')-C(12')-C(20') | 120.5(4) |
| C(13')-C(12')-C(20') | 129.6(5) |
| C(12')-C(13')-N(18') | 105.1(4) |
| C(12')-C(13')-C(14') | 137.3(4) |
| N(18')-C(13')-C(14') | 117.3(4) |
| N(15')-C(14')-N(19') | 118.7(5) |
| N(15')-C(14')-C(13') | 122.1(4) |

TABLE 28-continued

Bond lengths (Å) and angles (°) for the Form I crystal structure.

| | |
|---|---|
| N(19')-C(14')-C(13') | 119.2(4) |
| C(14')-N(15')-C(16') | 117.7(5) |
| C(17')-C(16')-N(15') | 125.3(4) |
| C(17')-C(16')-H(16') | 117.3 |
| N(15')-C(16')-H(16') | 117.3 |
| C(16')-C(17')-N(18') | 116.7(5) |
| C(16')-C(17')-H(17') | 121.6 |
| N(18')-C(17')-H(17') | 121.6 |
| C(10')-N(18')-C(17') | 132.0(4) |
| C(10')-N(18')-C(13') | 107.1(3) |
| C(17')-N(18')-C(13') | 120.8(4) |
| C(14')-N(19')-H(19C) | 112(4) |
| C(14')-N(19')-H(19D) | 121(3) |
| H(19C)-N(19')-H(19D) | 110(5) |
| C(21')-C(20')-C(33') | 118.3(4) |
| C(21')-C(20')-C(12') | 123.1(4) |
| C(33')-C(20')-C(12') | 118.6(4) |
| C(22')-C(21')-C(20') | 121.3(5) |
| C(22')-C(21')-H(21') | 119.3 |
| C(20')-C(21')-H(21') | 119.3 |
| C(21')-C(22')-C(23') | 120.2(5) |
| C(21')-C(22')-H(22') | 119.9 |
| C(23')-C(22')-H(22') | 119.9 |
| C(32')-C(23')-C(22') | 117.9(5) |
| C(32')-C(23')-C(24') | 117.0(4) |
| C(22')-C(23')-C(24') | 125.1(4) |
| O(35')-C(24')-N(25') | 122.5(4) |
| O(35')-C(24')-C(23') | 121.0(4) |
| N(25')-C(24')-C(23') | 116.5(4) |
| C(24')-N(25')-C(26') | 125.5(4) |
| C(24')-N(25')-H(25') | 123(4) |
| C(26')-N(25')-H(25') | 111(4) |
| N(27')-C(26')-C(31') | 124.1(5) |
| N(27')-C(26')-N(25') | 113.5(4) |
| C(31')-C(26')-N(25') | 122.3(5) |
| C(28')-N(27')-C(26') | 116.5(5) |
| N(27')-C(28')-C(29') | 124.4(6) |
| N(27')-C(28')-H(28') | 117.8 |
| C(29')-C(28')-H(28') | 117.8 |
| C(28')-C(29')-C(30') | 118.4(5) |
| C(28')-C(29')-H(29') | 120.8 |
| C(30')-C(29')-H(29') | 120.8 |
| C(31')-C(30')-C(29') | 119.2(5) |
| C(31')-C(30')-H(30') | 120.4 |
| C(29')-C(30')-H(30') | 120.4 |
| C(30')-C(31')-C(26') | 117.4(6) |
| C(30')-C(31')-H(31') | 121.3 |
| C(26')-C(31')-H(31') | 121.3 |
| C(33')-C(32')-C(23') | 121.8(5) |
| C(33')-C(32')-H(32') | 119.1 |
| C(23')-C(32')-H(32') | 119.1 |
| C(32')-C(33')-C(20') | 120.4(5) |
| C(32')-C(33')-H(33') | 119.8 |
| C(20')-C(33')-H(33') | 119.8 |

TABLE 29

Hydrogen coordinates [×10^4] and isotropic displacement parameters [Å^2 × 10^3] for the Form I crystal structure.

| Atom | x | y | z | $U_{eq}$ | s.o.f. |
|---|---|---|---|---|---|
| H(1A) | −6178 | 5079 | 12092 | 153 | 1 |
| H(1B) | −4356 | 4281 | 12145 | 153 | 1 |
| H(1C) | −5145 | 4148 | 11237 | 153 | 1 |
| H(6A) | −68 | 5698 | 10586 | 57 | 1 |
| H(6B) | −452 | 6632 | 11490 | 57 | 1 |
| H(7A) | 2615 | 6200 | 10053 | 60 | 1 |
| H(7B) | 2383 | 6712 | 11121 | 60 | 1 |
| H(8A) | 1793 | 8851 | 10645 | 51 | 1 |
| H(8B) | 3009 | 8338 | 9638 | 51 | 1 |
| H(9) | −136 | 9423 | 9718 | 42 | 1 |
| H(16) | −1351 | 11404 | 6928 | 49 | 1 |
| H(17) | −1075 | 10553 | 8395 | 43 | 1 |
| H(19A) | 1750(70) | 8720(40) | 4820(30) | 38(15) | 1 |
| H(19B) | 2460(60) | 7530(50) | 5320(40) | 41(15) | 1 |
| H(21) | 1146 | 5365 | 6172 | 47 | 1 |
| H(22) | 2881 | 3660 | 5290 | 50 | 1 |
| H(25) | 4900(50) | 2800(50) | 4260(40) | 42(15) | 1 |
| H(28) | 7204 | 1182 | 1473 | 74 | 1 |
| H(29) | 9216 | −545 | 1706 | 81 | 1 |
| H(30) | 9788 | −946 | 3235 | 72 | 1 |
| H(31) | 8260 | 391 | 4513 | 54 | 1 |
| H(32) | 6876 | 4351 | 6352 | 44 | 1 |
| H(33) | 5129 | 6022 | 7253 | 42 | 1 |
| H(1'1) | 8252 | 5619 | −2426 | 81 | 1 |
| H(1'2) | 8403 | 6479 | −1568 | 81 | 1 |
| H(1'3) | 6772 | 5696 | −1446 | 81 | 1 |
| H(6'1) | 12664 | 4414 | −1075 | 55 | 1 |
| H(6'2) | 13481 | 3328 | −1872 | 55 | 1 |
| H(7'1) | 14809 | 3950 | −333 | 75 | 1 |
| H(7'2) | 15868 | 3464 | −1381 | 75 | 1 |
| H(8'1) | 15714 | 1821 | 65 | 55 | 1 |
| H(8'2) | 15577 | 1299 | −948 | 55 | 1 |
| H(9') | 13007 | 745 | −46 | 42 | 1 |
| H(16') | 14375 | −1427 | 2743 | 48 | 1 |
| H(17') | 14324 | −458 | 1261 | 41 | 1 |
| H(19C) | 11220(70) | 1220(50) | 4890(30) | 41(16) | 1 |
| H(19D) | 10600(50) | 2400(40) | 4440(40) | 22(12) | 1 |
| H(21') | 11948 | 4553 | 3699 | 52 | 1 |
| H(22') | 10185 | 6236 | 4584 | 50 | 1 |
| H(25') | 8300(50) | 7510(50) | 5450(50) | 41(15) | 1 |
| H(28') | 5814 | 8970 | 8239 | 57 | 1 |
| H(29') | 3650 | 10556 | 8004 | 62 | 1 |
| H(30') | 3120 | 10920 | 6446 | 56 | 1 |
| H(31') | 4770 | 9590 | 5188 | 49 | 1 |
| H(32') | 6404 | 5746 | 3281 | 47 | 1 |
| H(33') | 8180 | 4113 | 2376 | 42 | 1 |

Figure 54:
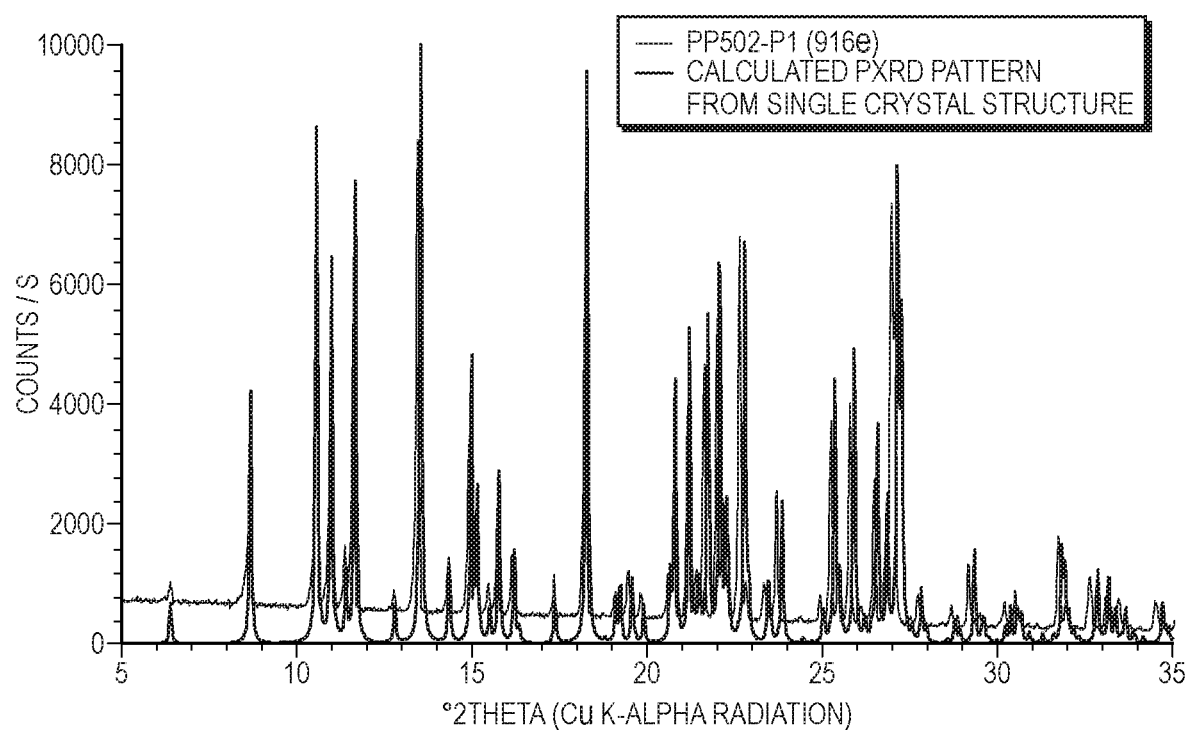
FIG. 54 compares the PXRD pattern of Form I to the pattern simulated using the crystal structure of Form I.

The PXRD pattern of Form I is compared to the pattern simulated using the crystal structure of Form I in FIG. 54. The patterns show agreement that indicates that the single crystal is representative of the same crystalline phase as Form I.

Example 11. Crystal Structure of Form III of the Formula (1) Free Base

A study of the crystal structure of Formula (1) free base Form III was also performed. The experimental methods are as described in Example 9, with the exception of the following. Water hydrogen atoms were positioned in assumed ideal positions and refined with O—H and H•••H distances restrained to 0.86(1) Å and 1.51(2) Å, respectively, and their thermal displacement parameters were set to 1.2$U_{eq}$ of the parent O atom. The O4W/O4W' water molecule was found to be disordered over two positions with relative occupancies of 0.85 and 0.15. The hydrogen atoms of the O4W/O4W' molecule could not be determined, but they are included in the molecular formula. The rings N5-C6-C7-C8-C9 of molecule A and N5'-C6'-C7'-C8'-C9' of molecule B are each disordered over two positions, with the relative occupancies for their major components of 0.70 and 0.61, respectively. Distance restraints were applied on equivalent bond and non-bond distances of the disorder component. The opposite atoms of disorder fragments were refined with equal anisotropic displacement parameters.

The results of the crystallographic experiments are summarized in Table 30.

TABLE 30

Crystal data and structure refinement for Form III.

| | |
|---|---|
| Identification code | 14thg422 PP502-Sol-DMF-H2O |
| Empirical formula | $C_{26}H_{27}N_7O_4$ |
| Moiety formula | $C_{26}H_{23}N_7O_2 \cdot 2H_2O$ |
| Formula weight | 501.54 |
| Temperature | 293(2)K |
| Wavelength | 1.54184 Å (Cu radiation) |
| Crystal system | Monoclinic |
| Space group | $P2_1$ |
| Unit cell dimensions | a = 8.3932(6) Å  α = 90° |
| | b = 21.1721(11) Å  β = 94.586(5)° |
| | c = 14.1298(7) Å  γ = 90° |
| Volume | 2502.9(3) Å³ |
| Z | 4 |
| Density (calculated) | 1.331 Mg/m³ |
| Absorption coefficient | 0.764 mm⁻¹ |
| F(000) | 1056 |
| Crystal | prism; colorless |
| Crystal size | 0.250 × 0.150 × 0.020 mm³ |
| Theta range for data collection | 3.769-62.794° |
| Index ranges | −9 ≤ h ≤ 9, −24 ≤ k ≤ 24, −15 ≤ l ≤ 16 |
| Reflections collected | 12795 |
| Independent reflections | 7704 [$R_{int}$ = 0.0441] |
| Absorption correction | Semi-empirical from equivalents |
| Max. and min. transmission | 1.00000 and 0.80527 |

TABLE 30-continued

Crystal data and structure refinement for Form III.

| | |
|---|---|
| Refinement method | Full-matrix least-squares on $F^2$ |
| Data/restraints/parameters | 7704/52/705 |
| Goodness-of-fit on $F^2$ | 1.048 |
| Final R indices [$F^2 > 2\sigma(F^2)$] | R1 = 0.0658, wR2 = 0.1685 |
| R indices (all data) | R1 = 0.0805, wR2 = 0.1883 |
| Absolute structure parameter | −0.1(2) |
| Extinction coefficient | 0.0030(6) |
| Largest diff. peak and hole | 0.327 and −0.228 e Å³ |

The asymmetric unit contains two molecules, denoted A and B, and four water positions, corresponding to a dihydrate. One water position is split. The compound is a dihydrate. The absolute configuration at both C9 and C9' was established as the (S)-configuration by anomalous-dispersion effects. The Flack x parameters, −0.1(3), was determined using 2360 quotients [(I+)−(I−)]/[(I+)+(I−)], as described in Parsons, et al., Acta Cryst. 2013, B69, 249-259).

The crystal structure does not contain any apparent solvent-accessible voids. The crystal structure contains classical N—H•••O, N—H•••N and O—H•••O bonds (listed in Table 31).

TABLE 31

Hydrogen bonds in the Form III crystal structure.

| D—H ... A | d(D—H) (Å) | d(H ... A) (Å) | d(D ... A) (Å) | DHA angle (°) |
|---|---|---|---|---|
| N(19)—H(19A) ... N(15')#1 | 0.867(15) | 2.17(2) | 3.030(7) | 171(7) |
| N(25)—H(25) ... O(2W)#2 | 0.861(15) | 2.16(3) | 2.964(9) | 155(5) |
| N(19')—H(19C) ... N(15)#3 | 0.866(15) | 2.214(17) | 3.079(7) | 176(7) |
| N(25')—H(25') ... O(1W) | 0.861(15) | 2.07(3) | 2.863(10) | 152(5) |
| O(1W)—H(1W) ... O(34) | 0.84(3) | 1.92(6) | 2.714(8) | 157(12) |
| O(2W)—H(3W) ... N(27)#4 | 0.81(3) | 2.23(7) | 2.90(4) | 141(8) |
| O(2W)—H(4W) ... O(34') | 0.82(3) | 2.13(6) | 2.867(9) | 149(10) |
| O(3W)—H(5W) ... O(35) | 0.85(3) | 2.24(7) | 2.977(11) | 144(11) |
| O(3W)—H(6W) ... N(11')#5 | 0.83(3) | 2.28(7) | 3.049(9) | 153(13) |

Symmetry transformations used to generate equivalent atoms:
1 −x + 1,y − 1/2,−z + 2
2 x,y,z − 1
3 −x + 1,y + 1/2, −z + 2
4 x,y,z + 1
5 −x + 2,y − 1/2,−z + 1

Additional results, including atomic coordinates for the Form III crystal structure, are given in Table 32, Table 33, and Table 34.

TABLE 32

Atomic coordinates (×10⁴), equivalent isotropic displacement parameters (Å² × 10³) and site occupancy factors for heavy atoms in the Form III crystal structure. $U_{eq}$ is defined as one third of the trace of the orthogonalized $U_{ij}$ tensor.

| Atom | x | y | z | Ueq | s.o.f. |
|---|---|---|---|---|---|
| C(1) | 7254(13) | 5083(4) | 7815(5) | 109(3) | 1 |
| C(2) | 6777(9) | 5436(3) | 6954(5) | 80(2) | 1 |
| C(3) | 6374(9) | 5707(3) | 6235(5) | 78(2) | 1 |
| C(4) | 5962(8) | 6018(3) | 5343(4) | 69(2) | 1 |
| N(5) | 4572(6) | 5852(2) | 4896(4) | 75(1) | 1 |
| C(6) | 4022(10) | 6145(4) | 3994(6) | 105(3) | 1 |
| C(7) | 2525(15) | 5791(7) | 3682(10) | 121(5) | 0.699(17) |
| C(8) | 1854(14) | 5636(13) | 4614(14) | 128(4) | 0.699(17) |
| C(7A) | 2244(18) | 6201(15) | 4070(20) | 121(5) | 0.301(17) |
| C(8A) | 1860(30) | 5600(30) | 4600(40) | 128(4) | 0.301(17) |
| C(9) | 3334(8) | 5457(3) | 5279(6) | 87(2) | 1 |
| C(10) | 3735(8) | 4767(3) | 5295(5) | 74(2) | 1 |
| N(11) | 4057(6) | 4430(2) | 4554(4) | 71(1) | 1 |
| C(12) | 4209(7) | 3815(3) | 4838(4) | 63(1) | 1 |

TABLE 32-continued

Atomic coordinates (×10⁴), equivalent isotropic displacement parameters (Å² × 10³) and site occupancy factors for heavy atoms in the Form III crystal structure. $U_{eq}$ is defined as one third of the trace of the orthogonalized $U_{ij}$ tensor.

| Atom | x | y | z | Ueq | s.o.f. |
|---|---|---|---|---|---|
| C(13) | 3912(7) | 3769(3) | 5788(4) | 63(1) | 1 |
| C(14) | 3665(7) | 3278(3) | 6463(4) | 65(1) | 1 |
| N(15) | 3411(8) | 3409(3) | 7350(4) | 82(2) | 1 |
| C(16) | 3324(11) | 4037(4) | 7594(5) | 96(2) | 1 |
| C(17) | 3371(9) | 4523(3) | 7006(5) | 87(2) | 1 |
| N(18) | 3645(6) | 4390(2) | 6065(4) | 69(1) | 1 |
| N(19) | 3695(7) | 2658(2) | 6211(4) | 72(1) | 1 |
| C(20) | 4578(7) | 3318(3) | 4162(4) | 63(1) | 1 |
| C(21) | 3901(8) | 3338(3) | 3233(4) | 75(2) | 1 |
| C(22) | 4268(8) | 2899(3) | 2575(5) | 82(2) | 1 |
| C(23) | 5353(7) | 2411(3) | 2823(4) | 70(2) | 1 |
| C(24) | 5740(8) | 1903(4) | 2146(5) | 78(2) | 1 |
| N(25) | 5343(7) | 2023(3) | 1207(4) | 82(2) | 1 |
| C(26) | 5402(6) | 1603(2) | 438(3) | 78(2) | 1 |
| N(27) | 5424(6) | 1895(2) | −399(3) | 90(2) | 1 |
| C(28) | 5407(7) | 1526(3) | −1180(3) | 108(3) | 1 |
| C(29) | 5320(7) | 880(3) | −1147(4) | 114(3) | 1 |
| C(30) | 5290(7) | 590(2) | −268(5) | 116(3) | 1 |
| C(31) | 5335(7) | 952(2) | 556(4) | 104(2) | 1 |
| C(32) | 6035(8) | 2391(3) | 3738(4) | 72(2) | 1 |
| C(33) | 5674(8) | 2835(3) | 4389(4) | 71(2) | 1 |
| O(34) | 6839(6) | 6408(2) | 4997(3) | 92(1) | 1 |
| O(35) | 6352(7) | 1410(3) | 2427(4) | 105(2) | 1 |
| C(1') | 7696(16) | 2764(5) | 7523(8) | 142(4) | 1 |
| C(2') | 7752(12) | 3245(4) | 8271(6) | 104(2) | 1 |
| C(3') | 7804(11) | 3640(3) | 8876(6) | 97(2) | 1 |
| C(4') | 7786(12) | 4089(3) | 9650(5) | 87(2) | 1 |
| N(5') | 9178(7) | 4331(2) | 9967(4) | 80(2) | 1 |
| C(6') | 10718(14) | 4074(10) | 9711(13) | 109(6) | 0.614(13) |
| C(7') | 11884(14) | 4463(6) | 10289(14) | 125(6) | 0.614(13) |
| C(8') | 11090(20) | 4550(20) | 11219(15) | 108(3) | 0.614(13) |
| C(6") | 10790(20) | 4240(20) | 9650(20) | 109(6) | 0.386(13) |
| C(7") | 11720(20) | 4083(10) | 10698(15) | 125(6) | 0.386(13) |
| C(8") | 10980(40) | 4550(30) | 11330(30) | 108(3) | 0.386(13) |
| C(9') | 9334(7) | 4700(3) | 10847(4) | 76(2) | 1 |
| C(10') | 9125(7) | 5389(3) | 10673(4) | 64(1) | 1 |
| N(11') | 9385(6) | 5712(2) | 9891(3) | 63(1) | 1 |
| C(12') | 9236(7) | 6337(3) | 10105(4) | 58(1) | 1 |
| C(13') | 8844(6) | 6404(3) | 11035(4) | 60(1) | 1 |
| C(14') | 8396(7) | 6902(3) | 11662(4) | 65(1) | 1 |
| N(15') | 8097(6) | 6786(3) | 12546(3) | 73(1) | 1 |
| C(16') | 8185(8) | 6172(3) | 12851(5) | 77(2) | 1 |
| C(17') | 8477(8) | 5671(3) | 12314(4) | 71(2) | 1 |
| N(18') | 8795(5) | 5792(2) | 11387(3) | 60(1) | 1 |
| N(19') | 8247(7) | 7499(2) | 11341(4) | 74(1) | 1 |
| C(20') | 9595(7) | 6820(2) | 9394(4) | 58(1) | 1 |
| C(21') | 8991(8) | 6766(3) | 8469(4) | 74(2) | 1 |
| C(22') | 9397(8) | 7207(3) | 7784(4) | 75(2) | 1 |
| C(23') | 10437(7) | 7698(2) | 8029(4) | 63(1) | 1 |
| C(24') | 10911(9) | 8199(3) | 7361(5) | 76(2) | 1 |
| N(25') | 10449(7) | 8119(3) | 6439(4) | 76(1) | 1 |
| C(26') | 10663(6) | 8542(2) | 5682(3) | 90(2) | 1 |
| N(27') | 10045(6) | 8313(3) | 4855(4) | 114(2) | 1 |
| C(28') | 10118(8) | 8689(4) | 4087(3) | 157(6) | 1 |
| C(29') | 10828(9) | 9274(4) | 4120(5) | 164(6) | 1 |
| C(30') | 11467(9) | 9497(2) | 4989(6) | 147(5) | 1 |
| C(31') | 11393(8) | 9130(3) | 5801(4) | 112(3) | 1 |
| C(32') | 11044(8) | 7747(3) | 8964(4) | 69(2) | 1 |
| C(33') | 10637(7) | 7311(3) | 9641(4) | 66(1) | 1 |
| O(34') | 6502(7) | 4225(2) | 9989(4) | 100(2) | 1 |
| O(35') | 11686(9) | 8659(2) | 7651(4) | 119(2) | 1 |
| O(1W) | 9679(9) | 7013(4) | 5330(5) | 135(2) | 1 |
| O(2W) | 4409(8) | 3159(3) | 10069(4) | 106(2) | 1 |
| O(3W) | 8713(12) | 472(4) | 1824(8) | 157(3) | 1 |
| O(4W) | 14547(14) | 9678(5) | 7332(8) | 170(5) | 0.848(14) |
| O(4W') | 14510(80) | 9400(30) | 8260(50) | 170(5) | 0.152(14) |

TABLE 33

Bond lengths (Å) and angles (°) for the Form III crystal structure.

| Bond | Value |
|---|---|
| C(1)—C(2) | 1.456(10) |
| C(1)—H(1A) | 0.96 |
| C(1)—H(1B) | 0.96 |
| C(1)—H(1C) | 0.96 |
| C(2)—C(3) | 1.193(9) |
| C(3)—C(4) | 1.438(9) |
| C(4)—O(34) | 1.234(7) |
| C(4)—N(5) | 1.328(8) |
| N(5)—C(6) | 1.458(9) |
| N(5)—C(9) | 1.472(8) |
| C(6)—C(7) | 1.499(11) |
| C(6)—C(7A) | 1.509(14) |
| C(6)—H(6A) | 0.97 |
| C(6)—H(6B) | 0.97 |
| C(6)—H(6A1) | 0.97 |
| C(6)—H(6A2) | 0.97 |
| C(7)—C(8) | 1.510(14) |
| C(7)—H(7A) | 0.97 |
| C(7)—H(7B) | 0.97 |
| C(8)—C(9) | 1.544(11) |
| C(8)—H(8A) | 0.97 |
| C(8)—H(8B) | 0.97 |
| C(7A)—C(8A) | 1.523(15) |
| C(7A)—H(7A1) | 0.97 |
| C(7A)—H(7A2) | 0.97 |
| C(8A)—C(9) | 1.538(14) |
| C(8A)—H(8A1) | 0.97 |
| C(8A)—H(8A2) | 0.97 |
| C(9)—C(10) | 1.497(9) |
| C(9)—H(9) | 0.98 |
| C(9)—H(9A) | 0.98 |
| C(10)—N(11) | 1.313(8) |
| C(10)—N(18) | 1.357(8) |
| N(11)—C(12) | 1.367(7) |
| C(12)—C(13) | 1.389(8) |
| C(12)—C(20) | 1.471(8) |
| C(13)—N(18) | 1.396(8) |
| C(13)—C(14) | 1.436(8) |
| C(14)—N(15) | 1.317(8) |
| C(14)—N(19) | 1.362(8) |
| N(15)—C(16) | 1.378(10) |
| C(16)—C(17) | 1.324(11) |
| C(16)—H(16) | 0.93 |
| C(17)—N(18) | 1.396(9) |
| C(17)—H(17) | 0.93 |
| N(19)—H(19A) | 0.867(15) |
| N(19)—H(19B) | 0.864(15) |
| C(20)—C(21) | 1.388(9) |
| C(20)—C(33) | 1.395(9) |
| C(21)—C(22) | 1.367(9) |
| C(21)—H(21) | 0.93 |
| C(22)—C(23) | 1.404(10) |
| C(22)—H(22) | 0.93 |
| C(23)—C(32) | 1.372(9) |
| C(23)—C(24) | 1.493(9) |
| C(24)—O(35) | 1.216(9) |
| C(24)—N(25) | 1.365(9) |
| N(25)—C(26) | 1.409(6) |
| N(25)—H(25) | 0.861(15) |
| C(26)—N(27) | 1.3363 |
| C(26)—C(31) | 1.3898 |
| N(27)—C(28) | 1.3505 |
| C(28)—C(29) | 1.3707 |
| C(28)—H(28) | 0.93 |
| C(29)—C(30) | 1.3874 |
| C(29)—H(29) | 0.93 |
| C(30)—C(31) | 1.3907 |
| C(30)—H(30) | 0.93 |
| C(31)—H(31) | 0.93 |
| C(32)—C(33) | 1.366(9) |
| C(32)—H(32) | 0.93 |
| C(33)—H(33) | 0.93 |
| C(1')—C(2') | 1.468(12) |
| C(1')—H(1'1) | 0.96 |
| C(1')—H(1'2) | 0.96 |
| C(1')—H(1'3) | 0.96 |
| C(2')—C(3') | 1.193(10) |
| C(3')—C(4') | 1.450(11) |
| C(4')—O(34') | 1.248(10) |
| C(4')—N(5') | 1.321(10) |
| N(5')—C(9') | 1.466(7) |
| N(5')—C(6") | 1.470(14) |
| N(5')—C(6') | 1.474(12) |
| C(6')—C(7') | 1.475(13) |
| C(6')—H(6'1) | 0.97 |
| C(6')—H(6'2) | 0.97 |
| C(7')—C(8') | 1.533(14) |
| C(7')—H(7'1) | 0.97 |
| C(7')—H(7'2) | 0.97 |
| C(8')—C(9') | 1.555(11) |
| C(8')—H(8'1) | 0.97 |
| C(8')—H(8'2) | 0.97 |
| C(6")—C(7") | 1.65(5) |
| C(6")—H(6"1) | 0.97 |
| C(6")—H(6"2) | 0.97 |
| C(7")—C(8") | 1.504(14) |
| C(7")—H(7"1) | 0.97 |
| C(7")—H(7"2) | 0.97 |
| C(8")—C(9') | 1.523(13) |
| C(8")—H(8"1) | 0.97 |
| C(8")—H(8"2) | 0.97 |
| C(9')—C(10') | 1.488(8) |
| C(9')—H(9') | 0.98 |
| C(9')—H(9") | 0.98 |
| C(10')—N(11') | 1.332(8) |
| C(10')—N(18') | 1.366(7) |
| N(11')—C(12') | 1.365(7) |
| C(12')—C(13') | 1.388(8) |
| C(12')—C(20') | 1.482(8) |
| C(13')—N(18') | 1.389(7) |
| C(13')—C(14') | 1.446(8) |
| C(14')—N(15') | 1.316(8) |
| C(14')—N(19') | 1.344(8) |
| N(15')—C(16') | 1.370(9) |
| C(16')—C(17') | 1.337(9) |
| C(16')—H(16') | 0.93 |
| C(17')—N(18') | 1.383(7) |
| C(17')—H(17') | 0.93 |
| N(19')—H(19C) | 0.866(15) |
| N(19')—H(19D) | 0.862(15) |
| C(20')—C(21') | 1.368(8) |
| C(20')—C(33') | 1.385(8) |
| C(21')—C(22') | 1.406(9) |
| C(21')—H(21') | 0.93 |
| C(22')—C(23') | 1.384(9) |
| C(22')—H(22') | 0.93 |
| C(23')—C(32') | 1.381(8) |
| C(23')—C(24') | 1.495(8) |
| C(24)—O(35') | 1.223(8) |
| C(24)—N(25') | 1.339(9) |
| N(25')—C(26') | 1.417(6) |
| N(25')—H(25') | 0.861(15) |
| C(26')—N(27') | 1.3318 |
| C(26')—C(31') | 1.3918 |
| N(27')—C(28') | 1.3508 |
| C(28')—C(29') | 1.3735 |
| C(28')—H(28') | 0.93 |
| C(29')—C(30') | 1.3825 |
| C(29')—H(29') | 0.93 |
| C(30')—C(31') | 1.3914 |
| C(30')—H(30') | 0.93 |
| C(31')—H(31') | 0.93 |
| C(32')—C(33') | 1.392(8) |
| C(32')—H(32') | 0.93 |
| C(33')—H(33') | 0.93 |
| O(1W)—H(1W) | 0.84(3) |
| O(1W)—H(2W) | 0.88(3) |
| O(2W)—H(3W) | 0.81(3) |
| O(2W)—H(4W) | 0.82(3) |
| O(3W)—H(5W) | 0.85(3) |
| O(3W)—H(6W) | 0.83(3) |
| C(2)—C(1)—H(1A) | 109.5 |
| C(2)—C(1)—H(1B) | 109.5 |
| H(1A)—C(1)—H(1B) | 109.5 |

TABLE 33-continued

Bond lengths (Å) and angles (°) for the Form III crystal structure.

| | |
|---|---|
| C(2)—C(1)—H(1C) | 109.5 |
| H(1A)—C(1)—H(1C) | 109.5 |
| H(1B)—C(1)—H(1C) | 109.5 |
| C(3)—C(2)—C(1) | 177.9(7) |
| C(2)—C(3)—C(4) | 176.8(7) |
| O(34)—C(4)—N(5) | 121.1(6) |
| O(34)—C(4)—C(3) | 122.9(6) |
| N(5)—C(4)—C(3) | 115.9(5) |
| C(4)—N(5)—C(6) | 120.5(5) |
| C(4)—N(5)—C(9) | 126.4(5) |
| C(6)—N(5)—C(9) | 112.3(5) |
| N(5)—C(6)—C(7) | 104.1(7) |
| N(5)—C(6)—C(7A) | 102.8(10) |
| N(5)—C(6)—H(6A) | 110.9 |
| C(7)—C(6)—H(6A) | 110.9 |
| N(5)—C(6)—H(6B) | 110.9 |
| C(7)—C(6)—H(6B) | 110.9 |
| H(6A)—C(6)—H(6B) | 109 |
| N(5)—C(6)—H(6A1) | 111.2 |
| C(7A)—C(6)—H(6A1) | 111.2 |
| N(5)—C(6)—H(6A2) | 111.2 |
| C(7A)—C(6)—H(6A2) | 111.2 |
| H(6A1)—C(6)—H(6A2) | 109.1 |
| C(6)—C(7)—C(8) | 102.4(10) |
| C(6)—C(7)—H(7A) | 111.3 |
| C(8)—C(7)—H(7A) | 111.3 |
| C(6)—C(7)—H(7B) | 111.3 |
| C(8)—C(7)—H(7B) | 111.3 |
| H(7A)—C(7)—H(7B) | 109.2 |
| C(7)—C(8)—C(9) | 104.3(10) |
| C(7)—C(8)—H(8A) | 110.9 |
| C(9)—C(8)—H(8A) | 110.9 |
| C(7)—C(8)—H(8B) | 110.9 |
| C(9)—C(8)—H(8B) | 110.9 |
| H(8A)—C(8)—H(8B) | 108.9 |
| C(6)—C(7A)—C(8A) | 102.5(15) |
| C(6)—C(7A)—H(7A1) | 111.3 |
| C(8A)—C(7A)—H(7A1) | 111.3 |
| C(6)—C(7A)—H(7A2) | 111.3 |
| C(8A)—C(7A)—H(7A2) | 111.3 |
| H(7A1)—C(7A)—H(7A2) | 109.2 |
| C(7A)—C(8A)—C(9) | 106.5(14) |
| C(7A)—C(8A)—H(8A1) | 110.4 |
| C(9)—C(8A)—H(8A1) | 110.4 |
| C(7A)—C(8A)—H(8A2) | 110.4 |
| C(9)—C(8A)—H(8A2) | 110.4 |
| H(8A1)—C(8A)—H(8A2) | 108.6 |
| N(5)—C(9)—C(10) | 113.3(6) |
| N(5)—C(9)—C(8A) | 102.2(9) |
| C(10)—C(9)—C(8A) | 112(2) |
| N(5)—C(9)—C(8) | 101.2(7) |
| C(10)—C(9)—C(8) | 114.7(13) |
| N(5)—C(9)—H(9) | 109.1 |
| C(10)—C(9)—H(9) | 109.1 |
| C(8)—C(9)—H(9) | 109.1 |
| N(5)—C(9)—H(9A) | 109.8 |
| C(10)—C(9)—H(9A) | 109.8 |
| C(8A)—C(9)—H(9A) | 109.8 |
| N(11)—C(10)—N(18) | 110.4(5) |
| N(11)—C(10)—C(9) | 125.3(6) |
| N(18)—C(10)—C(9) | 123.9(6) |
| C(10)—N(11)—C(12) | 107.7(5) |
| N(11)—C(12)—C(13) | 109.3(5) |
| N(11)—C(12)—C(20) | 120.7(5) |
| C(13)—C(12)—C(20) | 129.9(5) |
| C(12)—C(13)—N(18) | 104.5(5) |
| C(12)—C(13)—C(14) | 137.7(5) |
| N(18)—C(13)—C(14) | 117.4(5) |
| N(15)—C(14)—N(19) | 117.3(5) |
| N(15)—C(14)—C(13) | 121.5(5) |
| N(19)—C(14)—C(13) | 121.1(5) |
| C(14)—N(15)—C(16) | 117.2(6) |
| C(17)—C(16)—N(15) | 126.0(6) |
| C(17)—C(16)—H(16) | 117 |
| N(15)—C(16)—H(16) | 117 |
| C(16)—C(17)—N(18) | 117.1(6) |
| C(16)—C(17)—H(17) | 121.4 |
| N(18)—C(17)—H(17) | 121.4 |
| C(10)—N(18)—C(17) | 132.0(5) |
| C(10)—N(18)—C(13) | 108.0(5) |
| C(17)—N(18)—C(13) | 120.0(5) |
| C(14)—N(19)—H(19A) | 118(4) |
| C(14)—N(19)—H(19B) | 113(4) |
| H(19A)—N(19)—H(19B) | 121(3) |
| C(21)—C(20)—C(33) | 116.9(5) |
| C(21)—C(20)—C(12) | 120.0(6) |
| C(33)—C(20)—C(12) | 123.0(5) |
| C(22)—C(21)—C(20) | 121.6(6) |
| C(22)—C(21)—H(21) | 119.2 |
| C(20)—C(21)—H(21) | 119.2 |
| C(21)—C(22)—C(23) | 120.5(6) |
| C(21)—C(22)—H(22) | 119.7 |
| C(23)—C(22)—H(22) | 119.7 |
| C(32)—C(23)—C(22) | 118.1(6) |
| C(32)—C(23)—C(24) | 119.1(6) |
| C(22)—C(23)—C(24) | 122.7(6) |
| O(35)—C(24)—N(25) | 122.8(7) |
| O(35)—C(24)—C(23) | 121.1(7) |
| N(25)—C(24)—C(23) | 116.1(7) |
| C(24)—N(25)—C(26) | 127.6(6) |
| C(24)—N(25)—H(25) | 119(4) |
| C(26)—N(25)—H(25) | 112(4) |
| N(27)—C(26)—C(31) | 124.7 |
| N(27)—C(26)—N(25) | 113.2(4) |
| C(31)—C(26)—N(25) | 121.9(4) |
| C(26)—N(27)—C(28) | 117 |
| N(27)—C(28)—C(29) | 123.1 |
| N(27)—C(28)—H(28) | 118.4 |
| C(29)—C(28)—H(28) | 118.4 |
| C(28)—C(29)—C(30) | 118.4 |
| C(28)—C(29)—H(29) | 120.8 |
| C(30)—C(29)—H(29) | 120.8 |
| C(29)—C(30)—C(31) | 120.3 |
| C(29)—C(30)—H(30) | 119.8 |
| C(31)—C(30)—H(30) | 119.8 |
| C(26)—C(31)—C(30) | 116.3 |
| C(26)—C(31)—H(31) | 121.8 |
| C(30)—C(31)—H(31) | 121.8 |
| C(33)—C(32)—C(23) | 121.0(6) |
| C(33)—C(32)—H(32) | 119.5 |
| C(23)—C(32)—H(32) | 119.5 |
| C(32)—C(33)—C(20) | 121.8(6) |
| C(32)—C(33)—H(33) | 119.1 |
| C(20)—C(33)—H(33) | 119.1 |
| C(2')—C(1')—H(1'1) | 109.5 |
| C(2')—C(1')—H(1'2) | 109.5 |
| H(1'1)—C(1')—H(1'2) | 109.5 |
| C(2')—C(1')—H(1'3) | 109.5 |
| H(1'1)—C(1')—H(1'3) | 109.5 |
| H(1'2)—C(1')—H(1'3) | 109.5 |
| C(3')—C(2')—C(1') | 179.5(12) |
| C(2')—C(3')—C(4') | 175.6(10) |
| O(34')—C(4')—N(5') | 123.3(6) |
| O(34')—C(4')—C(3') | 120.2(8) |
| N(5')—C(4')—C(3') | 116.6(8) |
| C(4')—N(5')—C(9'') | 120.7(6) |
| C(4')—N(5')—C(6'') | 131.2(14) |
| C(9')—N(5')—C(6'') | 107.6(13) |
| C(4')—N(5')—C(6') | 122.9(8) |
| C(9')—N(5')—C(6') | 112.6(7) |
| N(5')—C(6')—C(7') | 102.4(10) |
| N(5')—C(6')—H(6'1) | 111.3 |
| C(7')—C(6')—H(6'1) | 111.3 |
| N(5')—C(6')—H(6'2) | 111.3 |
| C(7')—C(6')—H(6'2) | 111.3 |
| H(6'1)—C(6')—H(6'2) | 109.2 |
| C(6')—C(7')—C(8') | 103.1(13) |
| C(6)—C(7)—H(7'1) | 111.1 |
| C(8)—C(7)—H(7'1) | 111.1 |
| C(6)—C(7)—H(7'2) | 111.1 |
| C(8)—C(7)—H(7'2) | 111.1 |
| H(7'1)—C(7')—H(7'2) | 109.1 |
| C(7')—C(8')—C(9') | 101.6(10) |
| C(7)—C(8)—H(8'1) | 111.4 |

TABLE 33-continued

Bond lengths (Å) and angles (°) for the Form III crystal structure.

| | |
|---|---|
| C(9')—C(8")—H(8'1) | 111.4 |
| C(7")—C(8")—H(8'2) | 111.4 |
| C(9')—C(8")—H(8'2) | 111.4 |
| H(8'1)—C(8")—H(8'2) | 109.3 |
| N(5')—C(6")—C(7") | 98.1(18) |
| N(5')—C(6")—H(6"1) | 112.2 |
| C(7")—C(6")—H(6"1) | 112.2 |
| N(5')—C(6")—H(6"2) | 112.2 |
| C(7")—C(6")—H(6"2) | 112.2 |
| H(6"1)—C(6")—H(6"2) | 109.8 |
| C(8")—C(7")—C(6") | 102.1(19) |
| C(8")—C(7")—H(7"1) | 111.3 |
| C(6")—C(7")—H(7"1) | 111.3 |
| C(8")—C(7")—H(7"2) | 111.3 |
| C(6")—C(7")—H(7"2) | 111.3 |
| H(7"1)—C(7")—H(7"2) | 109.2 |
| C(7")—C(8")—C(9') | 105.9(12) |
| C(7")—C(8")—H(8"1) | 110.6 |
| C(9')—C(8")—H(8"1) | 110.6 |
| C(7")—C(8")—H(8"2) | 110.6 |
| C(9')—C(8")—H(8"2) | 110.6 |
| H(8"1)—C(8")—H(8"2) | 108.7 |
| N(5')—C(9')—C(10') | 112.4(5) |
| N(5')—C(9')—C(8") | 106.7(8) |
| C(10')—C(9')—C(8") | 112(3) |
| N(5')—C(9')—C(8') | 101.4(8) |
| C(10')—C(9')—C(8') | 110.5(18) |
| N(5')—C(9')—H(9') | 110.8 |
| C(10')—C(9')—H(9') | 110.8 |
| C(8')—C(9')—H(9') | 110.8 |
| N(5')—C(9')—H(9") | 108.7 |
| C(10')—C(9')—H(9") | 108.7 |
| C(8")—C(9')—H(9") | 108.7 |
| N(11')—C(10')—N(18') | 110.4(4) |
| N(11')—C(10')—C(9') | 128.0(5) |
| N(18')—C(10')—C(9') | 121.3(5) |
| C(10')—N(11')—C(12') | 106.8(4) |
| N(11')—C(12')—C(13') | 110.0(5) |
| N(11')—C(12')—C(20') | 119.5(5) |
| C(13')—C(12')—C(20') | 130.3(5) |
| C(12')—C(13')—N(18') | 105.0(5) |
| C(12')—C(13')—C(14') | 138.4(5) |
| N(18')—C(13')—C(14') | 116.4(5) |
| N(15')—C(14')—N(19') | 118.5(5) |
| N(15')—C(14')—C(13') | 121.5(5) |
| N(19')—C(14')—C(13') | 120.0(5) |
| C(14')—N(15')—C(16') | 117.9(5) |
| C(17')—C(16')—N(15') | 125.5(6) |
| C(17')—C(16')—H(16') | 117.2 |
| N(15')—C(16')—H(16') | 117.2 |
| C(16')—C(17')—N(18') | 116.7(6) |
| C(16')—C(17')—H(17') | 121.6 |
| N(18')—C(17')—H(17') | 121.6 |
| C(10')—N(18')—C(17') | 130.6(5) |
| C(10')—N(18')—C(13') | 107.8(4) |
| C(17')—N(18')—C(13') | 121.6(5) |
| C(14')—N(19')—H(19C) | 117(4) |
| C(14')—N(19')—H(19D) | 121(4) |
| H(19C)—N(19')—H(19D) | 120(3) |
| C(21')—C(20')—C(33') | 118.8(5) |
| C(21')—C(20')—C(12') | 120.7(5) |
| C(33')—C(20')—C(12') | 120.4(5) |
| C(20')—C(21')—C(22') | 120.7(6) |
| C(20')—C(21')—H(21') | 119.7 |
| C(22')—C(21')—H(21') | 119.7 |
| C(23')—C(22')—C(21') | 120.6(6) |
| C(23')—C(22')—H(22') | 119.7 |
| C(21')—C(22')—H(22') | 119.7 |
| C(32')—C(23')—C(22') | 118.2(5) |
| C(32')—C(23')—C(24') | 117.0(5) |
| C(22')—C(23')—C(24') | 124.7(6) |
| O(35')—C(24')—N(25') | 122.1(6) |
| O(35')—C(24')—C(23') | 120.9(6) |
| N(25')—C(24')—C(23') | 117.0(6) |
| C(24')—N(25')—C(26') | 127.6(6) |
| C(24')—N(25')—H(25') | 116(3) |
| C(26')—N(25')—H(25') | 116(3) |
| N(27')—C(26')—C(31') | 124.6 |
| N(27')—C(26')—N(25') | 111.7(4) |
| C(31')—C(26')—N(25') | 123.7(4) |
| C(26')—N(27')—C(28') | 116.8 |
| N(27')—C(28')—C(29') | 123.4 |
| N(27')—C(28')—H(28') | 118.3 |
| C(29')—C(28')—H(28') | 118.3 |
| C(28')—C(29')—C(30') | 118.3 |
| C(28')—C(29')—H(29') | 120.8 |
| C(30')—C(29')—H(29') | 120.8 |
| C(29')—C(30')—C(31') | 120.1 |
| C(29')—C(30')—H(30') | 120 |
| C(31')—C(30')—H(30') | 120 |
| C(30')—C(31')—C(26') | 116.7 |
| C(30')—C(31')—H(31') | 121.7 |
| C(26')—C(31')—H(31') | 121.7 |
| C(23')—C(32')—C(33') | 121.0(5) |
| C(23')—C(32')—H(32') | 119.5 |
| C(33')—C(32')—H(32') | 119.5 |
| C(20')—C(33')—C(32') | 120.7(5) |
| C(20')—C(33')—H(33') | 119.7 |
| C(32')—C(33')—H(33') | 119.7 |
| H(1W)—O(1W)—H(2W) | 102(4) |
| H(3W)—O(2W)—H(4W) | 116(5) |
| H(5W)—O(3W)—H(6W) | 108(5) |

TABLE 34

Hydrogen coordinates [×10$^4$] and isotropic displacement parameters [Å$^2$ × 10$^3$] for the Form III crystal structure.

| Atom | x | y | z | U$_{eq}$ | s.o.f. |
|---|---|---|---|---|---|
| H(1A) | 7145 | 5347 | 8359 | 163 | 1 |
| H(1B) | 8348 | 4953 | 7804 | 163 | 1 |
| H(1C) | 6585 | 4718 | 7850 | 163 | 1 |
| H(6A) | 4813 | 6101 | 3535 | 126 | 0.699(17) |
| H(6B) | 3799 | 6590 | 4079 | 126 | 0.699(17) |
| H(6A1) | 4258 | 5882 | 3462 | 126 | 0.301(17) |
| H(6A2) | 4508 | 6557 | 3927 | 126 | 0.301(17) |
| H(7A) | 2762 | 5410 | 3337 | 145 | 0.699(17) |
| H(7B) | 1792 | 6051 | 3286 | 145 | 0.699(17) |
| H(8A) | 1109 | 5285 | 4542 | 153 | 0.699(17) |
| H(8B) | 1310 | 5998 | 4858 | 153 | 0.699(17) |
| H(7A1) | 1671 | 6215 | 3442 | 145 | 0.301(17) |
| H(7A2) | 1984 | 6575 | 4420 | 145 | 0.301(17) |
| H(8A1) | 1652 | 5254 | 4154 | 153 | 0.301(17) |
| H(8A2) | 925 | 5663 | 4946 | 153 | 0.301(17) |
| H(9) | 3171 | 5596 | 5926 | 104 | 0.699(17) |
| H(9A) | 3144 | 5598 | 5921 | 104 | 0.301(17) |
| H(16) | 3224 | 4129 | 8230 | 115 | 1 |
| H(17) | 3227 | 4935 | 7212 | 105 | 1 |
| H(19A) | 3280(80) | 2380(20) | 6580(30) | 86 | 1 |
| H(19B) | 3640(80) | 2600(30) | 5603(12) | 86 | 1 |
| H(21) | 3179 | 3658 | 3054 | 90 | 1 |
| H(22) | 3795 | 2924 | 1958 | 99 | 1 |
| H(25) | 5230(60) | 2410(11) | 1030(40) | 50(14) | 1 |
| H(28) | 5456 | 1720 | −1768 | 129 | 1 |
| H(29) | 5282 | 642 | −1701 | 137 | 1 |
| H(30) | 5239 | 153 | −229 | 139 | 1 |
| H(31) | 5321 | 768 | 1153 | 125 | 1 |
| H(32) | 6753 | 2070 | 3918 | 86 | 1 |
| H(33) | 6172 | 2815 | 5000 | 85 | 1 |
| H(1'1) | 7861 | 2960 | 6926 | 213 | 1 |
| H(1'2) | 6672 | 2559 | 7482 | 213 | 1 |
| H(1'3) | 8520 | 2456 | 7671 | 213 | 1 |
| H(6'1) | 10840 | 4124 | 9038 | 131 | 0.614(13) |
| H(6'2) | 10824 | 3630 | 9877 | 131 | 0.614(13) |
| H(7'1) | 12053 | 4866 | 9985 | 151 | 0.614(13) |
| H(7'2) | 12901 | 4247 | 10397 | 151 | 0.614(13) |
| H(8'1) | 11562 | 4899 | 11589 | 130 | 0.614(13) |
| H(8'2) | 11152 | 4170 | 11600 | 130 | 0.614(13) |
| H(6"1) | 11198 | 4619 | 9374 | 131 | 0.386(13) |
| H(6"2) | 10838 | 3890 | 9216 | 131 | 0.386(13) |

TABLE 34-continued

Hydrogen coordinates [×10$^4$] and isotropic displacement parameters [Å$^2$ × 10$^3$] for the Form III crystal structure.

| Atom | x | y | z | U$_{eq}$ | s.o.f. |
|---|---|---|---|---|---|
| H(7"1) | 11527 | 3652 | 10891 | 151 | 0.386(13) |
| H(7"2) | 12864 | 4150 | 10694 | 151 | 0.386(13) |
| H(8"1) | 11622 | 4930 | 11400 | 130 | 0.386(13) |
| H(8"2) | 10880 | 4370 | 11955 | 130 | 0.386(13) |
| H(9') | 8585 | 4548 | 11294 | 91 | 0.614(13) |
| H(9") | 8518 | 4558 | 11258 | 91 | 0.386(13) |
| H(16') | 8027 | 6096 | 13485 | 92 | 1 |
| H(17') | 8467 | 5262 | 12553 | 85 | 1 |
| H(19C) | 7820(80) | 7770(20) | 11710(30) | 89 | 1 |
| H(19D) | 8310(90) | 7590(30) | 10749(16) | 89 | 1 |
| H(21') | 8305 | 6435 | 8292 | 88 | 1 |
| H(22') | 8963 | 7168 | 7160 | 90 | 1 |
| H(25') | 10060(50) | 7754(12) | 6280(30) | 44(13) | 1 |
| H(28') | 9663 | 8544 | 3505 | 188 | 1 |
| H(29') | 10879 | 9514 | 3572 | 197 | 1 |
| H(30') | 11947 | 9893 | 5031 | 176 | 1 |
| H(31') | 11809 | 9271 | 6393 | 135 | 1 |
| H(32') | 11735 | 8077 | 9144 | 83 | 1 |
| H(33') | 11068 | 7350 | 10265 | 80 | 1 |
| H(1W) | 8700(50) | 6930(50) | 5230(80) | 162 | 1 |
| H(2W) | 10010(120) | 6720(40) | 5740(70) | 162 | 1 |
| H(3W) | 4760(110) | 2910(30) | 9700(50) | 128 | 1 |
| H(4W) | 4670(120) | 3529(16) | 10000(70) | 128 | 1 |
| H(5W) | 8430(150) | 830(30) | 2010(100) | 189 | 1 |
| H(6W) | 9490(110) | 520(60) | 1500(80) | 189 | 1 |

Figure 55:
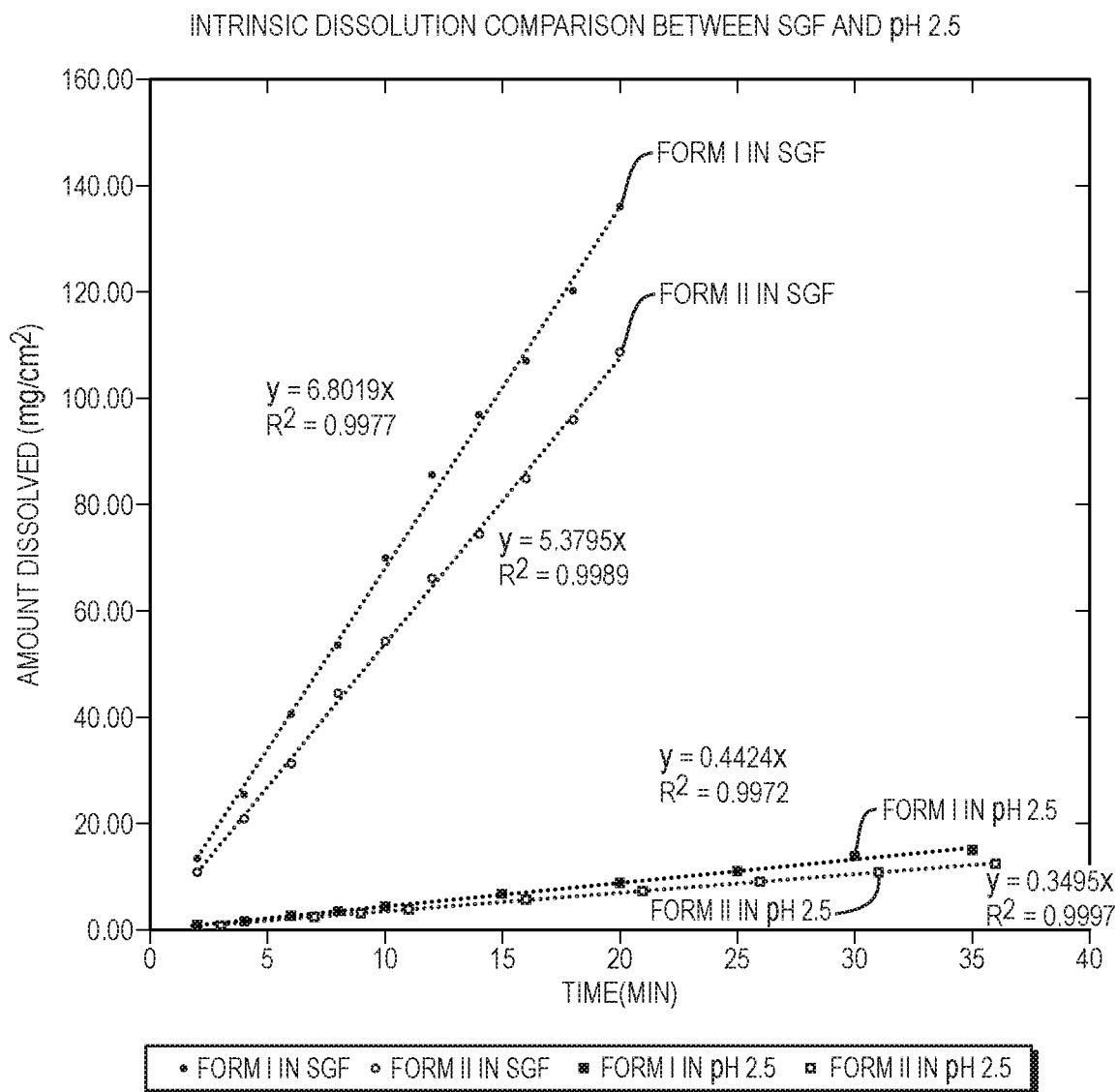
FIG. 55 shows intrinsic dissolution rate results for Forms I and II of Formula (1) free base.

Example 12. Comparison of Dissolution Rate and Exposure in Dogs for Free Base Form I and Free Base Form II The intrinsic dissolution rate (IDR) was measured for Forms I and II of the free base of Formula (1). IDR was measured using a paddle over stationary disc equipped dissolution apparatus with concentration determined using liquid chromatographic analysis against a standard. The y-intercept normalized results are shown in FIG. 55 with the slopes and regression coefficient displayed. Form I has an IDR of 6.8 mg/cm$^2$/min in simulated gastric fluid (SGF) (pH 1.2) and an IDR of 0.44 mg/cm$^2$/min in pH 2.5 HCl/NaCl buffer. Form II has an IDR of 5.4 mg/cm$^2$/min in SGF and an IDR of 0.35 mg/cm$^2$/min in pH 2.5 HCl/NaCl buffer. Form I therefore shows about a 26% increase in IDR at both conditions relative to Form II, which provides a significantly higher rate of dissolution that is advantageous.

Figure 56:
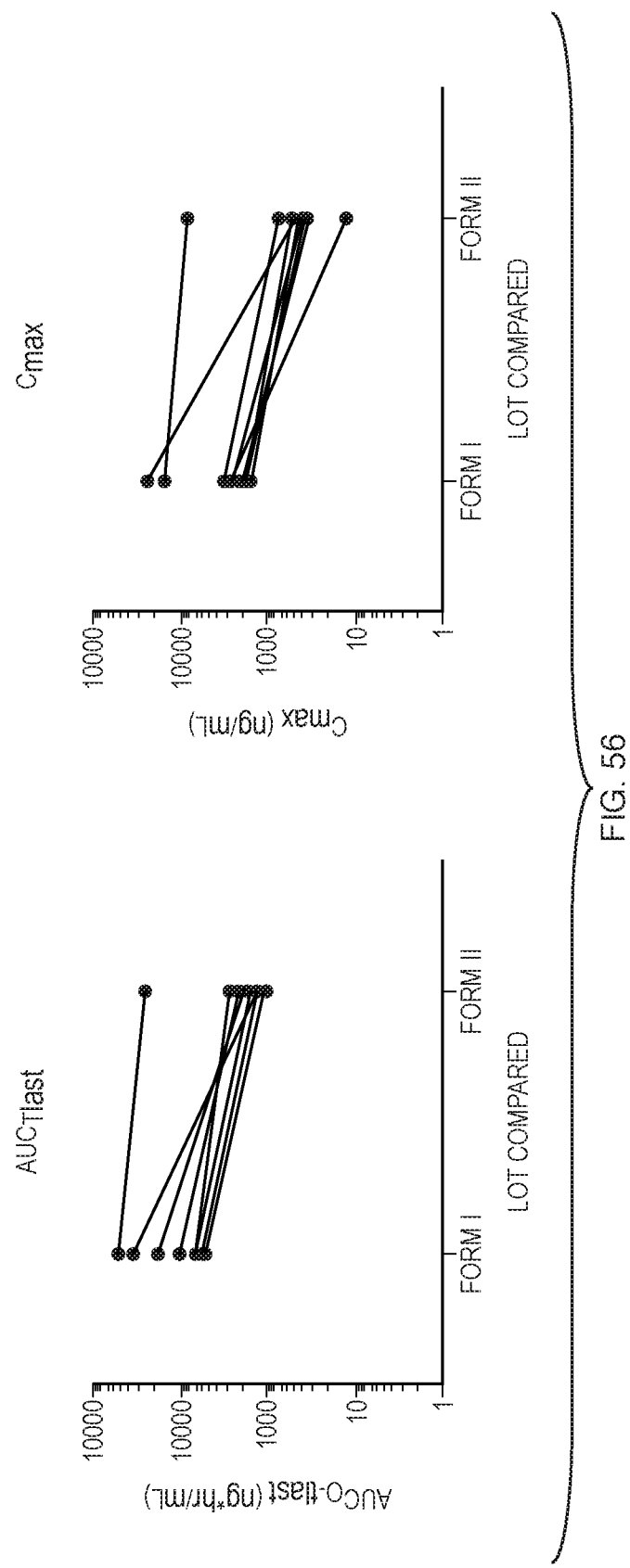
FIG. 56 shows exposure data in dogs for Forms I and II of Formula (1) free base.

The plasma exposure of Forms I and II of the free base of Formula (1) were compared in nine fasted beagle dogs after a single oral administration of 6 mg/kg of either form using batches with a similar particle size distribution. The experiment was performed in 5 weekly phases, with the Form II phase last. The area under the plasma drug concentration-time curve (AUC), shown in FIG. 56, reflects the exposure to drug after administration of each preparation of Formula (1) and is expressed in ng*h/L. Form II shows lower AUC than Form I in all dogs. Form II also shows lower C$_{max}$ (maximum concentration) than Form I in all dogs. It was concluded that Form I had higher exposure in the beagle than Form II. There was a good in vitro in vivo correlation for the dissolution rates of Form 1 and Form II, and the performance of each form of Formula (1) when delivered by oral capsule to dogs. The superior performance of Form I in this dog study demonstrates that more favorable dosing is possible in humans relative to Form II.

Example 13. Screening for Cocrystals, Salts, and Mixed Salts/Cocrystals of (S)-4-(8-Amino-3-(1-(but-2-ynoyl)pyrrolidin-2-yl)imidazo[1,5-a]pyrazin-1-yl)-N-(pyridin-2-yl)benzamide The cocrystal and salt formers given in Table 35 were employed in preliminary screening experiments using a high-throughput approach.

TABLE 35

Summary of cocrystal and salt formers used in preliminary screening experiments. The codes for each salt/cocrystal former are used in the batch identification numbers in the following sections.

| Salt/Co+13 crystal Former | Code | Formula | g/mol | Stock Solution |
|---|---|---|---|---|
| Acetylsalicylic acid | ASS | $C_9H_8O_4$ | 180.2 | 0.1M in acetone |
| Adipic acid | ADI | $C_6H_{10}O_4$ | 146.14 | 0.1M in acetone |
| Capric acid | CAP | $C_{10}H_{20}O_2$ | 172.27 | 0.1M in acetone |
| Caprylic acid | CPY | $C_8H_{16}O_2$ | 144.22 | 0.1M in acetone |
| Gentisic acid | GEN | $C_7H_6O_4$ | 154.12 | 0.1M in acetone |
| Glutaric acid | GLT | $C_5H_8O_4$ | 132.12 | 0.1M in acetone |
| Glutaric acid, 2-Oxo | OGL | $C_5H_6O_5$ | 146.1 | 0.1M in acetone |
| Glycolic acid | GLA | $C_2H_4O_3$ | 76.05 | 0.1M in acetone |
| Lactic acid, L- | LLA | $C_3H_6O_3$ | 90.08 | 0.1M in acetone |
| L-Malic acid | MLA | $C_4H_6O_5$ | 134.09 | 0.1M in acetone |
| Malonic acid | MLO | $C_3H_4O_4$ | 104.06 | 0.1M in acetone |
| Naphthoic acid, 1-hydroxy-2- | XIN | $C_{11}H_8O_3$ | 188.18 | 0.1M in acetone |
| Oxalic acid | OXA | $C_2H_2O_4$ | 90.04 | 0.1M in acetone |
| Toluenesulfonic acid | TOS | $C_7H_8O_3S \cdot H_2O$ | 190.22 | 0.1M in acetonitrile |
| Caffeine | CAF | $C_8H_{10}N_4O_2$ | 194.19 | 0.1M in acetone:$H_2O$ 9:1 |
| Ethylmaltol | ETM | $C_7H_8O_3$ | 140.14 | 0.1M in acetone |
| Maltol | MILL | $C_6H_6O_3$ | 126.11 | 0.1M in acetone |
| Menthol | MEN | $C_{10}H_{20}O$ | 156.27 | 0.1M in acetone |
| Nicotinamide | NCT | $C_6H_6N_2O$ | 122.13 | 0.1M in acetone |
| Proline, L- | PRO | $C_5H_9NO_2$ | 115.13 | 0.1M in methanol |

The preliminary results are summarized in Table 36.

TABLE 36

Summary of the preliminary results of cocrystal and salt screening experiments.

| Salt/Co-crystal Former | Result |
| --- | --- |
| Acetylsalicylic acid | poor |
| Adipic acid | poor |
| Capric acid | poor |
| Caprylic acid | poor |
| Gentisic acid | excellent |
| Glutaric acid | poor |
| Glutaric acid, 2-Oxo | medium |
| Glycolic acid | poor |
| Lactic acid, L- | medium |
| L-Malic acid | medium |
| Malonic acid | good |
| Naphthoic acid, 1-hydroxy-2- | good |
| Oxalic acid | excellent |
| Toluenesulfonic acid | medium |
| Caffeine | good |
| Ethylmaltol | medium |
| Maltol | medium |
| Menthol | medium |
| Nicotinamide | poor |
| Proline, L- | very good |
| Pyridoxine | medium |
| Sorbitol | good |
| Urea | good |
| Vanillin | poor |

More detailed screening experiments were performed. A total of 192 high-throughput screening experiments were carried out in a microtiter plate (MTP) made from quartz. The list of salt and co-crystal formers used for the experimentation is given in Table 37, and extends beyond the preliminary list in Table 35. The stock solutions of the 24 salt and co-crystal formers were filled into MTP well #A1-H3, A4-H6, A7-H9, and A10-H12. The same Formula (1) free base solution, which was prepared in THF:water (9:1) at a concentration of 0.05 M, was filled into each of the 96 MTP wells.

TABLE 37

List of salt and co-crystal formers used as starting materials in extended screening experiments.

| Salt/Co-crystal Former | Code | Formula | g/mol | Stock Solution |
| --- | --- | --- | --- | --- |
| Acetylsalicylic acid | ASA | $C_9H_8O_4$ | 180.2 | 0.1M in acetone |
| Adipic acid | ADI | $C_6H_{10}O_4$ | 146.14 | 0.1M in acetone |
| Capric acid | CAP | $C_{10}H_{12}O_2$ | 172.27 | 0.1M in acetone |
| Caprylic acid | CPY | $C_8H_{16}O_2$ | 144.22 | 0.1M in acetone |
| Gentisic acid | GEN | $C_7H_6O_4$ | 154.12 | 0.1M in acetone |
| Glutaric acid | GLT | $C_5H_8O_4$ | 132.12 | 0.1M in acetone |
| Glutaric acid, 2-oxo | OGL | $C_5H_6O_5$ | 146.1 | 0.1M in acetone |
| Glycolic acid | GLA | $C_2H_4O_3$ | 76.05 | 0.1M in acetone |
| Lactic acid, L- | LLA | $C_3H_6O_3$ | 90.08 | 0.1M in acetone |
| Malic acid, L- | MLA | $C_4H_6O_5$ | 134.09 | 0.1M in acetone |
| Malonic acid | MLO | $C_3H_4O_4$ | 104.06 | 0.1M in acetone |
| Naphthoic acid, 1-hydroxy-2- | XIN | $C_{11}H_8O_3$ | 188.18 | 0.1M in acetone |
| Oxalic acid | OXA | $C_2H_2O_4$ | 90.04 | 0.1M in acetone |
| Toluenesulfonic acid | TOS | $C_7H_8O_3S \cdot H_2O$ | 190.22 | 0.1M in acetonitrile |
| Caffeine | CAF | $C_8H_{10}N_4O_2$ | 194.19 | 0.1M in acetone:$H_2O$ 9:1 |
| Ethylmaltol | ETM | $C_7H_8O_3$ | 140.14 | 0.1M in acetone |
| Maltol | MILL | $C_6H_6O_3$ | 126.11 | 0.1M in acetone |
| Menthol | MEN | $C_{10}H_{20}O$ | 156.27 | 0.1M in acetone |
| Nicotinamide | NCT | $C_6H_6N_2O$ | 122.13 | 0.1M in acetone |
| Proline, L- | PRO | $C_5H_9NO_2$ | 115.13 | 0.1M in methanol |
| Pyridoxine | PYD | $C_8H_{11}NO_3$ | 169.18 | 0.1 in isopropanol |
| Solbitol | SBT | $C_6H_{14}O_6$ | 182.17 | 0.05M in methanol |
| Urea | URE | $CH_4N_2O$ | 60.06 | 0.1M in isopropanol |
| Vanillin | VLN | $C_8H_8O_3$ | 152.15 | 0.1M in acetone |

The amount of substance per experiment was about 3 mg and the outcome of the crystallization experiments was evaluated by light microscopy. Since the stock solutions of the salt and co-crystal formers were generally 0.1 M and the concentration of the stock solution of Form I of the free base of Formula (1) was 0.05 M, 100 µL of free base stock solution was mixed with 50 µL of salt or co-crystal former stock solution. The first series of 96 experiments the solvents were evaporated from the mixed stock solutions under a slight nitrogen flow at room temperature. The results of the microscopic investigation are summarized in Table 38.

TABLE 38

Results from visual (light microscopic) inspection of the MTP after the first series of evaporation experiments.

| Salt/Co-crystal Former | Well # | Mic | Well # | Mic | Well # | Mic | Well # | Mic |
|---|---|---|---|---|---|---|---|---|
| Acetylsalicylic acid | A1 | amo | A4 | amo | A7 | amo | A10 | amo |
| Adipic acid | B1 | amo | B4 | amo | B7 | amo | B10 | amo |
| Capric acid | C1 | amo | C4 | amo | C7 | amo | C10 | amo |
| Caprylic acid | D1 | amo | D4 | amo | D7 | amo | D10 | amo |
| Gentisic acid | E1 | pa-cry | E4 | pa-cry | E7 | cryst. | E10 | pa-cry |
| Glutaric acid | F1 | amo | F4 | amo | F7 | amo | F10 | amo |
| Glutaric acid, 2-oxo | G1 | amo | G4 | amo | G7 | amo | G10 | amo |
| Glycolic acid | H1 | amo | H4 | amo | H7 | amo | H10 | amo |
| Lactic acid, L- | A2 | amo | A5 | amo | A8 | amo | A11 | amo |
| Malic acid, L- | B2 | amo | B5 | amo | B8 | amo | B11 | amo |
| Malonic acid | C2 | amo | C5 | amo | C8 | amo | C11 | amo |
| 1-hydroxy-2-naphthoic acid | D2 | amo | D5 | amo | D8 | amo | D11 | amo |
| Oxalic acid | E2 | pa-cry | E5 | cryst | E8 | pa-cry | E11 | pa-cry |
| Toluenesulfonic acid | F2 | amo | F5 | amo | F8 | amo | F11 | amo |
| Caffeine | G2 | cryst | G5 | pa-cry | G8 | cryst | G11 | cryst |
| Ethylmaltol | H2 | amo | H5 | amo | H8 | amo | H11 | amo |
| Maltol | A3 | amo | A6 | amo | A9 | amo | A12 | po-cry |
| Menthol | B3 | amo | B6 | amo | B9 | amo | B12 | amo |
| Nicotinamide | C3 | amo | C6 | amo | C9 | amo | C12 | amo |
| Proline, L- | D3 | pa-cry | D6 | pa-cry | D9 | pa-cry | D12 | pa-cry |
| Pyridoxine | E3 | amo | E6 | amo | E9 | amo | E12 | amo |
| Sorbitol | F3 | amo | F6 | amo | F9 | pa-cry | F12 | pa-cry |
| Urea | G3 | pa-cry | G6 | pa-cry | G9 | pa-cry | G12 | pa-cry |
| Vanillin | H3 | amo | H6 | amo | H9 | amo | H12 | amo |

Abbreviations:
amo = amorphous,
pa-cry = partially crystalline,
po-cry = possibly crystalline.

After the first evaporation of the solvents the solids in the MTP were subjected to a second series of 96 experiments, where four different solvent systems were explored. To the dry residues of the first experiment 100 μL of solvent according to Table 39.

TABLE 39

Solvents and solvent mixtures used for the second set of experiments.

| MTP well # | Solvent System |
|---|---|
| A1 through H3 | acetone-water 95:5 |
| A4 through H6 | isopropanol-water 95:5 |
| A7 through H9 | acetonitrile |
| A10 through H12 | ethyl acetate-water 99:1 |

The suspensions were agitated at 25° C. for two days then the solvents were evaporated under a slight nitrogen flow and the MTP was examined by light microscopy. If the light microscopic image suggested the presence of crystalline material, then a Raman spectrum was measured. Visually amorphous samples; e.g., glassy residues observed in the MTP were not further investigated. The results are given in Table 40.

TABLE 40

Results from light microscopy of the MTP after the second set of experiments.

| Salt/Co-crystal Former | Well # | Mic | Well # | Mic | Well # | Mic | Well # | Mic |
|---|---|---|---|---|---|---|---|---|
| Acetylsalicylic acid | A1 | amo | A4 | amo | A7 | amo | A10 | amo |
| Adipic acid | B1 | amo | B4 | amo | B7 | amo | B10 | amo |
| Capric acid | C1 | amo | C4 | amo | C7 | amo | C10 | amo |
| Caprylic acid | D1 | amo | D4 | amo | D7 | amo | D10 | amo |
| Gentisic acid | E1 | cryst | E4 | amo | E7 | cryst | E10 | cryst |
| Glutaric acid | F1 | amo | F4 | amo | F7 | amo | F10 | cryst |
| Glutaric acid, 2-oxo | G1 | amo | G4 | amo | G7 | po-cry | G10 | amo |
| Glycolic acid | H1 | amo | H4 | amo | H7 | amo | H10 | amo |
| Lactic acid, L- | A2 | po-cry | A5 | amo | A8 | amo | A11 | amo |
| Malic acid, L- | B2 | amo | B5 | amo | B8 | amo | B11 | amo |
| Malonic acid | C2 | po-cry | C5 | amo | C8 | po-cry | C11 | po-cry |
| 1-hydroxy-2-naphthoic acid | D2 | po-cry | D5 | amo | D8 | po-cry | D11 | amo |
| Oxalic acid | E2 | po-cry | E5 | amo | E8 | cryst | E11 | pa-cry |
| Toluenesulfonic acid | F2 | po-cry | F5 | amo | F8 | po-cry | F11 | po-cry |
| Caffeine | G2 | cryst | G5 | pa-cry | G8 | cryst | G11 | cryst |
| Ethylmaltol | H2 | amo | H5 | amo | H8 | amo | H11 | cryst |

TABLE 40-continued

Results from light microscopy of the MTP after the second set of experiments.

| Salt/Co-crystal Former | Well # | Mic | Well # | Mic | Well # | Mic | Well # | Mic |
| --- | --- | --- | --- | --- | --- | --- | --- | --- |
| Maltol | A3 | amo | A6 | amo | A9 | amo | A12 | amo |
| Menthol | B3 | amo | B6 | amo | B9 | amo | B12 | amo |
| Nicotinamide | C3 | amo | C6 | amo | C9 | amo | C12 | amo |
| Proline, L- | D3 | cryst | D6 | pa-cry | D9 | pa-cry | D12 | cryst |
| Pyridoxine | E3 | po-cry | E6 | amo | E9 | amo | E12 | po-cry |
| Sorbitol | F3 | amo | F6 | pa-cry | F9 | pa-cry | F12 | cryst |
| Urea | G3 | pa-cry | G6 | pa-cry | G9 | pa-cry | G12 | cryst |
| Vanillin | H3 | amo | H6 | amo | H9 | amo | H12 | amo |

Abbreviations:
amo = amorphous,
pa-cry = partially crystalline,
po-cry = possibly crystalline.

The result from the above experimentation is a rating of the lead for each salt or co-crystal that was included in the screening program, which was classified as very good, good, intermediate, and poor. Salt and co-crystal leads that were classified as very good, good or intermediate are presented in Table 41. Poor leads were obtained for acetylsalicylic acid, adipic acid, capric acid, caprylic acid, glutaric acid, glycolic acid, nicotinamide, and vanillin; these are not listed in Table 41.

TABLE 41

Salt and co-crystal formers for which very good, good and intermediate leads were obtained. N is the number of scale-up experiments (including additional suspension experiments).

| Salt/Co-crystal former | Code | Lead classification | N | Scale-up result |
| --- | --- | --- | --- | --- |
| Gentisic acid | GEN | very good | 8 | crystalline salt |
| Glutaric acid, 2-oxo | OGL | intermediate | 0 | not applicable |
| Lactic acid, L- | LLA | intermediate | 0 | not applicable |
| L-Malic acid | MLA | intermediate | 0 | not applicable |
| Malonic acid | MLO | good | 1 | unsuccessful |
| Naphthoic acid, 1-Hydroxy-2- | XIN | good | 1 | amorphous |
| Oxalic acid | OXA | very good | 7 | crystalline salt |
| Toluenesulfonic acid | TOS | intermediate | 0 | not applicable |
| Caffeine | CAF | good | 1 | unsuccessful |
| Ethylmaltol | ETM | intermediate | 0 | not applicable |
| Maltol | MILL | intermediate | 0 | not applicable |
| Menthol | MEN | intermediate | 0 | not applicable |
| Proline, L- | PRO | very good | 8 | co-crystal |
| Pyridoxine | PYD | intermediate | 0 | not applicable |
| Sorbitol | SBT | good | 6 | co-crystal |
| Urea | URE | good | 1 | unsuccessful |

Experiments with a significant number of potentially useful salt and co-crystal formers were unsuccessful. For example, experimentation produced poor leads for acetylsalicylic acid, adipic acid, capric acid, caprylic acid, glutaric acid, glycolic acid, nicotinamide, and vanillin. Intermediate, good or very good leads can still turn out to be false upon further examination, because crystallization in presence of other compounds can potentially lead to a new crystal form or either compound present in the experiment. Furthermore, amorphous solid residues were obtained in all small scale experiments with adipic acid, ascorbic acid, aceturic acid (N-acetyl glycine), benzoic acid, nicotinic acid, and saccharin.

Example 14. The L-Arabitol Cocrystal of (S)-4-(8-Amino-3-(1-(but-2-ynoyl)pyrrolidin-2-yl)imidazo[1,5-a]pyrazin-1-yl)-N-(pyridin-2-yl)benzamide Example 14.1. Preparation of Form A of the L-Arabitol Cocrystal of Formula (1)

The L-arabitol cocrystal of Formula (1) can be prepared by dissolving both components in methanol or in 96% ethanol at reflux temperature, followed by cooling the solution to room temperature. For instance, 1 mmol of Formula (1) free base Form I and 2.25 mmol of L-arabitol are dissolved in methanol at reflux temperature and the solution is allowed to cool to room temperature. After stirring for several hours a suspension is obtained that contains the co-crystal (SP221-ARA-P3).

Example 14.2. Physical Characterization of Form A of the L-Arabitol Cocrystal of Formula (1)

$^1$H NMR spectroscopy of the product from experiment SP221-ARA-P3 revealed a ratio of free base to L-arabitol of about 1:1.9 (or 1:2). This estimation is based on the sum of the integrals of the aromatic protons of Formula (1) divided by the integral of two well separated protons of L-arabitol at 4.2 and 4.3 ppm divided by 5.

Another sample of the L-arabitol cocrystal of Formula (1) (SP221-ARA-P4) was also examined by determination of CHNO content by elemental composition analysis. The molecular formula of a 1:2 co-crystal of Formula (1) and L-arabitol would be $C_{36}H_{47}N_7O_{12}$ with a molecular weight of 769.8 g/mol. A dihydrate of this cocrystal would have the molecular formula of $C_{36}H_{51}N_7O_{14}$ and a molecular weight of 805.8 g/mol (with a theoretical water content of 4.5%). The results as presented in Table 42 are in good agreement with the molecular formula for a 1:2 cocrystal (2 moles of L-arabitol per mole of Formula (1)) dihydrate.

TABLE 42

Results from elemental composition analysis and water content determination.

| Element | % found | Fit for $C_{36}H_{51}N_7O_{14}$ |
| --- | --- | --- |
| C | 53.7 | 53.66 |
| H | 6.2 | 6.38 |
| N | 12.2 | 12.17 |
| O | 27.2 | 27.80 |
| water | 4.2 | 4.47 |

Based on elemental analysis and TG-FTIR mass loss, the stoichiometry of the co-crystal of Formula (1) with L-arabitol is a 1:2 cocrystal dihydrate (Form A) with the molecular formula $C_{36}H_{51}N_7O_{14}=[C_{26}H_{23}N_7O_2].2\ [C_5H_{12}O_5].2.H_2O$ and a molecular weight of 805.8 g/mol.

Figure 57:
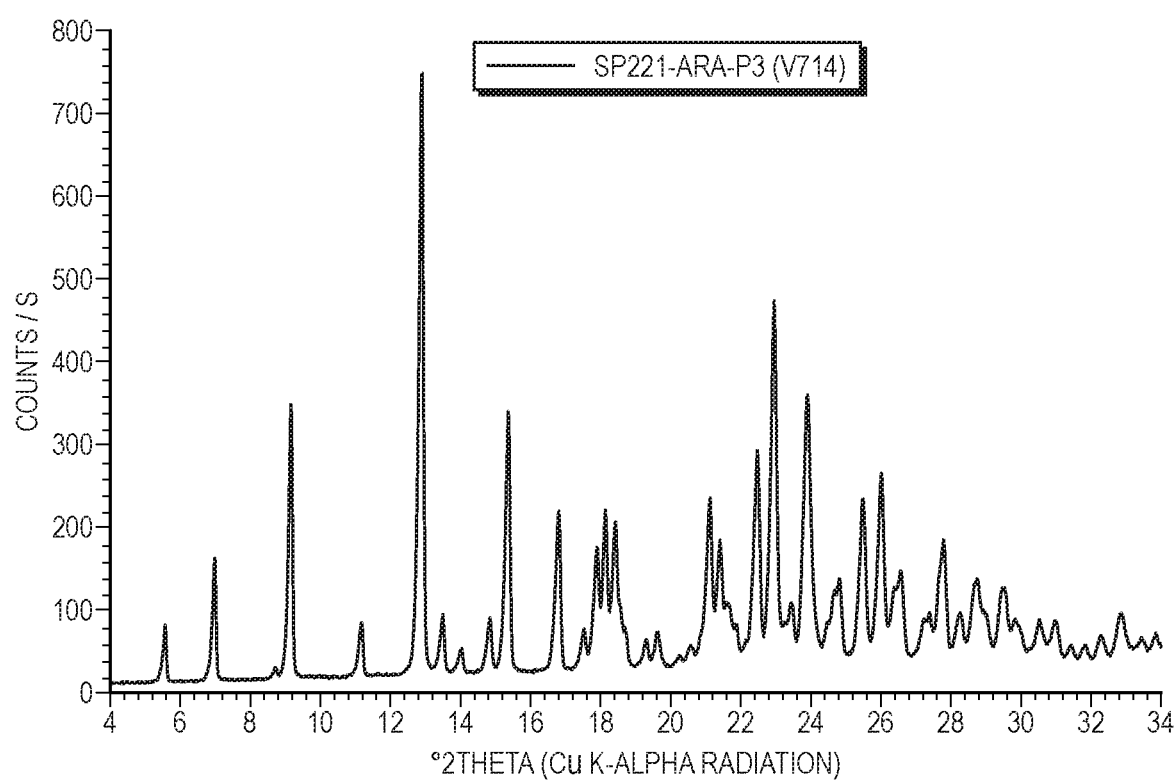
FIG. 57 illustrates a PXRD pattern of a sample of the L-arabitol cocrystal of Formula (1).

The PXRD pattern of the product from experiment SP221-ARA-P3 is displayed in FIG. 57. The PXRD pattern of sample SP221-ARA-P3 was verified against all known polymorphs of Formula (1) and the known PXRD pattern of L-arabitol. None of these forms can be detected in the PXRD pattern of the sample examined. All successfully produced samples of the co-crystal with L-arabitol exhibited the same PXRD pattern. The following peaks are characteristic of Form A of the 1:2 L-arabitol co-crystal of Formula (1): 5.6, 7.0, 9.2, 11.2, 12.9, 13.5, 14.0, 14.8, 15.3, 16.8, 17.9, 18.2, 18.4, 21.1, 21.4, 22.5, 22.9, 23.9, 24.8, 25.5, 26.0, 26.6, 27.7, 28.2, 28.8, and 29.4° 2θ±0.2° 2θ.

Optical microscopy of the L-arabitol cocrystal of Formula (1) (SP221-ARA-P4) shows crystalline material with predominantly needle-shaped particles with lengths of about 5 to 30 μm and widths of about 1 to 5 μm.

Raman spectroscopy was performed using a sample of the L-arabitol cocrystal of Formula (1) (SP221-ARA-P4). The Raman spectrum over the measured range from 100 cm$^{-1}$ to 3500 cm$^{-1}$ and the fingerprint region from 200 cm$^{-1}$ to 1800 cm$^{-1}$. The Raman spectrum was obtained in a similar manner as described in Example 1.2 for Form I. Characteristic Raman peaks for Form A of the L-arabitol cocrystal of Formula (1) are observed at 2917, 2241, 1674, 1610, 1581, 1565, 1529, 1494, 1455, 1348, 1325, 1309, 1264, 1242, 1189, 1164, 999, 872, and 279 (Raman shift, cm$^{-1}$±2 cm$^{-1}$).

IR spectroscopy was also performed using a sample of the L-arabitol cocrystal of Formula (1) (SP221-ARA-P4). The IR spectrum over the measured range from 600 cm$^{-1}$ to 3600 cm$^{-1}$ and the fingerprint region from 600 cm$^{-1}$ to 1800 cm$^{-1}$. The IR spectrum was obtained in a similar manner as described in Example 1.2 for Form I. Characteristic IR peaks for Form A of the L-arabitol cocrystal of Formula (1) are observed at 3471, 3188, 2924, 2239, 1670, 1637, 1621, 1603, 1579, 1524, 1505, 1435, 1346, 1306, 1274, 1242, 1203, 1135, 1090, 1049, 1009, 998, 950, 902, 892, 862, 821, 783, 739, 726, 711, 694, 637, and 621 (IR frequency, cm$^{-1}$±4 cm$^{-1}$).

The TG-FTIR thermogram suggests a water content of about 4.2%. This mass loss is close to the water content for a dihydrate for which the expected water content would be 4.47%. The DSC analysis in a closed sample pan reveals two endothermic events at about 110° C. and 127° C. (peak temperatures) that are followed by an exothermic signal with the peak maximum at 157° C.

Dynamic vapor sorption analysis of the L-arabitol co-crystal (sample SP221-ARA-P4) shows that the water content can strongly vary with changing relative humidity. The water content at the end of the test is in good agreement with the TG-FTIR mass loss. The fact that all water is removed at 0% RH suggests that the water is weakly bound in the co-crystal. The maximum water content of about 4.7% is reached at 95% RH. At the beginning of the test some excess water was present; however, the equilibrated water content at 50% RH is 4.1%. This result was corroborated by a second DVS test of the same sample.

Example 15. The Citrate Salt of (S)-4-(8-Amino-3-(1-(but-2-ynoyl)pyrrolidin-2-yl)imidazo[1,5-a]pyrazin-1-yl)-N-(pyridin-2-yl)benzamide Example 15.1. Preparation of Form A of Citrate Salt of Formula (1)

Citric acid has the molecular formula $C_6H_8O_7$ and a molecular mass of 192.12 g/mol. The $pK_a$ values of the three carboxylic acid groups in citric acid are 2.93, 4.76 and 6.40. Crystallization of the citrate salt from acetone-water mixtures led to samples that contained significant amounts of acetone and some water, while crystallization from 1-propanol led to a sample that contained a large amount of 1-propanol, indicating that both phases may be solvates.

Sample SP221-CIT-P4 was prepared as follows: 941 mg of free base of Formula (1) (PP502-P1) and 384.5 mg citric acid was dissolved in 22 mL of acetone-water (10:1) by heating the mixture to 50° C. Upon cooling to room temperature, a dilute suspension formed that was stirred in an open vial to let some solvent evaporate. More acetone was added, which led to a thicker suspension and which was filtered after stirring at room temperature for about one hour. About 436 mg of a white solid product was obtained after drying in air at room temperature. The product from experiment SP221-CIT-P4 was further dried in air at 40° C. for 24 hours to provide sample SP221-CIT-P4A. Batches produced by the procedures used for SP221-CIT-P4 and SP221-CIT-P4A may be additionally exposed to controlled humidity in order to exchange acetone for water.

Sample SP221-CIT-P6 was prepared as follows: 466 mg of free base of Formula (1) (PP502-P1) and 96.4 mg citric acid was dissolved in 10 mL 1-propanol 10:1 by heating the mixture to 70° C. At 50° C. the mixture was seeded with SP221-CIT-P4 and let cool to room temperature. A suspension formed from which the solid product was filtered off after stirring at room temperature for about one hour. About 660 mg of a white solid product was obtained after drying in air at room temperature. Batches produced by the procedure used for SP221-CIT-P6 may be additionally exposed to controlled humidity in order to exchange 1-propanol for water.

Example 15.2. Physical Characterization of Form A of the Citrate Salt of Formula (1)

$^1$H NMR spectroscopy of the product from experiment SP221-CIT-P4 revealed a ratio of Formula (1) to citric acid of about 2:1 (1.83) based on the sum of the integrals for the 10 aromatic protons of Formula (1) divided by the integral from the four protons from the methylene groups of citric acid between 2.6 and 2.9 ppm. The 1:2 citric acid:Formula (I) may be a phase containing both ionized citric acid (as in a salt) and non-ionized citric acid (as in a cocrystal). The molecular formula of a 2:1 salt or co-crystal of Formula (1) with citric acid is $2.[C_{26}H_{23}N_7O_2]+C_6H_8O_7$ with a molecular weight of 1123.1 g/mol. In an initial attempt to convert the acetone solvate into a hydrate sample, SP221-CIT-P4 was subjected to suspension equilibration in water at 25° C. for 24 hours, which resulted in conversion to Form III of the free base of Formula (1) (the dihydrate).

Figure 58:
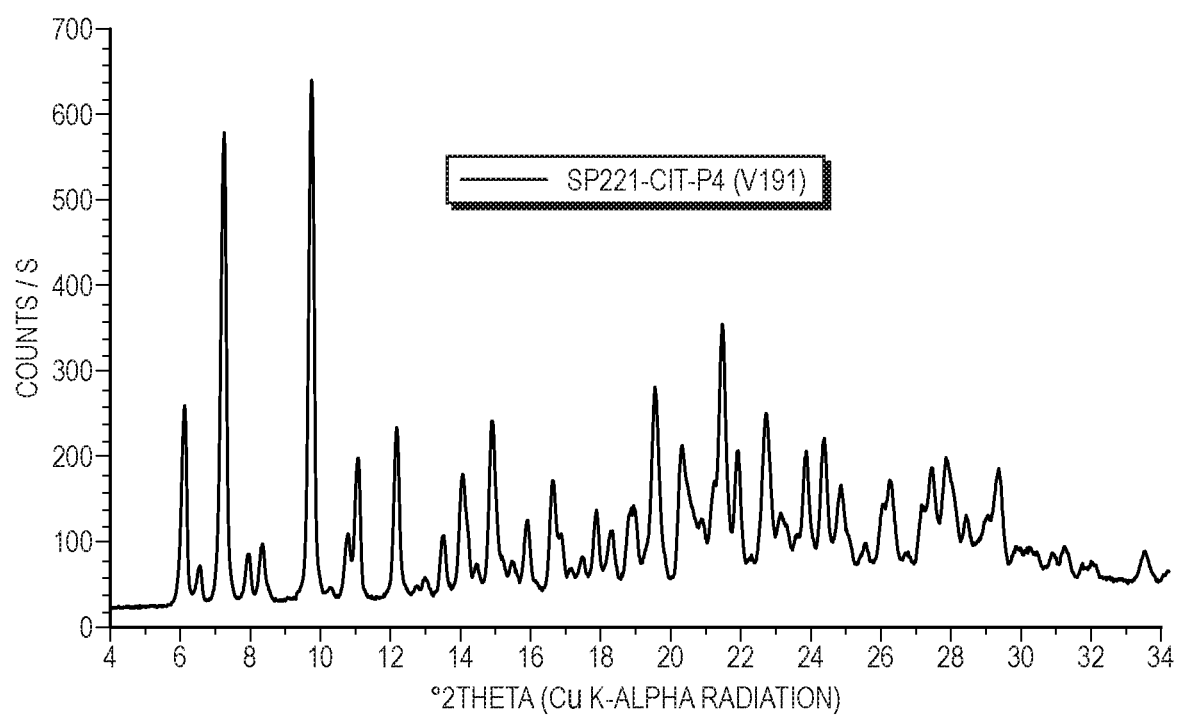
FIG. 58 illustrates a PXRD pattern of Form A of the citrate salt of Formula (1) (sample SP211-CIT-P4) crystallized from acetone-water.

Reflection PXRD patterns of the citrate salt obtained from acetone-water (SP221-CIT-P4) and 1-propanol (SP221-CIT-P6) are shown in FIG. 58. An overlay of the two PXRD patterns illustrates that the PXRD patterns of the two forms show remarkable similarities, indicating a similar crystal lattice for both samples, and thus the two patterns likely represent two different solvation states of a single host structure comprising citrate and Formula (1). Both samples are therefore designated Form A. Form A of the citrate salt of Formula (1) can also include other small organic solvents and water in variable amounts. The following peaks are characteristic of Form A of the citrate salt of Formula (1), when in the approximate solvation state of sample SP221-CIT-P4a: 6.1, 6.6, 7.2, 7.9, 8.3, 9.7, 10.8, 11.1, 12.2, 13.5, 14.1, 14.9, 15.9, 16.6, 17.5, 17.9, 18.3, 18.9, 19.5, 20.3, 21.5, 21.9, 22.7, 23.8, 24.4, 24.8, 26.1, 26.3, 27.2, 27.4, 27.9, and 29.3° 2θ±0.2° 2θ. The following peaks are characteristic of Form A of the citrate salt of Formula (1), when in the approximate solvation state of sample SP221-CIT-P6: 6.1, 6.4, 7.2, 7.9, 8.2, 9.6, 10.9, 12.0, 13.4, 13.8, 14.0, 14.9, 15.5, 15.9, 16.4, 17.3, 17.5, 18.2, 18.6, 19.3, 20.1, 20.4, 21.4, 21.6, 22.6, 23.2, 23.7, 24.3, 26.0, 27.0, 27.3, 27.8, and 29.2° 2θ±0.2° 2θ. The foregoing characteristic peaks may vary in their position with the exchange of solvent into this crystalline phase.

Figure 59:
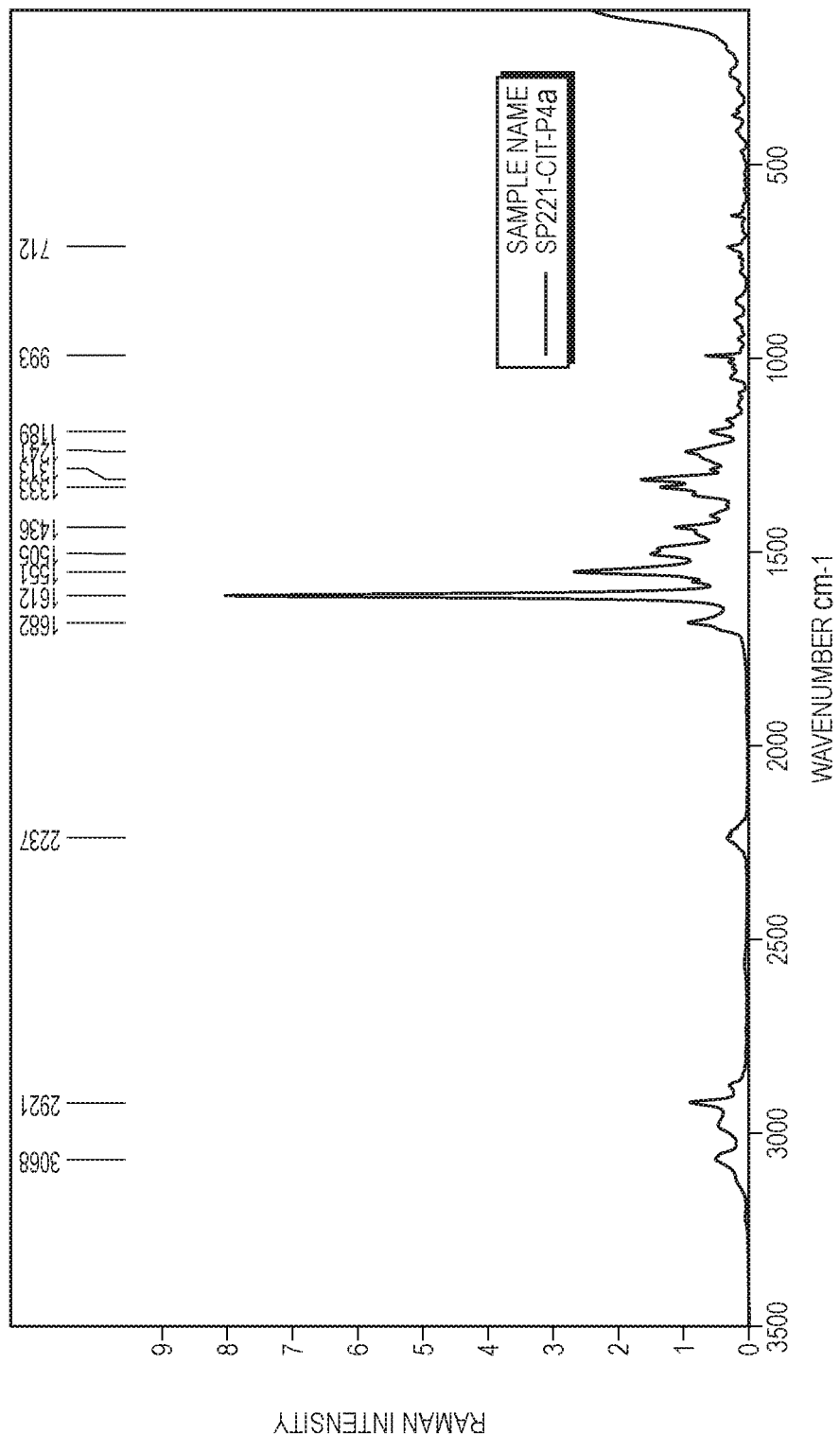
FIG. 59 illustrates a Raman spectrum of a sample of Form A of the citrate salt of Formula (1).

Raman spectroscopy over a spectral range of 100 cm$^{-1}$ to 3500 cm$^{-1}$, of Form A of the citrate salt of Formula (1) was performed on samples SP221-CIT-P4 a Characteristic Raman peaks for Form A of the citrate salt of Formula (1), when in the approximate solvation state of sample SP221-CIT-P4a, are observed at 3068, 2921, 2237, 1682, 1612, 1551, 1505, 1436, 1332, 1313, 1241, 1188, 993 and 712 (Raman shift, cm$^{-1}$±2 cm$^{-1}$) (FIG. 59). Characteristic Raman peaks for Form A of the citrate salt of Formula (1), when in the approximate solvation state of sample SP221-CIT-P6, are observed at 3055, 2920, 2237, 1685, 1612, 1549, 1504, 1436, 1333, 1313, 1286, 1240, 1187, 993 and 712 (Raman shift, cm$^{-1}$±2 cm$^{-1}$). The foregoing characteristic peaks may vary in their positions with the exchange of solvent into this crystalline phase.

ATR-IR spectroscopy of Form A, measured from 600 cm$^{-1}$ to 3600 cm$^{-1}$, of the citrate salt of Formula (1) was performed on samples SP221-CIT-P4a and SP221-CIT-P6. Characteristic IR peaks for Form A of the citrate salt of Formula (1), when in the approximate solvation state of sample SP221-CIT-P4a, are observed at 3396, 2234, 1673, 1606, 1537, 1428, 1304, 1264, 1200, 1092, 1008, 893, 866, 773, 735, and 693 (IR frequency, cm$^{-1}$±4 cm$^{-1}$). Characteristic IR peaks for Form A of the citrate salt of Formula (1), when in the approximate solvation state of sample SP221-CIT-P6, are observed at 3403, 2960, 2872, 2233, 1678, 1608, 1582, 1538, 1434, 1403, 1352, 1302, 1253, 1201, 1094, 1055, 1010, 967, 895, 813, 772, 750, 693, and 612 (IR frequency, cm$^{-1}$±4 cm$^{-1}$). The foregoing characteristic peaks may vary in their positions with the exchange of solvent into this crystalline phase.

TG-FTIR analysis was carried out on three different samples of the citrate salt. The results show that the sample contains both water and acetone and that the water is less strongly bound than the acetone. A sample of SP221-CIT-P4 was stored for three months after preparation at ambient conditions and denoted sample SP221-CIT-P3. TG-FTIR analysis of this sample revealed that most of the mass loss was due to water. This provides evidence that acetone was slowly replaced by water over time, with a water content increase to about 8%. This observation is supported by the finding that typically the mass loss occurs in two steps. In the first step water and some acetone is released and in the second step the mass loss is predominantly due to acetone. The theoretical acetone content for a Formula (1): citrate 2:1 salt acetone monosolvate would be 5% and the theoretical water content for a pentahydrate would be 8%. Therefore, in addition to an acetone solvate (or a mixed acetone solvate-hydrate), a pure hydrated state of Form A of the citrate salt of Formula (1) can be prepared. The result from TG-FTIR analysis of the 1-propanol solvate shows two distinct steps, which may indicate that a second 1-propanol solvate phase with a different stoichiometry exists.

Sample SP221-CIT-P3 of Form A of the citrate salt of Formula (1) was selected for a DSC test in a closed sample pan and was observed to exhibit a broad endotherm that obscured melting. For a second DSC experiment, the citrate sample SP221-CIT-P3 was stored under 33% relative humidity for several days of equilibration. The resulting DSC thermogram did not show any significant differences. The maximum of the endothermic signal is at 90° C.; however, the deviation from the baseline begins even below 60° C. and a pronounced shoulder is found at about 82° C. The exotherm that begins at about 140° C. is likely the result of thermal degradation.

Dynamic vapor sorption (DVS) analysis of the citrate salt (sample SP221-CIT-P4) shows that the given salt form absorbs a substantial amount of water at high humidity conditions and that at the end of the test the water content is about 7.5% by weight. It is likely that part of the acetone that was found by TG-FTIR was exchanged by water during the DVS test.

Example 16. The Gentisate Salt of (S)-4-(8-Amino-3-(1-(but-2-ynoyl)pyrrolidin-2-yl)imidazo[1,5-a]pyrazin-1-yl)-N-(pyridin-2-yl)benzamide Example 16.1. Preparation of Form A and Other Forms of the Gentisate Salt of Formula (1)

Gentisic acid has the chemical name 2,5-dihydroxybenzoic acid, the molecular formula $C_7H_6O_4$, and a molecular mass of 154.12 g/mol. The pK$_a$ of gentisic acid is 2.93. The gentisate salt was first identified in the screen described above (sample SP221-GEN-P1) and was reproduced by crystallization from an acetone-water mixture as an acetone hemisolvate (SP221-GEN-P2). Suspension equilibration of the acetone hemisolvate in acetonitrile led to a crystalline sample that did not contain residual organic solvent (sample SP221-GEN-P3). TG-FTIR showed that this sample contained about 2.6% of water. This result agreed well with the theoretical water content for a gentisate monohydrate of 2.8%.

Sample SP221-GEN-P1 was prepared as follows: 235.6 mg of Formula (1) free base (PP502-P1, 0.5 mmol) was dissolved in 4.0 mL of acetone-water (9:1) at 57° C. and 5.0 mL of a 0.1 M stock solution of gentisic acid in acetone was added. The mixture was allowed to cool to room temperature and stirred while the cap was kept open to let acetone evaporate. After a suspension with a volume of about 3 mL was obtained, the solid product was filtered off and dried in air at room temperature.

Sample SP221-GEN-P2 was prepared as follows: 470 mg of Formula (1) free base (PP502-P1, 0.5 mmol) was dissolved in 11.0 mL of a 0.1 M stock solution of gentisic acid in acetone. 2.0 mL of water was added to this solution. The solution was seeded with a small amount of SP221-GEN-P1 and stirred in an open vial to allow solvent evaporation. The solution was allowed to cool to room temperature and was stirred while the cap was left open to continue to allow acetone to evaporate. After a suspension with a volume of about 3 mL was obtained, the solid product was filtered off and dried in air at room temperature.

Sample SP221-GEN-P3 was prepared as follows: 2.0 mL of acetonitrile was added to 58 mg of sample SP221-GEN-P2, and the resulting suspension was stirred at room temperature for three days. The solids were filtered and dried in air at room temperature.

Sample SP221-GEN-P4 was prepared as follows: 466 mg of PP502-P1 (0.5 mmol) and 154 mg of gentisic acid dissolved in 10.0 mL of 2-propanol by heating to 70° C. To facilitate dissolution, 0.2 mL of formic acid was added. The solution was allowed to cool to room temperature and was seeded with SP221-GEN-P2 at about 45° C., and 5.0 mL of 2-propanol was added. Within about four hours a suspension was obtained from which the solid product was filtered off and dried in air at room temperature.

An additional batch (sample SP221-GEN-P5) of the gentisate salt of Formula (1) monohydrate was prepared by a similar method as was used to prepare SP221-GEN-P3. To about 400 mg of sample SP221-GEN-P4 was added 4.2 mL of acetonitrile containing 5% water. The resulting suspension was stirred at room temperature for one day. The solids were filtered off and dried product in air at room temperature. Sample SP221-GEN-P5A was prepared by keeping sample SP221-GEN-P5 at 33% relative humidity for two weeks.

A second hydrate, possibly a dihydrate, was obtained as the solid residue after a solubility test (sample SP221-GEN-P6).

Example 16.2. Physical Characterization of Form A and Other Forms of the Gentisate Salt of Formula (1)

$^1$H NMR spectroscopy of the product from experiment SP221-GEN-P5 revealed a ratio of Formula (1) free base to gentisic acid of 1:1 based upon the sum of integrated signals of four aromatic protons of Formula (1) between 7.5 and 8.5 ppm and two aromatic protons of gentisic acid that appear between 6.6 and 7.0 ppm. The $^1$H NMR spectrum also confirmed that the obtained material is essentially free of organic solvent.

In addition, sample SP221-GEN-P5 was analyzed for CHNO content by elemental composition analysis. The molecular formula of a 1:1 salt of Formula (1) with gentisic acid is expected to be $C_{33}H_{29}N_7O_6$ with a molecular weight of 619.6 g/mol. A monohydrate of a 1:1 salt of Formula (1) with gentisic acid would have the molecular formula of $C_{33}H_{31}N_7O_7$ and a molecular weight of 637.65 g/mol (with a water content of 2.8%). The results as presented in Table 43 are in agreement with the expected formula for a monohydrate.

TABLE 43

Results from elemental composition analysis and water content determination for sample SP221-GEN-P5.

| Element | % found | $C_{33}H_{31}N_7O_7$ |
|---|---|---|
| C | 60.9 | 62.16 |
| H | 5.1 | 4.90 |
| N | 15.0 | 15.38 |
| O | 16.5 | 17.56 |
| water | 2.6* | 2.82 |

*This value was taken from the TG-FTIR analysis of sample SP221-GEN-P3, as described below.

Optical microscopy of the gentisate salt of Formula (1) monohydrate (sample SP221-GEN-P5) showed crystalline material with predominantly needle-shaped particles with lengths of about 5 to 50 μm and widths of about 1 to 10 μm.

Figure 60:
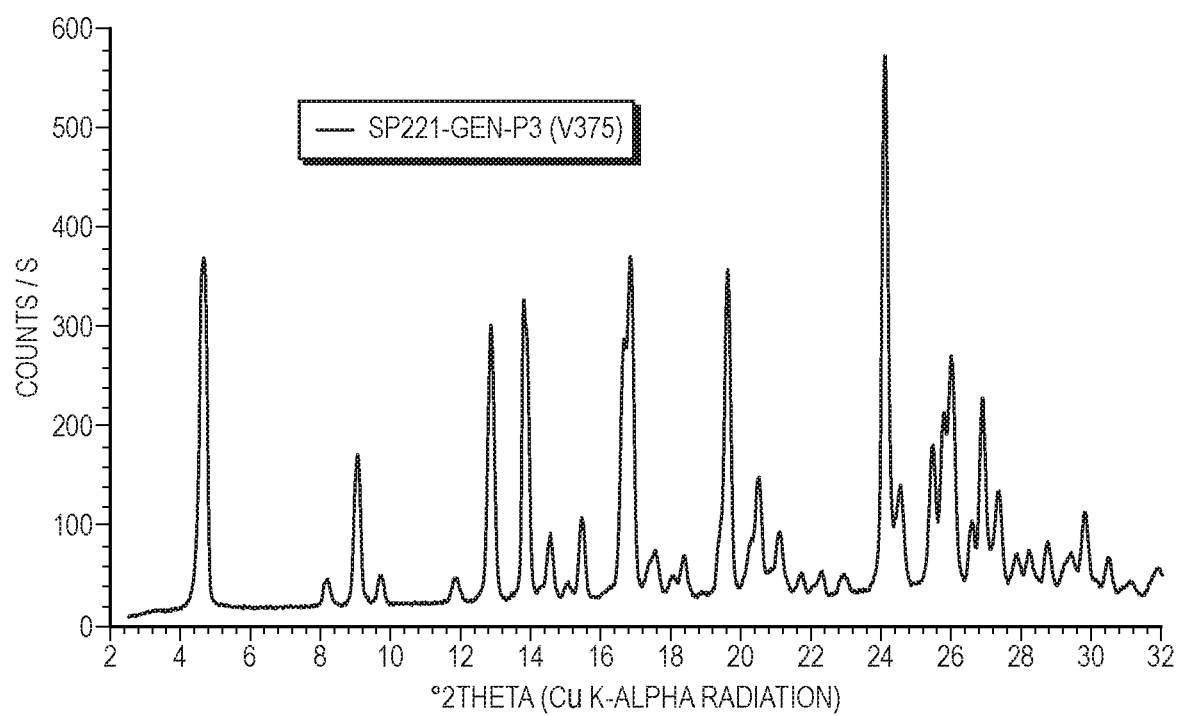
FIG. 60 illustrates a PXRD pattern of a sample of Form A of the gentisate salt of Formula (1) monohydrate.

A reflection PXRD pattern of the gentisate salt of Formula (1) monohydrate is shown in FIG. 60 (sample SP221-GEN-P3). The PXRD pattern of sample SP221-GEN-P5 (not shown) was indistinguishable from the pattern of sample SP221-GEN-P3, indicating that both samples are representative of the same crystalline phase. This crystalline phase is designated Form A (monohydrate) of the gentisate salt of Formula (1). The following peaks are characteristic of Form A (monohydrate) of the gentisate salt of Formula (1): 4.6, 8.2, 9.0, 9.7, 11.8, 12.9, 13.8, 14.5, 15.5, 16.6, 16.8, 18.4, 19.6, 20.5, 21.1, 24.1, 24.5, 25.5, 25.8, 26.0, 26.6, 26.9, 27.4, and 29.8° 2θ±0.2° 2θ.

Raman spectroscopy was measured in a range from 100 cm$^{-1}$ to 3500 cm$^{-1}$ using a sample of Form A (monohydrate) of the gentisate salt of Formula (1) (sample SP221-GEN-P5). The Raman spectrum was obtained in a similar manner as described in Example 1.2 for Form I. Characteristic Raman peaks for Form A (monohydrate) of the gentisate salt of Formula (1) are observed at 3057, 2919, 2223, 1681, 1613, 1576, 1552, 1518, 1437, 1333, 1312, 1228, 1192, 1156, 990, 716, 485, and 257 (Raman shift, cm$^{-1}$±2 cm$^{-1}$).

IR spectroscopy was measured in a range from 600 cm$^{-1}$ to 3600 cm$^{-1}$ using a sample of Form A (monohydrate) of the gentisate salt of Formula (1) (sample SP221-GEN-P5). The IR spectrum was obtained in a similar manner as described in Example 1.2 for Form I. Characteristic IR peaks for Form A (monohydrate) of the gentisate salt of Formula (1) are observed at 2957, 1682, 1668, 1602, 1574, 1523, 1504, 1481, 1429, 1377, 1346, 1302, 1274, 1228, 1157, 1092, 1010, 939, 896, 865, 826, 810, 778, 748, 734, 686, 660, and 617 (IR frequency, cm$^{-1}$±4 cm$^{-1}$).

The TG-FTIR thermogram of Form A (monohydrate) was measured for the gentisate salt of Formula (1) (sample SP221-GEN-P3). Differential scanning calorimetry of Form A (monohydrate) of the gentisate salt of Formula (1) (sample SP221-GEN-P5A), revealed two small endothermic peaks at 106° C. and 121° C. These peaks are unlikely to correspond to melting of the salt, but can be assigned to phase transformations. The deviation from the baseline at 180° C. is tentatively attributed to the beginning of a melting process; however, thermal degradation is the dominating phenomenon above 195° C. and a distinct melting point could not be identified by DSC.

DVS analysis of Form A (monohydrate) of the gentisate salt of Formula (1) (sample SP221-GEN-P5) reveals several steps when scanning from high to lower RH. This suggests that more than one hydrate might exist. Even though the observed hysteresis is not symmetrical, a second test of the same sample has shown that the entire DVS hydration-dehydration cycle is reversible. PXRD of the sample recovered from the DVS sample pan showed the same pattern as the solid residue of the solubility experiments. The water content of 5.2% essentially corresponds to the water content of a dihydrate. The following peaks are characteristic of the dihydrate gentisate salt of Formula (1) obtained after the DVS test: 4.6, 8.7, 11.7, 12.5, 12.8, 13.1, 14.1, 15.1, 15.6, 16.5, 16.8, 19.7, 24.1, 24.5, 25.3, 25.7, 25.9, 26.6, 26.9, and 29.4° 2θ±0.2° 2θ.

Example 17. Characterization of the Oxalate Salt of (S)-4-(8-Amino-3-(1-(but-2-ynoyl)pyrrolidin-2-yl) imidazo[1,5-a]pyrazin-1-yl)-N-(pyridin-2-yl)benzamide Example 17.1. Preparation of Form A of the Oxalate Salt of Formula (1)

Oxalic acid has the molecular formula $C_2H_2O_4$ with a molecular mass of 90.04 g/mol. The $pK_a$ values of the two acid groups are 1.27 and 4.27. The oxalate salt was first identified in the screen described above.

Sample SP221-OXA-P1 was prepared as follows: 236 mg of sample PP502-P1 and 45.4 mg of oxalic acid (Sigma Aldrich #75688) were added to 5.0 mL of acetone:water (95:5) and the mixture was heated to about 55° C. The compound did not dissolve; the mixture was allowed to cool to room temperature and stirred overnight, after which the solid was filtered off and dried in air at room temperature.

Sample SP221-OXA-P2 was prepared as follows: 468.2 mg of sample PP502-P1 and 90.9 mg of oxalic acid (Sigma Aldrich #75688) was added to 10.0 mL of 1-propanol and heated to 70° C. An essentially unstirable gel was obtained to which another 15.0 mL of 1-propanol and 1.0 mL of water were added. Stirring was continued at room temperature for three days before the solid was filtered off and examined by PXRD after short drying in air at room temperature.

Sample SP221-OXA-P3 was prepared as follows: 468 mg of sample PP502-P1 was dissolved in 10.0 mL of methanol at reflux, and 90 mg of oxalic acid dissolved in 2.0 mL of methanol was added. The material was cooled to room temperature, seeded with SP221-OXA-P2, and about half of the suspension was taken and stirred at room temperature then heated again to 50° C.; after which all solids dissolved. The solution was allowed to cool to room temperature again and stirred before part of the sample was filtered and solid investigated after drying in air at room temperature. This sample was designated SP221-OXA-P3A. To the other half of the suspension from was added 3.0 mL of water. All solid immediately dissolved, then the mixture was stirred under nitrogen purge at room temperature until all solvents were removed. To the dry residue was added 2.0 mL of acetonitrile, 2.0 mL of ethanol and 0.2 mL of water and stirred for two days at room temperature. A suspension was obtained from which the solid was filtered off and dried in air at room temperature. This sample was designated SP221-OXA-P3B.

Sample SP221-OXA-P4 was prepared as follows: 468 mg of sample PP502-P1 was dissolved in 10.0 mL of acetone and 1.0 mL of water at reflux, and 45 mg of oxalic acid (Sigma Aldrich #75688) dissolved in 1.0 mL of water was added. No crystallization was observed. An additional 46 mg of solid oxalic acid and 5.0 mL of acetone were added and stirring at room temperature was continued while the vial was kept open. After overnight stirring, a thick paste was obtained. Heating the mixture to 50° C. led to complete dissolution and cooling to room temperature again led to a very thick suspension. Part of the suspension was filtered and the solid dried in air at room temperature.

Sample SP221-OXA-P5 was prepared as follows: 470 mg of sample PP502-P1 and 90 mg of oxalic acid (Sigma Aldrich #75688) were combined in 10.0 mL of tetrahydrofuran and 1.0 mL of methanol heated to reflux to achieve dissolution of the solids. Upon seeding with SP221-OXA-P2 and cooling to room temperature, a thick paste was obtained that was heated to 60° C. to 65° C. and stirred for two days before the solid was filtered off and dried in air at room temperature.

Sample SP221-OXA-P7 was prepared as follows: the remaining products from experiments SP221-OXA-P4 and SP221-OXA-P5 (about 300 mg) were combined and were suspended in 5.0 mL of water. The mixture was stirred at room temperature for four days. The suspension was filtered and the solids were dried in air at room temperature for 24 hours.

Example 17.2. Physical Characterization of Form A of the Oxalate Salt of Formula (1)

$^1$H NMR spectroscopy of the oxalate was not carried out because of the lack of non-exchangeable hydrogens in oxalic acid. The CHNO content of SP221-OXA-P1 was determined by elemental composition analysis, with the results shown in Table 44. The molecular formula of a 1:1 salt of Formula (1) with oxalic acid is predicted to be $C_{28}H_{25}N_7O_6$ with a molecular weight of 555.55 g/mol. A hydrate with a stoichiometry of 2.5 moles of water to 1 mole of Formula (1) would have the molecular formula of $C_{28}H_{30}N_7O_{8.5}$ and a molecular weight of 602.6 g/mol (with a water content of 7.5%). The results as presented for sample SP221-OXA-P7 are in fair agreement with the molecular formula for such a "2.5 hydrate." An assumed water content of about 7.5% is based on the result from TG-FTIR which revealed a mass loss of 8.3% essentially attributable to water. A trihydrate would contain 8.9% of water and therefore a trihydrate is also possible.

TABLE 44

Results from elemental composition analysis of oxalate salts and theoretical compositions.

| Element | % found for SP221-OXA-P1 | % found for SP221-OXA-P7 | % theoretical for anhydrous form | % theoretical for monohydrate | % theoretical for 2.5 hydrate |
|---|---|---|---|---|---|
| C | 57.4 | 53.8 | 60.54 | 58.63 | 55.81 |
| H | 4.9 | 5.3 | 4.54 | 4.74 | 5.35 |
| N | 16.6 | 15.9 | 17.65 | 17.09 | 16.27 |
| O | 17.4 | 21.1 | 17.28 | 19.53 | 22.57 |
| Sum | 96.3% | 96.1% | 100% | 100% | 100% |

Figure 61:
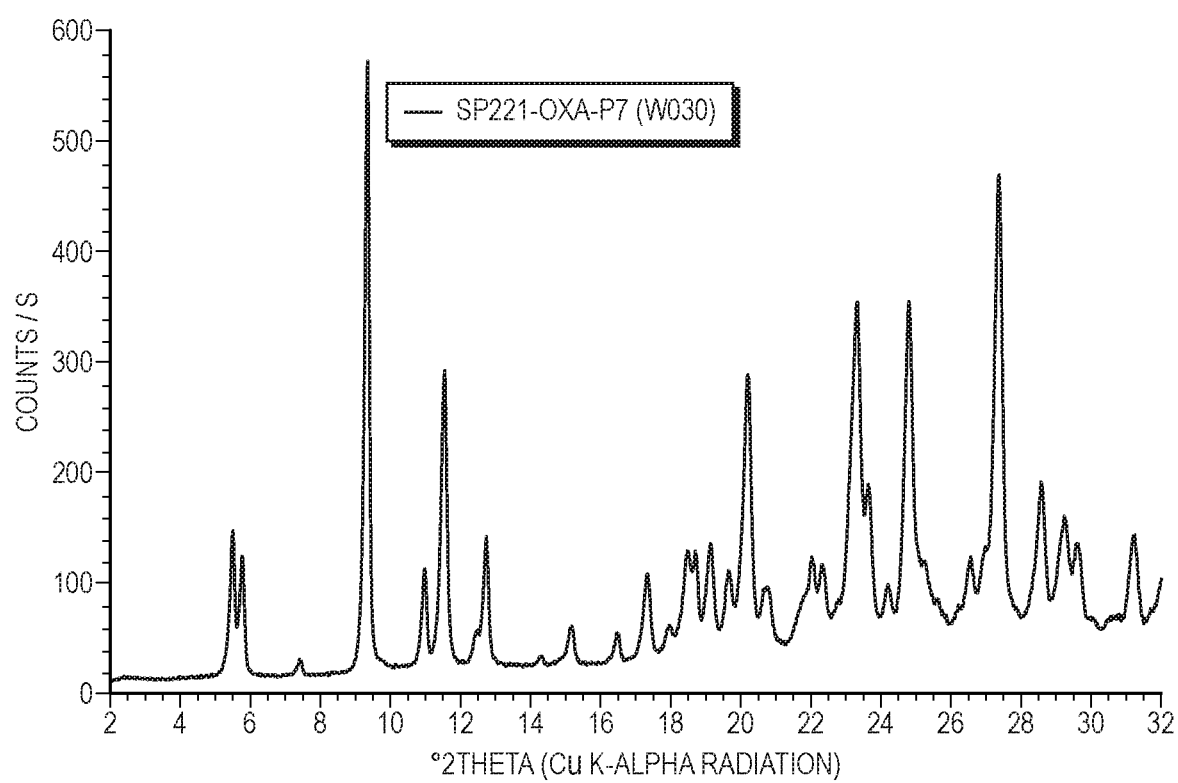
FIG. 61 illustrates a PXRD pattern of Form A of the oxalate salt of Formula (1).

A reflection PXRD pattern of the oxalate salt of Formula (1) monohydrate is shown in FIG. 61 (sample SP221-OXA-P7). This crystalline phase is designated Form A (2.5 hydrate) of the oxalate salt of Formula (1). The following peaks are characteristic of Form A (2.5 hydrate) of the oxalate salt of Formula (1): 5.5, 5.8, 7.4, 9.3, 11.0, 11.5, 12.7, 15.2, 16.5, 17.3, 18.5, 18.7, 19.1, 19.7, 20.2, 20.8, 22.0, 22.3, 23.3, 23.6, 24.8, 27.4, 28.6, 29.3, 29.6, 31.2, and 33.1° 2θ±0.2° 2θ.

Raman spectroscopy was measured over the range from 100 cm$^{-1}$ to 3500 cm$^{-1}$ using a sample of Form A (2.5 hydrate) of the oxalate salt of Formula (1) (sample SP221-OXA-P7). The Raman spectrum was obtained in a similar manner as described in Example 1.2 for Form I. Characteristic Raman peaks for Form A (2.5 hydrate) of the oxalate salt of Formula (1) are observed at 3073, 2992, 2950, 2922, 2247, 1671, 1612, 1584, 1552, 1504, 1469, 1440, 1336, 1311, 1273, 1235, 1191, 1162, 1095, 1012, 897, 718, 633, 409, 370, and 263 (Raman shift, cm$^{-1}$±2 cm$^{-1}$).

IR spectroscopy was measured over the range from 600 cm$^{-1}$ to 3600 cm$^{-1}$ using a sample of Form A (2.5 hydrate) of the oxalate salt of Formula (1) (sample SP221-OXA-P7). The IR spectrum was obtained in a similar manner as described in Example 1.2 for Form I. Characteristic IR peaks for Form A (2.5 hydrate) of the oxalate salt of Formula (1) are observed at 3419, 2249, 1670, 1615, 1544, 1503, 1438, 1391, 1334, 1304, 1262, 1195, 1151, 1126, 1093, 1013, 894, 877, 823, 783, 765, 738, and 652 (IR frequency, cm$^{-1}$±4 cm$^{-1}$).

The TG-FTIR thermogram of Form A (2.5 hydrate) of the oxalate salt of Formula (1) (sample SP221-OXA-P7) was measured. The observed mass loss, likely due to water, is between the expected water content for a trihydrate (8.9%) and a dihydrate (6.1%). The water appears to be weakly bound, because the beginning of the mass loss is essentially at room temperature. Differential scanning calorimetry results for Form A (2.5 hydrate) of the oxalate salt of Formula (1) (sample SP221-OXA-P7). DSC revealed a melting endotherm at 127° C. with an enthalpy of fusion of about 70 J/g. Thermal events observed in the DSC above 150° C. are likely due to thermal decomposition.

DVS analysis of Form A (2.5 hydrate) of the oxalate salt of Formula (1) (sample SP221-OXA-P7) reveals that the water is removed at 0% RH. PXRD of the sample recovered from the DVS sample pan showed the same pattern as pattern before the start of the DVS test. At 50% RH, the water content is about 5.5% and at 95% RH, the water content is about 6.5%. This result suggests that Form A may form a stable dihydrate.

Figure 62:
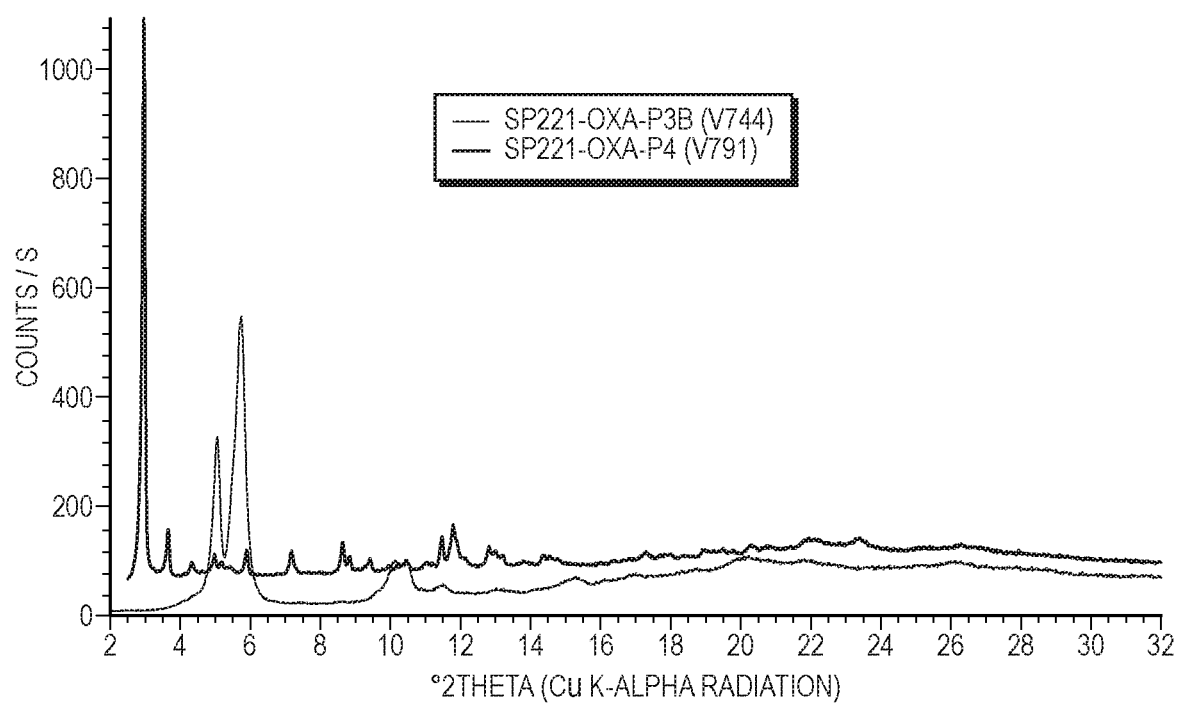
FIG. 62 illustrates PXRD patterns of materials likely to be other forms of oxalate salts of Formula (1).

Two additional PXRD patterns were obtained from preparations of oxalate salts. PXRD patterns of samples SP221-OXA-P3B and SP221-OXA-P4 are shown in FIG. 62. Based on their PXRD patterns, these samples likely represent other crystalline oxalate salts of Formula (1).

Example 18. Characterization of the L-Proline Cocrystal of (S)-4-(8-amino-3-(1-(but-2-ynoyl)pyrrolidin-2-yl)imidazo[1,5-a]pyrazin-1-yl)-N-(pyridin-2-yl)benzamide

Example 18.1. Preparation of Form A of the L-Proline Cocrystal of Formula (1)

Cocrystals of Formula (1) with L-proline was prepared as follows. Sample SP221-PRO-P1 was prepared using 235 mg of Formula (1) free base (PP502-P1) and 57.5 mg L-proline, which were dissolved in 6.0 mL of acetone-water (95:5), after which the solution was heated to about 58° C. An essentially clear solution was obtained, that was allowed to cool to room temperature and stirred overnight. After about 20 hours the obtained suspension was filtered and the solid product dried in air at room temperature.

Sample SP221-PRO-P2 was prepared as follows: 41.2 mg of L-proline was dissolved in 5.0 mL of ethanol containing about 1% of water. 168 mg of Formula (1) free base (PP502-P1) was dissolved in 7.0 mL of ethanol at about 60° C. The L-proline solution was then added to the Formula (1) solution, and the combined solution was allowed to cool to room temperature and stirred overnight. About 5 mL of ethanol was allowed to evaporate, and the solids were filtered.

Sample SP221-PRO-P3 was prepared as follows: 235 mg PP502-P1 and 80.4 mg of L-proline were suspended in 8.0 mL of ethanol and heated to 70° C. Another 1.5 ml of ethanol was added at 70° C. in order to obtain an essentially clear solution. The solution was allowed to cool to room temperature within about one hour and was stirred at room temperature for about 2 hours. The solids were filtered and the solid product was dried in air at room temperature.

Sample SP221-PRO-P6 was prepared as follows: 940 mg of PP502-P1 was dissolved in 15.0 mL of ethanol and 1.0 mL of water by heating to about 75° C., and 345 mg of L-proline was dissolved in 4.0 mL ethanol:water (3:1) and combined. The solution was allowed to cool to 40° C. and stirred at 40° C. under a steady flow of nitrogen. Over three days all solvents evaporated and a dry residue was obtained. The solid was resuspended solid in 3.0 mL of acetonitrile, 1.0 mL of methanol and 0.2 mL of water and stirred at room temperature. As the suspension was too concentrated, 2.0 mL of acetonitrile and 4.0 mL methanol were added, and after about 2 hours an in-process sample was isolated and tested.

Example 18.2. Physical Characterization of the L-Proline Cocrystal of Formula (1)

$^1$H NMR spectroscopy of the product from experiment SP221-PRO-P6 revealed a spectrum with signals assignable to proline, which are consistent with the ratio expected for a cocrystal, although overlapping signals prevented more detailed quantitative analysis.

The CHNO content of SP221-PRO-P1 was determined by elemental composition analysis, with the results shown in Table 45.

TABLE 45

Results from elemental composition analysis of sample SP221-PRO-P1.

| Element | % found | Calculated for $C_{36}H_{41}N_9O_6$ | Calculated for $C_{36}H_{41}N_9O_6$. 0.15 $H_2O$ |
|---|---|---|---|
| C | 61.6 | 62.15 | 61.91 |
| H | 6.3 | 5.94 | 5.96 |
| N | 18 | 18.12 | 18.05 |
| O | 13.9 | 13.80 | 14.09 |

Figure 63:
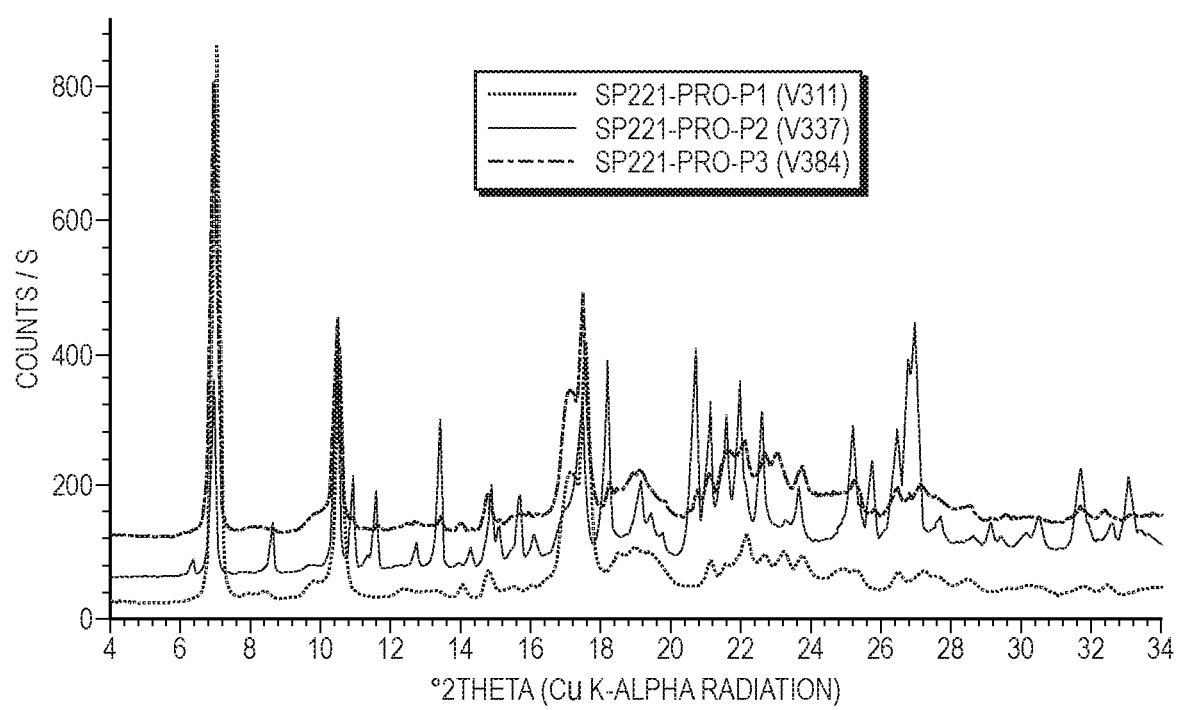
FIG. 63 illustrates PXRD patterns of Formula (1) L-proline cocrystal samples.

The PXRD patterns of three samples of this cocrystal, two of which are likely to be the same crystalline phase (samples SP221-PRO-P1 and SP221-PRO-P3), are shown in FIG. 63. The crystalline phase of samples SP221-PRO-P1 and SP221-PRO-P3 is designated Form A of L-proline cocrystal of Formula (1). The following peaks are characteristic of Form A L-proline cocrystal of Formula (1) (as measured for sample SP221-PRO-P1): 7.0, 10.5, 14.0, 14.8, 17.1, 17.6, 21.1, and 22.1° 2θ±0.2° 2θ. PXRD analysis of sample SP221-PRO-P6 (not shown) showed that this material was the same phase as that obtained for sample SP221-PRO-P1. The PXRD pattern of sample SP221-PRO-P2 shows evidence of the presence of a substantial amount of Form I of the free base of Formula (1).

Raman spectroscopy was measured over the range from 100 cm$^{-1}$ to 3500 cm$^{-1}$ using a sample of Form A of the L-proline cocrystal of Formula (1) (sample SP221-PRO-P1). The Raman spectrum was obtained in a similar manner as described in Example 1.2 for Form I. Characteristic Raman peaks for Form A of the L-proline cocrystal of Formula (1) are observed at 3064, 2971, 2919, 2881, 2242, 1675, 1607, 1577, 1530, 1484, 1454, 1434, 1344, 1323, 1311, 1264, 1243, 1185, 1157, 1035, 1020, 993, 370, 275, 190, and 153 (Raman shift, cm$^{-1}$±2 cm$^{-1}$).

IR spectroscopy was measured over the range from 600 cm$^{-1}$ to 3600 cm$^{-1}$ using a sample of Form A of the L-proline cocrystal of Formula (1) (sample SP221-PRO-P1). The IR spectrum was obtained in a similar manner as described in Example 1.2 for Form I. Characteristic IR peaks for Form A of the L-proline cocrystal of Formula (1) are observed at 3471, 3310, 3108, 2358, 1672, 1615, 1526, 1495, 1452, 1431, 1399, 1342, 1305, 1262, 1241, 1184, 1148, 1091, 1038, 1014, 991, 944, 890, 872, 837, 816, 775, 756, 737, 713, and 668 (IR frequency, cm$^{-1}$±4 cm$^{-1}$).

The TG-FTIR thermogram of Form A of the L-proline cocrystal of Formula (1) (sample SP221-PRO-P1) was obtained. A small mass loss of about 0.7% observed for sample SP221-PRO-P1 is attributable to water, and no other solvent loss was observed. The TG-FTIR thermogram of another sample of Form A of the L-proline cocrystal of Formula (1) (sample SP221-PRO-P3). This sample showed a much larger mass loss, identified as a mixture of ethanol and water by TG-FTIR, which may result from residual solvent.

Example 19. Characterization of the D-Sorbitol Cocrystal of (S)-4-(8-Amino-3-(1-(but-2-ynoyl)pyrrolidin-2-yl)imidazo[1,5-a]pyrazin-1-yl)-N-(pyridin-2-yl)benzamide

Example 19.1. Preparation of Form A of the D-Sorbitol Cocrystal of Formula (1)

A cocrystal of Formula (1) with D-sorbitol was identified in the screening experiments describe previously. Sample SP221-SBT-P1 was prepared as follows. 235 mg of Formula (1) free base (PP502-P1) was dissolved in 12.0 mL of a 0.05 M stock solution of D-sorbitol in methanol by gentle heating to reflux temperature. The solution was cooled to room temperature and stirred. After several days, no formation of solid was observed, and some of the methanol was evaporated under nitrogen flow. Within three days a suspension was formed, from which the solid was filtered off and examined by PXRD.

Sample SP221-SBT-P2 was prepared as follows: to the remaining sample SP22-SBT-P1 was added 3.0 mL of ethanol. The resulting suspension was stirred at room temperature for four days. The solids were filtered, dried in air at room temperature, and examined by PXRD.

Sample SP221-SBT-P4 was prepared as follows: 510 mg of Formula (1) free base (PP502-P1) and 200 mg of sorbitol (Sigma #S1876) were dissolved in 10.0 mL of ethanol and 3.333 mL of water by gentle heating. The solution was cooled to room temperature while purging with a slight nitrogen flow. After three days, a white suspension was obtained from which the solid was filtered off and dried in air at room temperature for a yield of about 250 mg. Optical microscopy showed the presence of a very fine needle shaped crystalline material.

Example 19.2. Physical Characterization of the D-Sorbitol Cocrystal of Formula (1)

$^1$H NMR spectroscopy of the product from experiment SP221-SBT-P4 revealed a ratio of Formula (1) free base to D-sorbitol of 3:2.

In addition, sample SP221-SBT-P4 was analyzed for CHNO content by elemental composition analysis, with the results shown in Table 46. The molecular sum formula of a 1:0.66 cocrystal of Formula (1) and D-sorbitol would be $C_{26}H_{23}N_7O_2 \cdot 0.66 [C_6H_{14}O_6]$ with a molecular weight of 586.95 g/mol. A tetrahydrate would be expected to have a molecular weight of 659.0 g/mol (with a water content of 10.9%). The results for C, H, and N are in good agreement with a tetrahydrate, however, the oxygen content found is too low and is more consistent with an anhydrous phase.

TABLE 46

Results from elemental composition (CHNO analysis) and water content (TG-FTIR) analysis for sample SP221-SBT-P4.

| Element | % found | $C_{33}H_{31}N_7O_7$ |
|---|---|---|
| C | 54.8 | 54.68 |
| H | 5.5 | 6.17 |
| N | 15.1 | 14.88 |
| O | 17.2 | 24.28 |
| water | 11.0 | 10.9 |

*This value was taken from the TG-FTIR analysis of SP221-SBT-P4, as described below.

Optical microscopy of the D-sorbitol cocrystal of Formula (1) (sample SP221-SBT-P4) showed crystalline material with predominantly with very fine needle-shaped particles with lengths of about 50 to 150 μm and widths of about 1 to 5 μm.

Figure 64:
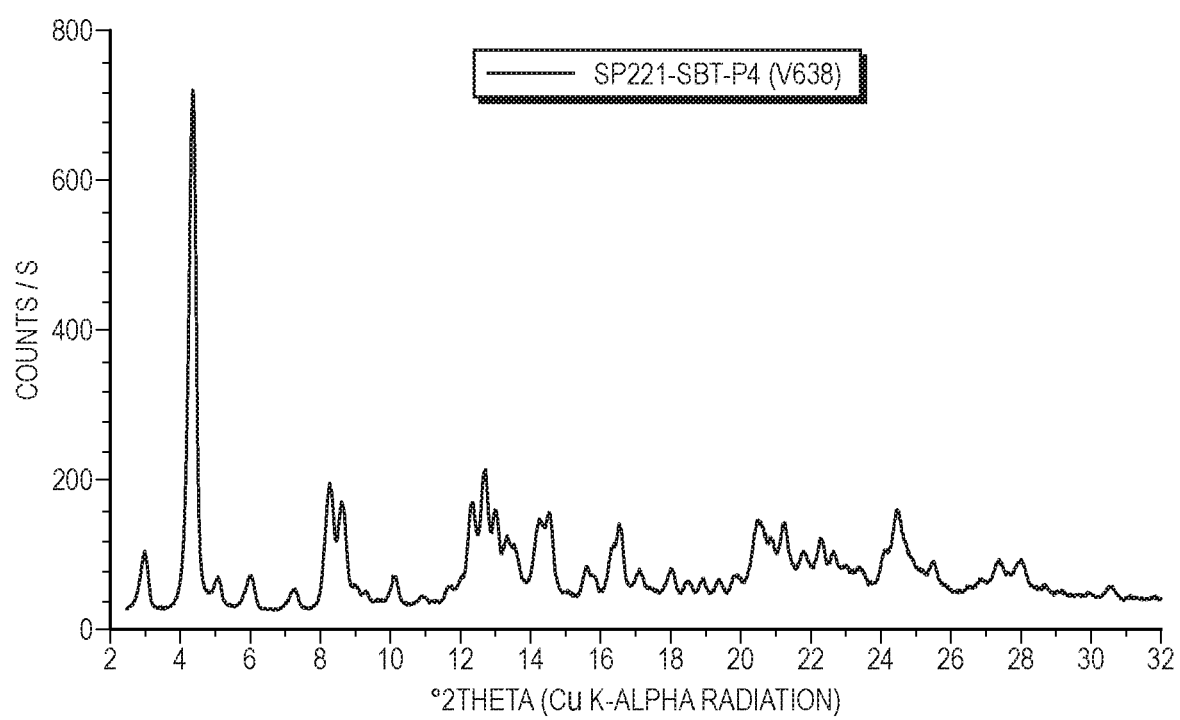
FIG. 64 illustrates a PXRD pattern of Form A of the D-sorbitol cocrystal of Formula (1).

A PXRD pattern of the D-sorbitol cocrystal of Formula (1) is shown in FIG. 64 (sample SP221-SBT-P4). This crystalline phase is designated Form A of the D-sorbitol cocrystal of Formula (1). The following peaks are characteristic of Form A of the D-sorbitol cocrystal of Formula (1): 3.0, 4.4, 5.1, 6.0, 7.3, 8.3, 8.6, 10.1, 12.3, 12.7, 13.4, 13.0, 14.3, 14.5, 15.6, 16.5, 17.1, 18.0, 18.5, 19.0, 19.4, 19.8, 20.5, 21.2, 21.8, 22.3, 22.6, 24.4, 25.5, 27.3, 28.0, and 32.9° 2θ±0.2° 2θ.

Raman spectroscopy was measured over the range from 100 cm$^{-1}$ to 3500 cm$^{-1}$ using a sample of Form A of the D-sorbitol cocrystal of Formula (1) (sample SP221-SBT-P4). The Raman spectrum was obtained in a similar manner as described in Example 1.2 for Form I. Characteristic Raman peaks for Form A of the D-sorbitol cocrystal of Formula (1) are observed at 3071, 2921, 2246, 1682, 1610, 1579, 1531, 1493, 1453, 1437, 1343, 1311, 1246, 1183, 1162, 1039, 1000, 950, and 646 (Raman shift, cm$^{-1}$±2 cm$^{-1}$).

IR spectroscopy was measured over the range from 600 cm$^{-1}$ to 3600 cm$^{-1}$ using a sample of Form A of the D-sorbitol cocrystal of Formula (1) (sample SP221-SBT-P4). The IR spectrum was obtained in a similar manner as described in Example 1.2 for Form I. Characteristic IR peaks for Form A of the D-sorbitol cocrystal of Formula (1) are observed at 3207, 2244, 1681, 1666, 1651, 1615, 1578, 1548, 1531, 1504, 1463, 1434, 1418, 1398, 1311, 1243, 1207, 1149, 1112, 1093, 1052, 1017, 1004, 948, 891, 867, 821, 777, 735, 724, 707, 643, and 618 (IR frequency, cm$^{-1}$±4 cm$^{-1}$).

The TG-FTIR thermogram of Form A of the D-sorbitol cocrystal of Formula (1) (sample SP221-SBT-P4) indicates a water content of about 11%. This water content is consistent with the expected water content for a 3:2 cocrystal of Formula (1): D-sorbitol tetrahydrate for which the water content would be 10.9%. The water appears to be weakly bound, because the mass loss essentially begins with the beginning of the heating phase, even from a sample pan with a pinhole as used in the TG-FTIR testing. Differential scanning calorimetry of Form A of the D-sorbitol cocrystal of Formula (1) (sample SP221-SBT-P4) shows an endotherm at 102° C. with a shoulder at 107° C. that may be assigned to the melting of the cocrystal. The endotherm is followed by exothermic event with a peak temperature of 178° C. that may correspond to recrystallization of the free base Form I or thermal degradation.

The results of DVS analysis of Form A of the D-sorbitol cocrystal of Formula (1) (sample SP221-SBT-P4) show that tested sample can absorb up to about 13% of water at high humidity and that all water is removed at 0% RH. A small hysteresis is observed below 20% RH; this suggests the existence of multiple hydrate forms.

Example 20. Characterization of the Succinic Acid Complex of (S)-4-(8-Amino-3-(1-(but-2-ynoyl)pyrrolidin-2-yl)imidazo[1,5-a]pyrazin-1-yl)-N-(pyridin-2-yl)benzamide Example 20.1. Preparation of Form A of the Succinic Acid Complex of Formula (1)

Sample SP221-SUC-P4 was prepared as follows: 941 mg of Formula (1) free base (PP502-P1) and 237.9 mg succinic acid were dissolved in 20.0 mL of acetone and 3.0 mL of water at 55° C. The solution was cooled to room temperature and stirred in an open vial for three days at room temperature. After three days the volume of the obtained suspension was about 7 mL. The suspension was filtered and the solid dried in air at room temperature.

Sample SP221-SUC-P1 was prepared as follows: 3.0 mL of stock solution of Formula (1) (batch SP221-FBL2) was mixed with 3.0 mL stock solution of 0.05 M succinic acid in ethanol and allowed to evaporate from an open vial at room temperature. A yellow glassy residue was obtained, to which was added 3 mL acetonitrile with continued stirring, after which evaporation occurred and solids were obtained.

Sample SP221-SUC-P7 was prepared as follows: to 466 mg of Formula (1) free base (batch PP502-P1) and 118 mg of succinic acid were combined in 10 mL of 1-propanol. The mixture was heated to 70° C., and 0.1 mL of formic acid was added to achieve dissolution. The solution was allowed to cool to room temperature, and after overnight stirring a suspension was obtained from which the solid product was filtered off and dried in air at room temperature. A yield of about 395 mg was obtained.

Sample SP221-SUC-P2 was prepared as follows: 115.5 mg of Formula (1) free base (batch PP502-P1) and 29.0 mg succinic acid were vigorously ground in an agate mortar with 200 acetone:water 4:1. A sticky paste was obtained, to which acetonitrile was added; the material remained sticky after evaporation of the acetonitrile. The mortar was washed out with 15 mL of methanol and 2.0 mL of acetonitrile, and the wash solution was placed in a glass vial and stirred with the lid open at 40° C. After four days, the suspension was filtered and solids were dried in air at room temperature.

Preparation of hydrates of cocrystals of Formula (1) and succinic acid may be achieved by exposing the foregoing organic solvates to water by vapor exchange.

Example 20.2. Physical Characterization of Form A of the Succinic Acid Complex of Formula (1)

$^1$H NMR spectroscopy of the product from experiment SP221-SUC-P4 determined a ratio of Formula (1) free base to succinic acid of about 1:1 based on the integral for the aromatic proton of Formula (1) near 8.4 ppm and the four protons from the methylene groups of succinic acid between 2.4 ppm.

The pK$_a$ values of succinic acid are 4.21, and 5.64. Since the lower pK$_a$ of succinic acid is just about 1.6 units below the pK$_a$ value of basic function of ACP-196 free base, co-crystal formation is likely to be favored over salt formation.

Figure 65:
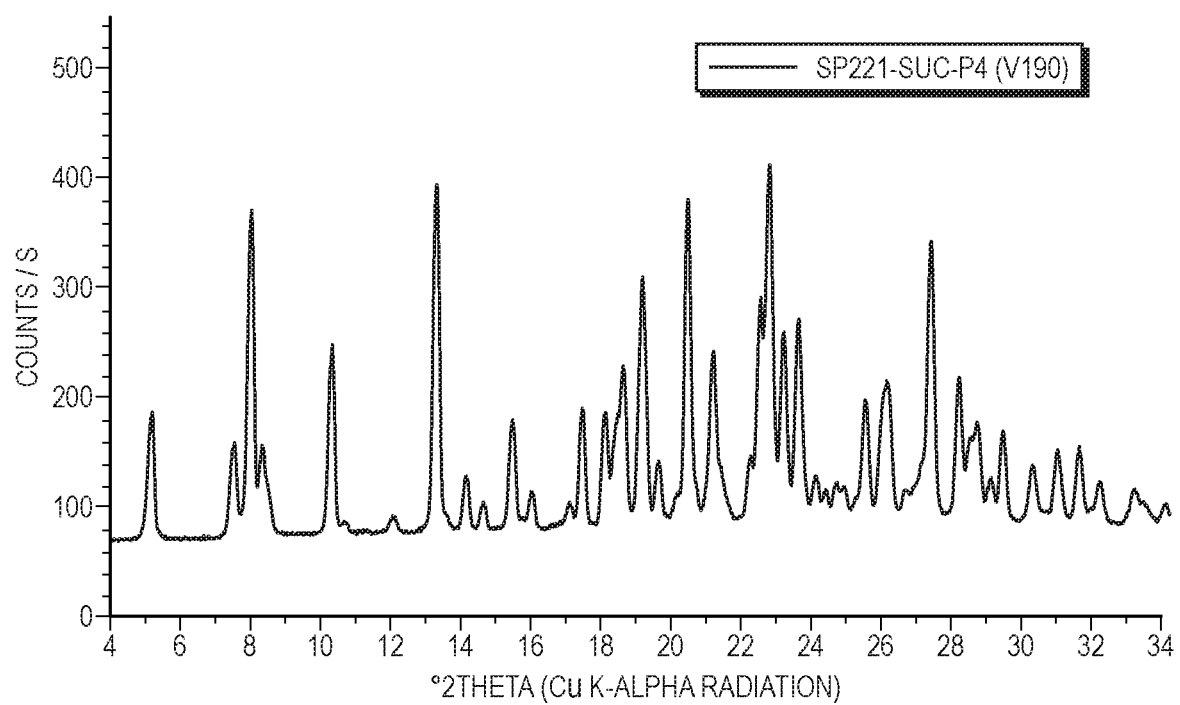
FIG. 65 illustrates a PXRD pattern of Form A of the succinic acid cocrystal of Formula (1).

A reflection PXRD pattern of a succinic acid cocrystal of Formula (1) is shown in FIG. 65 (sample SP221-SUC-P4). This crystalline phase is designated Form A of the succinic acid cocrystal of Formula (1). The following peaks are characteristic of Form A (acetone solvate) of the succinic acid cocrystal of Formula (1): 5.2, 7.5, 8.0, 8.4, 10.3, 12.1, 13.3, 14.2, 14.7, 15.5, 16.0, 17.1, 17.5, 18.1, 18.6, 19.2, 19.6, 20.5, 21.2, 22.5, 22.8, 23.2, 23.6, 25.5, 26.2, 27.4, 28.2, 28.7, 29.4, 30.3, 31.0, 31.6, 32.2, 33.2, and 35.59° 2θ±0.2° 2θ.

Raman spectroscopy was measured over a range from 100 cm$^{-1}$ to 3500 cm$^{-1}$ using a sample of Form A (acetone solvate) of the succinic acid cocrystal of Formula (1) (sample SP221-SUC-P4). The Raman spectrum was obtained in a similar manner as described in Example 1.2 for Form I. Characteristic Raman peaks for Form A (acetone solvate) of the succinic acid cocrystal of Formula (1) are observed at 2973, 2922, 2252, 1670, 1613, 1580, 1566, 1545, 1529, 1496, 1450, 1347, 1330, 1307, 1270, 1244, 1190, 1160, 1036, 1010, 844, 728, 634, 411, 237, 200, and 138 (Raman shift, cm$^{-1}$±2 cm$^{-1}$).

IR spectroscopy was measured over a range from 600 cm$^{-1}$ to 3600 cm$^{-1}$ using a sample of Form A (acetone solvate) of the succinic acid cocrystal of Formula (1) (sample SP221-SUC-P4). The IR spectrum was obtained in a similar manner as described in Example 1.2 for Form I. Characteristic IR peaks for Form A (acetone solvate) of the succinic acid cocrystal of Formula (1) are observed at 2359, 1712, 1668, 1620, 1603, 1578, 1526, 1494, 1432, 1417, 1403, 1367, 1346, 1304, 1246, 1220, 1174, 1162, 1130, 1096, 1035, 1009, 993, 965, 950, 896, 863, 851, 838, 778, 754, 734, 726, 712, 672, 636, 624, and 606 (IR frequency, cm$^{-1}$±4 cm$^{-1}$).

The TG-FTIR thermogram of Form A of the succinic acid cocrystal of Formula (1) (sample SP221-SUC-P4) shows a significant mass loss of approximately 7.5%, identified as acetone, indicates that this sample is an acetone solvate. The TG-FTIR thermogram of the acetonitrile solvate of the succinic acid cocrystal of Formula (1) (sample SP221-SUC-P2), which showed a similar PXRD pattern compared to sample SP221-SUC-P1. A mass loss of nearly 4%, attributable mainly to acetonitrile, indicates that this sample is an acetonitrile solvate. The TG-FTIR thermogram of the acetonitrile solvate of the succinic acid cocrystal of Formula (1) (sample SP221-SUC-P7) shows a mass loss of nearly 9.5%, attributable mainly to 1-propanol, indicates that this sample is a 1-propanol solvate.

Example 21. Characterization of the Sulfate Salt of (S)-4-(8-Amino-3-(1-(but-2-ynoyl)pyrrolidin-2-yl) imidazo[1,5-a]pyrazin-1-yl)-N-(pyridin-2-yl)benzamide Example 21.1. Preparation of Form A of the Sulfate Salt of Formula (1)

A sulfate salt of Formula (1) (sample SP221-SO4-P1) was prepared as follows. To 5.0 mL of a 0.1 M stock solution of Formula (1) free base in acetone-water (sample SL20150415FB, 0.1 M) was added one equivalent of sulfuric acid in form of concentrated sulfuric acid (27.8 μL), which was heated to 50° C. and allowed to cool to room temperature. As crystallization did not occur the mixture was seeded with a few mg of crystalline phosphate salt. After overnight stirring at room temperature a yellow/white suspension was obtained from which the solid was filtered off and dried in air at room temperature.

Sample SP221-SO4-P3 was prepared by repetition of the experiment used to produce SP221-SO4-P1 using a 1:1 ratio of sulfuric acid to free base.

Sample SP221-SO4-P4 was prepared by dissolving 941 mg of sample PP502-P1 in 22 mL of acetone-water 10:1 at about 50° C. and adding one equivalent of concentrated sulfuric acid (112 μL). A suspension formed at 50° C.; the mixture was allowed to cool to room temperature and then stirred overnight at room temperature before solid was filtered off and dried in air. About 880 mg of slightly yellowish solid was obtained.

Sample SP221-SO4-P5 was prepared by adding 300 mg of SP221-SO4-P4 to 3.0 mL of acetonitrile and 0.3 mL of water. The suspension was stirred at room temperature for one day. The suspension was filtered, and solids were dried in air at room temperature.

Sample SP221-SO4-P6 was prepared by adding 944 mg of Formula (1) free base (batch PP502-P1) to 15.0 mL of acetone:water (9:1) and heating to reflux to achieve dissolution. Sulfuric acid (0.8 mL/1 equivalent) was then added in the form of a 2.5 M aqueous solution. The solution was seeded with SP221-SO4-P1 and allowed to cool to 35° C. while stirring was continued overnight. A suspension was obtained that was reheated to 50° C. for about three hours then allowed to cool again to room temperature and stirred for two hours before the solid was filtered off and dried in air at room temperature. A yield of about 950 mg was obtained.

Example 21.2. Physical Characterization of Form A of the Sulfate Salt of Formula (1)

$^1$H NMR spectroscopy (spectrum not shown) of the product from experiment SP221-SO4-P4 was consistent with Formula (1). Samples SP221-SO4-P4 and SP221-SO4-P5 were analyzed by CHONS elemental composition analysis, with the results shown in Table 47. The molecular sum formula expected for a solvent-free monostoichiometric sulfate salt of Formula (1) is $C_{26}H_{25}N_7O_6S$, with a molecular weight of 563.6 g/mol. A trihydrate monostoichiometric sulfate salt of Formula (1) is expected to have a sum molecular formula of $C_{26}H_{31}N_7O_9S$ and a molecular weight of 617.6 g/mol (with a water content of 8.7%). A tetrahydrate monostoichiometric sulfate salt of Formula (1) is expected to have a molecular sum formula of $C_{26}H_{33}N_7O_{10}S$ and a molecular weight of 635.7 g/mol (with a water content of 11.3%). The best fit to the experimental values for sample SP221-SO4-P4 is to a tetrahydrate with an excess of sulfuric acid equivalent to a molar ratio of about 1.25. The best fit to the experimental values for sample SP221-SO4-P5 was found for a monosulfate tetrahydrate salt, wherein good agreement with the theoretically expected hydrogen, oxygen and sulfur content was found, with only a slight discrepancy found for carbon and nitrogen.

TABLE 47

Results from elemental composition (CHNOS analysis) analysis for samples SP221-SO4-P4 and SP221-SO4-P5 of the sulfate salt of Formula (1).

| Element | SP221-SO4-P4 (% found, experimental) | SP221-SO4-P5 (% found, experimental) | $C_{26}H_{33.5}N_7O_{11}S_{1.25}$ tetrahydrate sulfate salt (theoretical) | Tetrahydrate monosulfate salt (theoretical) |
|---|---|---|---|---|
| C | 47.4 | 46.8 | 47.30 | 49.13 |
| H | 4.9 | 4.7 | 5.11 | 5.23 |
| N | 14.9 | 14.4 | 14.85 | 15.42 |
| O | not determined | 25.0 | 26.66 | 25.17 |
| S | 6.2 | 5.0 | 6.07 | 5.04 |
| water* | 10.6 | not available | 10.9 | 11.3 |

*Water content was determined by Karl Fischer titration.

Optical microscopy of sample SP221-SO4-P5 showed crystalline material with predominantly needle-shaped particles. The particles in sample SP221-SO4-P5 were considerably smaller than those for sample SP221-SO4-P6, which showed particle lengths up to about 100 μm and widths of about 5 to 10 μm.

Figure 66:
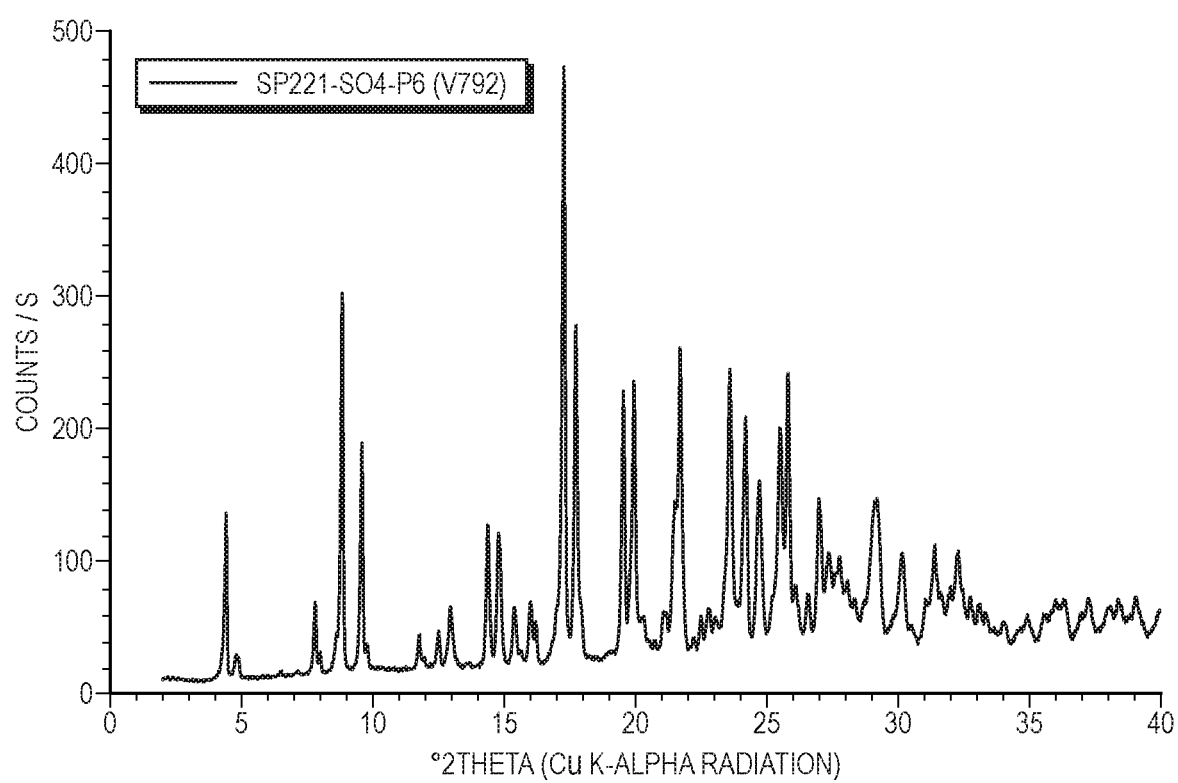
FIG. 66 illustrates a PXRD pattern of a sample of Form A of a sulfate salt of Formula (1).

The reflection PXRD pattern of sample SP221-SO4-P6 is shown in FIG. 66. This crystalline phase is designated Form A of the sulfate salt of Formula (1). The following peaks are characteristic of Form A of the sulfate salt of Formula (1): 4.6, 5.0, 8.0, 9.0, 9.8, 12.0, 12.7, 13.2, 14.6, 15.0, 15.6, 16.2, 17.5, 18.0, 19.8, 20.2, 21.9, 23.8, 24.4, 24.9, 25.7, 26.0, 27.2, 29.5, 30.4, 31.6, and 32.5° 2θ±0.2° 2θ.

Raman spectroscopy was measured over a range from 100 cm$^{-1}$ to 3500 cm$^{-1}$ using a sample of Form A of the sulfate salt cocrystal of Formula (1) (sample SP221-SO4-P4). The Raman spectrum was obtained in a similar manner as described in Example 1.2 for Form I. Characteristic Raman peaks for Form A of the sulfate salt of Formula (1) are observed at 3115, 2977, 2926, 2224, 1675, 1611, 1537, 1498, 1449, 1409, 1361, 1327, 1310, 1288, 1243, 1198, 1155, 1042, 1009, 978, 948, 906, 849, 771, 713, 652, 632, 464, 370, and 254 (Raman shift, cm$^{-1}$±2 cm$^{-1}$).

IR spectroscopy was measured over a range from 600 cm$^{-1}$ to 3600 cm$^{-1}$ using a sample of Form A of the sulfate salt of Formula (1) (sample SP221-SO4-P4). The IR spectrum was obtained in a similar manner as described in Example 1.2 for Form I. Characteristic IR peaks for Form A of the sulfate salt of Formula (1) are observed at 3430, 3101, 3029, 2225, 1667, 1633, 1615, 1598, 1563, 1557, 1508, 1428, 1350, 1328, 1308, 1276, 1225, 1088, 1036, 1018, 925, 891, 848, 816, 783, 736, 723, 694, and 612 (IR frequency, cm$^{-1}$±4 cm$^{-1}$).

The TG-FTIR thermogram of Form A of the sulfate salt of Formula (1) (sample SP221-SO4-P4) shows a mass loss of 10.1% is due to water. The water loss begins with heating and is complete by about 110° C. using a heating rate of 10° C. per minute. Differential scanning calorimetry results for Form A of the sulfate salt of Formula (1) (sample SP221-SO4-P4). DSC showed a melting endotherm with a peak temperature of 118° C. and an enthalpy of fusion of about 92 J/g. DSC revealed a melting endotherm at 127° C. with an enthalpy of fusion of about 70 J/g.

DVS analysis was performed for Form A of the sulfate salt of Formula (1) (sample SP221-SO4-P4) show that the water is not completely removed at 0% RH after five hours. The initial water content of the given sulfate sample was determined by Karl Fischer titration. At the end of the test, the water content is almost the same as at the beginning of the measurement.

Example 22. Overcoming the Effects of Acid Reducing Agents with Formulations of (S)-4-(8-Amino-3-(1-(but-2-ynoyl)pyrrolidin-2-yl)imidazo[1,5-a]pyrazin-1-yl)-N-(pyridin-2-yl)benzamide Acid-reducing agents, such as omeprazole, may limit the exposure of Formula (1) free base in mammals because of previously-discussed pH-solubility profile of Formula (1). This is a significant issue in the treatment of patients with cancer, inflammatory diseases, immune diseases, and autoimmune diseases, since these patients are commonly co-administered acid reducing agents for gastric irritation that often accompanies their conditions. Acid reducing agents are the most commonly prescribed medications in North America and Western Europe. Of recently approved oral cancer therapeutics, >50% have pH-dependent solubility, and therefore have a potential drug-drug interaction with regards to acid reducing agents. In cancer patients, it is estimated that 20-33% of all patients are using some form of acid-reducing agent. In particular cancers, such as pancreatic cancer or gastrointestinal cancers, acid reducing agent use is as high as 60-80% of patients. Smelick, et al., *Mol. Pharmaceutics* 2013, 10, 4055-4062.

The concern of potential drug-drug interactions with acid reducing agents for weakly basic drugs has led to the development of risk assessment strategies and drug-drug interaction studies designs for new drugs that exhibit pH dependent solubility and dissolution. Smelick, et al., *Mol. Pharmaceutics* 2013, 10, 4055-4062. Acid reducing agents include proton pump inhibitors, such as omeprazole, esomeprazole, lansoprazole, dexlansoprazole, pantoprazole, rabeprazole, and ilaprazole; H2 receptor antagonists, such as cimetidine, ranitidine, and famotidine; and antacids such as bicarbonates, carbonates, and hydroxides of aluminium, calcium, magnesium, potassium, and sodium. Mixtures of antacids plus agents targeting mechanisms of gastric secretion may also be used as prescription or non-prescription acid-reducing agents. Any other acid reducing agent known in the art may also be used. In some cases, the effect of an acid-reducing agent is transient and depends on presence of the agent in the stomach. In other cases, the effect of an acid-reducing agent may be pronounced throughout the treatment interval, providing a constant elevation of gastric pH to levels greater than pH 4.

The terms hypochlorhydria and achlorhydria refer to conditions where gastric secretion of hydrochloric acid is lower than normal or severely reduced to nonexistent. The natural pH of the stomach is lowered by acid secretions in response to food stimulation; in certain medical conditions the ability of the gastric proton pump to secrete acid is compromised. Infections with *H. pylori* have been associated with impaired secretion of gastric acid (hypochlorhydria or achlorhydria). Other disease states, including those in which gastric parietal cells are destroyed or depleted, or the signaling to gastric parietal cells is altered, can lead to hypochlorhydria or achlorhydria. Long-term use of proton pump inhibitors or H2 receptor antagonists may also result in these conditions. The evaluation of gastric pH over the course of a day (through meals) may be monitored in patients with in situ pH probes, if needed, as a diagnostic aid.

Dissolution of Form 1 of Formula (1) into aqueous media such as stomach fluid is pH dependent (see, e.g., FIG. 67 and FIG. 68, discussed in more detail below). The bioavailability of Formula (1) may therefore be modified by factors that improve its dissolution. Alternate forms of Formula (1), and acidification of the formulation of Form 1 of Formula (1) were tested in dogs treated with omeprazole 10 mg/day to evaluate the extent to which an alternate form of Formula (1) can overcome the effects of acid-reducing agents.

Dogs were treated with Formula (1) 100 mg capsules in several related studies using the same animals and a strict dosing schedule to minimize intra- and inter-animal variability. All doses were chased with 35 mL of distilled H$_2$O by oral gavage to standardize the dissolution volume with each dose administration. Dogs were conditioned to receive sham capsules and chase water on non-dosing days; food was also controlled to reduce the variability associated with gastric acid secretions in response to presentation and consumption of chow. The conditioning regimen was followed continuously for at least six months, and the same 12 dogs were used for all studies described below.

Figure 69:
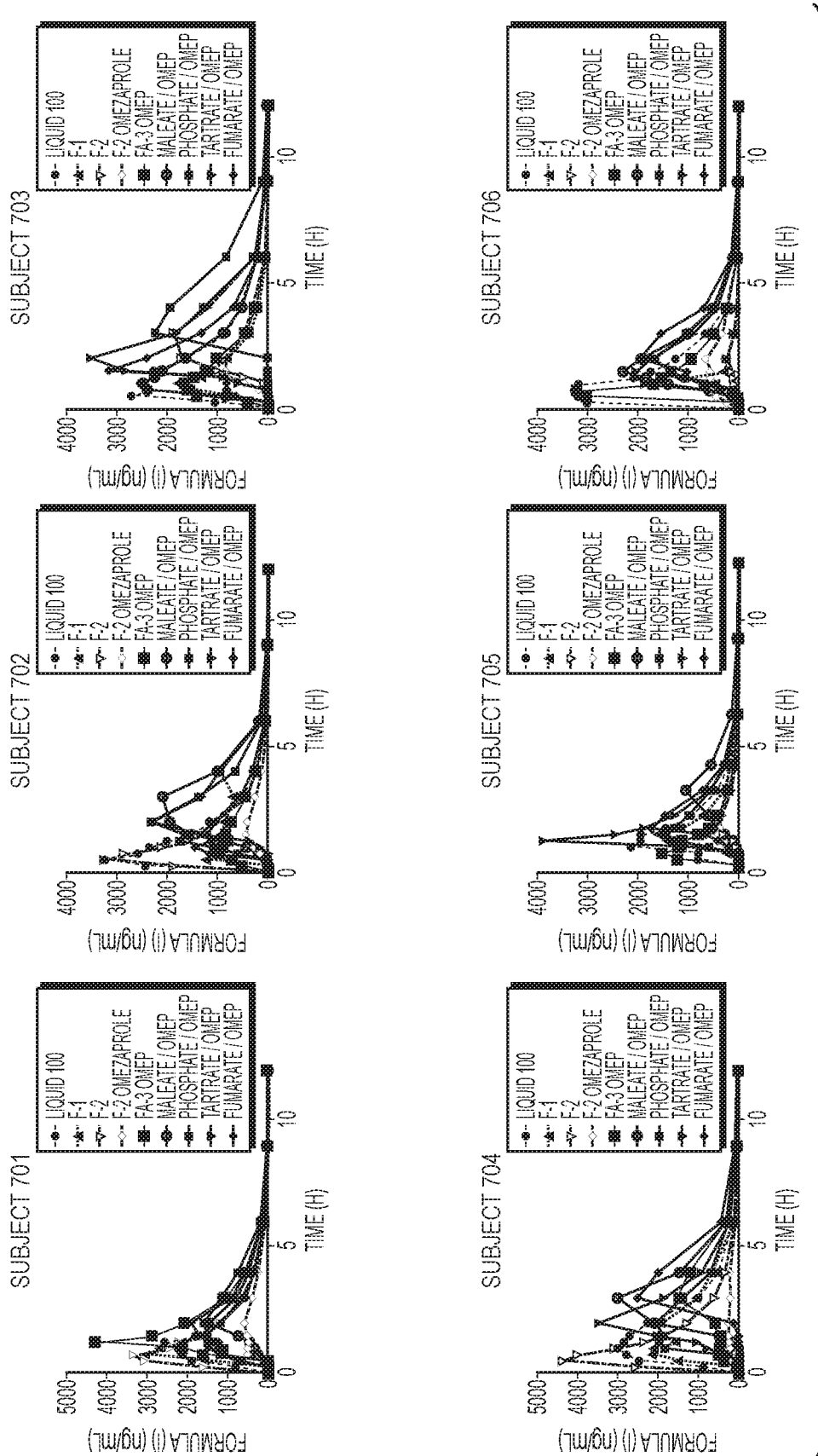
FIG. 69 shows individual concentration-time profiles from dogs in the omeprazole/Formula (1) study. Conditioned dogs were dosed with 100 mg of Formula (1) in sequential dosing phases separated by washout periods of 4-7 days. Liquid capsules or solid capsules containing Form I of Formula (1) were administered; for comparison, a clinical formulation or hand-filled capsules with an Avicel blend were administered. After these initial study phases, dogs were treated with 10 mg/day omeprazole throughout the remainder of the study. After four days of omeprazole treatment, 100 mg of Form I of Formula (1) was administered in the clinical formulation, in a formulation containing acidulants, or in capsules containing 100 mg free base equivalent of the Formula (1) salts of maleate, phosphate, fumarate or tartrate, and plasma concentrations of Formula (1) were measured at the indicated times.
Figure 69:
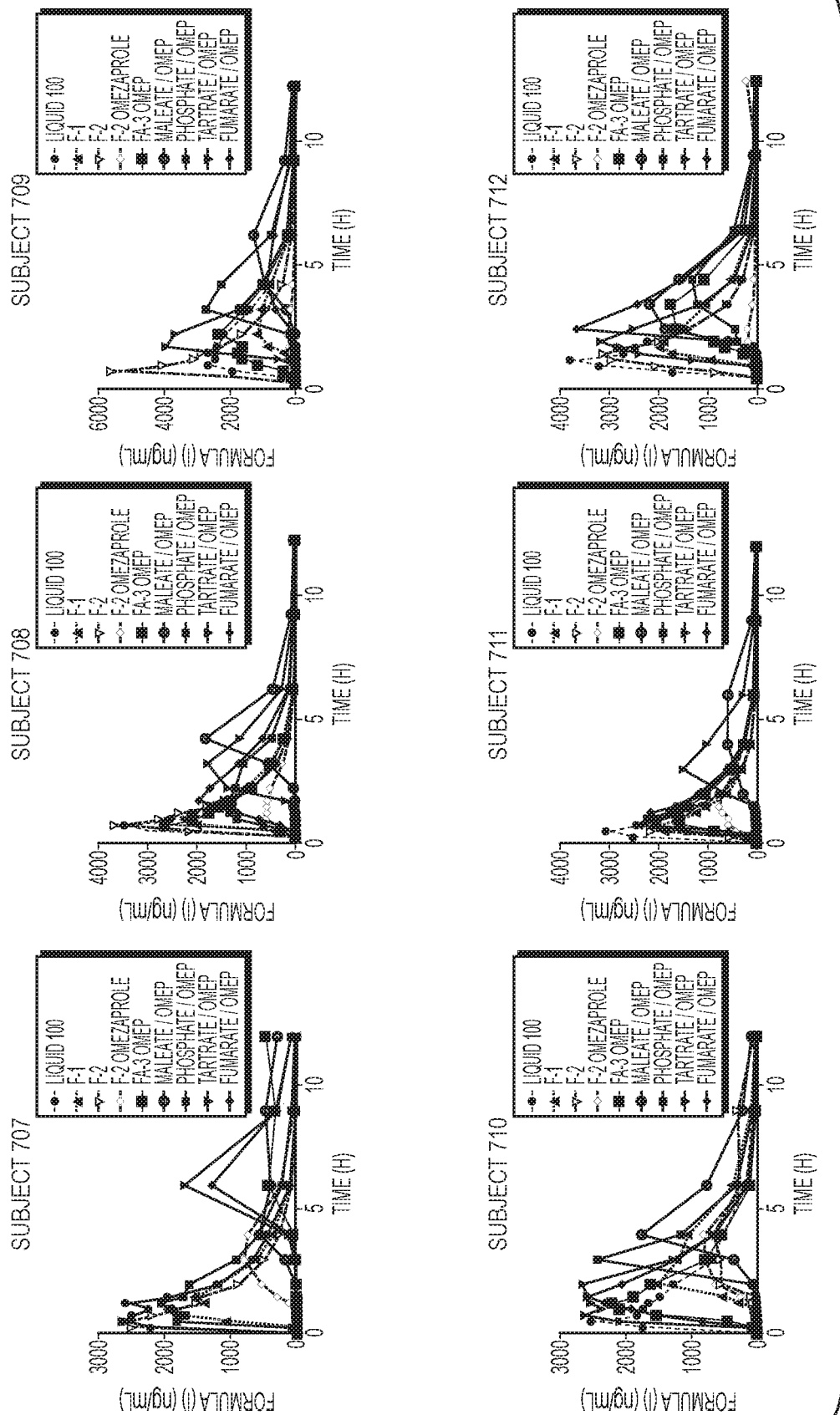

Study 2219-057 used 100 mg of Formula (1) in liquid capsules (hydroxyl-β-cyclodextrin/citrate, 2 doses) to set the bar for absorption without a dissolution component associated with solid form. Study 2219-059 used Formula (1) with formulation F-1 and Study 2219-061 used Formula (1) with formulation F-2 alone or following pre-treatment of the dogs with omeprazole, then proceeded to test Formula (1) salt forms in the F-1 formulation and an acidic formulation of Form I of Formula (1) designated FA-3 (see Example 23 below for the preparation of formulations). FIG. 69 shows individual concentration-time profiles for all dogs included in this series of studies. For simplicity, the mean concentration-time profiles are presented in FIG. 69 for studies with repeated doses of the same form/formulation of Formula (1). The Y axes in FIG. 69 are set for each dog individually, to emphasize the within-dog effects of salt forms and prototype acid formulation.

Study 2219-061 used Form I of Formula (1) recrystallized from ethanol, as described in Example 8, and the maleate, phosphate, fumarate and tartrate salt forms of Formula (1). Following collection of pharmacokinetics data after one dose administration of 100 mg capsules in the F-2 formulation, omeprazole treatment (10 mg/day) was initiated as a part of the conditioning regimen. The remaining study phases were conducted in omeprazole treated dogs. After 4 days on omeprazole, the dogs were dosed with experimental Formula (1) drug forms or formulation on top of the continuing daily omeprazole dose. Salt forms were dosed to equal 100 mg of Formula (1) free base. The F-1 formulation was used for dosing the salt forms after correction for counterion and water content. The prototype acid formulation (FA-3) used both fumaric acid and alginic acid as an extra-granular mix with the granulated Formula (1) in formulation F-2.

Figure 70:
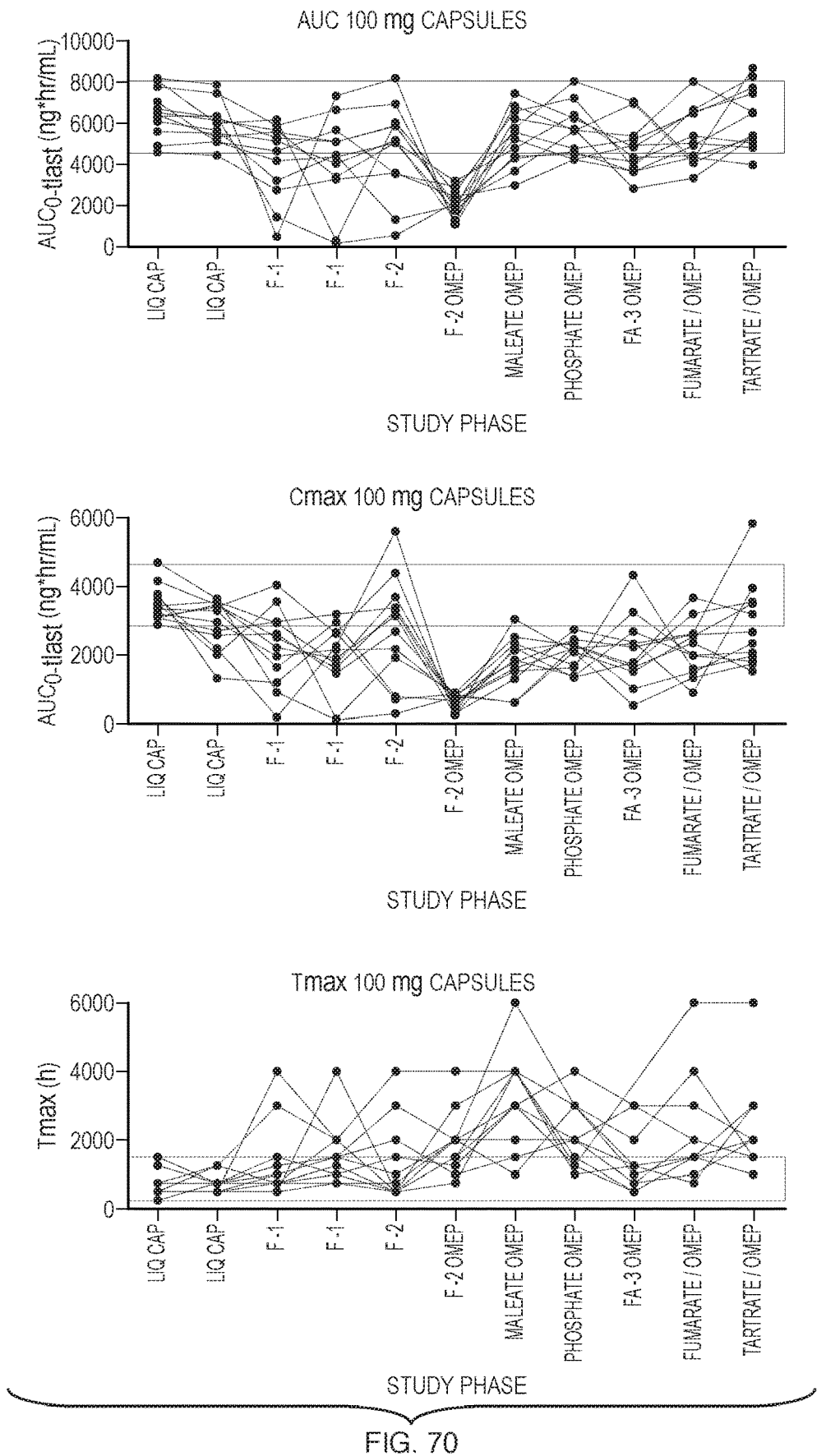
FIG. 70 shows trends in the AUC, $C_{max}$, and $T_{max}$ for conditioned dogs treated with various solid forms of Formula (1). Liquid capsules (100 mg) were administered for comparison with the solid forms. Solid capsules of 100 mg strength in the clinical formulation of Form I of Formula (1) were administered to dogs prior to or following daily treatment with omeprazole to reduce stomach acidity. The subsequent study phases followed 4 days of dosing with omeprazole (10 mg/day); omeprazole treatment continued throughout the study. An acidulant formulation of Form I of Formula (1) was compared with the maleate, phosphate, fumarate or tartrate salts of Formulation 1 (F-1) administered as 100 mg equivalent of free base in capsules. Exposures of salts and the capsules of Form I of Formula (1) formulated with acidulant were increased, relative to exposure of Form I in the presence of omeprazole.

FIG. 70 shows changes in the AUC, $C_{max}$ and $T_{max}$ by study phase, with each study or study phase presented sequentially. The initial study using liquid formulation in capsules to deliver 100 mg Formula (1) in solution was designed to show exposures following this dose (i.e., not dissolution limited), and to characterize the variability in dogs when dissolution-associated variance is removed. The higher mean exposure and smaller within- and between-animal variability observed following administration of the fully dissolved Formula (1) in liquid capsules to conditioned dogs demonstrate that dissolution of Form I of Formula (1) plays a role in limiting oral absorption, indicating that optimal dissolution will enhance absorption.

The remaining variance in pharmacokinetic parameters observed following administration of liquid capsules may be due to intrinsic factors that vary between the inbred beagle dogs. This effect has also been demonstrated using 25 mg liquid capsules and Form I of Formula (1) capsules using a dose scaled version of F-1. Between-animal variability following administration of a liquid capsule or matching solid capsules containing Form 1 of Formula (1) at a fixed dose, may result from small variations in the mg/kg dosage of test article as well as other intrinsic factors such as those governing drug metabolism and elimination. Adding a weight-based normalization for the AUC's in the solid form experiments with this group of dogs will further tighten the between-animal variance at each dosing interval. Dose adjusted AUC and $C_{max}$ values can be compared most accurately for statistical analysis of the experimental results.

After administration of the salt forms or Form I of Formula (1) in acidic formulation to overcome the omeprazole effect, $T_{max}$ increased in most of the dogs. Although there was a trend towards a lower mean $C_{max}$ in these study phases (FIG. 69 and FIG. 70), the pattern was not observed with every phase or for all dogs. A similar trend has been observed in dogs and humans when Form I of Formula (1) is administered with food. Notably, the mean AUC levels in dogs treated with salt forms of Formula (1) or with the acidic formulation of Form I, were similar to AUCs observed in dogs after administration of Form I without omeprazole. There was a trend to decrease between-animal variability when these experimental dosage forms were administered, compared with the Form I capsules administered in conditioned dogs without omeprazole treatment. Therefore, exposure after oral dosing with Formula (1) in a salt form are increased in the presence of omeprazole, and variability in exposure is decreased in both omeprazole-treated dogs and conditioned dogs without omeprazole treatment. The prototype acidic formulation for Form I of Formula (1) has a similar effect.

The observed effect of alternate salt forms and acidulents with Formula (1) on oral absorption in omeprazole-treated dogs is novel and surprising. The pH-dependence of Formula (1) dissolution is associated with the stability of acidic and basic species in aqueous solutions, and with the free energy of dissolution during phase transition. In vitro-in vivo correlations demonstrated that dissolution limitations were associated with poor absorption of Form I of Formula (1) in omeprazole-treated dogs (or dogs treated with alternate gastric acid reducing agents, such as famotidine, calcium carbonate, or the other treatments listed above). In a human Phase 1, single-center, open-label, fixed-sequence, 2-period, 3-part study to evaluate the one-way interaction of calcium carbonate, omeprazole, or rifampin on Formula (1) in healthy adult subjects, treatment of subjects with acid reducing agents prior to administration of Form I of Formula (1) resulted in significant decreases in exposure. The role of pH in dissolution of Formula (1) was demonstrated in vitro, and the dissolution limitation on absorption was postulated in vivo. The addition of acidulants to the formulation, or the administration of fully dissolved Formula (1), are methods to facilitate dissolution by lowering pH in the microenvironment, or to circumvent the dissolution step for a proof-of-concept in vivo model. In contrast, dosing with the alternate salt forms of Formula (1), which were expected to have little impact on gastric pH, demonstrated that the solid form of Formula (1) has significant and unexpected effects on oral absorption characteristics in mammals.

Figure 71:
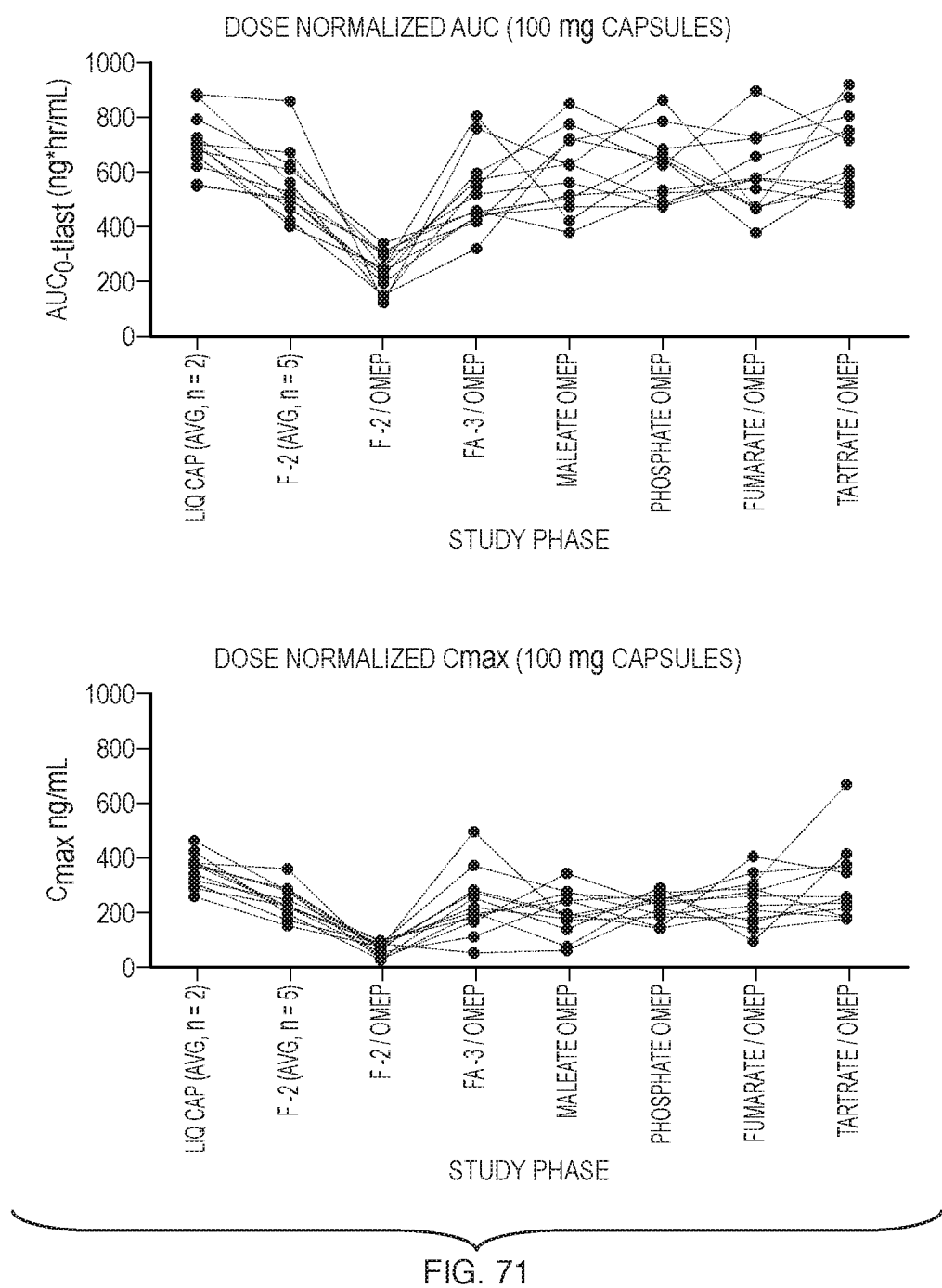
FIG. 71 illustrates dose-normalized AUC and $C_{max}$ for Formula (1) in dogs, comparing liquid capsules ("Liq Caps") (average of n=2), formulation F-2 (average of n=5), formulation F-2 with omeprazole ("F-2/Omep," showing loss of exposure for Formula (1)), and five formulations of the present invention that restore exposure in the presence of omeprazole: FA-3 (with acidulant, "FA-3/Omep"), F-1 maleate ("Maleate/Omep"), F-1 phosphate ("Phosphate/Omep"), F-1 fumarate ("Fumarate/Omep"), and F-1 tartrate ("Tartrate/Omep").

FIG. 71 compares dose-normalized AUC and $C_{max}$, with additional averaging of repeated exposures for dogs for liquid capsules (n=2 per dog) and F-2 (n=5 per dog). The results again show that Formula (1) exposure can be recovered in the presence of omeprazole using the FA-3 acidulant formulation of the present invention as well as the salts of the present invention.

These studies demonstrate that good exposures can be achieved in omeprazole treated dogs via either an enabling formulation for Form I of Formula (1), or by generating a new salt form of Formula (1). The exposures obtained using formulation FA-3 with acidulant and the salts with omeprazole are surprisingly similar to exposures observed without omeprazole, and would be expected to perform well for other salts and acidulants as well as for other acid-reducing agents. The dissolution-mediated absorption observed in human subjects can be modeled in dogs. The in vitro dissolution assay is also a good predictor of in vivo absorption characteristics of different encapsulated formulations of Form I of Formula (1).

A separate PK comparability study (2219-060) has been completed to characterize exposures from the acetone-recrystallized and ethanol-recrystallized drug substance in capsules manufactured with the F-2 formulation. These data more fully characterize the between- and within-dog variability associated with absorption of Formula (1) in conditioned dogs that are not treated with omeprazole and indicate that ethanol-recrystallized drug substance is suitable for late-phase clinical development.

Example 23. Formulations of (S)-4-(8-Amino-3-(1-(but-2-ynoyl)pyrrolidin-2-yl)imidazo[1,5-a]pyrazin-1-yl)-N-(pyridin-2-yl)benzamide Formulations of Formula (1) solid forms (salts and free base Form I) were prepared as shown in Table 48.

TABLE 48

Description of Formulation 1 (F-1) and acidic salt formulations.

| | F-1 free base (Form I) w/w % | F-1 maleate (Form A) w/w % | F-1 fumarate (Form A) w/w % | F-1 L-tartrate (Form A) w/w % | F-1 phosphate (Form A) w/w % |
|---|---|---|---|---|---|
| Formula (1) | 10-50% | 10-50% | 10-50% | 10-50% | 10-50% |
| Microcrystalline Cellulose | 50-90% | 50-90% | 50-90% | 50-90% | 50-90% |

Additional formulations were prepared as shown in Table 49 using the following procedure. Formula (1) dry-granulate was blended with extragranular acidulants. The blends were then filled into hard gelatin capsules (in the case of FA-1, FA-2, FA-4, and FA-5) or compressed into a tablet (in the case of FA-4).

TABLE 49

Formulations of Formula (1), showing intragranular components and extragranular components.

| | | | FORMULA (1) | SILICIFIED MICROCRYSTALLINE CELLULOSE | PARTIALLY PRE-GELATINIZED MAIZE STARCH | SODIUM STARCH GLYCOLATE | MAGNESIUM STEARATE |
|---|---|---|---|---|---|---|---|
| F-2 | w/w % | Intragranular | 25-50% | 25-33% | 20-33% | 0-5% | 0.05-1% |
| FA-1 | w/w % | | 25-35% | 15-35% | 20-33% | 0-5% | 0.05-1% |
| FA-2 | w/w % | | 25-35% | 15-35% | 20-33% | 0-5% | 0.05-1% |
| FA-3 | w/w % | | 25-35% | 15-35% | 20-33% | 0-5% | 0.05-1% |
| FA-4 | w/w % | | 25-35% | 15-35% | 20-33% | 0-5% | 0.05-1% |
| FA-5 | w/w % | | 25-35% | 15-35% | 20-33% | 0-5% | 0.05-1% |

| | | | MAGNESIUM STEARATE | FUMARIC ACID | ALGINIC ACID | POLOXAMER 407 | HYDROXYPROPYL METHYLCELLULOSE |
|---|---|---|---|---|---|---|---|
| F-2 | w/w % | Extragranular | 0.05-1% | — | — | — | — |
| FA-1 | w/w % | | 0.05-1% | 25-33% | — | — | 1-5% |
| FA-2 | w/w % | | 0.05-1% | — | 15-33% | — | — |
| FA-3 | w/w % | | 0.05-1% | 15-33% | 5-15% | — | — |
| FA-4 | w/w % | | 0.05-1% | 15-33% | 5-15% | — | — |
| FA-5 | w/w % | | 0.05-1% | 15-33% | 5-15% | 0.5-5% | — |

1. Polaxamer 407 refers to triblock copolymer of polypropylene glycol and polyethylene glycol (available from BASF, Inc., under the tradename PLURONIC F127).

Figure 67:
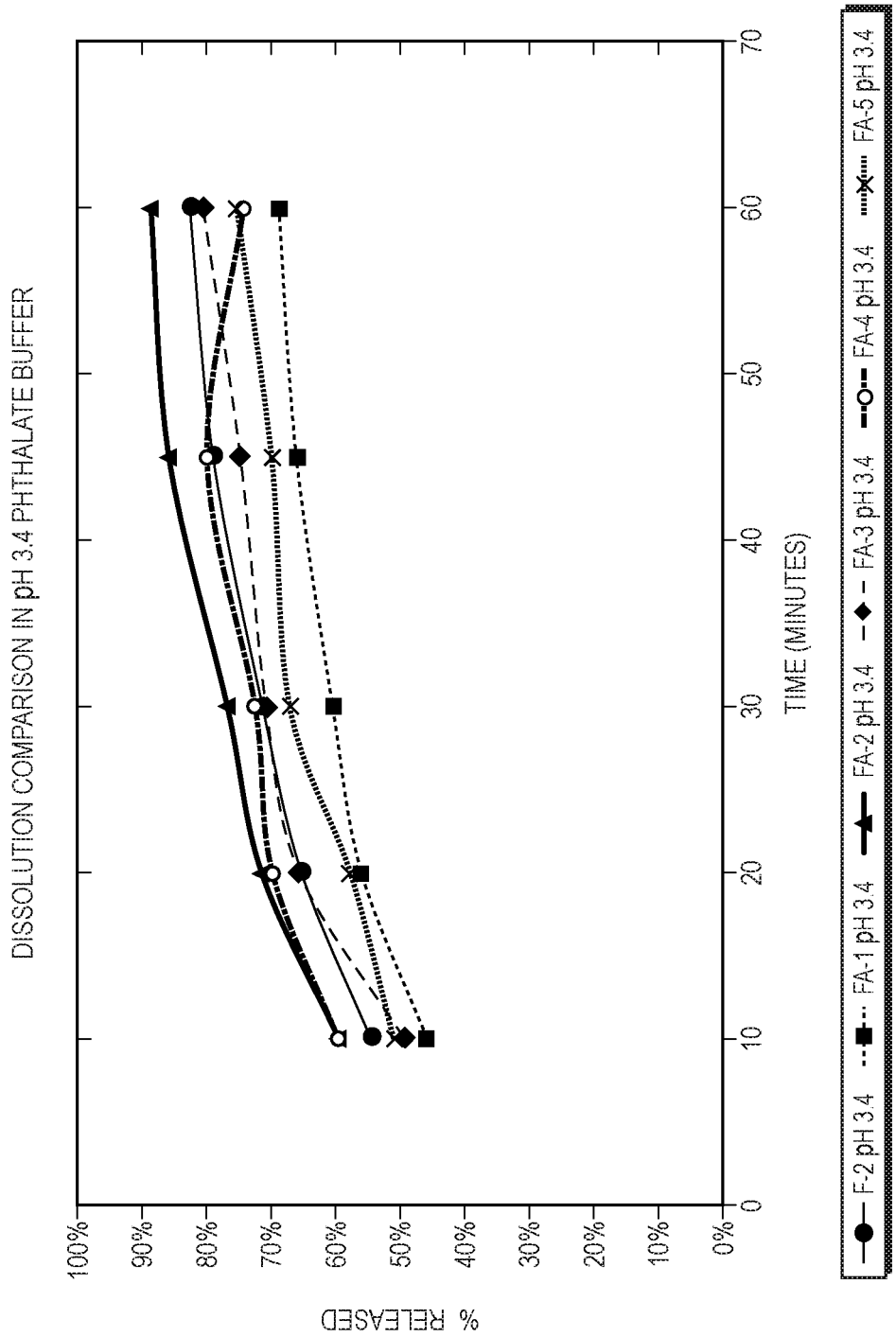
FIG. 67 illustrates a comparison of the dissolution profiles of formulations of Formula (1) at a pH of 3.4.
Figure 68:
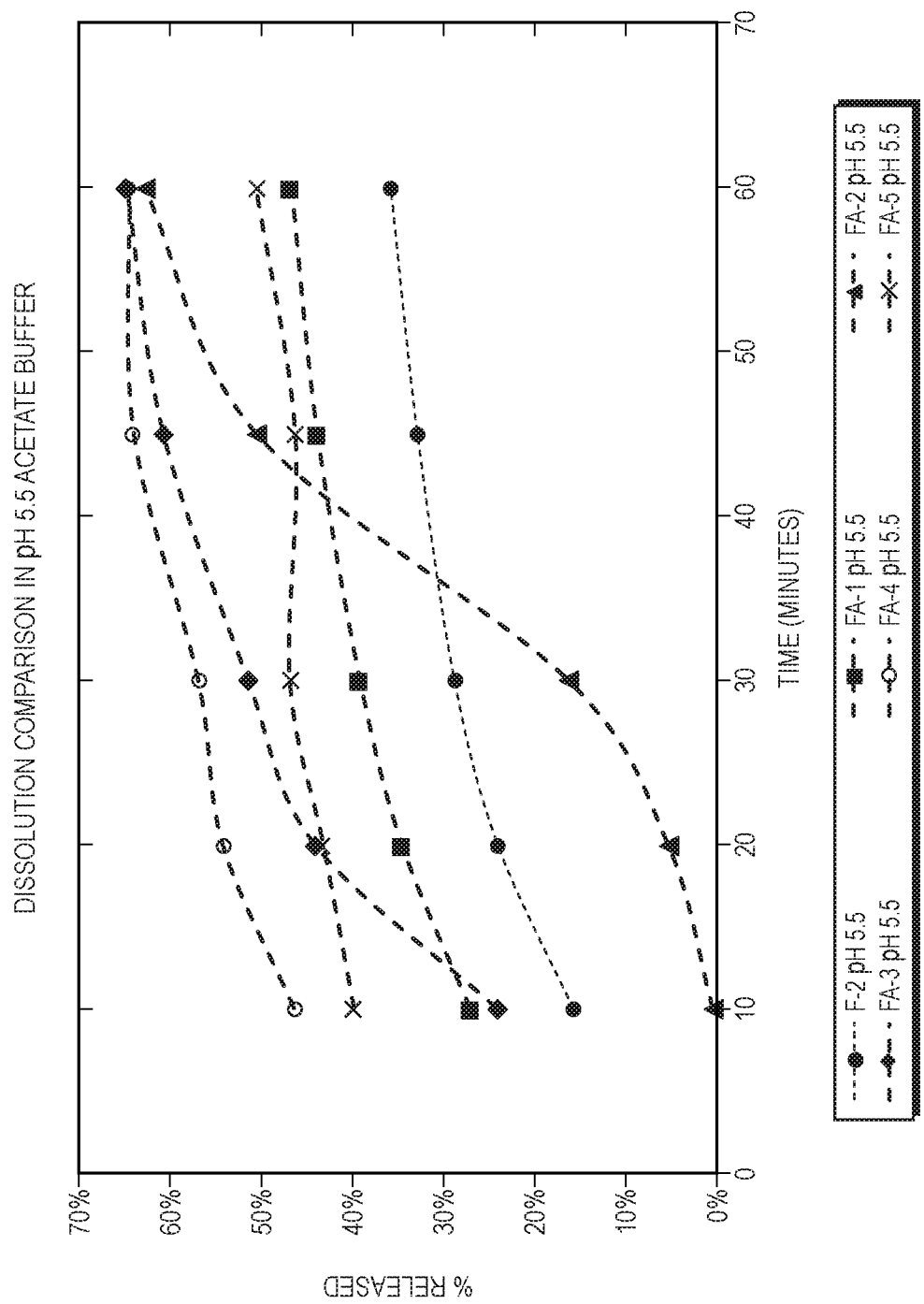
FIG. 68 illustrates a comparison of the dissolution profiles of formulations of Formula (1) at a pH of 5.5.

The results of dissolution experiments using formulations representative of those in Table 49 at two different pH values are shown in FIG. 67 and FIG. 68. The dissolution system was a U.S. Pharmacopeia Type II apparatus equipped with paddles (at 50 rpm) and 900 mL vessels equilibrated at 37° C. Samples are taken at intervals using a cannula at a set depth through an in-line filter and analyzed by reversed phase HPLC with UV spectroscopic detection. Capsules were tested in sinkers, and the tablet was tested neat.

Additional formulations were prepared according to Table 50. Intragranular formulations may be prepared by the following procedure. Materials are pre-blended in a 250 mL V-blender for 300 revolutions. After blending, lubricant is added and blending is performed for 100 additional revolutions. The blend is roller compacted on a TF-mini roller compactor and then feed through an oscillating granulator equipped with a 20 mesh screen. Extragranular formulations may be prepared by the following procedure. When extragranular acids or polymers are added, they are added to the preblended or neat extragranular material and then add granulated in a 250 mL V-blender and for 300 revolutions. After blending, lubricant is added and blending is performed for an additional 100 revolutions. Lubricated granules are then filled into size 1 hard gelatin capsules using a dosing disk or dosator-equipped semi-automatic or automatic encapsulator. Alternately, material may be compressed on a tablet press or mold.

TABLE 50

Formulations of Formula (1).

| | | | FORMULA (1) | SILICIFIED MICRO-CRYSTALLINE CELLULOSE | PARTIALLY PRE-GELATINIZED MAIZE STARCH | SODIUM STARCH GLYCOLATE | TARTARIC ACID | MAG-NESIUM STEARATE | ALGINIC ACID |
|---|---|---|---|---|---|---|---|---|---|
| FA-7 | w/w % | Intragranular | 25-50% | 25-33% | 20-33% | 0-5% | 15-33% | 0.05-1% | 5-15% |
| FA-8 | w/w % | | 25-35% | 15-35% | 20-33% | 0-5% | — | 0.05-1% | — |
| FA-9 | w/w % | | 25-35% | 15-35% | 20-33% | 0-5% | — | 0.05-1% | — |
| FA-10 | w/w % | | 25-35% | 15-35% | 20-33% | 0-5% | — | 0.05-1% | — |

| | | | MAGNESIUM STEARATE | TARTARIC ACID | ALGINIC ACID | ASCORBIC ACID | CARBOPOL 971P[1] | HYDROXYPROPYL METHYLCELLULOSE |
|---|---|---|---|---|---|---|---|---|
| FA-7 | w/w % | Extragranular | 0.05-1% | — | — | — | — | — |
| FA-8 | w/w % | | 0.05-1% | 25-33% | 5-15% | — | — | — |
| FA-9 | w/w % | | 0.05-1% | — | 15-33% | — | — | 7.5-15% |
| FA-10 | w/w % | | 0.05-1% | — | — | 20-50% | 2.5-10% | — |

[1]Carbopol 971P (Lubrizol, Inc.) is also referred to as carboxypolymethylene or "carbomers" (e.g., in pharmaceutical monographs such as USP/NF or Ph. Eur.).

In addition to the formulations described in Table 49 and Table 50, other acidulants may also be used as described herein, including fumaric acid, succinic acid, D-tartaric acid, L-tartaric acid, racemic tartaric acid, ascorbic acid, isoascorbic acid (also known as erythorbic acid and D-araboascorbic acid), alginic acid, Protacid F 120 NM, Protacid AR 1112 (also known as Kelacid NF), Carbopol 971P (carboxypolymethylene), and Carbomer 941 (polyacrylic acid).

Additional non-limiting formulations are given in Table 51, and may be prepared as described above or by using methods known in the art. These formulations, and all of the foregoing formulations, may be prepared as capsules or tablets, with or without coating.

TABLE 51

Formulations of Formula (1).

|  |  |  | FORMULA (I) (FORM I FREE BASE) | SILICIFIED MICRO-CRYSTALLINE CELLULOSE | PARTIALLY PRE-GELATINIZED MAIZE STARCH | SODIUM STARCH GLYCOLATE | TARTARIC ACID | MAGNESIUM STEARATE |
|---|---|---|---|---|---|---|---|---|
| FA-11 | w/w % | Intragranular | 25-50% | 10-25% | 10-25% | 0-5% | 10-30% | 0.05-1% |
| FA-12 | w/w % |  | 25-50% | 10-25% | 10-25% | 0-5% | — | 0.05-1% |

|  |  | ALGINIC ACID | HYDROXYPROPYL METHYLCELLULOSE |  | MAGNESIUM STEARATE | TARTARIC ACID | SODIUM STARCH GLYCOLATE |
|---|---|---|---|---|---|---|---|
| FA-11 | w/w % | 10-30% | — | Extragranular | 0.05-2% | — | 0-6% |
| FA-12 | w/w % | — | 0-20% |  | 0.05-2% | 10-35% | 0-6% |

Example 24. Amorphous Dispersions of (S)-4-(8-Amino-3-(1-(but-2-ynoyl)pyrrolidin-2-yl)imidazo[1,5-a]pyrazin-1-yl)-N-(pyridin-2-yl)benzamide The feasibility of the formation of amorphous solid dispersions of Formula (1) in following polymers was explored in a variety of polymers, including KOLLIDON VA64, polyvinylpyrollidone (PVP-10 and PVP-40), HPMC, Kolliphor P188, HPMCAS-L, HPMCAS-H, EUDRAGIT L100-5, and EUDRAGIT L100. Drug substance concentrations in the amorphous solid dispersions were generally about 11 to 20%. Aqueous solubilities of the amorphous solid dispersions were measured at pH~6.8 in phosphate buffer. Typical solubilities were between 100 μg/mL and 160 μg/mL, which is about twice the solubility of Form I of the free base of Formula (1), but less than the solubility of the amorphous form of the free base of Formula (1). The polymers used for the preparation of amorphous solid dispersions are summarized in Table 52.

TABLE 52

Polymers used for amorphous solid dispersions.

| Polymer | Supplier | Lot Number |
|---|---|---|
| Vinylpyrrolidone-vinyl acetate copolymer (PVP-VA) (KOLLIDON VA64) | BASF | 50347977 |
| Polyvinylpyrrolidone (PVP-10, average molecular weight 10 kDa) | Sigma Aldrich | BCBF4168V |
| Polyvinylpyrrolidone (PVP-40, average molecular weight 40 kDa) | Sigma Aldrich | BCBG0598V |
| Hydroxypropylmethylcellulose (HPMC) | Sigma Aldrich | BCBC9084V |
| Kolliphor (Poloxamere) P188 | Sigma Aldrich | SLBJ6719V |
| Hydroxypropylmethylcellulose acetate succinate, HPMCAS-LF (AQOAT AS-LF)[1] | Shin-Etsu | 3093208 |
| Hydroxypropylmethylcellulose acetate succinate, HPMCAS-HF (AQOAT AS-HF)[2] | Shin-Etsu | 4073131 |
| Methacrylic acid:ethyl acrylate copolymer (1:1) (EUDRAGIT L100-55) | Evonik | B141104042 |
| Methacrylic acid:methyl methacrylate copolymer (1:1) (EUDRAGIT L100) | Evonik | B14003011 |

[1] LF grade refers to HPMCAS polymer with an acetyl content of 5 to 9%, a succinoyl content of 14 to 18%, a methoxyl content of 20 to 24%, and a hydroxypropyl content of 5 to 9%.
[2] HF grade refers to HPMCAS polymer with an acetyl content of 10 to 14%, a succinoyl content of 4 to 8%, a methoxyl content of 22 to 26%, and a hydroxypropyl content of 6 to 10%.

Batch PP502-P111 was prepared as follows: 1.008 g of PVP-K25 (BASF) was dissolved in water. To 2.0 mL of the PVP solution was added 24 mg of Formula (1) free base (batch PP502-P1), and dissolution was achieved by additionally adding 2.0 mL of water, 0.2 mL of acetone, and 0.2 mL of acetic acid. A clear solution obtained, from which the solvents were allowed to evaporate at room temperature.

Batch PP502-P112 was prepared as follows: 6.0 mL of THF was added to the remaining PVP-K25 (form BASF) solution from experiment PP502-P111 (18 mL). An aliquot of 3 mL of this new solution was taken, and 33 mg of Formula (1) free base batch PP502-P1 was added to this aliquot. Full dissolution was not achieved, and 0.1 mL of acetic acid was added. A clear solution was then obtained, from which the solvents were allowed to evaporate at room temperature.

Batch PP502-P116 was prepared as follows: 2.007 g of PVP-10 (Sigma-Aldrich/CR-1104921) was dissolved in 20 mL of water and 202.9 mg of Formula (1) free base batch PP502-P1 was separately dissolved in 4.3 mL of acetone:water (4:1). The two solutions were combined and a new clear solution was obtained that was subjected to freeze drying. A slightly yellow powder was obtained.

Batch PP502-P119, a 10% w/w dispersion of Formula (1) in Kolliphor P188, was prepared as follows: 1.999 g Kolliphor P188 (poloxamer P188, obtained from Sigma-Aldrich #K4894) was dissolved in 20 mL of water, and 240 mg of PP502-P1 was separately dissolved into 9.5 mL of acetone:water (4:1). The solution containing Formula (1) was filtered into the polymer solution and the mixture was freeze dried. A solid product was obtained after freeze drying.

Batch PP502-P128, a 16% w/w dispersion of Formula (1) in PVP-VA (KOLLIDON VA64), was prepared as follows. Stock solution SL20150715 was first prepared by dissolving 1.532 g of batch PP502-P1 of Formula (1) free base in 33.0 mL of acetone:water (4:1), yielding a solution with a concentration of 45 mg/mL of Formula (1). 1.01 g of PVP-VA was dissolved in 10 mL of water, to which was added 4.3 mL of stock solution SL20150715 (292 mg, to achieve 11% w/w drug loading). A solution was obtained and freeze dried to yield solid product.

Batch PP502-P129, a 16% w/w dispersion of Formula (1) in PVP10, was prepared as follows: 999 mg of PVP-10 was dissolved in 10 mL of water, to which was added 4.3 mL of the aforementioned stock solution SL20150715 (193 mg, to achieve 16% w/w drug loading). A solution was obtained and freeze dried to yield solid product.

Batch PP502-P130, a 16% w/w dispersion of Formula (1) in PVP40, was prepared as follows: 1.01 g of PVP-40 was dissolved in 10 mL of water, to which was added 4.3 mL of the aforementioned stock solution SL20150715 (193 mg, to achieve 16% w/w drug loading). A solution was obtained and freeze dried to yield solid product.

Batch PP502-P131, an 11% w/w dispersion of Formula (1) in PVP-VA and HPMC, was prepared as follows: 1.02 g of PVP-VA and 506 mg HPMC (for a 2:1 polymer ratio) were dissolved in 10 mL of water, to which was added 6.5 mL of SL20150715 (292 mg, to achieve 11% drug loading). A solution was obtained and freeze dried to yield solid product.

Batch PP502-P136, a 17% w/w dispersion of Formula (1) in EUDRAGIT L100-55, was prepared as follows. 1009 mg of Eudragit L100-55 and 201 mg of PP502-P1 (16.6%) were placed in a 250 mL round-bottom flask and were dissolved in 14.0 mL of THF:water (4:1). A yellow-colored solution was obtained. The THF was evaporated in a rotary evaporator at 38° C., and then the remaining solution was freeze dried until the next day at a pressure of 0.09 mbar. Part of the obtained solid material was isolated as batch PP502-P136. The remaining part of this material was further dried at 60° C. under vacuum for about 18 hours, and was designated batch PP502-P136A.

Batch PP502-P137, a 17% w/w dispersion of Formula (1) in EUDRAGIT L100, was prepared as follows: 1011 mg of Eudragit L100 and 200 mg of PP502-P1 (16.6%) were placed in a 250 mL round-bottom flask and were dissolved in 20.0 mL of THF:water (4:1). A yellow-colored solution was obtained. The THF was evaporated in a rotary evaporator at 38° C. and then the remaining solution was freeze dried until the next day at a pressure of 0.09 mbar. Part of the obtained solid material was isolated as batch PP502-P137. The remaining part of this material was further dried at 60° C. under vacuum for about 18 hours, and was designated batch PP502-P137A.

Batch PP502-P138, a 20% w/w dispersion of Formula (1) in HPMCAS-LF, was prepared as follows: 998 mg of HPMCAS-LF and 250 mg of PP502-P1 (20%) were placed in a 250 mL round flask and dissolved in 25.0 mL of THF:water (4:1). A yellow-colored solution was obtained. The THF was evaporated in a rotary evaporator at 38° C., and then the remaining solution was freeze dried until the next day at a pressure of 0.09 mbar. Part of the obtained solid material was isolated as batch PP502-P138. The remaining part of this material was further dried at 60° C. under vacuum for about 18 hours, and was designated batch PP502-P138A.

Batch PP502-P139, a 20% w/w disperion of Formula (1) in HPMCAS-HF, was prepared as follows: 1036 mg of HPMCAS-HF and 250 mg of PP502-P1 (20%) were placed in a 250 mL round flask and dissolved in 25.0 mL of THF:water (4:1). A yellow-colored solution was obtained. The THF was evaporated in a rotary evaporator at 38° C., and then the remaining solution was freeze dried until the next day at a pressure of 0.09 mbar. Part of the obtained solid material was isolated as batch PP502-P139. The remaining part of this material was further dried at 60° C. under vacuum for about 18 hours, and was designated batch PP502-P139A.

Figure 72:
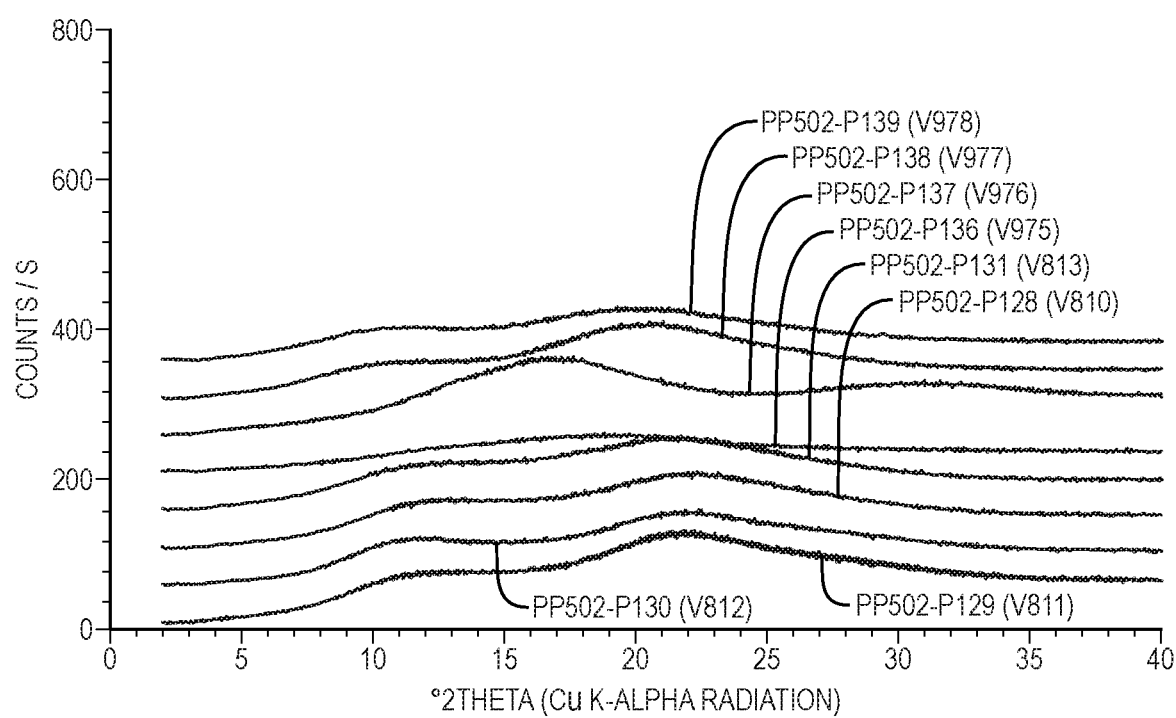
FIG. 72 shows PXRD patterns for amorphous solid dispersions (samples PP502-P128, PP502-P129, PP502-P130, PP502-P131, PP502-P132, PP502-P136, PP502-P137, PP502-P138, and PP502-P139).

PXRD results for several batches are given in FIG. 72. The lack of any discernable Bragg reflections in each PXRD pattern demonstrates a lack of detectable crystalline content in each sample, and indicates that each sample is amorphous. DSC results are summarized in Table 53. The appearance of a single $T_g$, rather than separate $T_g$ events for the polymer and the drug, indications formation of an amorphous solid molecular dispersion. TG-FTIR results are also summarized in Table 53.

TABLE 53

Summary of DSC and TG-FTIR results for amorphous solid dispersions.

| Sample identifier | Dispersion | DSC result ($T_g$ and $\Delta C_p$) | TG-FTIR result |
|---|---|---|---|
| PP502-P128 | 16% Formula (1) in PVP-VA | $T_g$~115° C., $\Delta C_p$~0.72 J/g/K[1]<br>$T_g$~111° C., $\Delta C_p$~0.48 J/g/K[2] | $\Delta m$ = −3.8% at 160° C. attributable to water, no organic solvent |
| PP502-P129 | 16% Formula (1) in PVP-10 | $T_g$~126° C., $\Delta C_p$~0.99 J/g/K[1]<br>$T_g$~110° C., $\Delta C_p$~0.48 J/g/K[2] | $\Delta m$ = −4.2% at 140° C., attributable to water, no organic solvent, at higher temperature degradation possible |
| PP502-P130 | 16% Formula (1) in PVP-40 | $T_g$~153° C., $\Delta C_p$~0.57 J/g/K[1]<br>$T_g$~152° C., $\Delta C_p$~0.37 J/g/K[2] | $\Delta m$ = −5.2% at 140° C., attributable to water, no organic solvent, at higher temperature degradation possible |
| PP502-P131 | 11% Formula (1) in PVP-VA:HPMC (2:1) | $T_g$~120° C., $\Delta C_p$~0.63 J/g/K[1]<br>$T_g$~114° C., $\Delta C_p$~0.53 J/g/K[2] | $\Delta m$ = −3.1% at 140° C., attributable to water, no organic solvent, at higher temperature degradation possible |
| PP502-P136A | 17% Formula (1) in EUDRAGIT L100-55 | $T_g$~134° C., $\Delta C_p$~0.55 J/g/K | $\Delta m$ = −~03.5% at 160° C., attributable to THF |
| PP502-P137A | 17% Formula (1) in EUDRAGIT L100 | $T_g$~143° C., $\Delta C_p$~0.39 J/g/K | $\Delta m$ = −~03.5% at 160° C., attributable to THF |
| PP502-P138A | 20% Formula (1) in HPMCAS-LF | $T_g$~114° C., $\Delta C_p$~0.48 J/g/K | $\Delta m$ = −~02.5% at 160° C., THF and water |
| PP502-P139A | 20% Formula (1) in HPMCAS-HF | $T_g$~111° C., $\Delta C_p$~0.49 J/g/K | $\Delta m$ = −~01.5% at 160° C., attributable to water |

[1]Measured in closed sample pan.
[2]Measured in open sample pan.

HPMCAS-LF and 250 mg of PP502-P1 (20%) were placed in a 250 mL round flask and dissolved in 25.0 mL of THF:water (4:1). A yellow-colored solution was obtained. The THF was evaporated in a rotary evaporator at 38° C., and then the remaining solution was freeze dried until the next day at a pressure of 0.09 mbar. Part of the obtained solid Additional amorphous solid dispersions with different concentrations of Formula (1) can also be produced using the procedures described above.

The apparent aqueous solubility of selected amorphous solid dispersions was tested in phosphate buffer at pH 6.8, with the results shown in Table 54.

TABLE 54

Summary of solubility testing results for amorphous solid dispersions.

| Sample identifier | Dispersion | Solubility (1 hour) (mg/ml) | pH (1 hour) | Solubility (24 hours) (mg/ml) | pH (24 hours) |
|---|---|---|---|---|---|
| PP502-P128 | 16% Formula (1) in PVP-VA | 0.157 | 6.79 | 0.105 | 6.78 |
| PP502-P129 | 16% Formula (1) in PVP-10 | 0.110 | 6.80 | 0.07 | 6.78 |

TABLE 54-continued

Summary of solubility testing results for amorphous solid dispersions.

| Sample identifier | Dispersion | Solubility (1 hour) (mg/ml) | pH (1 hour) | Solubility (24 hours) (mg/ml) | pH (24 hours) |
|---|---|---|---|---|---|
| PP502-P130 | 16% Formula (1) in PVP-40 | 0.130 | 6.80 | 0.09 | 6.80 |
| PP502-P131 | 11% Formula (1) in PVP-VA:HPMC (2:1) | 0.160 | 6.82 | 0.088 | 6.81 |
| PP502-P136 | 17% Formula (1) in EUDRAGIT L100-55 | 0.018 | 6.49 | 0.015 | 6.39 |
| PP502-P137 | 17% Formula (1) in EUDRAGIT L100 | 0.059 | 6.71 | 0.043 | 6.59 |
| PP502-P138 | 20% Formula (1) in HPMCAS-LF | 0.106 | 6.49 | 0.091 | 6.34 |
| PP502-P139 | 20% Formula (1) in HPMCAS-HF | 0.100 | 6.54 | 0.135 | 6.58 |

Example 25. Comparison of Processability for Free Base Form I and Free Base Form II Both Form I and Form II of Formula (1) free base were processed under similar parameters using the process and composition for formulation F-2 (as described above). Formula (1) was blended with the ingredients and then lubricated, then roller compacted with a top feeding roller compacter with a separate granulation step. The granules were then lubricated. The resultant granules from the Form I and Form II were then characterized for tapped and aerated density. The Form II granules showed a general trend towards poor flow and poor uniformity.

Flowability typically affects the ease of handling pharmaceutical product during processing. When flowability is very poor, problems occur with handling and processing during blending, granulation and filling/compression. The flowability based on interparticulate interactions can be measured using the Hausner ratio or the compressibility index by measuring the aerated and tapped density of the powders. These values are calculated and ranked as outlined in the U.S. Pharmacoepia Monograph USP <1174> monograph. Hausner, *Int. J. Powder Metall.* 1967, 3, 7-13; Carr, *Chem. Eng.* 1965, 72, 163-168. The U.S. Pharmacoepia Monograph USP <1174> defines the following categories of flow character: Excellent (compressability index≤10%, Hausner's ratio 1.00 to 1.11); Good (compressability index 11-15%, Hausner's ratio 1.12 to 1.18); Fair (compressability index 16-20%, Hausner's ratio 1.19 to 1.25); Passable (compressability index 21-25%, Hausner's ratio 1.26 to 1.34); Poor (compressability index 26-31%, Hausner's ratio 1.35 to 1.45); Very poor (compressability index 32-37%, Hausner's ratio 1.46 to 1.59); and Very, very poor (compressability index>38%, Hausner's ratio>1.60).

The Hausner ratio and compressibility index for the Form I granules was 1.33 and 25% respectively while the Form II granules exhibited a Hausner ratio of 1.47 and compressibility index of 32%. The results thus indicates that Form I granules have a passable flow while Form II granules have poor to very poor flow.

The blends were then filled into capsules using an automated encapsulator operating on the dosing disc principle. After filling to a target weight, capsules are checked for weight uniformity with out of weight capsules being rejected. The Form I capsules have a yield of 90-100% acceptable capsules while the Form II containing capsules had a yield of only 40-60%.

Upon measuring the content uniformity as defined by the U.S. Pharmacoepia Monograph USP <905> for a hard gelatin capsule, the Form II containing capsules have an acceptance value greater than 15, while the Form I containing capsules have an acceptance value below 15.

The results are summarized in Table 55.

TABLE 55

Results of Processability Tests for Form I and Form II of Formula (1) free base.

| Lot | Bulk Density g/cc | Tap Density g/cc | Hausner ratio | Compressibility Index (%) |
|---|---|---|---|---|
| F-2 using Form I | 0.527 | 0.703 | 1.33 | 25 |
| F-2 using Form II | 0.438 | 0.644 | 1.47 | 32 |

We claim:

1. A crystal form of (S)-4-(8-amino-3-(1-(but-2-ynoyl)pyrrolidin-2-yl)imidazo[1,5-a]pyrazin-1-yl)-N-(pyridin-2-yl)benzamide maleate, or hydrate thereof, characterized by a reflection X-ray powder diffraction pattern comprising at least five peaks selected from the group consisting of 5.3°±0.2° 2θ, 9.8°±0.2° 2θ, 10.6°±0.2° 2θ, 11.6°±0.2° 2θ, 13.5°±0.2° 2θ, 13.8°±0.2° 2θ, 13.9°±0.2° 2θ, 14.3°±0.2° 2θ, 15.3°±0.2° 2θ, 15.6°±0.2° 2θ, 15.8°±0.2° 2θ, 15.9°±0.2° 2θ, 16.6°±0.2° 2θ, 17.4°±0.2° 2θ, 17.5°±0.2° 2θ, 18.7°±0.2° 2θ, 19.3°±0.2° 2θ, 19.6°±0.2° 2θ, 19.8°±0.2° 2θ, 20.0°±0.2° 2θ, 20.9°±0.2° 2θ, 21.3°±0.2° 2θ, 22.1°±0.2° 2θ, 22.3°±0.2° 2θ, 22.7°±0.2° 2θ, 23.2°±0.2° 2θ, 23.4°±0.2° 2θ, 23.7°±0.2° 2θ, 23.9°±0.2° 2θ, 24.5°±0.2° 2θ, 24.8°±0.2° 2θ, 25.2°±0.2° 2θ, 25.6°±0.2° 2θ, 26.1°±0.2° 2θ, 26.4°±0.2° 2θ, 26.7°±0.2° 2θ, 26.9°±0.2° 2θ, 27.1°±0.2° 2θ, 27.6°±0.2° 2θ, 28.8°±0.2° 2θ, 29.5°±0.2° 2θ, 30.0°±0.2° 2θ, 30.3°±0.2° 2θ, 30.9°±0.2° 2θ, 31.5°±0.2° 2θ, 31.9°±0.2° 2θ, 32.5°±0.2° 2θ, 34.0°±0.2° 2θ, and 35.1°±0.2° 2θ.

2. The crystal form of claim 1, or hydrate thereof, wherein the reflection X-ray powder diffraction pattern of the crystal form, or hydrate thereof, comprises peaks at 5.3°±0.2° 2θ, 9.8°±0.2° 2θ, 10.6°±0.2° 2θ, 11.6°±0.2° 2θ, and 19.3°±0.2° 2θ.

3. The crystal form of claim 2, or hydrate thereof, wherein the peaks are present when the reflection X-ray powder diffraction is carried out using Cu-Kα radiation.

4. The crystal form of claim 2, or hydrate thereof, wherein the peaks are present when the reflection X-ray powder diffraction is carried out using a Bruker D8 Advance powder X-ray diffractometer equipped with a LynxEye detector and operating in Bragg-Brentano reflection geometry mode, a tube voltage of 40 kV and current of 40 mA, a variable divergence slit with a 3° window, a step size of 0.02° 2θ, a sample rotation of 0.5 revolution per second, and a step time of 37 seconds.

5. The crystal form of claim 2, or hydrate thereof, wherein the crystal form, or hydrate thereof, is further characterized by a differential scanning calorimetry thermogram comprising an endothermic peak at 174° C.

6. The crystal form of claim 2, or hydrate thereof, wherein the crystal form, or hydrate thereof, is further characterized by a dynamic vapor sorption isotherm exhibiting a water content change of 0.5% between 20% relative humidity and 80% relative humidity.

7. The crystal form of claim 2, or hydrate thereof, wherein the crystal form, or hydrate thereof, is further characterized by a differential scanning calorimetry thermogram comprising an endothermic peak at 174° C. and a dynamic vapor sorption isotherm exhibiting a water content change of 0.5% between 20% relative humidity and 80% relative humidity.

8. The crystal form of claim 2, or hydrate thereof, wherein the crystal form, or hydrate thereof, is micronized.

9. The crystal form of claim 8, or hydrate thereof, wherein the micronized crystal form, or hydrate thereof, has a particle size distribution ranging from 10 μm to 100 μm.

10. The crystal form of claim 2, or hydrate thereof, wherein the crystal form is a crystal hydrate.

11. The crystal form of claim 10, wherein the crystal hydrate is a monohydrate.

12. The crystal form of claim 11, wherein the crystal monohydrate is micronized.

13. The crystal form of claim 12, wherein the micronized crystal monohydrate has a particle size distribution ranging from 10 μm to 100 μm.

14. A pharmaceutical composition comprising at least one pharmaceutically acceptable excipient and a crystal form of (S)-4-(8-amino-3-(1-(but-2-ynoyl)pyrrolidin-2-yl)imidazo[1,5-a]pyrazin-1-yl)-N-(pyridin-2-yl)benzamide maleate, or hydrate thereof, characterized by a reflection X-ray powder diffraction pattern comprising at least five peaks selected from the group consisting of 5.3°±0.2° 2θ, 9.8°±0.2° 2θ, 10.6°±0.2° 2θ, 11.6°±0.2° 2θ, 13.5°±0.2° 2θ, 13.8°±0.2° 2θ, 13.9°±0.2° 2θ, 14.3°±0.2° 2θ, 15.3°±0.2° 2θ, 15.6°±0.2° 2θ, 15.8°±0.2° 2θ, 15.9°±0.2° 2θ, 16.6°±0.2° 2θ, 17.4°±0.2° 2θ, 17.5°±0.2° 2θ, 18.7°±0.2° 2θ, 19.3°±0.2° 2θ, 19.6°±0.2° 2θ, 19.8°±0.2° 2θ, 20.0°±0.2° 2θ, 20.9°±0.2° 2θ, 21.3°±0.2° 2θ, 22.1°±0.2 2θ, 22.3°±0.2° 2θ, 22.7°±0.2° 2θ, 23.2°±0.2° 2θ, 23.4°±0.2° 2θ, 23.7°±0.2° 2θ, 23.9°±0.2° 2θ, 24.5°±0.2° 2θ, 24.8°±0.2° 2θ, 25.2°±0.2° 2θ, 25.6°±0.2° 2θ, 26.1°±0.2° 2θ, 26.4°±0.2° 2θ, 26.7°±0.2° 2θ, 26.9°±0.2° 2θ, 27.1°±0.2° 2θ, 27.6°±0.2° 2θ, 28.8°±0.2° 2θ, 29.5°±0.2° 2θ, 30.0°±0.2° 2θ, 30.3°±0.2° 2θ, 30.9°±0.2° 2θ, 31.5°±0.2° 2θ, 31.9°±0.2° 2θ, 32.5°±0.2° 2θ, 34.0°±0.2° 2θ, and 35.1°±0.2° 2θ.

15. The pharmaceutical composition of claim 14, wherein the pharmaceutical composition is a tablet.

16. The pharmaceutical composition of claim 14, wherein the pharmaceutical composition is a solid pharmaceutical composition for oral administration.

17. The pharmaceutical composition of claim 16, wherein the pharmaceutical composition is a tablet.

18. The pharmaceutical composition of claim 14, wherein the pharmaceutical composition is a solid pharmaceutical composition for oral administration comprising 100 mg free base equivalent weight of the crystalline maleate.

19. The pharmaceutical composition of claim 18, wherein the pharmaceutical composition is a tablet.

20. The pharmaceutical composition of claim 14, wherein the crystal form, or hydrate thereof, is micronized.

21. The pharmaceutical composition of claim 20, wherein the micronized crystal form, or hydrate thereof, has a particle size distribution ranging from 10 μm to 100 μm.

22. The pharmaceutical composition of claim 14, wherein the reflection X-ray powder diffraction pattern of the crystal form, or hydrate thereof, comprises peaks at 5.3°±0.2° 2θ, 9.8°±0.2° 2θ, 10.6°±0.2° 2θ, 11.6°±0.2° 2θ, and 19.3°±0.2° 2θ.

23. The pharmaceutical composition of claim 22, wherein the pharmaceutical composition is a solid pharmaceutical composition for oral administration.

24. The pharmaceutical composition of claim 23, wherein the solid pharmaceutical composition for oral administration is a tablet.

25. The pharmaceutical composition of claim 22, wherein the pharmaceutical composition is a solid pharmaceutical composition for oral administration comprising 100 mg free base equivalent weight of the crystalline maleate.

26. The pharmaceutical composition of claim 22, wherein the peaks are present when the reflection X-ray powder diffraction is carried out using Cu-Kα radiation.

27. The pharmaceutical composition of claim 22, wherein the peaks are present when the reflection X-ray powder diffraction is carried out using a Bruker D8 Advance powder X-ray diffractometer equipped with a LynxEye detector and operating in Bragg-Brentano reflection geometry mode, a tube voltage of 40 kV and current of 40 mA, a variable divergence slit with a 3° window, a step size of 0.02° 2θ, a sample rotation of 0.5 revolution per second, and a step time of 37 seconds.

28. The pharmaceutical composition of claim 22, wherein the crystal form, or a hydrate thereof, is further characterized by a differential scanning calorimetry thermogram comprising an endothermic peak at 174° C.

29. The pharmaceutical composition of claim 22, wherein the crystal form, or hydrate thereof, is further characterized by a dynamic vapor sorption isotherm exhibiting a water content change of 0.5% between 20% relative humidity and 80% relative humidity.

30. The pharmaceutical composition of claim 22, wherein the crystal form, or hydrate thereof, is further characterized by a differential scanning calorimetry thermogram comprising an endothermic peak at 174° C. and a dynamic vapor sorption isotherm exhibiting a water content change of 0.5% between 20% relative humidity and 80% relative humidity.

31. The pharmaceutical composition of claim 22, wherein the crystal form, or hydrate thereof, is micronized.

32. The pharmaceutical composition of claim 31, wherein the micronized crystal form, or hydrate thereof, has a particle size distribution ranging from 10 μm to 100 μm.

33. The pharmaceutical composition of claim 22, wherein the crystal form is a crystal hydrate.

34. The pharmaceutical composition of claim 33, wherein the crystal hydrate is a monohydrate.

35. A method for inhibiting Bruton's tyrosine kinase activity in a human, comprising orally administering to the human a solid pharmaceutical composition comprising at least one pharmaceutically acceptable excipient and a crystal form of (S)-4-(8-amino-3-(1-(but-2-ynoyl)pyrrolidin-2-yl)imidazo[1,5-a]pyrazin-1-yl)-N-(pyridin-2-yl)benzamide maleate, or hydrate thereof, characterized by a reflection X-ray powder diffraction pattern comprising at least five peaks selected from the group consisting of 5.3°±0.2° 2θ, 9.8°±0.2° 2θ, 10.6°±0.2° 2θ, 11.6°±0.2° 2θ, 13.5°±0.2° 2θ, 13.8°±0.2° 2θ, 13.9°±0.2° 2θ, 14.3°±0.2° 2θ, 15.3°±0.2° 2θ, 15.6°±0.2° 2θ, 15.8°±0.2° 2θ, 15.9°±0.2° 2θ, 16.6°±0.2° 2θ, 17.4°±0.2° 2θ, 17.5°±0.2° 2θ, 18.7°±0.2° 2θ, 19.3°±0.2° 2θ, 19.6°±0.2° 2θ, 19.8°±0.2° 2θ, 20.0°±0.2° 2θ, 20.9°±0.2° 2θ, 21.3°±0.2° 2θ, 22.1°±0.2° 2θ, 22.3°±0.2° 2θ, 22.7°±0.2° 2θ, 23.2°±0.2° 2θ, 23.4°±0.2° 2θ, 23.7°±0.2° 2θ, 23.9°±0.2° 2θ, 24.5°±0.2° 2θ, 24.8°±0.2° 2θ, 25.2°±0.2° 2θ, 25.6°±0.2° 2θ, 26.1°±0.2° 2θ, 26.4°±0.2° 2θ, 26.7°±0.2° 2θ, 26.9°±0.2° 2θ, 27.1°±0.2° 2θ, 27.6°±0.2° 2θ, 28.8°±0.2° 2θ, 29.5°±0.2° 2θ, 30.0°±0.2° 2θ, 30.3°±0.2° 2θ, 30.9°±0.2° 2θ, 31.5°±0.2° 2θ, 31.9°±0.2° 2θ, 32.5°±0.2° 2θ, 34.0°±0.2° 2θ, and 35.1°±0.2° 2θ.

36. The method of claim 35, wherein the reflection X-ray powder diffraction pattern of the crystal form, or hydrate thereof, comprises peaks at 5.3°±0.2° 2θ, 9.8°±0.2° 2θ, 10.6°±0.2° 2θ, 11.6°±0.2° 2θ, and 19.3°±0.2° 2θ.

37. The method of claim 36, wherein the human suffers from a hyperproliferative disease.

38. The method of claim 37, wherein the hyperproliferative disease is Waldenström's macroglobulinemia.

39. The method of claim 37, wherein the hyperproliferative disease is mantle cell lymphoma.

40. The method of claim 37, wherein the hyperproliferative disease is small lymphocytic lymphoma.

41. The method of claim 37, wherein the hyperproliferative disease is chronic lymphocytic leukemia.

42. The method of claim 37, wherein the hyperproliferative disease is diffuse large B cell lymphoma.

* * * * *